(12) United States Patent
Cushing et al.

(10) Patent No.: US 8,575,183 B2
(45) Date of Patent: Nov. 5, 2013

(54) HETEROCYCLIC COMPOUNDS AND THEIR USES

(75) Inventors: Timothy David Cushing, Pacifica, CA (US); Jason A. Duquette, Millbrae, CA (US); Xiao He, Foster City, CA (US); Julia Lohman, San Francisco, CA (US); Youngsook Shin, Emeryville, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/078,192

(22) Filed: Apr. 1, 2011

(65) Prior Publication Data

US 2011/0245257 A1     Oct. 6, 2011

Related U.S. Application Data

(60) Provisional application No. 61/320,378, filed on Apr. 2, 2010.

(51) Int. Cl.
*A01N 43/90* (2006.01)
*A61K 31/519* (2006.01)
*C07D 239/02* (2006.01)

(52) U.S. Cl.
USPC ..... 514/265.1; 544/224; 544/322; 548/361.1; 548/469; 549/49; 549/200

(58) Field of Classification Search
USPC ............... 544/224, 322; 548/361.1, 469, 459; 549/49, 200; 514/265.1
See application file for complete search history.

(56) References Cited

U.S. PATENT DOCUMENTS

| | | | |
|---|---|---|---|
| 7,109,337 B2 * | 9/2006 | Kath et al. ............ | 544/324 |
| 2005/0256145 A1 * | 11/2005 | Kath et al. ............ | 514/275 |
| 2007/0244131 A1 * | 10/2007 | Lim et al. ............ | 514/256 |

FOREIGN PATENT DOCUMENTS

| | | | |
|---|---|---|---|
| EP | 0 252 507 A1 | | 1/1988 |
| EP | 0 530 149 A1 | | 3/1993 |
| EP | 2 194 044 A1 | | 6/2010 |
| WO | WO03040141 | * | 5/2003 |
| WO | WO2008039882 | * | 4/2008 |
| WO | 2009/041521 A1 | | 4/2009 |
| WO | 2009/128520 A1 | | 10/2009 |
| WO | 2010/061180 A1 | | 6/2010 |
| WO | 2010/092340 A1 | | 8/2010 |
| WO | 2010/151740 A2 | | 12/2010 |
| WO | 2011/075628 A1 | | 6/2011 |

OTHER PUBLICATIONS

Saudi et al., Synthesis of substituted pyrimidinedione derivatives as potential schistosomicidal agents Letters in Drug Design & Discovery (2009), 6(4), 268-277 CODEN: LDDDAW; ISSN: 1875-628X URL: http://www.benthamdirect.org/pages/b_byvolumeissue.php; English.*
Che et al, Che, Xin; Zheng, Lianyou; Dang, Qun; Bai, XuThe Center for Combinatorial Chemistry and Drug Discovery, Jilin University, Changchun, Jilin,130012, Peop. Rep. China Source: Journal of Organic Chemistry (2008), 73(3),1147-1149.*
McMahon et al Pinedo et al.*
Berndt, at al., "The p110δ structure: Mechanisms for selectivity and potency of new PI(3)K inhibitors" Nature Chemical Biology, Jan. 10, 2010 pp. 1-8.
Berndt, et al., "Supplementary Methods and Results the p110δ structure: Mechanisms for selectivity and potency of new PI(3)K inhibitors" Nature Chemical Biology, Jan. 2010 pp. 1-34.
Liu, Chemical Abstract, "Synthesis of benzoxepinoquinolinones" 1987.
Wang, Chemical Abstract, "Synthesis and elucidation of indoprofen analogues" 2003.
Bhat, Chemical Abstract, "Syntheses of 3-chloro-5, 8-disubstituted-6,7- or 8-monosubstituted-2-(substituted, . . . )"1982.
Agoh, Chemical-abstract, 1991.
Chemical_abstract, Dec. 28, 2008.
Chemical-abstract, Jun. 26, 2007.

* cited by examiner

Primary Examiner — Paul V. Ward
(74) Attorney, Agent, or Firm — Richard V. Person

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity, The present invention also enables methods for treating cancers that are mediated, dependent on or associated with p110δ activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

5 Claims, No Drawings

HETEROCYCLIC COMPOUNDS AND THEIR USES

This application claims the benefit of U.S. Provisional Application No. 61/320,378, filed Apr. 2, 2010, which is hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274: 8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Stepmmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of the AGC family. Members of the Tec family containing PH domains with apparent selectivity for PtdIns (3,4,5)P$_3$ include Tec, Btk, Itk and Etk. Binding of PH to PIP$_3$ is critical for tyrosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu Rev. Immunol. 22_563-598 (2004)). In vitro, some isoforms of protein kinase C (PKC) are directly activated by PIP3. (Burgering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan et al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85 α, p55 α and p50α proteins (Deane and Fruman, Annu Rev. Immunol. 22: 563-598

(2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3Kgamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p10'-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and G13γ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Froman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274: 10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p 110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinaemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CD5+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ<sup>D910A</sup> mice have been studied extensively and have elucidated the diverse role that delta plays in the immune system. T cell dependent and T cell independent immune responses are severely attenuated in p110δ<sup>D910A</sup> and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unknown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)). Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equipotently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosus (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ<sup>D910A</sup>) it was shown that in addition to playing a key role in B and T cell activation, delta is also partially involved in neutrophil migration and primed neutrophil respiratory burst leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ¹)<sup>910A</sup> mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ<sup>D910A</sup> mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

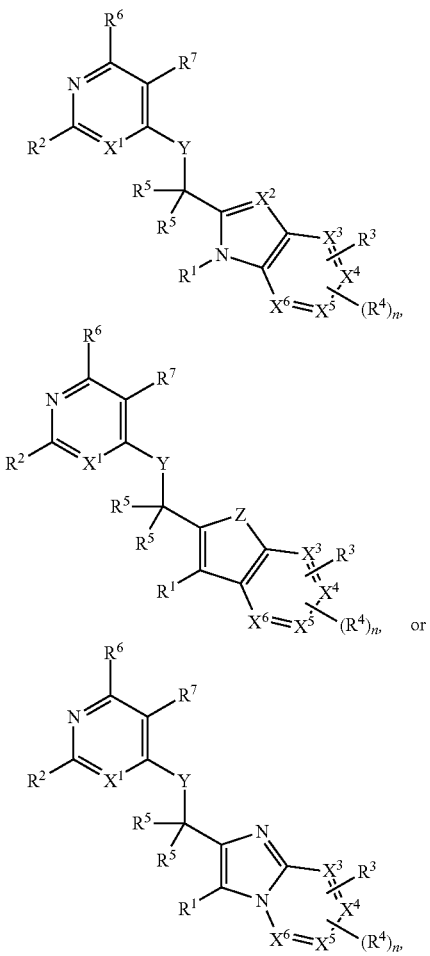

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the invention relates to compounds having the structure:

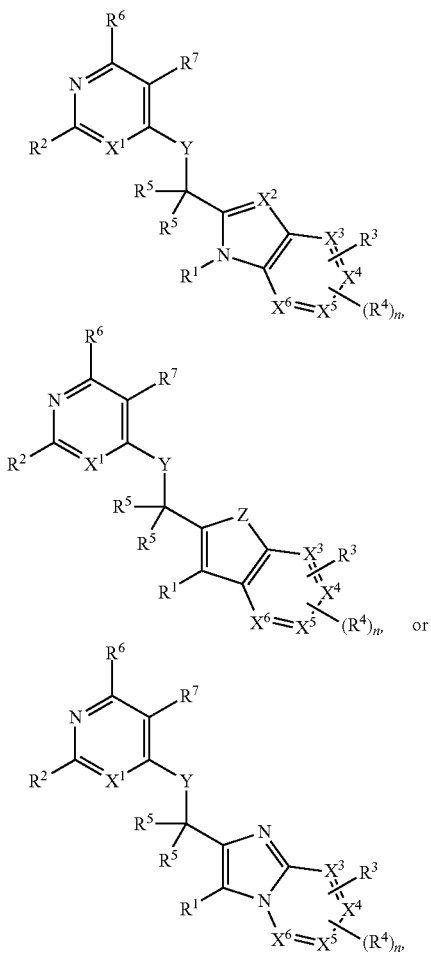

or any pharmaceutically-acceptable salt thereof, wherein:
$X^1$ is $C(R^{10})$ or N;
$X^2$ is $C(R^{12})$ or N;
$X^3$ is C or N;
$X^4$ is C or N;
$X^5$ is C or N;
$X^6$ is C or N; wherein at least two of $X^3$, $X^4$, $X^5$ and $X^6$ are C;
Y is $N(R^8)$, O or S;
Z is S, O, or $NR^{11}$;
n is 0, 1, 2 or 3;

$R^1$ is a direct-bonded, $C_{1-4}$alk-linked, $OC_{1-2}$alk-linked, $C_{1-2}$alkO-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$; wherein the available carbon atoms of the ring are additionally substituted by 0, 1 or 2 oxo or thioxo groups; and wherein the ring is additionally substituted by 0 or 1 saturated 5- or 6-membered monocyclic ring containing 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk and cyano; or $R^1$ is $C_{1-4}$alk substituted by 1 or 2 substituents selected from cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$;

$R^2$ is selected from H, halo, $C_{1-6}$alk, $C_{1-4}$haloalk, cyano, nitro, O$R^a$, N$R^aR^a$, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^3$ is selected from H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk, $C_{1-4}$haloalk, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$; or $R^3$ is an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —O$C_{1-4}$alk, —NH$_2$, —NH$C_{1-4}$alk, —N($C_{1-4}$alk)$C_{1-4}$alk;

$R^4$ is, independently, in each instance, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk or $C_{1-4}$haloalk;

$R^5$ is, independently, in each instance, H, halo, $C_{1-6}$alk, $C_{1-4}$haloalk, or $C_{1-6}$alk substituted by 1, 2 or 3 substituents selected from halo, cyano, OH, O$C_{1-4}$alk, $C_{1-4}$alk, $C_{1-3}$haloalk, O$C_{1-4}$alk, NH$_2$, NH$C_{1-4}$alk, N($C_{1-4}$alk)$C_{1-4}$alk; or both $R^5$ groups together form a $C_{3-6}$-spiroalk substituted by 0, 1, 2 or 3 substituents selected from halo, cyano, OH, O$C_{1-4}$alk, $C_{1-4}$alk, $C_{1-3}$haloalk, O$C_{1-4}$alk, NH$_2$, NH$C_{1-4}$alk, N($C_{1-4}$alk)$C_{1-4}$alk;

$R^6$ is H, halo, NH$R^9$ or OH;

R[7] is selected from H, halo, $C_{1-4}$haloalk, cyano, nitro, —C(=O)R[a], —C(=O)OR[a], —C(=O)NR[a]R[a], —C(=NR[a])NR[a]R[a], —OR[a], —OC(=O)R[a], —OC(=O)NR[a]R[a], —OC(=O)N(R[a])S(=O)$_2$R[a], —OC$_{2-6}$alkNR[a]R[a], —OC$_{2-6}$alkOR[a], —SR[a], —S(=O)R[a], —S(=O)$_2$R[a], —S(=O)$_2$NR[a]R[a], —S(=O)$_2$N(R[a])C(=O)R[a], —S(=O)$_2$N(R[a])C(=O)OR[a], —S(=O)$_2$N(R[a])C(=O)NR[a]R[a], —NR[a]R[a], —N(R[a])C(=O)R[a], —N(R[a])C(=O)OR[a], —N(R[a])C(=O)NR[a]R[a], —N(R[a])C(=NR[a])NR[a]R[a], —N(R[a])S(=O)$_2$R[a], —N(R[a])S(=O)$_2$NR[a]R[a], —NR[a]C$_{2-6}$alkNR[a]R[a], —NR[a]C$_{2-6}$alkOR[a] and $C_{1-6}$alk, wherein the $C_{1-6}$alk is substituted by 0, 1 2 or 3 substituents selected from halo, $C_{1-4}$haloalk, cyano, nitro, —C(=O)R[a], —C(=O)OR[a], —C(=O)NR[a]R[a], —C(=NR[a])NR[a]R[a], —OR[a], —OC(=O)R[a], —OC(=O)NR[a]R[a], —OC(=O)N(R[a])S(=O)$_2$R[a], —OC$_{2-6}$alkNR[a]R[a], —OC$_{2-6}$alkOR[a], —SR[a], —S(=O)R[a], —S(=O)$_2$R[a], —S(=O)$_2$NR[a]R[a], —S(=O)$_2$N(R[a])C(=O)R[a], —S(=O)$_2$N(R[a])C(=O)OR[a], —S(=O)$_2$N(R[a])C(=O)NR[a]R[a], —NR[a]R[a], —N(R[a])C(=O)R[a], —N(R[a])C(=O)OR[a], —N(R[a])C(=O)NR[a]R[a], —N(R[a])C(=NR[a])NR[a]R[a], —N(R[a])S(=O)$_2$R[a], —N(R[a])S(=O)$_2$NR[a]R[a], —NR[a]C$_{2-6}$alkNR[a]R[a] and —NR[a]C$_{2-6}$alkOR[a], and the $C_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, $C_{1-4}$alk, $OC_{1-4}$alk, $OC_{1-4}$haloalk, $NHC_{1-4}$alk, $N(C_{1-4}$alk)$C_{1-4}$alk and $C_{1-4}$haloalk; or R[7] and R[8] together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, $C_{1-4}$haloalk, cyano, nitro, —C(=O)R[a], —C(=O)OR[a], —C(=O)NR[a]R[a], —C(=NR[a])NR[a]R[a], —OR[a], —OC(=O)R[a], —OC(=O)NR[a]R[a], —OC(=O)N(R[a])S(=O)$_2$R[a], —OC$_{2-6}$alkNR[a]R[a], —OC$_{2-6}$alkOR[a], —SR[a], —S(=O)R[a], —S(=O)$_2$R[a], —S(=O)$_2$NR[a]R[a], —S(=O)$_2$N(R[a])C(=O)R[a], —S(=O)$_2$N(R[a])C(=O)OR[a], —S(=O)$_2$N(R[a])C(=O)NR[a]R[a], —NR[a]R[a], —N(R[a])C(=O)R[a], —N(R[a])C(=O)OR[a], —N(R[a])C(=O)NR[a]R[a], —N(R[a])C(=NR[a])NR[a]R[a], —N(R[a])S(=O)$_2$R[a], —N(R[a])S(=O)$_2$NR[a]R[a], —NR[a]C$_{2-6}$alkNR[a]R[a] and —NR[a]C$_{2-6}$alkOR[a]; or R[7] and R[9] together form a —N=C— bridge wherein the carbon atom is substituted by H, halo, $C_{1-6}$alk, $C_{1-4}$haloalk, cyano, nitro, OR[a], NR[a]R[a], —C(=O)R[a], —C(=O)OR[a], —C(=O)NR[a]R[a], —C(=NR[a])NR[a]R[a], —S(=O)R[a], —S(=O)$_2$R[a], —S(=O)$_2$NR[a]R[a];

R[8] is H or $C_{1-6}$alk;
R[9] is H, $C_{1-6}$alk or $C_{1-4}$haloalk;
R[10] is H, halo, $C_{1-3}$alk, $C_{1-3}$haloalk or cyano;
R[11] is H or $C_{1-4}$alk;
R[12] is H or $C_{1-4}$alk;
R[a] is independently, at each instance, H or R[b]; and
R[b] is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk.

In another embodiment, in conjunction with the above and below embodiments, the structure is:

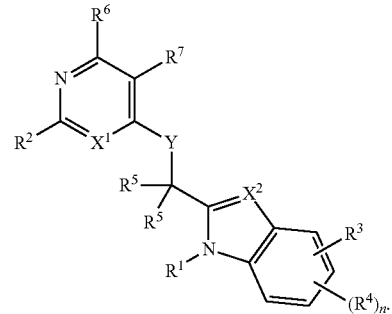

In another embodiment, in conjunction with the above and below embodiments, the structure is:

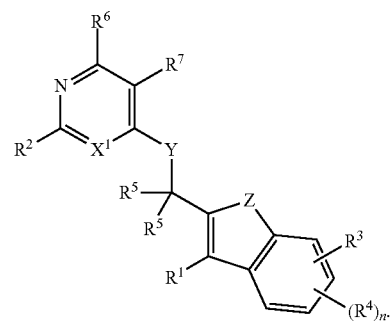

In another embodiment, in conjunction with the above and below embodiments, the structure is:

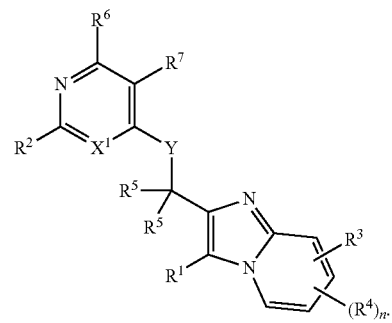

In another embodiment, in conjunction with the above and below embodiments, $X^3$ is C; $X^4$ is C; $X^5$ is C; and $X^6$ is C.
In another embodiment, in conjunction with the above and below embodiments, $X^3$ is N; $X^4$ is C; $X^5$ is C; and $X^6$ is C.
In another embodiment, in conjunction with the above and below embodiments, $X^3$ is C; $X^4$ is N; $X^5$ is C; and $X^6$ is C.
In another embodiment, in conjunction with the above and below embodiments, $X^3$ is C; $X^4$ is C; $X^5$ is N; and $X^6$ is C.
In another embodiment, in conjunction with the above and below embodiments, $X^3$ is C; $X^4$ is C; $X^5$ is C; and $X^6$ is N.
In another embodiment, in conjunction with the above and below embodiments, $R^1$ is a direct-bonded, $C_{1-4}$alk-linked, $OC_{1-2}$alk-linked, $C_{1-2}$alkO-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; wherein the available carbon atoms of the ring are additionally substituted by 0, 1 or 2 oxo or thioxo groups; and wherein the ring is additionally substituted by 0 or 1 saturated 5- or 6-membered monocyclic ring containing 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk and cyano.

In another embodiment, in conjunction with the above and below embodiments, $R^1$ is a direct-bonded, $C_{1-4}$alk-linked, $OC_{1-2}$alk-linked, $C_{1-2}$alkO-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; wherein the available carbon atoms of the ring are additionally substituted by 0, 1 or 2 oxo or thioxo groups; and wherein the ring is additionally substituted a saturated 5- or 6-membered monocyclic ring containing 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk and cyano.

In another embodiment, in conjunction with the above and below embodiments, $R^1$ is a direct-bonded, $C_{1-4}$alk-linked, $OC_{1-2}$alk-linked, $C_{1-2}$alkO-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; wherein the available carbon atoms of the ring are additionally substituted by 0, 1 or 2 oxo or thioxo groups; and wherein the ring is additionally substituted phenyl or pyridyl, either of which is substituted by 0, 1, 2 or 3 substituents independently selected from halo, $C_{1-6}$alk, $C_{1-4}$haloalk and cyano.

In another embodiment, in conjunction with the above and below embodiments, $R^1$ is a direct-bonded phenyl or pyridyl, either of which is substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is a direct-bonded phenyl or pyridyl, either of which is substituted by 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is a direct-bonded phenyl or pyridyl.

In another embodiment, in conjunction with the above and below embodiments, $R^1$ is a direct-bonded phenyl or pyridyl, either of which is substituted by 1, 2 or 3 substituents independently selected from halo, —S$R^a$, —S(=O)$R^a$ and —S(=O)$_2R^a$.

In another embodiment, in conjunction with the above and below embodiments, $R^1$ is a direct-bonded phenyl or pyridyl, either of which is substituted by 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is $C_{1-4}$alk substituted by 1 or 2 substituents selected from cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is $C_{2-4}$alk substituted by —O$R^a$.

In another embodiment, in conjunction with the above and below embodiments, $R^1$ is a direct-bonded, $C_{1-4}$alk-linked, $OC_{1-2}$alk-linked, $C_{1-2}$alkO-linked or O-linked cyclopropyl substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; wherein the available carbon atoms of the ring are additionally substituted by 0, 1 or 2 oxo or thioxo groups; and wherein the ring is additionally substituted by 0 or 1 saturated 5- or 6-membered monocyclic ring containing 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk and cyano.

In another embodiment, in conjunction with the above and below embodiments, $R^1$ is cyclopropyl.

In another embodiment, in conjunction with the above and below embodiments, $R^1$ is cyclopropylmethyl.

In another embodiment, in conjunction with the above and below embodiments, $X^1$ is N.

In another embodiment, in conjunction with the above and below embodiments, $X^2$ is N.

In another embodiment, in conjunction with the above and below embodiments, $X^2$ is C($R^{12}$).

In another embodiment, in conjunction with the above and below embodiments, Y is N($R^8$).

In another embodiment, in conjunction with the above and below embodiments, $R^1$ is a direct-bonded saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with the above and below embodiments, $R^1$ is a direct-bonded unsaturated 6-membered monocyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$.

In another embodiment, in conjunction with the above and below embodiments, $R^1$ is phenyl, pyridyl or pyrimidinyl, all of which are substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is phenyl substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^1$ is phenyl, pyridyl or pyrimidinyl, all of which are substituted by 1, 2 or 3 substituents independently selected from halo, $C_{1-6}$alk, and $C_{1-4}$haloalk.

In another embodiment, in conjunction with the above and below embodiments, $R^1$ is phenyl which is substituted by 1, 2 or 3 substituents independently selected from halo, $C_{1-6}$alk, and $C_{1-4}$haloalk.

In another embodiment, in conjunction with the above and below embodiments, $R^2$ is H.

In another embodiment, in conjunction with the above and below embodiments, $R^3$ is selected from H and halo.

In another embodiment, in conjunction with the above and below embodiments, $R^3$ is selected from halo, nitro, cyano, $C_{1-4}$alk, O$C_{1-4}$alk, O$C_{1-4}$haloalk, NH$C_{1-4}$alk, N($C_{1-4}$alk)$C_{1-4}$alk, $C_{1-4}$haloalk, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with the above and below embodiments, $R^5$ is, independently, in each instance, H, halo, $C_{1-6}$alk, and $C_{1-4}$haloalk.

In another embodiment, in conjunction with the above and below embodiments, one $R^5$ is H and the other $R^5$ is $C_{1-6}$alk.

In another embodiment, in conjunction with the above and below embodiments, one $R^5$ is H and the other $R^5$ is methyl.

In another embodiment, in conjunction with the above and below embodiments, one $R^5$ is H and the other $R^5$ is (R)-methyl.

In another embodiment, in conjunction with the above and below embodiments, one $R^5$ is H and the other $R^5$ is (S)-methyl.

In another embodiment, in conjunction with the above and below embodiments, $R^6$ is NH$R^9$.

In another embodiment, in conjunction with the above and below embodiments, $R^7$ is cyano.

In another embodiment, in conjunction with the above and below embodiments, $R^7$ and $R^8$ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, $C_{1-4}$haloalk, cyano, nitro, —C(=O)$R^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with the above and below embodiments, $R^7$ and $R^9$ together form a —N=C— bridge wherein the carbon atom is substituted by H, halo, $C_{1-4}$alk, $C_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$.

In another embodiment, in conjunction with the above and below embodiments, $R^7$ and $R^9$ together form a —N=C— bridge wherein the carbon atom is substituted by H or halo.

In another embodiment, in conjunction with the above and below embodiments, the structure has the general formula:

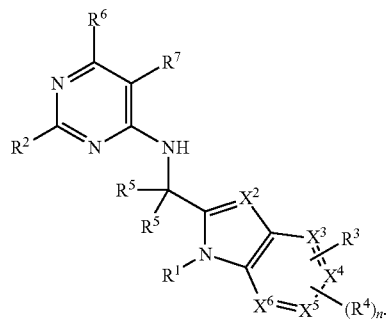

In another embodiment, in conjunction with the above and below embodiments, the structure has the general formula:

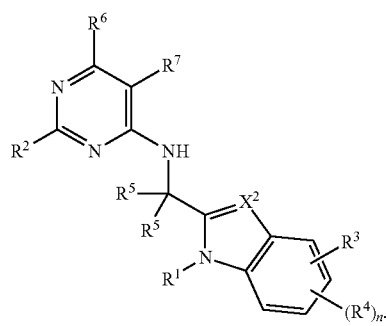

In another embodiment, in conjunction with the above and below embodiments, the structure has the general formula:

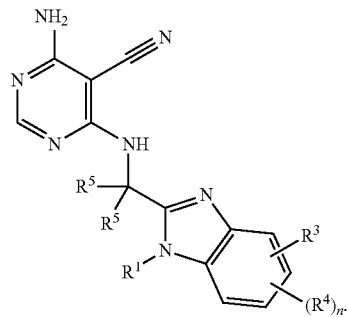

In another embodiment, in conjunction with the above and below embodiments, the structure has the general formula:

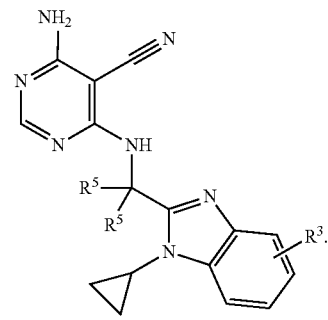

In another embodiment, in conjunction with the above and below embodiments, the structure has the general formula:

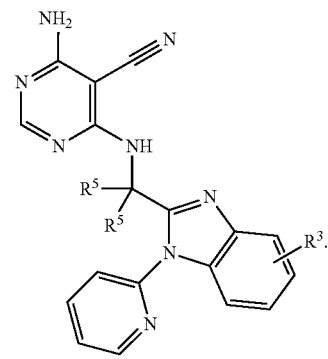

In another embodiment, in conjunction with the above and below embodiments, the structure has the general formula:

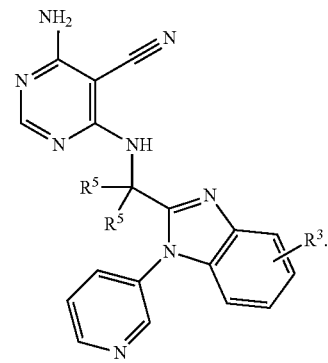

In another embodiment, in conjunction with the above and below embodiments, the structure has the general formula:

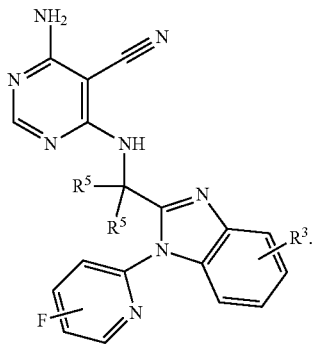

In another embodiment, in conjunction with the above and below embodiments, the structure has the general formula:

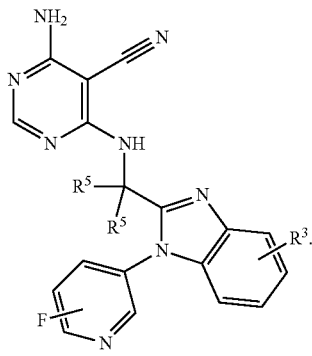

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha\text{-}\beta}$alk" means an alk group comprising a minimum of a and a maximum of 13 carbon atoms in a branched, cyclical or linear relationship or any combination of the three, wherein α and β represent integers. The alk groups described in this section may also contain one or two double or triple bonds. Examples of $C_{1\text{-}6}$alk include, but are not limited to the following:

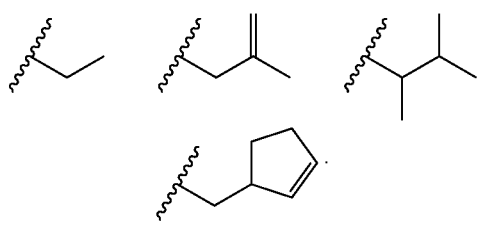

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalk" means an alk group, as described above, wherein any number—at least one—of the hydrogen atoms attached to the alk chain are replaced by F, Cl, Br or I.

"Heterocycle" means a ring comprising at least one carbon atom and at least one other atom selected from N, O and S. Examples of heterocycles that may be found in the claims include, but are not limited to, the following:

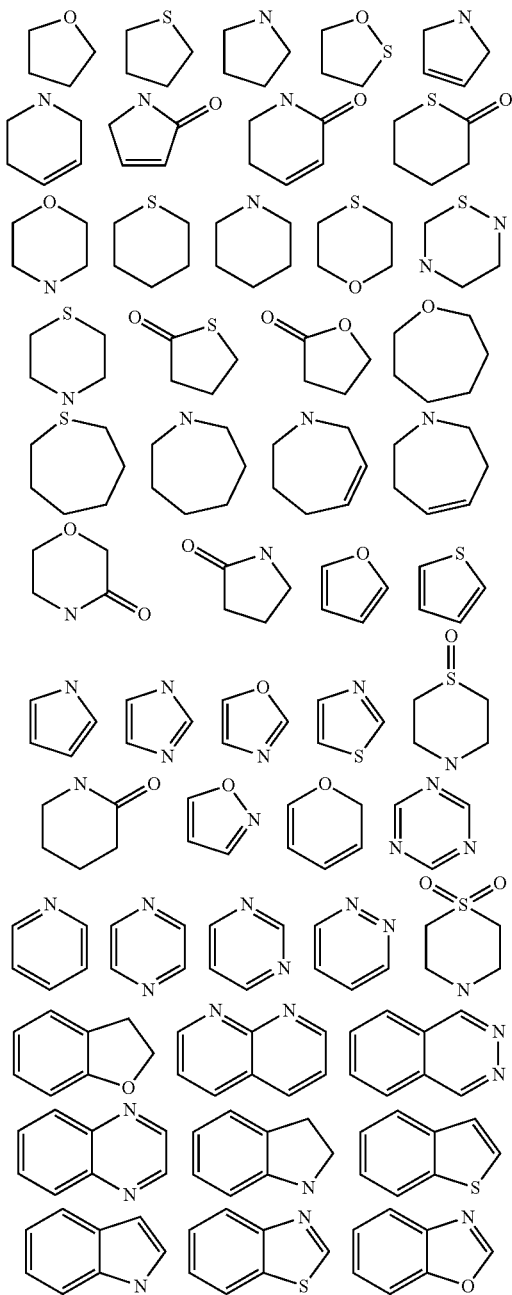

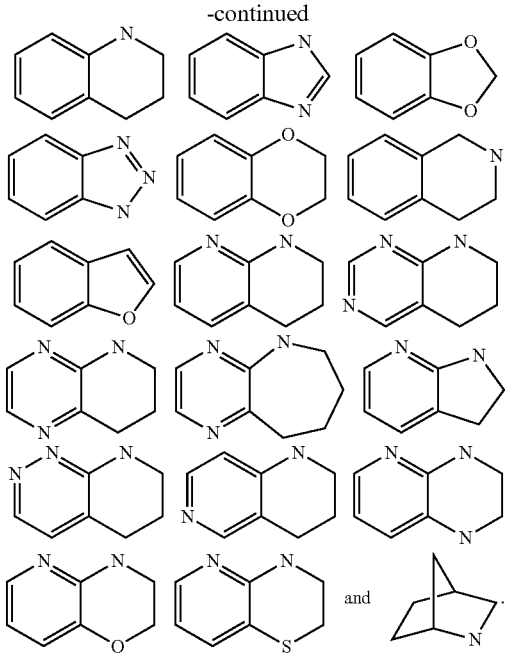

and .

"Available nitrogen atoms" are those nitrogen atoms that are part of a heterocycle and are joined by two single bonds (e.g. piperidine), leaving an external bond available for substitution by, for example, H or CH$_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralk, substituted aralk, cycloalkenylalk and substituted cycloalkenyl alk, allyl, substituted allyl, acyl, alkoxycarbonyl, aralkoxycarbonyl, silyl and the like. Examples of aralk include, but are not limited to, benzyl, ortho-methylbenzyl, trityl and benzhydryl, which can be optionally substituted with halogen, alk, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalk or substituted cycloalkenylalk radicals, preferably have 6-10 carbon atoms, include, but are not limited to, cyclohexenyl methyl and the like.

Suitable acyl, alkoxycarbonyl and aralkoxycarbonyl groups include benzyloxycarbonyl, t-butoxycarbonyl, isobutoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralk group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalk rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralk groups. Alk groups are also suitable groups for protecting hydroxy and mercapto groups, such as tert-butyl.

Silyl protecting groups are silicon atoms optionally substituted by one or more alk, aryl and aralk groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

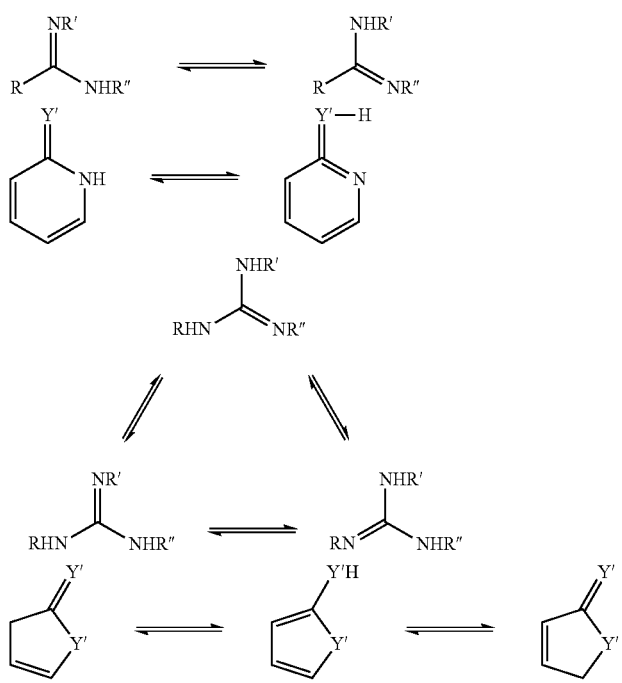

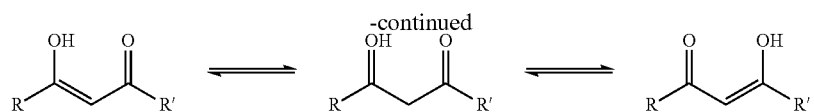

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alk (for example, methyl, ethyl), cycloalk (for example, cyclohexyl), aralk (for example, benzyl, p-methoxybenzyl), and alkcarbonyloxyalk (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)).

Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Experimental

The following abbreviations are used:
AcOH—glacial acetic acid
aq.—aqueous
BINAP—2,2'-bis(diphenylphosphino)-1,1'-binaphthyl
concd.—concentrated
DCM—dichloromethane
DIEA—N,N-diisopropyl ethylamine
DMF—N,N-dimethylformamide
DMS—dimethyl sulfide
EDCHCl N-(3-dimethylaminopropyl)-N'-ethylcarbodiimide hydrochloride
eqv.—equivalent
Et$_2$O—diethyl ether
EtOAc—ethyl acetate
EtOH—ethyl alcohol
h—hour(s)
min—minutes
MeOH—methyl alcohol
MsCl—methanesulfonyl chloride
NaOAc—sodium acetate
rt—room temperature
satd.—saturated
TFA—trifluoroacetic acid
THF—tetrahydrofuran General Reagents and solvents used below can be obtained from commercial sources. $^1$H-NMR spectra were recorded on a Bruker 400 MHz and 500 MHz NMR spectrometer. Significant peaks are tabulated in the order: multiplicity (s, singlet; d, doublet; t, triplet; q, quartet; m, multiplet; br s, broad singlet), coupling constant(s) in hertz (Hz) and number of protons. Mass spectrometry results are reported as the ratio of mass over charge, followed by the relative abundance of each ion (in parentheses electrospray ionization (ESI) mass spectrometry analysis was conducted on a Agilent 1100 series LC/MSD electrospray mass spectrometer. All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 μm column (4.6×150 mm) as the stationary phase and eluting with acetonitrile:water with 0.1% TFA. Reverse phase semi-prep HPLC was carried out using a Agilent 1100 Series on a Phenomenex Gemini™ 10 μm C18 column (250×21.20 mm) as the stationary phase and eluting with acetonitrile:water with 0.1% TFA. semi-prep supercritical fluid chromatography (SFC) was carried out using a Thar 350 SFC with a Daicel™ AD-H column (250×30 mm) as the stationary phase and eluting with methanol (20 mM NH$_3$):CO$_2$ as the mobile phase.

General Procedures

Preparation of (S)-benzyl 4-bromo-3-oxobutan-2-ylcarbamate (A)

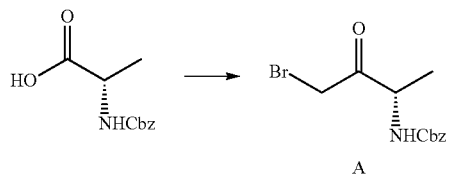

To a solution of N-{(benzyloxy)carbonyl} L-alanine (20 g, 89.64 mmol) in THF (400 mL) at −20° C. was added NMM (13.5 g, 133.2 mmol), followed by isobutyl chloroformate (14.6 g, 107 mmol). After stirring for 1.5 h at −20° C., this mixture was filtered off under cooling and the filtrate was treated with excess freshly prepared diazomethane/Et$_2$O solution (prepared from 30.0 g of N-methyl nitroso urea, 200 mL 40% KOH/100 mL Et$_2$O) with stirring until a yellow color persisted. The mixture was allowed to warm to 0° C. and the solution was then warmed to rt and stirred for 1 h, re-cooled to 0° C. and treated with a solution of HBr (45% aqueous)/AcOH (1/1 (v/v), 50 mL) for 30 minutes, reaction was monitored by TLC, after completion of reaction, reaction mass was diluted with EtOAc (500 mL) and water (200 mL). The organic phase was separated, washed with water, dried over Na$_2$SO$_4$, filtered and concentrated. The crude product was purified by column chromatography on silical gel using hexanes/EtOAc (2:1) as eluent to give the desired product (S)-benzyl 4-bromo-3-oxobutan-2-ylcarbamate: $^1$H NMR (400 MHz, DMSO-d$_6$): δ 7.35-7.38 (m, 5H), δ5.4 (bs, 1H), δ5.0-5.1 (s, 2H), δ4.6-4.7 (q, 1H), δ4.01-4.09 (q, 2H), δ1.41-1.43 (d, 3H); LC-MS (ESI) m/z 300.11 [M+H ($^{79}$Br)]$^+$ and 302.12 [M+H ($^{81}$Br)]$^+$ Preparation of 4-amino-6-chloro-5-pyrimidinecarbonitrile (B)

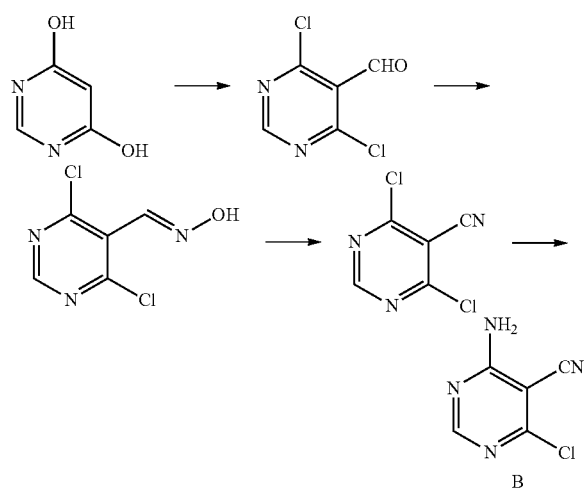

4,6-Dichloro-5-pyrimidinecarbaldehyde

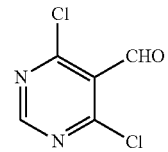

A mixture of DMF (64 mL) and POCl$_3$ (200 mL) at 0° C. was stirred for 1 h, treated with 4,6-pyrimidinediol (50.0 g, 446 mmol), and stirred for 0.5 h at rt, and then refluxed for 3 h. The volatiles were removed under reduced pressure, and the residue was poured into ice water and extracted six times with Et$_2$O. The organic phase was washed with satd. aq. NaHCO$_3$ and water, dried over Na$_2$SO$_4$, concentrated, and crystallized (EtOAc-petroleum ether) to give 4,6-dichloro-5-pyrimidinecarbaldehyde; LC-MS (ESI) m/z 177 [M+H]$^+$.

4,6-Dichloro-5-pyrimidinecarbaldehyde oxime

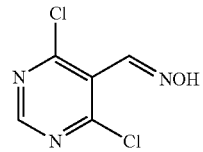

A mixture of 4,6-dichloro-5-pyrimidinecarbaldehyde (8.00 g, 44.8 mmol), NaOAc (3.7 g, 1.0 eq) and NH$_2$OH.HCl (3.1 g, 1.0 eq) in EtOH (320 mL) was stirred at rt for 2 h. The reaction mixture was filtered, concentrated and purified by column chromatography on silica gel (dry loading, first DCM then DCM/EtOAc, 1/9) to give 4,6-dichloro-5-pyrimidinecarbaldehyde oxime as a white solid.

4,6-Dichloro-5-pyrimidinecarbonitrile

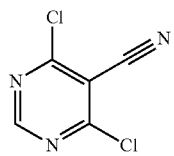

4,6-Dichloro-5-pyrimidinecarbaldehyde oxime (8 g) was dissolved in CHCl$_3$ (40 mL) and treated with SOCl$_2$ (6 mL) for 2 h at rt. The solvent was removed and the residue triturated with DCM (5 mL) to give a white solid, which was filtered and washed with DCM (5 mL). The filtrate was concentrated under reduced pressure and purified by column chromatography on silica gel (dry loading, DCM/hexane, 3/1) to give a white solid. The two solids were combined to provide 4,6-dichloro-5-pyrimidinecarbonitrile.

4-Amino-6-chloro-5-pyrimidinecarbonitrile (B)

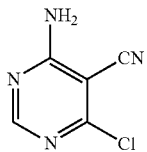

The white solid, 4,6-dichloro-5-pyrimidinecarbonitrile (5.82 g, 33.5 mmol) was dissolved in THF (66.9 mL) in a 500 mL of round-bottom flask and ammonia gas (0.570 g, 33.5 mmol) was bubbled through for 3 min every 10 min for 50 min with stirring. A white precipitate (ammonium chloride) was formed. The precipitate was filtered and washed with THF (100 mL). To the filtrate was added silica gel and concentrated under reduced pressure. The mixture was purified by column chromatography on a 120 g of Redi-Sep column using 0 to 100% gradient of EtOAc in hexane over 27 min and then 100% isocratic of EtOAc in hexane for 20 min as eluent to give 4-amino-6-chloropyrimidine-5-carbonitrile as an off-white solid. The off-white solid was suspended in EtOAc-hexane (1:1, 20 mL), filtered, washed with EtOAc-hexane (1:1, 30 mL), and dried to give 4-amino-6-chloro-5-pyrimidinecarbonitrile (B) as a white solid: $^1$H NMR (500 MHz, DMSO-$d_6$) δ ppm 7.91-8.77 (3H, m); LC-MS (ESI) m/z 154.9 [M+H]$^+$.

General Procedure C for Imidazopyridine Analogs

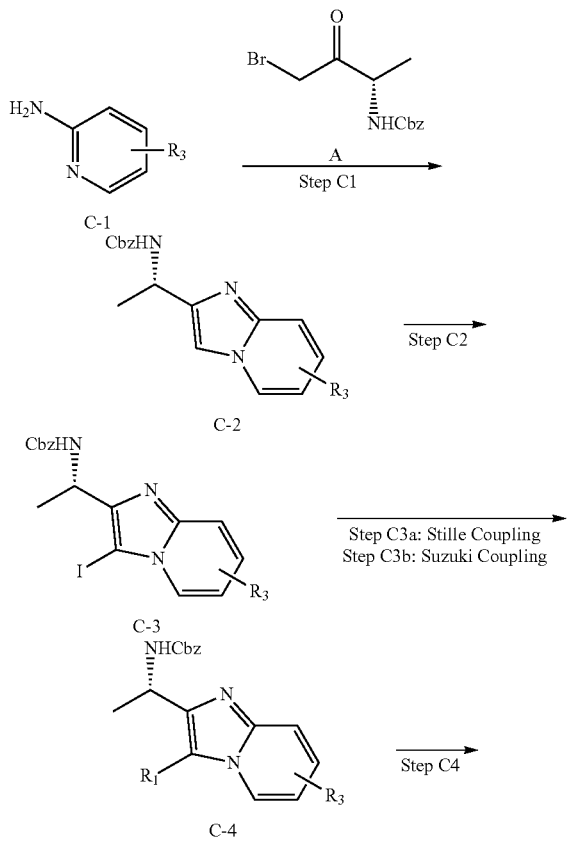

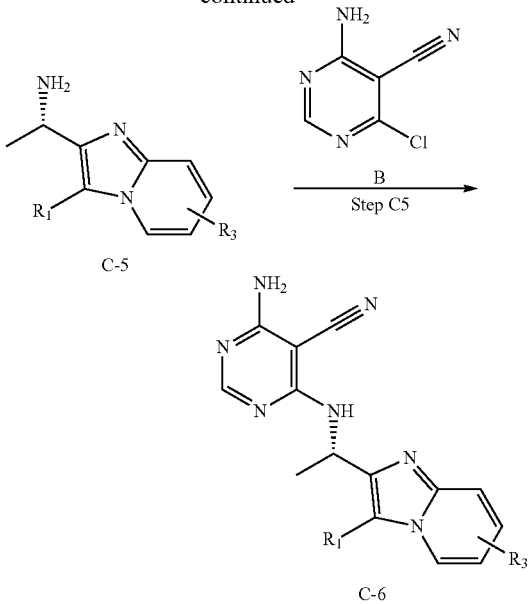

Step C1. Synthesis of C-2. A mixture of (S)-benzyl 4-bromo-3-oxobutane-2-ylcarbamate (23.32 mmol) and C-1 (23.32 mmol) in EtOH was heated to reflux overnight. After the completion of the reaction, the mixture was cooled to rt. EtOH was removed under reduced pressure and the residue was dissolved in EtOAc. The organic layer was washed with satd. aq. NaHCO$_3$ solution, dried over Na$_2$SO$_4$, filtered and concentrated under reduced pressure. The crude residue was purified by column chromatography on silica gel (100-200 mesh) using 0 to 8% gradient of MeOH in DCM as eluent to give C-2.

Step C2. Synthesis of C-3. To a solution of C-2 (12.11 mmol) in acetonitrile was added N-iodosuccinimide (12.11 mmol). The reaction mixture was stirred overnight at rt. After completion of the reaction by TLC, the mixture was diluted with water and extracted with EtOAc. The organic layer was washed with satd. aq. NaHCO$_3$ solution, dried over Na$_2$SO$_4$, filtered and concentrated. The crude residue obtained was purified by column chromatography on silica gel (100-200 mesh) using 0 to 50% gradient of EtOAc in hexane as eluent to give C3 as solid.

Step C3a. Stille Coupling. Synthesis of C-4. A mixture of C-3 (1 eqv.), tin reagent (1.2 eqv.), and Pd(PPh$_3$)$_4$ (0.1 eqv.) in 1,4-Dioxane was stirred at 110° C. for overnight. After completion of the reaction by TLC, the reaction mixture was cooled to rt, and concentrated under reduced pressure to give a brownish liquid. The brownish liquid was purified using a Biotage Companion™ with 100 g of silica gel column and eluting with 0 to 40% gradient of EtOAc in hexane to give C4 as a solid.

Step C3b. Suzuki reaction. Synthesis of C-4. A mixture of boronic acid (0.854 mmol), C-3 (0.569 mmol), Pd(Ph$_3$P)$_4$ (0.028 mmol), and Na$_2$CO$_3$ (1.138 mmol) in acetonitrile-water (3:1) was heated at 100° C. for 2 h. The reaction mixture was partitioned between water and EtOAc. The organic layer was separated, dried with Na$_2$SO$_4$, filtered, and concentrated. The residue was dissolved in DCM and loaded onto a silica gel cartridge. The compound was purified by column chromatography on a 12 g of Redi-Sep™ column using 0 to 70% gradient of EtOAc in hexane as eluent. The desired fractions were combined and concentrated to yield a sticky amber colored residue, C-4.

Step C4. Synthesis of C-5.

The mixture of the C-4 (1.16 mmol) and DMS (0.4 mL in TFA (1.6 mL)) was stirred at rt overnight. After the completion of the reaction, according to TLC, the mixture was concentrated under vacuum, dissolved in EtOAc (100 mL), and washed with satd. aq. $NaHCO_3$ solution. The organic layer was dried over $Na_2SO_4$, filtered and concentrated to yield the crude product C-6, which was carried on crude without purification for the next step.

Step C5. Synthesis of C-6.

A mixture of 4-amino-6-chloropyrimidine-5-carbonitrile (B) (1.0 eqv.), C-5 (1.0 eqv.) and DIEA (3.0 eqv.) in n-butanol was stirred at 110° C. for overnight. The reaction was monitored by TLC, after completion of reaction the reaction mixture was concentrated under reduced pressure. The residue was purified by column chromatography on silica gel using 0 to 10% gradient of MeOH in DCM as eluent to give C-6.

General Procedure D for Benzimidazole Analogs

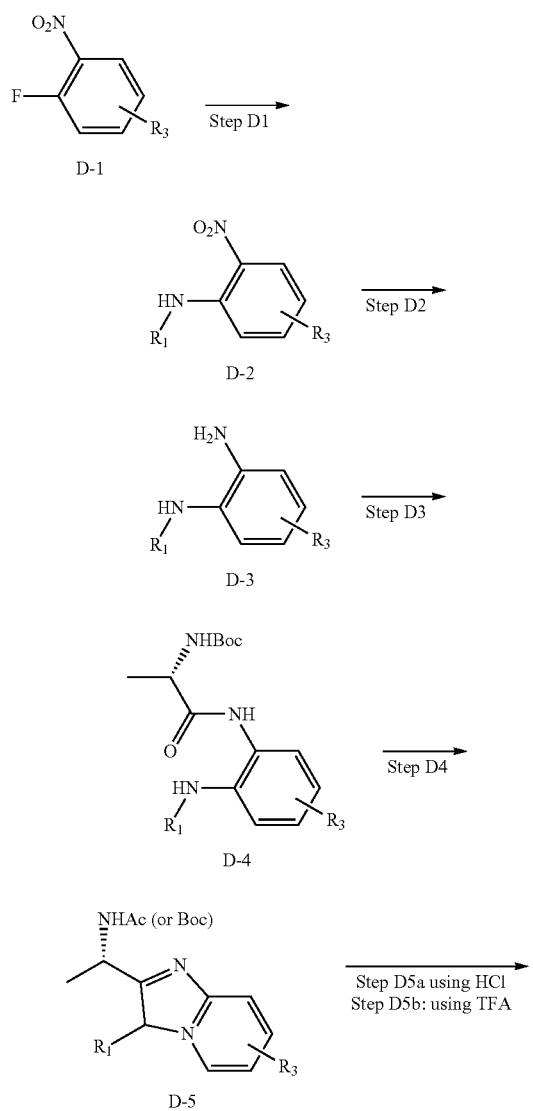

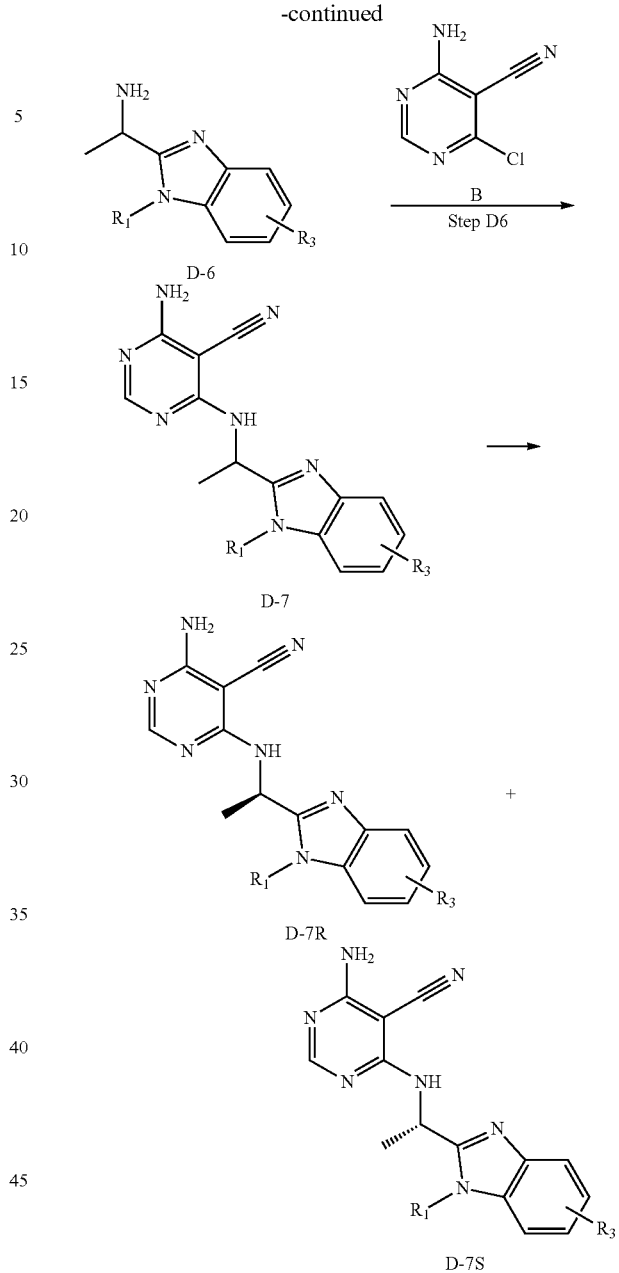

Step D1. Synthesis of D-2. A mixture of D-1 (16.02 mmol) and substituted aniline (16.02 mmol) was stirred at 130° C. After 92 h, the mixture was cooled to rt and a black solid was formed. The mixture containing the black solid was dissolved in DCM (50 mL) and washed with satd. aq. $NaHCO_3$ solution (30 mL×1). The organic layer was dried over $MgSO_4$, filtered, and concentrated under reduced pressure. The residue was purified by column chromatography on a 120 g of Redi-Sep™ column using 0 to 50% gradient of EtOAc in hexane over 27 min and then 50% isocratic of EtOAc in hexane for 27 min as eluent to give D-2.

Step D2. Synthesis of D-3. A mixture of D-2 (2.80 mmol) and tin(II) chloride dihydrate (14.00 mmol) in EtOAc (18.67 mL) was heated under reflux with stirring. After 5 h, the mixture was cooled to rt, and poured into 10 M aqueous NaOH solution (50 mL). The mixture was extracted with EtOAc (50 mL×2). The combined organic layers were washed with water (50 mL×2) and brine (50 mL×1), dried over Mg₂SO₄, filtered, and concentrated under reduced pressure. The residue was purified by column chromatography on a 40 g of Redi-Sep™ column using 0 to 20% gradient of EtOAc in hexane over 14 min and then 20% isocratic of EtOAc in hexane for 14 min as eluent to give D-3.

Step D3. Synthesis of D-4. To a −10° C. solution (NaCl-ice bath) of Boc-L-Ala-OH (0.965 g, 5.10 mmol) and N-methylmorpholine (0.589 mL, 5.35 mmol) in DCM (12.75 mL) was added isobutyl chloroformate (0.667 mL, 5.10 mmol). The resulting cloudy colorless mixture was stirred at −10° C. After 1 h, a solution of D-3 (2.55 mmol) in DCM (12.75 mL) was added to the mixture. The resulting mixture was stirred at −10° C. for 40 min, then allowed to warm to rt. After 24 h, satd. aq. NH₄Cl solution (50 mL) was added to the mixture and the organic layer separated. The aqueous mixture was extracted with DCM (50 mL×1). The combined organic layers were dried over MgSO₄, filtered, and concentrated under reduced pressure to give a pink solid. The pink solid was purified by column chromatography on a 40 g of Redi-Sep™ column using 0 to 20% gradient of EtOAc in hexane over 14 min, then 20% isocratic of EtOAC in hexane for 14 min, then 20 to 50% gradient of EtOAc in hexane over 14 min, and then 50% isocratic of EtOAC in hexane for 14 min as eluent to give D-4.

Step D4. Synthesis of D-5a or D-5b. A solution of D-4 (2.485 mmol) in AcOH (8.28 mL) was heated at 100° C. with stirring. After 92 h, the mixture was cooled to rt and poured into DCM (50 mL) and satd. aq. NaHCO₃ solution (50 mL). The aqueous layer was separated. The organic layer was washed with satd. aq. NaHCO₃ solution (50 mL×1), washed with water (50 mL×1) and brine (50 mL×1), dried over MgSO₄, filtered, and concentrated under reduced pressure to give D-5a or D-5b. Epimerization occurred during cyclization, and Boc-protecting group was cleaved and the free amine was re-protected with acetyl group during the reaction to give D-5b.

Step D5a. Synthesis of D-6. A solution of D-5a (2.117 mmol) and 2 N HCl (16.94 mL, 33.9 mmol) was heated at 100° C. After 22 h, the mixture was cooled to rt. The acidic aqueous mixture was washed with DCM (30 mL×2) to remove organic impurities and then basified to ~pH 10 with 10 N NaOH (3.5 mL), extracted with DCM (50 mL×3). The combined organic layers were washed with water (100 mL×1), brine (100 mL×1), and dried over MgSO₄, filtered, and concentrated under reduced pressure to give D-6. The crude product D-6 was carried on without purification to the next step.

Step D5b. Synthesis of D-6. To a mixture of D-5b (1.589 mmol) in DCM (10.59 mL) was added dropwise TFA (138 mmol) at rt with stirring. The reaction mixture became clear and the solution was stirred at rt. for 1.5 h. The mixture was then concentrated under reduced pressure to give a yellow syrup. The syrup was dissolved in DCM (50 mL), washed with satd. aq. NaHCO₃ solution (50 mL×1), water (50 mL×1), brine (50 mL×1), dried over MgSO₄, filtered, and concentrated under reduced pressure to give D-6. The crude product D-6 was carried on crude without purification for the next step.

Step D6. Synthesis of D-7. A mixture of 4-amino-6-chloropyrimidine-5-carbonitrile (B) (0.257 g, 1.662 mmol), D-6 (1.662 mmol), and DIEA (0.868 mL, 4.99 mmol) in n-butanol (16.62 mL) was stirred at 120° C. After 24 h, the heat was removed and left at rt. After cooling, the mixture was concentrated under reduced pressure to give a brown solid, which was suspended in water (50 mL), sonicated, filtered, and washed with water (100 mL) to give a tan solid. The tan solid was suspended in EtOAc-hexane (1:4, 20 mL), filtered, washed with EtOAc-hexane (1:4, 20 mL), and dried to give D-7 as a racemic mixture.

Example 1

Preparation of 4-amino-6-((1-(6-fluoro-1-(3-(methylsulfonyl)phenyl)-1H-benzimidazol-2-yl)ethyl)amino)-5-pyrimidinecarbonitrile, 4-amino-6-(((1R)-1-(6-fluoro-1-(3-(methylsulfonyl)phenyl)-1H-benzimidazol-2-yl)ethyl)amino)-5-pyrimidinecarbonitrile, and 4-amino-6-(((1S)-1-(6-fluoro-1-(3-(methylsulfonyl)phenyl)-1H-benzimidazol-2-yl)ethyl)amino)-5-pyrimidinecarbonitrile 5-Fluoro-N-(3-(methylsulfonyl)phenyl)-2-nitroaniline

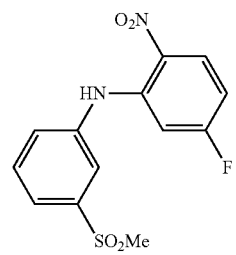 [SMILES: CS(=O)(=O)c1cccc(Nc2cc(F)ccc2[N+](=O)[O-])c1]

Prepared according to Step D1 in General Procedure D using 2,4-difluoronitro-benzene (0.571 mL, 5.20 mmol) and 3-(methylsulfonyl)aniline (0.891 g, 5.20 mmol) to give 5-fluoro-N-(3-(methylsulfonyl)phenyl)-2-nitroaniline as a bright yellow solid: $^1$H NMR (400 MHz, DMSO-d$_6$) δ ppm 9.65 (1H, s), 8.25 (1H, dd, J=9.6, 6.1 Hz), 7.85-7.89 (1H, m), 7.64-7.75 (3H, m), 6.98 (1H, dd, J=11.4, 2.6 Hz), 6.79-6.87 (1H, m), 3.24 (3H, s); LC-MS (ESI) m/z 311.0 [M+H]$^+$.

5-Fluoro-N1-(3-(methylsulfonyl)phenyl)benzene-1,2-diamine

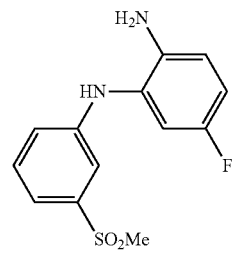 [SMILES: CS(=O)(=O)c1cccc(Nc2cc(F)ccc2N)c1]

Prepared according to Step D2 in General Procedure D using 5-fluoro-N-(3-(methylsulfonyl)phenyl)-2-nitroaniline (0.805 g, 2.59 mmol) to give 5-fluoro-N1-(3-(methylsulfonyl)phenyl)benzene-1,2-diamine as a colorless syrup: $^1$H NMR (400 MHz, DMSO-d$_6$) δ ppm 7.82 (1H, s), 7.36-7.43 (1H, m), 7.18-7.25 (2H, m), 7.01 (1H, ddd, J=8.2, 2.2, 1.1

Hz), 6.83-6.89 (1H, m), 6.71-6.79 (2H, m), 4.71 (2H, s), 3.14 (3H, s); LC-MS (ESI) m/z 281.0 [M+H]⁺

(S)-tert-Butyl 1-(4-fluoro-2-(3-(methylsulfonyl)phenylamino)phenylamino)-1-oxopropan-2-ylcarbamate

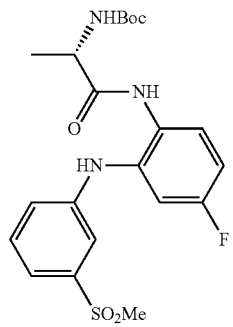 [SMILES: C[C@H](NC(=O)OC(C)(C)C)C(=O)Nc1ccc(F)cc1Nc1cccc(S(C)(=O)=O)c1]

Prepared according to Step D3 in General Procedure D using 5-fluoro-N1-(3-(methylsulfonyl)phenyl)benzene-1,2-diamine to give (S)-tert-butyl 1-(4-fluoro-2-(3-(methylsulfonyl)phenylamino)phenylamino)-1-oxopropan-2-ylcarbamate as a solid: ¹H NMR (500 MHz, DMSO-d₆) δ ppm 9.40 (1H, s), 7.86 (1H, s), 7.48 (2H, q, J=8.0 Hz), 7.40 (1H, br. s.), 7.35 (1H, d, J=7.3 Hz), 7.23 (1H, d, J=7.8 Hz), 7.13 (1H, d, J=6.4 Hz), 7.09 (1H, dd, J=10.5, 2.7 Hz), 6.87 (1H, td, J=8.2, 1.5 Hz), 4.05-4.11 (1H, m), 3.16 (3H, s), 1.35 (9H, s), 1.16-1.21 (3H, m); LC-MS (ESI) positive mode m/z 452.1 [M+H]⁺ and negative mode m/z 450.1 [M−H]⁺.

N-(1-(6-Fluoro-1-(3-(methylsulfonyl)phenyl)-1H-benzo[d]imidazol-2-yl)-ethyl)acetamide

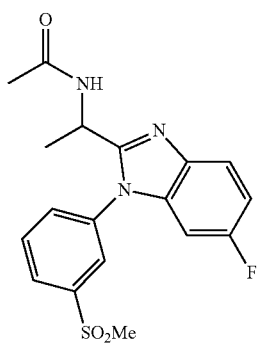 [SMILES: CC(=O)NC(C)c1nc2ccc(F)cc2n1-c1cccc(S(C)(=O)=O)c1]

Prepared according to Step D4 in General Procedure D using (S)-tert-butyl 1-(4-fluoro-2-(3-(methylsulfonyl)phenylamino)phenylamino)-1-oxopropan-2-ylcarbamate (0.9788 g, 2.168 mmol) to give N-(1-(6-fluoro-1-(3-(methylsulfonyl)phenyl)-1H-benzo[d]imidazol-2-yl)ethyl)acetamide as a pink solid: ¹H NMR (400 MHz, DMSO-d₆) δ ppm 8.40 (1H, d, J=8.0 Hz), 8.07-8.14 (1H, m), 8.04 (1H, br. s.), 7.89 (2H, d, J=4.5 Hz), 7.75 (1H, dd, J=8.8, 4.9 Hz), 7.15 (1H, ddd, J=9.9, 8.9, 2.5 Hz), 7.01 (1H, dd, J=9.0, 2.3 Hz), 4.98-5.13 (1H, m), 3.32 (3H, s), 1.59 (3H, s), 1.45 (3H, d, J=6.8 Hz); LC-MS (ESI) m/z 376.0 [M+H]⁺ Epimerization occurred during cyclization.

1-(6-Fluoro-1-(3-(methylsulfonyl)phenyl)-1H-benzo[d]imidazol-2-yl)ethanamine

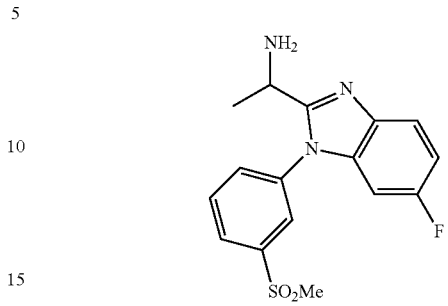

Prepared according to Step D5a in General Procedure D using (S)—N-(1-(6-fluoro-1-(3-(methylsulfonyl)phenyl)-1H-benzo[d]imidazol-2-yl)ethyl)acetamide (0.6713 g, 1.788 mmol) to give 1-(6-fluoro-1-(3-(methylsulfonyl)phenyl)-1H-benzo[d]imidazol-2-yl)ethanamine as a white solid: ¹H NMR (400 MHz, DMSO-d₆) δ ppm 8.16-8.20 (1H, m), 8.09-8.15 (1H, m), 7.97-8.03 (1H, m), 7.89-7.95 (1H, m), 7.71 (1H, dd, J=8.8, 4.9 Hz), 7.12 (1H, ddd, J=10.0, 8.8, 2.5 Hz), 7.01 (1H, dd, J=9.0, 2.3 Hz), 3.96 (1H, q, J=6.7 Hz), 3.35 (3H, s), 1.95 (2H, br. s.), 1.36 (3H, d, J=6.7 Hz); LC-MS (ESI) m/z 334.0 [M+H]⁺

4-Amino-6-((-1-(6-fluoro-1-(3-(methylsulfonyl)phenyl)-1H-benzimidazol-2-yl)ethyl)amino)-5-pyrimidinecarbonitrile

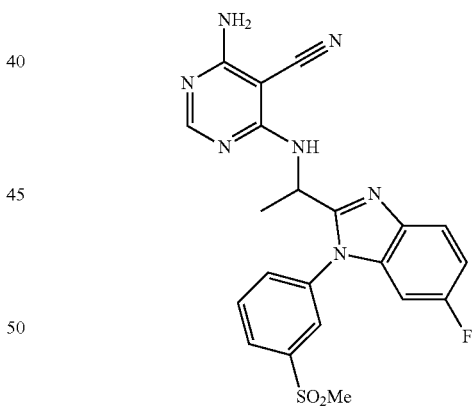

Prepared according to Step D6 in General Procedure D using (S)-1-(6-fluoro-1-(3-(methylsulfonyl)phenyl)-1H-benzo[d]imidazol-2-yl)ethanamine (0.2992 g, 0.897 mmol) to give 4-amino-6-(1-(6-fluoro-1-(3-(methylsulfonyl)phenyl)-1H-benzo[d]imidazol-2-yl)ethylamino)pyrimidine-5-carbonitrile as a tan solid: ¹H NMR (400 MHz, DMSO-d₆) δ ppm 8.14 (1H, t, J=1.9 Hz), 8.03 (1H, dt, J=7.8, 1.4 Hz), 7.87-7.96 (1H, m), 7.84 (1H, s), 7.72-7.83 (3H, m), 7.09-7.25 (3H, m), 6.97 (1H, dd, J=8.9, 2.4 Hz), 5.50 (1H, quin, J=7.0 Hz), 3.26 (3H, s), 1.55 (3H, d, J=6.8 Hz); LC-MS (ESI) m/z 452.0 [M+H]⁺.

4-Amino-6-(((1R)-1-(6-fluoro-1-(3-(methylsulfonyl)phenyl)-1H-benzimidazol-2-yl)ethyl)amino)-5-pyrimidinecarbonitrile, and 4-amino-6-(((1S)-1-(6-fluoro-1-(3-(methylsulfonyl)phenyl)-1H-benzimidazol-2-yl)ethyl)amino)-5-pyrimidinecarbonitrile

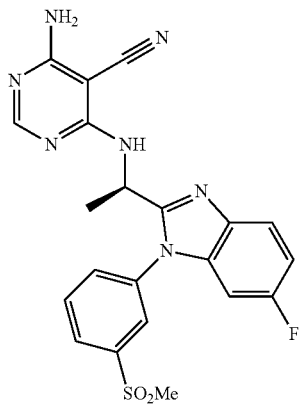

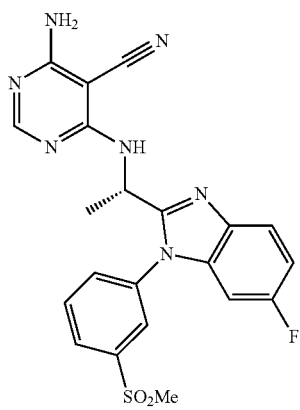 [SMILES: CC(Nc1ncnc(N)c1C#N)c1nc2ccc(F)cc2n1-c1cccc(S(C)(=O)=O)c1]

The racemic mixture (190.63 mg) was separated on AD-H column using Preparative SFC to give two fractions:

First peak on OD-H column: (R)-4-amino-6-(1-(6-fluoro-1-(3-(methylsulfonyl)phenyl)-1H-benzo[d]imidazol-2-yl)ethylamino)pyrimidine-5-carbonitrile as a light yellow solid: $^1$H NMR (400 MHz, DMSO-d$_6$) δ ppm 8.14 (1H, t, J=2.0 Hz), 8.03 (1H, ddd, J=8.0, 1.3, 1.1 Hz), 7.91 (1H, d, J=7.2 Hz), 7.84 (1H, s), 7.80 (1H, t, J=7.9 Hz), 7.71-7.78 (2H, m), 7.08-7.25 (3H, m), 6.97 (1H, dd, J=8.9, 2.4 Hz), 5.45-5.55 (1H, m), 3.26 (3H, s), 1.55 (3H, d, J=6.8 Hz); LC-MS (ESI) m/z 452.0 [M+H]$^+$.

Second peak on OD-H column: (S)-4-amino-6-(1-(6-fluoro-1-(3-(methylsulfonyl)phenyl)-1H-benzo[d]imidazol-2-yl)ethylamino)pyrimidine-5-carbonitrile as a light yellow solid: $^1$H NMR (400 MHz, DMSO-d$_6$) δ ppm 8.14 (1H, t, J=1.9 Hz), 8.00-8.05 (1H, m), 7.91 (1H, d, J=7.4 Hz), 7.84 (1H, s), 7.80 (1H, t, J=7.9 Hz), 7.72-7.78 (2H, m), 7.10-7.24 (3H, m), 6.97 (1H, dd, J=8.7, 2.4 Hz), 5.50 (1H, qd, J=6.9, 6.7 Hz), 3.26 (3H, s), 1.55 (3H, d, J=6.8 Hz); LC-MS (ESI) m/z 452.0 [M+H]$^+$.

Example 2

Preparation of 4-amino-6-(((1S)-1-(6-fluoro-3-(3-(methylsulfonyl)phenyl)imidazo[1,2-a]pyridin-2-yl)ethyl)amino)-5-pyrimidinecarbonitrile

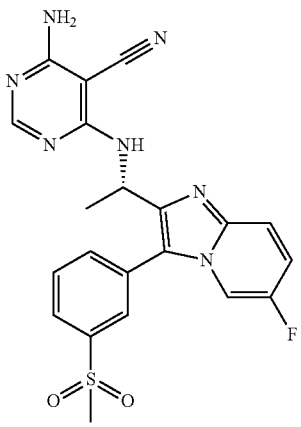 [SMILES: C[C@H](Nc1ncnc(N)c1C#N)c1nc2ccc(F)cn2c1-c1cccc(S(C)(=O)=O)c1]

Prepared according to General Procedure C to give 4-amino-6-(((1S)-1-(6-fluoro-3-(3-(methylsulfonyl)phenyl)imidazo[1,2-a]pyridin-2-yl)ethyl)amino)-5-pyrimidinecarbonitrile: $^1$H NMR (400 MHz, MeOH-d$_4$) δ ppm 8.31 (s, 1H) 8.13-8.16 (m, 1H) 8.07-8.11 (m, 1H) 8.00 (s, 1H) 7.87-7.90 (m, 1H) 7.79-7.85 (m, 1H) 7.62-7.67 (m, 1H) 7.34-7.41 (m, 1H) 5.61 (q, J=7.30 Hz, 1H) 3.21 (s, 3H) 1.63 (d, J=7.04 Hz, 3H); LC-MS (ESI) m/z 452.0 [M+H]$^+$.

Example 3

Preparation of 4-amino-6-((1-(5-fluoro-1-(3-(methylsulfanyl)phenyl)-1H-benzimidazol-2-yl)ethyl)amino)-5-pyrimidinecarbonitrile, 4-amino-6-(((1R)-1-(5-fluoro-1-(3-(methylsulfanyl)phenyl)-1H-benzimidazol-2-yl)ethyl)amino)-5-pyrimidinecarbonitrile, and 4-amino-6-(((1S)-1-(5-fluoro-1-(3-(methylsulfanyl)phenyl)-1H-benzimidazol-2-yl)ethyl)amino)-5-pyrimidinecarbonitrile 5-Fluoro-N-(3-(methylthio)phenyl)-2-nitroaniline

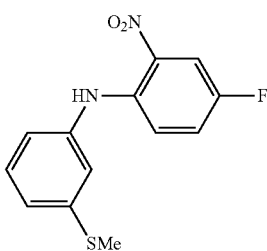 [SMILES: CSc1cccc(Nc2ccc(F)cc2[N+](=O)[O-])c1]

Prepared according to Step D1 in General Procedure D using 1,4-difluoro-2-nitrobenzene (3.251 g, 20.43 mmol) and 3-(methylthio)aniline (2.52 mL, 20.43 mmol) to give 5-fluoro-N-(3-(methylthio)phenyl)-2-nitroaniline as an orange solid: $^1$H NMR (400 MHz, DMSO-d$_6$) δ ppm 9.17 (1H, s), 7.93 (1H, dd, J=9.2, 3.1 Hz), 7.49 (1H, ddd, J=9.4, 7.5, 3.2 Hz), 7.25-7.34 (2H, m), 7.17 (1H, t, J=2.0 Hz), 7.01-7.07 (2H, m), 2.47 (3H, s); LC-MS (ESI) m/z 277.0 [M−H]⁻.

4-Fluoro-N1-(3-(methylthio)phenyl)benzene-1,2-diamine

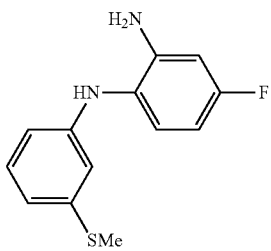 [SMILES: CSc1cccc(Nc2ccc(F)cc2N)c1]

Prepared according to Step D2 in General Procedure D using 4-fluoro-N-(3-(methylthio)phenyl)-2-nitroaniline (1.7261 g, 6.20 mmol) to give 4-fluoro-N1-(3-(methylthio)phenyl)benzene-1,2-diamine as an orange syrupy solid: ¹H NMR (400 MHz, DMSO-d₆) δ ppm 7.13 (1H, s), 7.03 (1H, t, J=7.9 Hz), 6.93 (1H, dd, J=8.4, 6.3 Hz), 6.46-6.55 (3H, m), 6.37 (1H, ddd, J=8.1, 2.2, 1.0 Hz), 6.31 (1H, td, J=8.5, 2.9 Hz), 5.08 (2H, s), 2.38 (3H, s); LC-MS (ESI) m/z 249.1 [M+H]⁺.

(S)-tert-Butyl 1-(5-fluoro-2-(3-(methylthio)phenylamino)phenylamino)-1-oxopropan-2-ylcarbamate

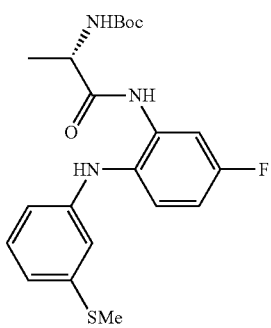 [SMILES: CSc1cccc(Nc2ccc(F)cc2NC(=O)[C@H](C)NC(=O)OC(C)(C)C)c1]

Prepared according to Step D3 in General Procedure D using 4-fluoro-N1-(3-(methylthio)phenyl)benzene-1,2-diamine (1.0765 g, 4.34 mmol) to give (S)-tert-butyl 1-(5-fluoro-2-(3-(methylthio)phenylamino)phenylamino)-1-oxopropan-2-ylcarbamate as an off-white syrupy solid: ¹H NMR (400 MHz, DMSO-d₆) δ ppm 9.31 (1H, br. s.), 7.76 (1H, dd, J=10.9, 2.2 Hz), 7.34 (1H, s), 7.15-7.26 (2H, m), 7.08 (1H, t, J=7.9 Hz), 6.95 (1H, td, J=8.5, 3.0 Hz), 6.60-6.66 (1H, m), 6.57 (1H, br. s.), 6.42-6.49 (1H, m), 4.06-4.15 (1H, m, J=7.3, 7.0, 6.9, 6.9 Hz), 2.38 (3H, s), 1.33 (9H, s), 1.12-1.19 (3H, m); LC-MS (ESI) m/z 420.1 [M+H]⁺.

tert-Butyl 1-(5-fluoro-1-(3-(methylthio)phenyl)-1H-benzo[d]imidazol-2-yl)-ethylcarbamate

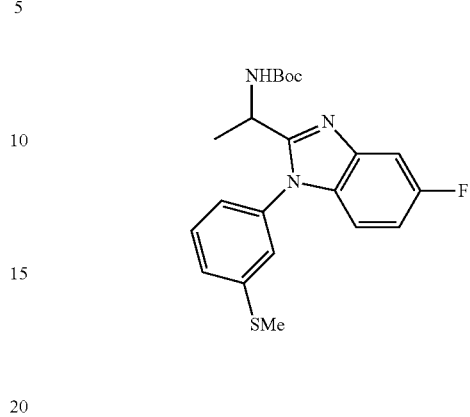

Prepared according to Step D4 in General Procedure D using (S)-tert-butyl 1-(5-fluoro-2-(3-(methylthio)phenylamino)phenylamino)-1-oxopropan-2-ylcarbamate (1.6781 g, 4.00 mmol to give tert-butyl 1-(5-fluoro-1-(3-(methylthio)phenyl)-1H-benzo[d]imidazol-2-yl)ethylcarbamate as an off-white solid: ¹H NMR (400 MHz, DMSO-d₆) δ ppm 7.48-7.57 (2H, m), 7.39-7.46 (2H, m), 7.36 (1H, d, J=7.4 Hz), 7.26 (1H, d, J=7.8 Hz), 7.02-7.10 (2H, m), 4.79 (1H, dq, J=7.1, 6.9 Hz), 2.52 (3H, s), 1.38 (3H, d, J=6.7 Hz), 1.29 (9H, s); LC-MS (ESI) m/z 402.1 [M+H]⁺. Epimerization occurred during cyclization.

1-(5-Fluoro-1-(3-(methylthio)phenyl)-1H-benzo[d]imidazol-2-yl)ethanamine

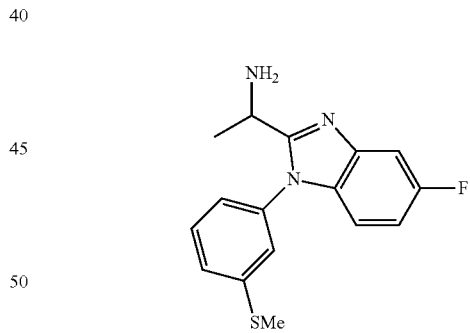

Prepared according to Step D5b in General Procedure D using tert-butyl 1-(5-fluoro-1-(3-(methylthio)phenyl)-1H-benzo[d]imidazol-2-yl)ethylcarbamate (0.2878 g, 0.717 mmol) to give 1-(5-fluoro-1-(3-(methylthio)phenyl)-1H-benzo[d]imidazol-2-yl)ethanamine as a light yellow syrup: ¹H NMR (400 MHz, DMSO-d₆) δ ppm 7.56 (1H, t, J=8.0 Hz), 7.43-7.52 (3H, m), 7.33 (1H, d, J=7.6 Hz), 7.02-7.14 (2H, m), 3.95 (1H, q, J=6.7 Hz), 2.53 (3H, s), 1.96 (2H, s), 1.34 (3H, d, J=6.7 Hz); LC-MS (ESI) m/z 302.0 [M+H]⁺. The light yellow syrup was carried on crude without purification for the next step.

4-Amino-6-((1-(5-fluoro-1-(3-(methylsulfanyl)phenyl)-1H-benzimidazol-2-yl)-Nethyl)amino)-5-pyrimidinecarbonitrile

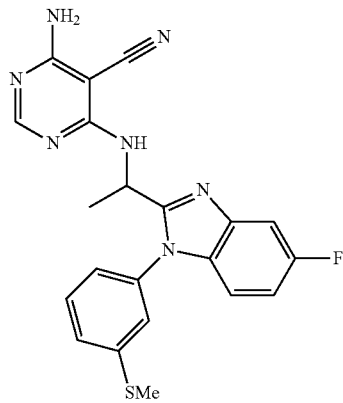 [SMILES: CSc1cccc(-n2c(C(C)Nc3ncnc(N)c3C#N)nc3cc(F)ccc32)c1]

Prepared according to Step D6 in General Procedure D using 1-(5-fluoro-1-(3-(methylthio)phenyl)-1H-benzo[d]imidazol-2-yl)ethanamine (0.1816 g, 0.603 mmol) give 4-amino-6-(1-(5-fluoro-1-(3-(methylthio)phenyl)-1H-benzo[d]-imidazol-2-yl)ethylamino)pyrimidine-5-carbonitrile as an off-white solid: $^1$H NMR (400 MHz, DMSO-$d_6$) δ ppm 7.86 (1H, s), 7.68 (1H, d, J=7.4 Hz), 7.54 (1H, ddd, J=9.6, 2.2, 0.8 Hz), 7.44 (1H, t, J=7.9 Hz), 7.39 (1H, t, J=1.9 Hz), 7.32 (1H, d, J=8.2 Hz), 7.24-7.28 (1H, m), 7.03-7.22 (4H, m), 5.54 (1H, t, J=6.7 Hz), 2.48 (3H, s), 1.52 (3H, d, J=6.8 Hz); LC-MS (ESI) m/z 420.1 [M+H]$^+$.

4-Amino-6-(((1R)-1-(5-fluoro-1-(3-(methylsulfanyl)phenyl)-1H-benzimidazol-2-yl)ethyl)amino)-5-pyrimidinecarbonitrile and 4-amino-6-(((1S)-1-(5-fluoro-1-(3-(methylsulfanyl)phenyl)-1H-benzimidazol-2-yl)ethyl)amino)-5-pyrimidinecarbonitrile

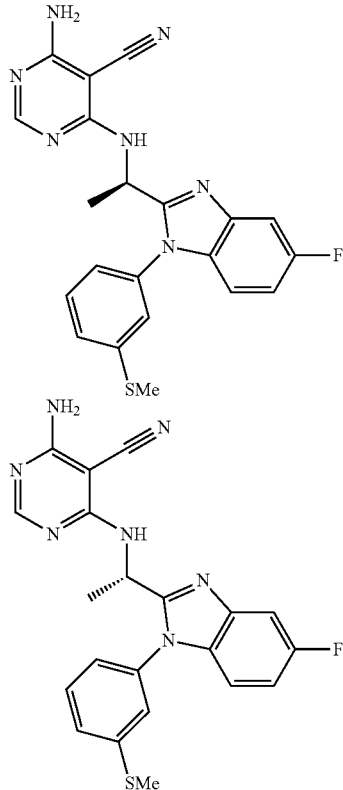

The racemic mixture (127.49 mg) was separated on IA column using Preparative SFC to give two fractions:

First peak on IA column: (R)-4-amino-6-(1-(5-fluoro-1-(3-(methylthio)phenyl)-1H-benzo[d]imidazol-2-yl)ethylamino)pyrimidine-5-carbonitrile as a tan solid: $^1$H NMR (400 MHz, DMSO-$d_6$) δ ppm 7.86 (1H, s), 7.69 (1H, d, J=7.4 Hz), 7.55 (1H, ddd, J=9.7, 2.1, 0.8 Hz), 7.44 (1H, t, J=7.9 Hz), 7.39 (1H, t, J=1.9 Hz), 7.32 (1H, d, J=7.4 Hz), 7.26 (1H, d, J=7.4 Hz), 7.17 (2H, br. s.), 7.04-7.12 (2H, m), 5.49-5.59 (1H, m), 2.48 (3H, s), 1.52 (3H, d, J=6.7 Hz); LC-MS (ESI) m/z 420.1 [M+H]$^+$.

Second peak on IA column: (S)-4-amino-6-(1-(5-fluoro-1-(3-(methylthio)phenyl)-1H-benzo[d]imidazol-2-yl)ethylamino)pyrimidine-5-carbonitrile as a tan solid: $^1$H NMR (400 MHz, DMSO-$d_6$) δ ppm 7.86 (1H, s), 7.69 (1H, d, J=7.4 Hz), 7.55 (1H, ddd, J=9.6, 2.1, 0.7 Hz), 7.44 (1H, t, J=7.8 Hz), 7.39 (1H, t, J=1.8 Hz), 7.32 (1H, d, J=7.4 Hz), 7.26 (1H, d, J=7.6 Hz), 7.17 (2H, br. s.), 7.04-7.12 (2H, m), 5.50-5.59 (1H, m), 2.48 (3H, s), 1.52 (3H, d, J=6.7 Hz); LC-MS (ESI) m/z 420.1 [M+H]$^+$.

Example 4

Preparation of 4-amino-6-((-1-(5-fluoro-1-(3-(methylsulfonyl)phenyl)-1H-benzimidazol-2-yl)ethyl)amino)-5-pyrimidinecarbonitrile, 4-amino-6-(((1R)-1-(5-fluoro-1-(3-(methylsulfonyl)phenyl)-1H-benzimidazol-2-yl)ethyl)amino)-5-pyrimidinecarbonitrile, and 4-amino-6-(((1S)-1-(5-fluoro-1-(3-(methylsulfonyl)phenyl)-1H-benzimidazol-2-yl)ethyl)amino)-5-pyrimidinecarbonitrile tert-Butyl 1-(5-fluoro-1-(3-(methylsulfonyl)phenyl)-1H-benzo[d]imidazol-2-yl)ethylcarbamate

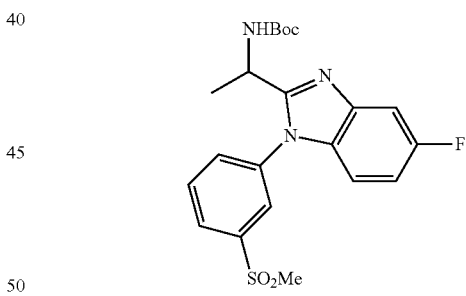

To a mixture of tert-butyl 1-(5-fluoro-1-(3-(methylthio)phenyl)-1H-benzo[d]-imidazol-2-yl)ethylcarbamate (0.7397 g, 1.842 mmol) in THF (13.82 mL) and water (4.61 mL) was added oxone (2.83 g, 4.61 mmol) and the mixture was stirred at rt. After 3 h, water (50 mL) was added to the mixture, and extracted with DCM (50 mL×2). The combined organic layers were dried over Na$_2$SO$_4$, filtered, concentrated under reduced pressure to give a white solid, which was purified by column chromatography on a 24 g of Redi-Sep™ Gold column using 0 to 50% gradient of EtOAc in hexane over 5 min and then 50% isocratic of EtOAC for 20 min as eluent to give tert-butyl 1-(5-fluoro-1-(3-(methylsulfonyl)phenyl)-1H-benzo[d]imidazol-2-yl)ethylcarbamate as a white solid. $^1$H NMR (400 MHz, DMSO-$d_6$) δ ppm 8.05-8.15 (2H, m), 7.90 (2H, d, J=4.9 Hz), 7.56 (1H, dd, J=9.5, 2.2 Hz), 7.35 (1H, d, J=8.0 Hz), 7.06-7.18 (2H, m), 4.82-4.95 (1H, m), 3.33 (3H, s), 1.44 (3H, d, J=6.8 Hz), 1.23 (9H, s); LC-MS (ESI) m/z 434.0 [M+H]⁺.

1-(5-Fluoro-1-(3-(methylsulfonyl)phenyl)-1H-benzo[d]imidazol-2-yl)ethanamine

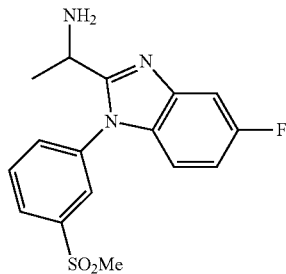 [SMILES: CC(N)c1nc2cc(F)ccc2n1-c1cccc(S(C)(=O)=O)c1]

Prepared according to Step D5b in General Procedure D using tert-butyl 1-(5-fluoro-1-(3-(methylsulfonyl)phenyl)-1H-benzo[d]imidazol-2-yl)ethylcarbamate (0.6889 g, 1.589 mmol) to give 1-(5-fluoro-1-(3-(methylsulfonyl)phenyl)-1H-benzo[d]imidazol-2-yl)ethanamine as white solid: ¹H NMR (400 MHz, DMSO-d₆) δ ppm 8.18 (1H, t, J=1.7 Hz), 8.11-8.15 (1H, m), 7.98-8.03 (1H, m), 7.93 (1H, t, J=7.8 Hz), 7.53 (1H, dd, J=9.7, 2.4 Hz), 7.13-7.19 (1H, m), 7.05-7.12 (1H, m), 3.96 (1H, q, J=6.7 Hz), 3.35 (3H, s), 1.98 (2H, s), 1.37 (3H, d, J=6.7 Hz); LC-MS (ESI) m/z 334.0 [M+H]⁺. The white solid was carried on crude without purification for the next step.

4-Amino-6-((-1-(5-fluoro-1-(3-(methylsulfonyl)phenyl)-1H-benzimidazol-2-yl)ethyl)amino)-5-pyrimidinecarbonitrile

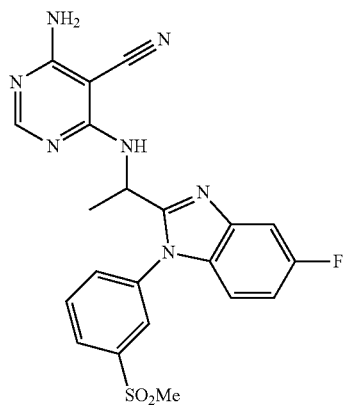 [SMILES: CC(Nc1ncnc(N)c1C#N)c1nc2cc(F)ccc2n1-c1cccc(S(C)(=O)=O)c1]

Prepared according to Step D6 in General Procedure D using 1-(5-fluoro-1-(3-(methylsulfonyl)phenyl)-1H-benzo[d]imidazol-2-yl)ethanamine (0.4657 g, 1.397 mmol) to give a brown solid. The brown solid was suspended in EtOAc-hexane (1:4, 10 mL), filtered, washed with EtOAc-hexane (1:4, 20 mL), and dried to give 4-amino-6-((-1-(5-fluoro-1-(3-(methylsulfonyl)phenyl)-1H-benzimidazol-2-yl)-ethyl)amino)-5-pyrimidinecarbonitrile as a tan solid: ¹H NMR (400 MHz, DMSO-d₆) δ ppm 8.15 (1H, t, J=1.9 Hz), 8.04 (1H, dt, J=7.8, 1.4 Hz), 7.93 (1H, d, J=7.4 Hz), 7.75-7.87 (3H, m), 7.58 (1H, dt, J=9.2, 1.3 Hz), 7.06-7.27 (4H, m), 5.50 (1H, qd, J=6.9, 6.7 Hz), 3.26 (3H, s), 1.56 (3H, d, J=6.8 Hz); LC-MS (ESI) m/z 452.0 [M+H]⁺.

4-Amino-6-(((1R)-1-(5-fluoro-1-(3-(methylsulfonyl)phenyl)-1H-benzimidazol-2-yl)ethyl)amino)-5-pyrimidinecarbonitrile and 4-amino-6-(((1S)-1-(5-fluoro-1-(3-(methylsulfonyl)phenyl)-1H-benzimidazol-2-yl)ethyl)amino)-5-pyrimidinecarbonitrile

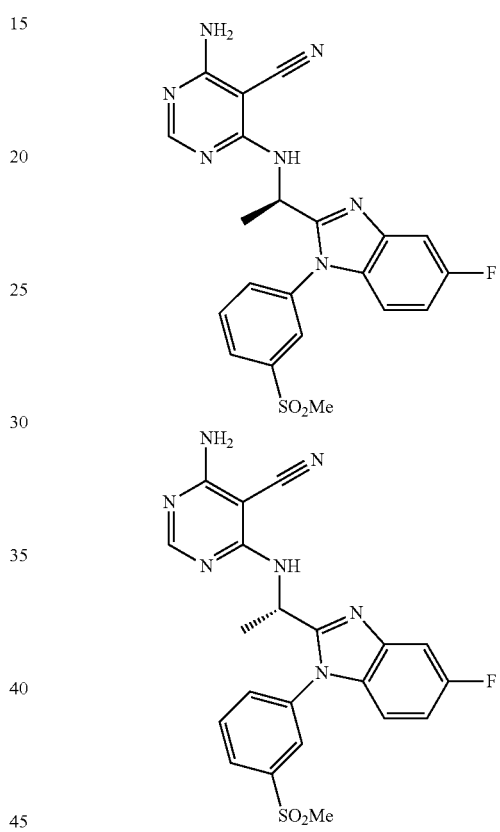

The racemic mixture (367.3 mg) was separated on AD-H column using preparative SFC to give two fractions:

First peak on AD-H column: (R)-4-amino-6-(1-(5-fluoro-1-(3-(methylsulfonyl)phenyl)-1H-benzo[d]imidazol-2-yl)ethylamino)pyrimidine-5-carbonitrile as a brown solid: ¹H NMR (400 MHz, DMSO-d₆) δ ppm 8.15 (1H, t, J=1.9 Hz), 8.04 (1H, dt, J=7.9, 1.4 Hz), 7.92 (1H, d, J=7.0 Hz), 7.74-7.86 (3H, m), 7.55-7.60 (1H, m), 7.07-7.26 (4H, m), 5.50 (1H, qd, J=7.0, 6.8 Hz), 3.26 (3H, s), 1.56 (3H, d, J=6.8 Hz); LC-MS (ESI) m/z 452.0 [M+H]⁺.

Second peak on AD-H column: (S)-4-amino-6-(1-(5-fluoro-1-(3-(methylsulfonyl)phenyl)-1H-benzo[d]imidazol-2-yl)ethylamino)pyrimidine-5-carbonitrile as a brown solid: ¹H NMR (400 MHz, DMSO-d₆) δ ppm 8.15 (1H, t, J=1.9 Hz), 8.01-8.06 (1H, m), 7.92 (1H, d, J=7.6 Hz), 7.74-7.86 (3H, m), 7.54-7.60 (1H, m), 7.05-7.27 (4H, m), 5.50 (1H, quin, J=6.8 Hz), 3.26 (3H, s), 1.56 (3H, d, J=6.8 Hz); LC-MS (ESI) m/z 452.0 [M+H]⁺.

Example 5

Preparation of 4-amino-6-(((1S)-1-(3-(3,5-difluorophenyl)-6-fluoroimidazo[1,2-a]pyridin-2-yl)ethyl)amino)-5-pyrimidinecarbonitrile

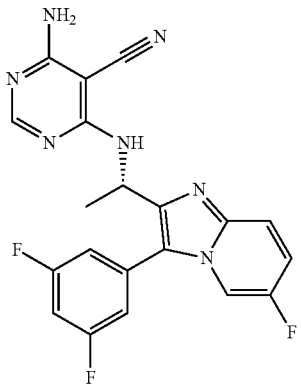 [SMILES: C[C@H](Nc1ncnc(N)c1C#N)c1nc2ccc(F)cn2c1-c1cc(F)cc(F)c1]

Prepared according to General Procedure C to give 4-amino-6-(((1S)-1-(3-(3,5-difluorophenyl)-6-fluoroimidazo[1,2-a]pyridin-2-yl)ethyl)amino)-5-pyrimidinecarbonitrile: $^1$H NMR (400 MHz, MeOH-d$_4$) δ ppm 8.40-8.47 (m, 1H) 8.01 (s, 1H) 7.88-7.94 (m, 1H) 7.79-7.86 (m, 1H) 7.20-7.33 (m, 3H) 5.68 (d, J=7.04 Hz, 1H) 1.71 (d, J=7.24 Hz, 3H); LC-MS (ESI) 410.0 [M+H]$^+$.

Example 6

Preparation of 4-amino-6-(((1S)-1-(6-fluoro-3-(4-fluorophenyl)imidazo[1,2-a]pyridin-2-yl)ethyl)amino)-5-pyrimidinecarbonitrile

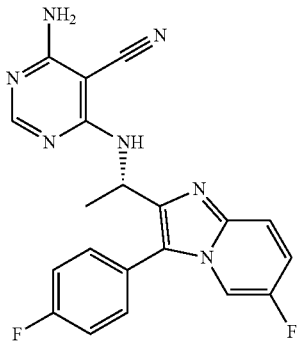 [SMILES: C[C@H](Nc1ncnc(N)c1C#N)c1nc2ccc(F)cn2c1-c1ccc(F)cc1]

Prepared according to General Procedure C to give 4-amino-6-(((1S)-1-(6-fluoro-3-(4-fluorophenyl)imidazo[1,2-a]pyridin-2-yl)ethyl)amino)-5-pyrimidinecarbonitrile: $^1$H NMR (400 MHz, MeOH-d$_4$) δ ppm 8.00-8.05 (m, 1H) 7.92 (s, 1H) 7.59-7.64 (m, 1H) 7.50-7.57 (m, 2H) 7.27-7.36 (m, 3H) 5.58 (q, J=7.04 Hz, 1H) 1.61 (d, J=6.85 Hz, 3H); LC-MS (ESI) 392.2 [M+H]$^+$.

Example 7

Preparation of 4-amino-6-((−1-(1-(3,5-difluorophenyl)-6-fluoro-1H-benzimidazol-2-yl)ethyl)amino)-5-pyrimidinecarbonitrile, 4-amino-6-(((1R)-1-(1-(3,5-difluorophenyl)-6-fluoro-1H-benzimidazol-2-yl)ethyl)amino)-5-pyrimidinecarbonitrile, and 4-amino-6-(((1S)-1-(1-(3,5-difluorophenyl)-6-fluoro-1H-benzimidazol-2-yl)ethyl)amino)-5-pyrimidinecarbonitrile N-(3,5-Difluorophenyl)-5-fluoro-2-nitroaniline

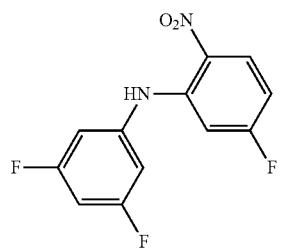 [SMILES: O=[N+]([O-])c1ccc(F)cc1Nc1cc(F)cc(F)c1]

Prepared according to Step D1 in General Procedure D using 2,4-difluoronitrobenzene (1.757 mL, 16.02 mmol) and 3,5-difluoroaniline (2.069 g, 16.02 mmol) to give N-(3,5-difluorophenyl)-5-fluoro-2-nitroaniline as an orange solid: $^1$H NMR (400 MHz, DMSO-d$_6$) δ ppm 9.48 (1H, s), 8.23 (1H, dd, J=9.4, 6.1 Hz), 7.05-7.17 (3H, m), 6.99 (1H, tt, J=9.4, 2.3 Hz), 6.84-6.91 (1H, m); LC-MS (ESI) m/z 267.0 [M−H]$^−$.

N1-(3,5-Difluorophenyl)-5-fluorobenzene-1,2-diamine

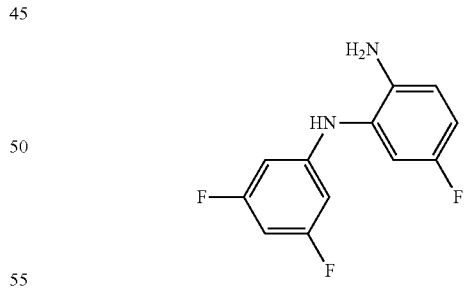

Prepared according to Step D2 in General Procedure D using N-(3,5-difluorophenyl)-5-fluoro-2-nitroaniline (0.7511 g, 2.80 mmol) to give N1-(3,5-difluorophenyl)-5-fluorobenzene-1,2-diamine as a light yellow syrup: $^1$H NMR (400 MHz, DMSO-d$_6$) δ ppm 7.85 (1H, s), 6.85 (1H, dd, J=10.0, 2.3 Hz), 6.72-6.81 (2H, m), 6.41 (1H, tt, J=9.4, 2.3 Hz), 6.24-6.33 (2H, m), 4.71 (2H, s); LC-MS (ESI) m/z 239.1 [M+H]$^+$.

(S)-tert-Butyl 1-(2-(3,5-difluorophenylamino)-4-fluorophenylamino)-1-oxopropan-2-ylcarbamate

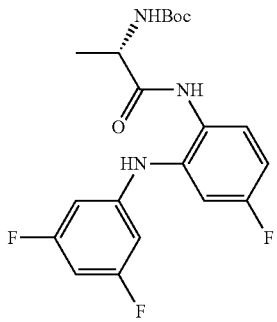 [SMILES: C[C@H](NC(=O)OC(C)(C)C)C(=O)Nc1ccc(F)cc1Nc1cc(F)cc(F)c1]

Prepared according to Step D3 in General Procedure D using N1-(3,5-difluorophenyl)-5-fluorobenzene-1,2-diamine (0.6074 g, 2.55 mmol) to give (S)-tert-butyl 1-(2-(3,5-difluorophenylamino)-4-fluorophenylamino)-1-oxopropan-2-ylcarbamate as a white solid: $^1$H NMR (400 MHz, DMSO-$d_6$) δ ppm 9.41 (1H, br. s.), 7.87 (1H, br. s.), 7.50 (1H, dd, J=8.6, 6.5 Hz), 7.07-7.20 (2H, m), 6.87-6.96 (1H, m), 6.43-6.62 (3H, m), 3.95-4.13 (1H, m), 1.37 (9H, s), 1.17 (3H, d, J=7.0 Hz); LC-MS (ESI) m/z 410.2 [M+H]$^+$.

N-(1-(1-(3,5-Difluorophenyl)-6-fluoro-1H-benzo[d]imidazol-2-yl)ethyl)acetamide

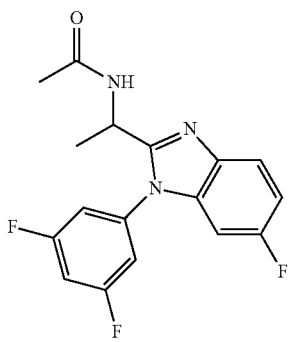 [SMILES: CC(=O)NC(C)c1nc2ccc(F)cc2n1-c1cc(F)cc(F)c1]

Prepared according to Step D4 in General Procedure D using (S)-tert-butyl 1-(2-(3,5-difluorophenylamino)-4-fluorophenylamino)-1-oxopropan-2-ylcarbamate (1.0173 g, 2.485 mmol) to give N-(1-(1-(3,5-difluorophenyl)-6-fluoro-1H-benzo[d]imidazol-2-yl)ethyl)acetamide as a brown solid: $^1$H NMR (400 MHz, DMSO-$d_6$) δ ppm 8.38 (1H, d, J=7.4 Hz), 7.72 (1H, dd, J=8.8, 4.9 Hz), 7.51 (1H, tt, J=9.5, 2.3 Hz), 7.41 (2H, dd, J=7.9, 1.7 Hz), 7.13 (1H, ddd, J=9.8, 8.8, 2.5 Hz), 7.03-7.09 (1H, m), 5.07 (1H, qd, J=7.1, 6.8 Hz), 1.64 (3H, s), 1.44 (3H, d, J=6.8 Hz); LC-MS (ESI) m/z 334.1 [M+H]$^+$. Epimerization occurred during cyclization.

1-(1-(3,5-Difluorophenyl)-6-fluoro-1H-benzo[d]imidazol-2-yl)ethanamine

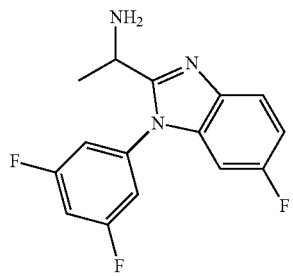 [SMILES: CC(N)c1nc2ccc(F)cc2n1-c1cc(F)cc(F)c1]

Prepared according to Step D5a in General Procedure D using N-(1-(1-(3,5-difluorophenyl)-6-fluoro-1H-benzo[d]imidazol-2-yl)ethyl)acetamide (0.7057 g, 2.117 mmol) to give 1-(1-(3,5-difluorophenyl)-6-fluoro-1H-benzo[d]imidazol-2-yl)ethanamine as a pink solid: $^1$H NMR (400 MHz, DMSO-$d_6$) δ ppm 7.69 (1H, dd, J=8.8, 4.9 Hz), 7.49-7.58 (3H, m), 7.04-7.15 (2H, m), 4.01 (1H, q, J=6.6 Hz), 1.95 (2H, br. s.), 1.36 (3H, d, J=6.5 Hz); LC-MS (ESI) m/z 292.0 [M+H]$^+$. The pink solid was carried on crude without purification.

4-Amino-6-((-1-(1-(3,5-difluorophenyl)-6-fluoro-1H-benzimidazol-2-yl)ethyl)amino)-5-pyrimidinecarbonitrile

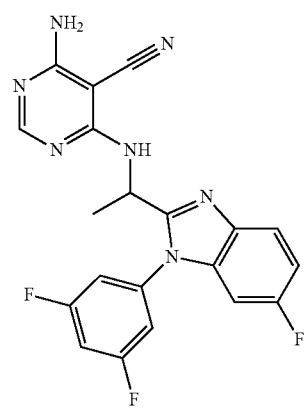

Prepared according to Step D6 in General Procedure D using 1-(1-(3,5-difluorophenyl)-6-fluoro-1H-benzo[d]imidazol-2-yl)ethanamine (0.4841 g, 1.662 mmol) to give 4-Amino-6-((-1-(1-(3,5-difluorophenyl)-6-fluoro-1H-benzimidazol-2-yl)-ethyl)amino)-5-pyrimidinecarbonitrile as a tan solid: $^1$H NMR (400 MHz, DMSO-$d_6$) δ ppm 7.87 (1H, s), 7.68-7.77 (2H, m), 7.29-7.41 (3H, m), 7.09-7.25 (3H, m), 7.05 (1H, dd, J=9.0, 2.3 Hz), 5.59-5.70 (1H, m), 1.56 (3H, d, J=6.8 Hz); LC-MS (ESI) m/z 410.0 [M+H]$^+$.

4-Amino-6-(((1R)-1-(1-(3,5-difluorophenyl)-6-fluoro-1H-benzimidazol-2-yl)-ethyl)amino)-5-pyrimidinecarbonitrile and 4-amino-6-(((1S)-1-(1-(3,5-difluorophenyl)-6-fluoro-1H-benzimidazol-2-yl)ethyl)amino)-5-pyrimidinecarbonitrile

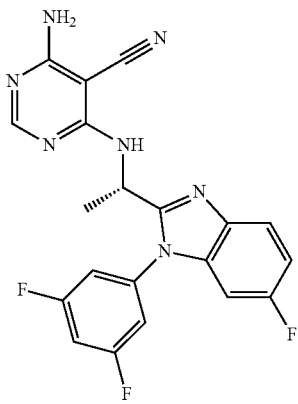 [SMILES: CC(Nc1ncnc(N)c1C#N)c1nc2ccc(F)cc2n1-c1cc(F)cc(F)c1]

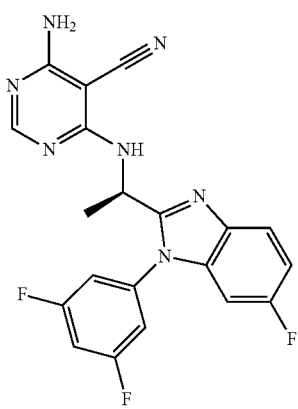

The racemic mixture (471 mg) was separated on IA column using preparative SFC to give two fractions:

First peak on IA column and second peak on OD-H column: 4-amino-6-(((1R)-1-(1-(3,5-difluorophenyl)-6-fluoro-1H-benzimidazol-2-yl)ethyl)amino)-5-pyrimidinecarbonitrile as an off-white solid: $^1$H NMR (400 MHz, DMSO-$d_6$) δ ppm 7.87 (1H, s), 7.68-7.78 (2H, m), 7.29-7.40 (3H, m), 7.09-7.25 (3H, m), 7.05 (1H, dd, J=8.9, 2.4 Hz), 5.60-5.69 (1H, m, J=7.1, 7.1, 6.9, 6.7 Hz), 1.56 (3H, d, J=6.8 Hz); LC-MS (ESI) m/z 410.0 [M+H]$^+$. Second peak on IA column and first peak on OD-H column: 4-amino-6-(((1S)-1-(1-(3,5-difluorophenyl)-6-fluoro-1H-benzimidazol-2-yl)ethyl)amino)-5-pyrimidinecarbonitrile as an off-white solid: $^1$H NMR (400 MHz, DMSO-$d_6$) δ ppm 7.87 (1H, s), 7.68-7.78 (2H, m), 7.29-7.40 (3H, m), 7.09-7.24 (3H, m), 7.05 (1H, dd, J=8.9, 2.4 Hz), 5.59-5.69 (1H, m), 1.56 (3H, d, J=6.8 Hz); LC-MS (ESI) m/z 410.0 [M+H]$^+$.

Example 8

Synthesis of 4-amino-6-(((8-chloro-3-phenylimidazo[1,2-a]pyridin-2-yl)methyl)amino)-5-pyrimidinecarbonitrile 3-Bromo-8-chloro-2-(chloromethyl)imidazo[1,2-a]pyridine

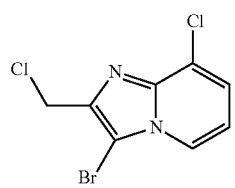 [SMILES: ClCc1nc2c(Cl)cccn2c1Br]

Acetonitrile (8.5 ml) was added to 8-chloro-2-(chloromethyl)imidazo[1,2-a]-pyridine (341 mg, 1.7 mmol). N-bromosuccinimide (302 mg, 1.7 mL) was added and the mixture was stirred at rt until complete. The reaction mixture was partitioned with EtOAc and satd. aq. NaHCO$_3$ solution. The organic layer was dried with Na$_2$SO$_4$, filtered, and concentrated under reduced pressure. The residue was taken up in DCM and purified by chromatography on a 23 g silica gel column using 0 to 70% gradient of EtOAc in hexane. The desired fractions were combined and concentrated under reduced pressure to give 3-bromo-8-chloro-2-(chloromethyl)imidazo[1,2-a]pyridine as a white crystalline solid.

2-((3-Bromo-8-chloroimidazo[1,2-a]pyridin-2-yl)methyl)isoindoline-1,3-dione

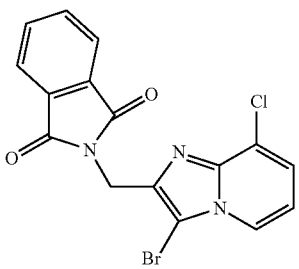 [SMILES: O=C1c2ccccc2C(=O)N1Cc1nc2c(Cl)cccn2c1Br]

DMF (4.6 ml) was added to a mixture of 3-bromo-8-chloro-2-(chloromethyl)imidazo[1,2-a]pyridine (258 mg, 0.922 mmol), phthalimide (136 mg, 0.922 mmol) and K$_2$CO$_3$ (55.6 μL, 0.922 mmol). The reaction was heated at 80° C. After the reaction was complete, the mixture was initially partitioned between EtOAc and water, but the product did not dissolve readily. The product was collected by filtration of (8-Chloro-3-phenylimidazo[1,2-a]pyridin-2-yl)methanamine

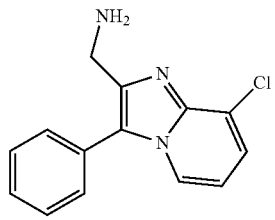 [SMILES: NCc1nc2c(Cl)cccn2c1-c1ccccc1]

2-((3-Bromo-8-chloroimidazo[1,2-a]pyridin-2-yl)methyl)isoindoline-1,3-dione was coupled with phenyl boronic acid according to Step C3b in General Procedure C. Partial hydrolysis of the phthalimide was observed under the reaction conditions. The crude intermediate was treated with DCM and TFA for a week. The reaction mixture was concentrated under reduced pressure and purified by reverse phase semi-prep HPLC. The fractions containing the desired product were lyophilized. The lyophilate was partitioned with satd. aq. NaHCO$_3$ solution and EtOAc. The aq. layer was extracted three times with EtOAc. The combined organic layers were dried with Na$_2$SO$_4$, filtered, and concentrated under reduced pressure to give (8-chloro-3-phenylimidazo[1,2-a]pyridin-2-yl)methanamine.

4-Amino-6-(((8-chloro-3-phenylimidazo[1,2-a]pyridin-2-yl)methyl)amino)-5-pyrimidinecarbonitrile

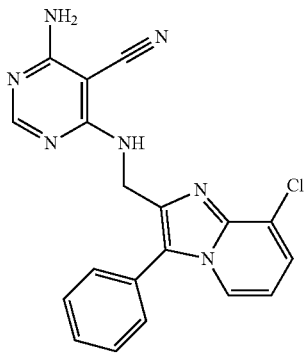 [SMILES: N#Cc1c(N)ncnc1NCc1nc2c(Cl)cccn2c1-c1ccccc1]

4-Amino-6-(((8-chloro-3-phenylimidazo[1,2-a]pyridin-2-yl)methyl)amino)-5-pyrimidinecarbonitrile was prepared from (8-chloro-3-phenylimidazo[1,2-a]pyridin-2-yl)methanamine according to Step C5 in General Procedure C: $^1$H NMR (500 MHz, DMSO-d$_6$) δ ppm 4.69 (d, J=5.38 Hz, 2H) 6.88 (t, J=7.09 Hz, 1H) 7.18 (br. s., 2H) 7.47-7.51 (m, 2H) 7.53-7.59 (m, 2H) 7.59-7.65 (m, 3H) 7.92 (s, 1H) 8.15 (dd, J=7.09, 0.98 Hz, 1H); LC-MS (ESI) m/z 376.1 [M+H]$^+$.

Example 9

Preparation of 4-amino-6-(((1S)-1-(3-(4-chlorophenyl)-6-fluoroimidazo[1,2-a]pyridin-2-yl)ethyl)amino)-5-pyrimidinecarbonitrile

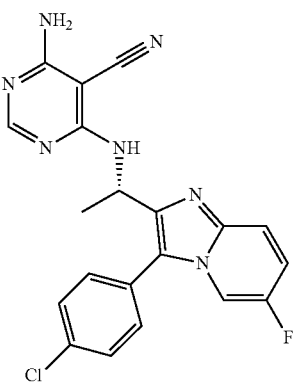 [SMILES: C[C@H](Nc1ncnc(N)c1C#N)c1nc2ccc(F)cn2c1-c1ccc(Cl)cc1]

Prepared according to General Procedure C to give 4-amino-6-(((1S)-1-(3-(4-chlorophenyl)-6-fluoroimidazo[1,2-a]pyridin-2-yl)ethyl)amino)-5-pyrimidinecarbonitrile: $^1$H NMR (400 MHz, DMSO-d$_6$): δ 8.2 (m, 1H), 7.9 (s, 1H), 7.71-7.74 (m, 1H), 7.6 (s, 4H), 7.3-7.4 (m, 1H), 7.2 (bs, 2H), 6.9 (d, 1H), 5.4 (m, 1H), 1.5 (d, 3H); LC-MS (ESI) m/z 407.11 [M+H]$^+$.

Example 10

Preparation of 4-amino-6-(((1S)-1-(6-fluoro-3-(2-(methylsulfonyl)phenyl)imidazo[1,2-a]pyridin-2-yl)ethyl)amino)-5-pyrimidinecarbonitrile

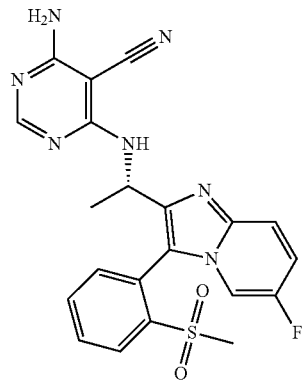 [SMILES: C[C@H](Nc1ncnc(N)c1C#N)c1nc2ccc(F)cn2c1-c1ccccc1S(C)(=O)=O]

Prepared according to General Procedure C including oxone oxidation between Step C3a and Step C4 to give 4-amino-6-(((1S)-1-(6-fluoro-3-(2-(methylsulfonyl)phenyl)imidazo[1,2-a]pyridin-2-yl)ethyl)amino)-5-pyrimidinecarbonitrile as a mixture of atropisomers that could be separated on Chiralpak™ OJ column using preparative SFC to give two fractions:

First peak on OJ column: $^1$H NMR (500 MHz, MeOH-d$_4$) δ ppm 8.18-8.23 (1H, m), 7.75-7.82 (3H, m), 7.68-7.71 (1H, m), 7.64 (1H, dd, J=9.9, 5.0 Hz), 7.52-7.55 (1H, m), 7.35 (1H, ddd, J=10.0, 7.9, 2.3 Hz), 5.65 (1H, q, J=7.0 Hz), 2.92 (3H, s), 1.65 (3H, d, J=6.8 Hz);

First peak on OJ column: ¹H NMR (500 MHz, MeOH-d₄) δ ppm 8.25-8.30 (1H, m), 7.88 (1H, s), 7.76-7.82 (1H, m), 7.59-7.69 (3H, m), 7.37 (1H, ddd, J=10.0, 7.9, 2.4 Hz), 7.25 (1H, dd, J=7.6, 1.2 Hz), 5.58 (1H, q, J=7.1 Hz), 2.87 (3H, s), 1.70 (3H, d, J=7.1 Hz); LC-MS (ESI) m/z 452.0 [M+H]⁺.

Example 11

Preparation of 4-amino-6-((-1-(6-fluoro-1-(4-fluorophenyl)-1H-benzimidazol-2-yl)ethyl)amino)-5-pyrimidinecarbonitrile, 4-amino-6-(((1R)-1-(6-fluoro-1-(4-fluorophenyl)-1H-benzimidazol-2-yl)ethyl)amino)-5-pyrimidinecarbonitrile, and 4-amino-6-(((1S)-1-(6-fluoro-1-(4-fluorophenyl)-1H-benzimidazol-2-yl)ethyl)amino)-5-pyrimidinecarbonitrile 5-Fluoro-N-(4-fluorophenyl)-2-nitroaniline

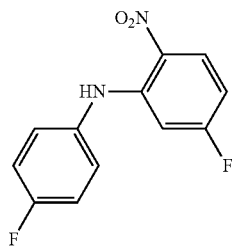

Prepared according to Step D1 in General Procedure D using 2,4-difluoronitro-benzene (2.068 mL, 18.86 mmol) and 4-fluoroaniline (1.811 mL, 18.86 mmol) to give 5-fluoro-N-(4-fluorophenyl)-2-nitroaniline as an orange solid: ¹H NMR (400 MHz, DMSO-d₆) δ ppm 9.56 (1H, s), 8.24 (1H, dd, J=9.5, 6.2 Hz), 7.36-7.44 (2H, m), 7.25-7.33 (2H, m), 6.67-6.74 (1H, m), 6.64 (1H, dd, J=11.8, 2.6 Hz); LC-MS (ESI) m/z 251.1 [M+H]⁺.

5-Fluoro-N1-(4-fluorophenyl)benzene-1,2-diamine

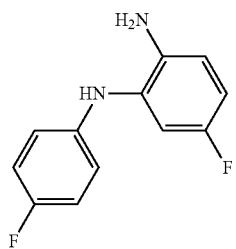 [SMILES: Nc1ccc(F)cc1Nc1ccc(F)cc1]

Prepared according to Step D2 in General Procedure D using 5-fluoro-N-(4-fluorophenyl)-2-nitroaniline (3.7432 g, 14.96 mmol) to give 5-fluoro-N1-(4-fluorophenyl)benzene-1,2-diamine as a brown syrup: ¹H NMR (400 MHz, DMSO-d₆) δ ppm 7.18 (1H, s), 6.98-7.07 (2H, m), 6.81-6.90 (2H, m), 6.65-6.76 (2H, m), 6.54-6.62 (1H, s); LC-MS (ESI) m/z 221.1 [M+H]⁺.

(S)-(9H-Fluoren-9-yl)methyl 1-(4-fluoro-2-(4-fluorophenylamino)phenylamino)-1-oxopropan-2-ylcarbamate

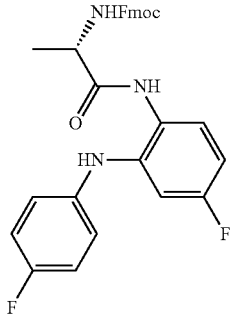

To a −10° C. solution (NaCl-ice bath) of Fmoc-L-Ala-OH (4.45 g, 14.30 mmol) and N-methylmorpholine (1.573 mL, 14.30 mmol) in DCM (34.1 mL) was added isobutyl chloroformate (1.782 mL, 13.62 mmol). The resulting cloudy colorless mixture was stirred at −10° C. for 30 min. To the mixture was then added a solution of 5-fluoro-N1-(4-fluorophenyl)benzene-1,2-diamine (1.500 g, 6.81 mmol) in DCM (12.75 mL). The resulting mixture was stirred at −10° C. for 1 h, to which the cold mixture was added satd. aq. NH₄Cl solution (100 mL). The precipitate was collected by filtration and washed with water (100 mL) to give (S)-(9H-fluoren-9-yl)methyl 1-(4-fluoro-2-(4-fluorophenylamino)phenylamino)-1-oxopropan-2-ylcarbamate as an off-white solid: ¹H NMR (400 MHz, DMSO-d₆) δ ppm 9.42 (1H, s), 7.89 (2H, d, J=7.6 Hz), 7.63-7.78 (3H, m), 7.22-7.46 (6H, m), 6.96-7.14 (4H, m), 6.83 (1H, dd, J=11.2, 2.7 Hz), 6.67 (1H, td, J=8.5, 2.8 Hz), 4.11-4.33 (4H, m), 1.28 (3H, d, J=7.0 Hz); LC-MS (ESI) m/z 514.2 [M+H]⁺. The off-white solid was carried on crude without purification.

(S)-(9H-Fluoren-9-yl)methyl 1-(6-fluoro-1-(4-fluorophenyl)-1H-benzo[d]imidazol-2-yl)ethylcarbamate

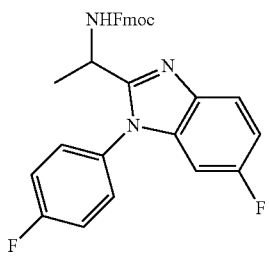

A Heterogeneous mixture of (S)-(9H-fluoren-9-yl)methyl 1-(4-fluoro-2-(4-fluorophenylamino)phenylamino)-1-oxopropan-2-ylcarbamate (3.500 g, 6.82 mmol) in acetic acid (45.4 mL) was heated at 100° C. with stirring. After 26 h, the mixture was cooled to rt and poured into DCM (100 mL) and satd. aq. NaHCO₃ solution (100 mL). The aq. layer was removed and the organic layer was washed with satd. aq. NaHCO₃ solution (100 mL×1), water (100 mL×1) and brine (100 mL×1), dried over MgSO₄, filtered, and concentrated under reduced pressure to give (S)-(9H-fluoren-9-yl)methyl 1-(6-fluoro-1-(4-fluorophenyl)-1H-benzo[d]imidazol-2-yl)ethylcarbamate as a dark brown syrup: LC-MS (ESI) m/z 496.1 [M+H]⁺. Epimerization occurred during cyclization and the dark brown syrup was carried on crude without further purification.

1-(6-Fluoro-1-(4-fluorophenyl)-1H-benzo[d]imidazol-2-yl)ethanamine

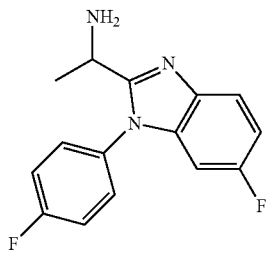 [SMILES: CC(N)c1nc2ccc(F)cc2n1-c1ccc(F)cc1]

To a solution of (9H-fluoren-9-yl)methyl 1-(6-fluoro-1-(4-fluorophenyl)-1H-benzo[d]imidazol-2-yl)ethylcarbamate (3.38 g, 6.82 mmol) in DCM (34.1 mL) was added piperidine (0.809 mL, 8.19 mmol) and the mixture was stirred at rt. After 4 days, the mixture was concentrated under reduced pressure to give a brown solid. The brown solid was purified by column chromatography on a 120 g of Redi-Sep column using 0 to 100% gradient of DCM:MeOH:NH₄OH (89:9:1) in DCM over 27 min and then 100% isocratic of DCM:MeOH:NH₄OH (89:9:1) for 5 min as eluent to give 1-(6-fluoro-1-(4-fluorophenyl)-1H-benzo[d]imidazol-2-yl)ethanamine over three steps as a pink syrupy solid. ¹H NMR (400 MHz, DMSO-d₆) δ ppm 7.67 (3H, td, J=8.8, 5.0 Hz), 7.48 (2H, t, J=8.8 Hz), 7.09 (1H, ddd, J=9.8, 8.8, 2.5 Hz), 6.88 (1H, dd, J=9.0, 2.3 Hz), 3.93 (1H, q, J=6.8 Hz), 1.92 (2H, br. s.), 1.33 (3H, d, J=6.7 Hz); LC-MS (ESI) m/z 274.0 [M+H]⁺.

4-Amino-6-((-1-(6-fluoro-1-(4-fluorophenyl)-1H-benzimidazol-2-yl)ethyl)amino)-5-pyrimidinecarbonitrile

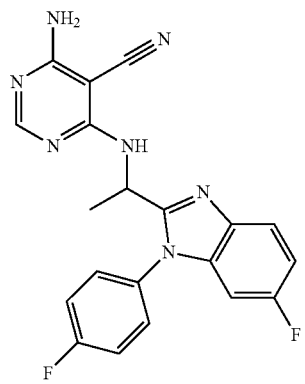 [SMILES: CC(Nc1ncnc(N)c1C#N)c1nc2ccc(F)cc2n1-c1ccc(F)cc1]

Prepared according to Step D6 in General Procedure D using 1-(6-fluoro-1-(4-fluorophenyl)-1H-benzo[d]imidazol-2-yl)ethanamine (0.8570 g, 3.14 mmol) to give 4-Amino-6-((-1-(6-fluoro-1-(4-fluorophenyl)-1H-benzimidazol-2-yl)ethyl)amino)-5-pyrimidinecarbonitrile as an off-white solid: ¹H NMR (400 MHz, DMSO-d₆) δ ppm 7.86 (1H, s), 7.72 (1H, dd, J=8.8, 4.9 Hz), 7.67 (1H, d, J=7.2 Hz), 7.54-7.63 (2H, m), 7.36 (2H, t, J=8.8 Hz), 7.19 (2H, br. s.), 7.10 (1H, ddd, J=9.8, 8.9, 2.4 Hz), 6.86 (1H, dd, J=8.9, 2.4 Hz), 5.46 (1H, quin, J=6.9 Hz), 1.52 (3H, d, J=6.8 Hz); LC-MS (ESI) m/z 392.0 [M+H]⁺.

4-Amino-6-(((1R)-1-(6-fluoro-1-(4-fluorophenyl)-1H-benzimidazol-2-yl)-ethyl)amino)-5-pyrimidinecarbonitrile and 4-amino-6-(((1S)-1-(6-fluoro-1-(4-fluorophenyl)-1H-benzimidazol-2-yl)ethyl)amino)-5-pyrimidinecarbonitrile

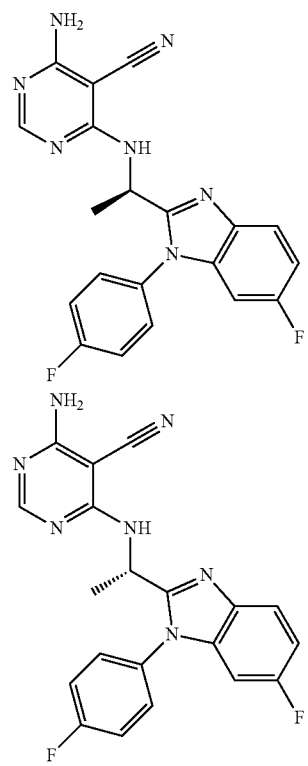

The racemic mixture (953.8 mg) was separated on AD-H column using Preparative SFC to give two fractions:

First peak on SFC AD-H column and second peak on analytical AD-H column: 4-Amino-6-(((1R)-1-(6-fluoro-1-(4-fluorophenyl)-1H-benzimidazol-2-yl)ethyl)amino)-5-pyrimidinecarbonitrile as an off-white solid: ¹H NMR (400 MHz, DMSO-d₆) δ ppm 7.86 (1H, s), 7.72 (1H, dd, J=8.8, 4.9 Hz), 7.67 (1H, d, J=7.4 Hz), 7.54-7.63 (2H, m), 7.36 (2H, t, J=8.8 Hz), 7.19 (2H, br. s.), 7.10 (1H, ddd, J=9.9, 8.9, 2.5 Hz), 6.86 (1H, dd, J=8.9, 2.4 Hz), 5.46 (1H, quin, J=6.9 Hz), 1.52 (3H, d, J=6.8 Hz); LC-MS (ESI) m/z 392.0 [M+H]⁺.

Second peak on SFC AD-H column and First peak on analytical AD-H column: 4-Amino-6-(((1S)-1-(6-fluoro-1-(4-fluorophenyl)-1H-benzimidazol-2-yl)ethyl)amino)-5-pyrimidinecarbonitrile as an off-white solid: ¹H NMR (400 MHz, DMSO-d₆) δ ppm 7.86 (1H, s), 7.72 (1H, dd, J=8.8, 4.9 Hz), 7.67 (1H, d, J=7.2 Hz), 7.55-7.63 (2H, m), 7.36 (2H, t, J=8.8 Hz), 7.19 (2H, br. s.), 7.10 (1H, ddd, J=9.7, 8.9, 2.5 Hz), 6.86 (1H, dd, J=8.9, 2.4 Hz), 5.46 (1H, quin, J=6.9 Hz), 1.52 (3H, d, J=6.8 Hz); LC-MS (ESI) m/z 392.0 [M+H]⁺.

Example 12

Preparation of 4-amino-6-(((1S)-1-(6-fluoro-3-(2-pyridinyl)imidazo[1,2-a]pyridin-2-yl)ethyl)amino)-5-pyrimidinecarbonitrile

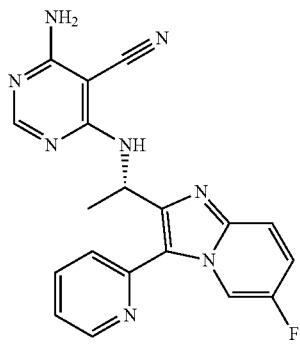 [SMILES: C[C@H](Nc1ncnc(N)c1C#N)c1nc2ccc(F)cn2c1-c1ccccn1]

Prepared according to General Procedure C to give 4-amino-6-((1S)-1-(6-fluoro-3-(2-pyridinyl)imidazo[1,2-a]pyridin-2-yl)ethyl)amino)-5-pyrimidinecarbonitrile as a white solid: $^1$H-NMR (400 MHz, DMSO-d$_6$): δ ppm 9.1 (d, 1H), 8.8 (d, 1H), 8.0 (m, 2H), 7.7-7.8 (m, 2H), 7.5 (m, 2H), 7.3 (bs, 2H), 6.8 (m, 1H), 5.7 (m, 1H), 1.49 (d, 3H): LC-MS (ESI) m/z 374.14 [M+H]$^+$.

Example 13

Preparation of 4-amino-6-(((1S)-1-(3-(3-chloro-5-fluorophenyl)-6-fluoroimidazo[1,2-a]pyridin-2-yl)ethyl)amino)-5-pyrimidinecarbonitrile

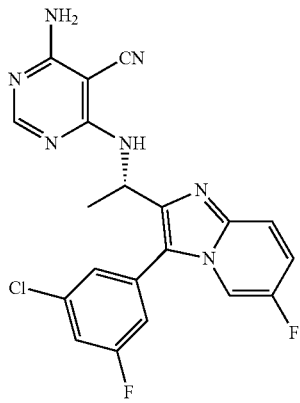 [SMILES: C[C@H](Nc1ncnc(N)c1C#N)c1nc2ccc(F)cn2c1-c1cc(F)cc(Cl)c1]

Prepared according to General Procedure C to give 4-amino-6-(((1S)-1-(3-(3-chloro-5-fluorophenyl)-6-fluoroimidazo[1,2-a]pyridin-2-yl)ethyl)amino)-5-pyrimidinecarbonitrile: $^1$H NMR (400 MHz, DMSO-d$_6$): δ 8.4 (d, 1H), 7.9 (s, 1H), 7.71-7.74 (m, 1H), 7.4-7.5 (m, 4H), 7.3 (bs, 2H), 7.0 (d, 1H), 5.4 (m, 1H), 1.5 (d, 3H); LC-MS (ESI) m/z 425.12 [M+H]$^+$.

Example 14

Preparation of 4-amino-6-(((1S)-1-(3-(4-chlorophenyl)-imidazo[1,2-a]pyridin-2-yl)ethyl)amino)-5-pyrimidinecarbonitrile

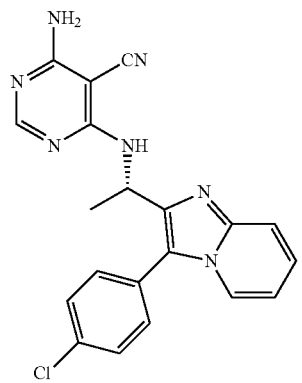 [SMILES: C[C@H](Nc1ncnc(N)c1C#N)c1nc2ccccn2c1-c1ccc(Cl)cc1]

Prepared according to General Procedure C to give 4-amino-6-(((1S)-1-(3-(4-chlorophenyl)imidazo[1,2-a]pyridin-2-yl)ethyl)amino)-5-pyrimidinecarbonitrile: $^1$H NMR (400 MHz, DMSO-d$_6$): (400 MHz, DMSO-d$_6$): δ 8.16 (d, 1H), 7.9 (s, 1H), 7.57-7.67 (m, 5H), 7.3 (dd, 1H), 7.2 (bs, 2H), 6.8 (m, 2H), 5.4 (m, 1H), 1.4 (d, 3H); LC-MS (ESI) m/z 389.12 [M+H]$^+$.

Example 15

Preparation of 4-amino-6-((-1-(6-fluoro-1-(3-(2-pyridinyl)phenyl)-1H-benzimidazol-2-yl)ethyl)amino)-5-pyrimidinecarbonitrile, 4-amino-6-(((1R)-1-(6-fluoro-1-(3-(2-pyridinyl)phenyl)-1H-benzimidazol-2-yl)ethyl)amino)-5-pyrimidinecarbonitrile, and 4-amino-6-(((1S)-1-(6-fluoro-1-(3-(2-pyridinyl)phenyl)-1H-benzimidazol-2-yl)ethyl)amino)-5-pyrimidinecarbonitrile 4-Amino-6-((-1-(6-fluoro-1-(3-(2-pyridinyl)phenyl)-1H-benzimidazol-2-yl)-ethyl)amino)-5-pyrimidinecarbonitrile

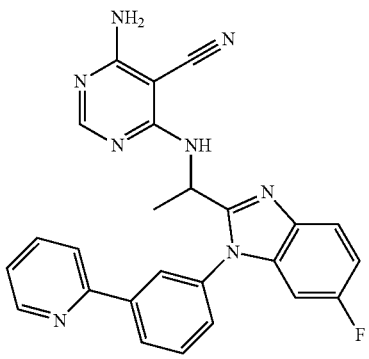 [SMILES: CC(Nc1ncnc(N)c1C#N)c1nc2ccc(F)cc2n1-c1cccc(-c2ccccn2)c1]

Prepared according to General Procedure D to give 4-amino-6-4-1-(6-fluoro-1-(3-(2-pyridinyl)phenyl)-1H-benzimidazol-2-yl)ethyl)amino)-5-pyrimidinecarbonitrile: $^1$H NMR (400 MHz, CHLOROFORM-d) δ ppm 8.70 (1H, d, J=4.5 Hz), 8.17 (2H, d, J=7.6 Hz), 7.98 (1H, s), 7.65-7.84 (4H, m), 7.48 (1H, d, J=7.4 Hz), 7.30 (1H, ddd, J=6.7, 4.9, 1.7 Hz), 7.02-7.10 (1H, m), 6.87 (1H, dd, J=8.4, 2.3 Hz), 6.23 (1H, d, J=7.8 Hz), 5.63 (1H, quin, J=7.1 Hz), 5.37 (2H, br. s.), 1.62 (3H, d, J=6.8 Hz); LC-MS (ESI) m/z 451.33 [M+H]+.

4-Amino-6-(((1R)-1-(6-fluoro-1-(3-(2-pyridinyl)phenyl)-1H-benzimidazol-2-yl)ethyl)amino)-5-pyrimidinecarbonitrile and 4-amino-6-(((1S)-1-(6-fluoro-1-(3-(2-pyridinyl)phenyl)-1H-benzimidazol-2-yl)ethyl)amino)-5-pyrimidinecarbonitrile

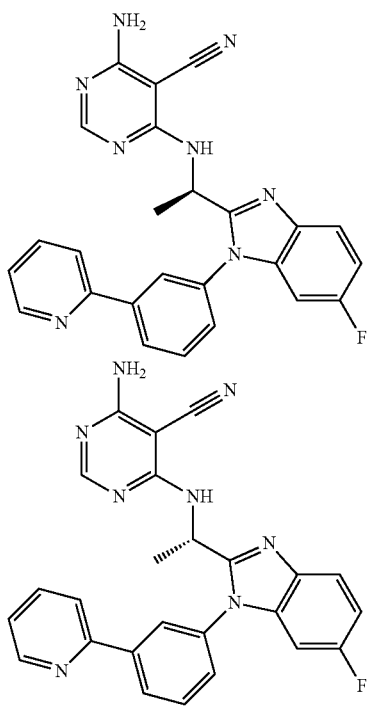

The racemic mixture (29 mg) was separated on AD-H column using Preparative SFC to give two fractions:

First peak on SFC AD-H column and Second peak on Chiralpak™ AD-H column: 4-Amino-6-(((1R)-1-(6-fluoro-1-(3-(2-pyridinyl)phenyl)-1H-benzimidazol-2-yl)ethyl)amino)-5-pyrimidinecarbonitrile as an off-white solid: ¹H NMR (400 MHz, CHLOROFORM-d) δ ppm 8.70 (1H, d, J=4.5 Hz), 8.17 (2H, d, J=7.6 Hz), 7.98 (1H, s), 7.65-7.84 (4H, m), 7.48 (1H, d, J=7.4 Hz), 7.30 (1H, ddd, J=6.7, 4.9, 1.7 Hz), 7.02-7.10 (1H, m), 6.87 (1H, dd, J=8.4, 2.3 Hz), 6.23 (1H, d, J=7.8 Hz), 5.63 (1H, quin, J=7.1 Hz), 5.37 (2H, br. s.), 1.62 (3H, d, J=6.8 Hz); LC-MS (ESI) m/z 451.1 [M+H]+.

Second peak on SFC AD-H column and First peak on Chiralpak™ AD-H column: 4-amino-6-(((1S)-1-(6-fluoro-1-(3-(2-pyridinyl)phenyl)-1H-benzimidazol-2-yl)ethyl)amino)-5-pyrimidinecarbonitrile as an off-white solid: ¹H NMR (400 MHz, CHLOROFORM-d) δ ppm 8.70 (1H, d, J=4.7 Hz), 8.17 (2H, d, J=7.6 Hz), 7.98 (1H, s), 7.66-7.84 (4H, m), 7.48 (1H, d, J=7.2 Hz), 7.30 (1H, ddd, J=6.7, 4.9, 1.7 Hz), 7.06 (1H, td, J=9.2, 2.3 Hz), 6.87 (1H, dd, J=8.6, 2.3 Hz), 6.24 (1H, d, J=7.6 Hz), 5.63 (1H, quin, J=7.0 Hz), 5.38 (2H, br. s.), 1.62 (3H, d, J=6.8 Hz); LC-MS (ESI) m/z 451.1 [M+H]+.

Example 16

Preparation of 4-amino-6-(((1S)-1-(6-fluoro-1-phenyl-1H-benzimidazol-2-yl)ethyl)amino)-5-pyrimidinecarbonitrile (S)-tert-Butyl 1-(6-fluoro-1H-benzo[d]imidazol-2-yl)ethylcarbamate

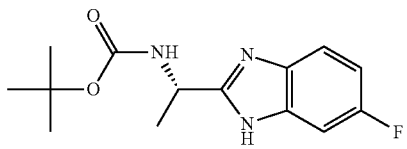 [SMILES: C[C@H](NC(=O)OC(C)(C)C)c1nc2ccc(F)cc2[nH]1]

Boc-L-Ala-OH (3.00 g, 15.86 mmol) and 3,4-diamino-1-fluorobenzene (2.00 g, 15.86 mmol) were mixed in pyridine (52.9 mL). EDCBCl (9.12 g, 47.6 mmol) was added and the mixture was stirred at ambient temperature for 20 min. The reaction mixture was diluted with EtOAc, washed with water, 1.0 N HCl and brine. The organic layer was dried with Na₂SO₄, filtered, and concentrated. The crude residue was purified by column chromatography on a 120 g of Redi-Sep™ column using 0 to 100% gradient of EtOAc in hexane as eluent. The desired fractions were combined and concentrated under reduced pressure to give the crude amide intermediate. The amide was dissolved in AcOH (26.9 mL) and heated in an oil bath at 70° C. for about 30 min. The reaction mixture was diluted with EtOAc and carefully neutralized with aq. K₂CO₃. The organic layer was washed with NaCl, dried with Na₂SO₄, and filtered. The filtrate was concentrated to dryness to yield (S)-tert-butyl 1-(6-fluoro-1H-benzo[d]imidazol-2-yl)ethylcarbamate: ¹H NMR (400 MHz, DMSO-d₆) δ ppm 12.23 (1H, br. s.), 7.15-7.61 (3H, m), 6.98 (1H, t, J=8.5 Hz), 4.78-4.89 (1H, m), 1.46 (3H, d, J=7.0 Hz), 1.40 (9H, s); LC-MS (ESI) m/z 280.1 [M+H]+.

(S)-tert-Butyl 1-(6-fluoro-1-phenyl-1H-benzo[d]imidazol-2-yl)ethylcarbamate and (S)-tert-butyl 1-(5-fluoro-1-phenyl-1H-benzo[d]imidazol-2-yl)ethylcarbamate

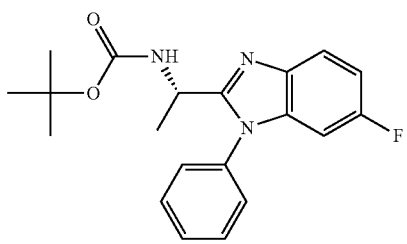

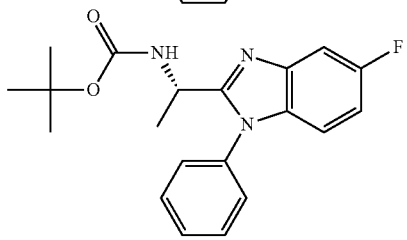

(S)-tert-Butyl 1-(6-fluoro-1H-benzo[d]imidazol-2-yl)ethylcarbamate (200 mg, 0.716 mmol), phenylboronic acid (175 mg, 1.432 mmol), DCM (9.5 mL) and pyridine (116 µL, 1.432 mmol) were added to a glass vial. Copper (II) acetate (104 µL, 1.074 mmol) was added and the loosely capped vial was left stirring at ambient temperature for 5 days. The reaction mixture was partitioned between satd. aq. NH$_4$Cl and DCM. The organic layer was washed with satd. aq. NH$_4$Cl and concentrated under reduced pressure. The residue was dissolved in MeOH and purified by reverse phase semi-prep HPLC. The fractions containing the desired product were combined to give 38 mg after lyophilization. The regioisomers were separated on AD-H column using Preparative SFC to give two fractions:

The first fraction was assigned as (S)-tert-butyl 1-(6-fluoro-1-phenyl-1H-benzo[d]imidazol-2-yl)ethylcarbamate based on the NOESY spectra for both fractions. The fraction was concentrated under reduced pressure to give 12 mg of a white solid: $^1$H NMR (500 MHz, MeOH-d$_4$) δ ppm 7.66 (m, 3H) 7.58-7.64 (m, 1H) 7.52 (br. s., 2H) 7.07 (m, 1H) 6.78 (dd, J=8.68, 2.32 Hz, 1H) 1.45 (d, J=7.09 Hz, 3H) 1.37 (s, 9H). The methyne signal was masked by the reference peak.

The second fraction was concentrated under reduced pressure to give 12 mg of (S)-tert-butyl 1-(5-fluoro-1-phenyl-1H-benzo[d]imidazol-2-yl)ethylcarbamate: $^1$H NMR (500 MHz, MeOH-d$_4$) δ ppm 7.58-7.68 (m, 3H) 7.53 (br. s., 2H) 7.38 (dd, J=9.29, 1.71 Hz, 1H) 7.00-7.08 (m, 2H) 1.45 (d, J=6.85 Hz, 3H) 1.33-1.41 (m, 9H). The methyne signal was masked by the reference peak.

(S)-1-(6-Fluoro-1-phenyl-1H-benzo[d]imidazol-2-yl)ethanamine

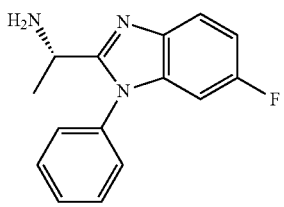 [SMILES: C[C@H](N)c1nc2ccc(F)cc2n1-c1ccccc1]

4.0 M HCl in 1,4-dioxane (1.0 mL) was added to a solution of (S)-tert-butyl 1-(6-fluoro-1-phenyl-1H-benzo[d]imidazol-2-yl)ethylcarbamate (12 mg, 0.034 mmol) in DCM (1 mL). After ~2 h the reaction mixture was concentrated under reduced pressure to dryness. The resulting solid was partitioned between DCM and satd. aq. NaHCO$_3$ solution. The aq. layer was extracted with DCM. The organic layers were combined, dried with Na$_2$SO$_4$, filtered and concentrated under reduced pressure to give (S)-1-(6-fluoro-1-phenyl-1H-benzo[d]imidazol-2-yl)ethanamine: LC-MS (ESI) m/z 256.1 [M+H]$^+$. The product was carried on crude without purification.

4-Amino-6-(((1S)-1-(6-fluoro-1-phenyl-1H-benzimidazol-2-yl)ethyl)amino)-5-pyrimidinecarbonitrile

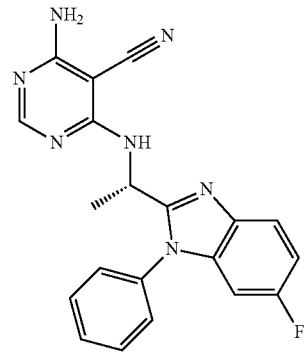

Prepared according to Step D6 in General Procedure D using (S)-1-(6-fluoro-1-phenyl-1H-benzo[d]imidazol-2-yl)ethanamine to give 4-amino-6-(((1S)-1-(6-fluoro-1-phenyl-1H-benzimidazol-2-yl)ethyl)amino)-5-pyrimidinecarbonitrile: $^1$H NMR (500 MHz, MeOH-d$_4$) δ ppm 7.86 (s, 1H) 7.67 (br. s., 1H) 7.56-7.62 (m, 2H) 7.46-7.56 (m, 3H) 7.07 (td, J=9.17, 2.45 Hz, 1H) 6.79 (dd, J=8.68, 2.57 Hz, 1H) 5.59 (q, J=7.01 Hz, 1H) 1.62 (d, J=7.09 Hz, 3H); LC-MS (ESI) m/z 374.1 [M+H]$^+$.

Example 17

Preparation of 4-amino-6-(((1S)-1-(5-fluoro-1-phenyl-1H-benzimidazol-2-yl)ethyl)amino)-5-pyrimidinecarbonitrile

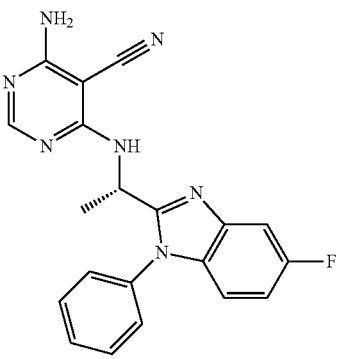 [SMILES: C[C@H](Nc1ncnc(N)c1C#N)c1nc2cc(F)ccc2n1-c1ccccc1]

Prepared according to the Procedure for Example 16 using (S)-tert-butyl 1-(5-fluoro-1-phenyl-1H-benzo[d]imidazol-2-yl)ethylcarbamate to give 4-amino-6-(((1S)-1-(5-fluoro-1-phenyl-1H-benzimidazol-2-yl)ethyl)amino)-5-pyrimidinecarbonitrile: $^1$H NMR (500 MHz, MeOH-d$_4$) δ ppm 7.86 (s, 1H) 7.57-7.62 (m, 2H) 7.46-7.57 (m, 3H) 7.38 (dd, J=8.93, 1.83 Hz, 1H) 7.00-7.09 (m, 2H) 5.56 (q, J=6.93 Hz, 1H) 1.62 (d, J=7.09 Hz, 3H); LC-MS (ESI) m/z 374.1 [M+H]$^+$.

Example 18

Preparation of 4-amino-6-((1-(1-(3,5-difluorophenyl)-4-fluoro-1H-benzimidazol-2-yl)ethyl)amino)-5-pyrimidinecarbonitrile, 4-amino-6-(((1R)-1-(1-(3,5-difluorophenyl)-4-fluoro-1H-benzimidazol-2-yl)ethyl)amino)-5-pyrimidinecarbonitrile, and 4-amino-6-(((1S)-1-(1-(3,5-difluorophenyl)-4-fluoro-1H-benzimidazol-2-yl)ethyl)amino)-5-pyrimidinecarbonitrile 4-Amino-6-((1-(1-(3,5-difluorophenyl)-4-fluoro-1H-benzimidazol-2-yl)ethyl)amino)-5-pyrimidinecarbonitrile

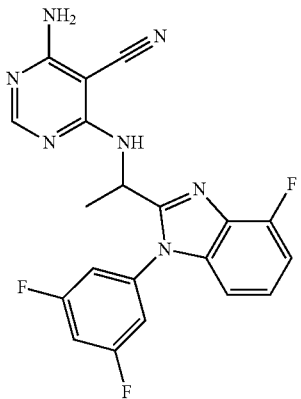 [SMILES: CC(Nc1ncnc(N)c1C#N)c1nc2c(F)cccc2n1-c1cc(F)cc(F)c1]

Prepared according to General Procedure D to give 4-amino-6-((1-(1-(3,5-difluorophenyl)-4-fluoro-1H-benzimidazol-2-yl)ethyl)amino)-5-pyrimidinecarbonitrile: $^1$H NMR (400 MHz, DMSO-$d_6$) δ ppm 7.87 (1H, s), 7.77 (1H, d, J=7.6 Hz), 7.32-7.42 (3H, m), 7.14-7.27 (3H, m), 7.07-7.14 (1H, m), 7.02 (1H, dd, J=8.0, 0.6 Hz), 5.64 (1H, quin, J=7.0 Hz), 1.59 (3H, d, J=6.8 Hz); LC-MS (ESI) m/z 410.1 [M+H]$^+$.

4-Amino-6-(((1R)-1-(1-(3,5-difluorophenyl)-4-fluoro-1H-benzimidazol-2-yl)ethyl)amino)-5-pyrimidinecarbonitrile and 4-amino-6-(((1S)-1-(1-(3,5-difluorophenyl)-4-fluoro-1H-benzimidazol-2-yl)ethyl)amino)-5-pyrimidinecarbonitrile

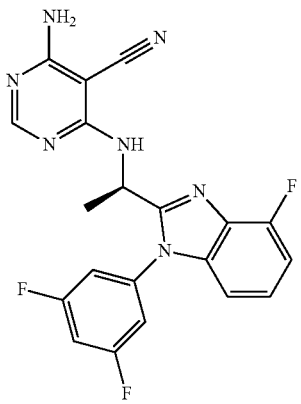

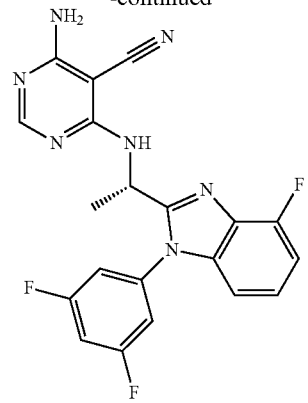

The racemic mixture (208 mg) was separated on AD-H column using Preparative SFC to give two fractions:

First peak on SFC AD-H column, first peak on Chiralpak™ AD-H column, and second peak on Chiralcel™ OD-H column: 4-amino-6-(((1R)-1-(1-(3,5-difluorophenyl)-4-fluoro-1H-benzimidazol-2-yl)ethyl)amino)-5-pyrimidinecarbonitrile as a tan solid: $^1$H NMR (400 MHz, DMSO-$d_6$) δ ppm 7.87 (1H, s), 7.77 (1H, d, J=7.6 Hz), 7.32-7.42 (3H, m), 7.14-7.27 (3H, m), 7.07-7.14 (1H, m), 7.02 (1H, dd, J=8.0, 0.6 Hz), 5.64 (1H, quin, J=7.0 Hz), 1.59 (3H, d, J=6.8 Hz); LC-MS (ESI) m/z 410.0 [M+H]$^+$.

Second peak on SFC AD-H column, second peak on Chiralpak™ AD-H column, and first peak on Chiralcel™ OD-H column: 4-amino-6-(((1S)-1-(1-(3,5-difluorophenyl)-4-fluoro-1H-benzimidazol-2-yl)ethyl)amino)-5-pyrimidinecarbonitrile as a tan solid: $^1$H NMR (400 MHz, DMSO-$d_6$) δ ppm 7.87 (1H, s), 7.77 (1H, d, J=7.8 Hz), 7.32-7.42 (3H, m), 7.14-7.27 (3H, m), 7.07-7.14 (1H, m), 7.02 (1H, dd, J=8.2, 0.8 Hz), 5.64 (1H, quin, J=7.0 Hz), 1.59 (3H, d, J=6.7 Hz); LC-MS (ESI) m/z 410.0 [M+H]$^+$.

Example 19

Preparation of 4-amino-6-((1-(6-fluoro-1-(2-(methylsulfonyl)phenyl)-1H-benzimidazol-2-yl)ethyl)amino)-5-pyrimidinecarbonitrile, 4-amino-6-(((1R)-1-(6-fluoro-1-(2-(methylsulfonyl)phenyl)-1H-benzimidazol-2-yl)ethyl)amino)-5-pyrimidinecarbonitrile, and 4-amino-6-(((1R)-1-(6-fluoro-1-(2-(methylsulfonyl)phenyl)-1H-benzimidazol-2-yl)ethyl)amino)-5-pyrimidinecarbonitrile 5-Fluoro-N-(2-(methylthio)phenyl)-2-nitroaniline

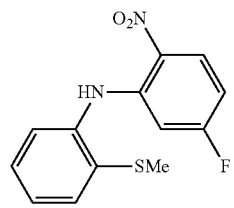 [SMILES: CSc1ccccc1Nc1cc(F)ccc1[N+](=O)[O-]]

Prepared according to Step D1 in General Procedure D using 2,4-difluoronitro-benzene (3.46 mL, 31.5 mmol) and 2-(methylthio)aniline (3.88 mL, 31.5 mmol) to give 5-fluoro- N-(2-(methylthio)phenyl)-2-nitroaniline as an orange solid: $^{1}$H NMR] (400 MHz, DMSO-$d_6$) δ ppm 9.52 (1H, s), 8.26 (1H, dd, J=9.4, 6.1 Hz), 7.34-7.45 (3H, m), 7.26-7.32 (1H, m), 6.67-6.75 (1H, m), 6.35 (1H, dd, J=11.6, 2.6 Hz), 2.43 (3H, s); LC-MS (ESI) m/z 279.0 [M+H]$^+$ at 2.176 min; m/z 277.0 [M−H]$^-$ at 2.169 min.

5-Fluoro-N1-(2-(methylthio)phenyl)benzene-1,2-diamine

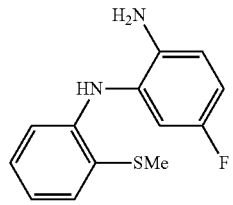 [SMILES: CSc1ccccc1Nc1cc(F)ccc1N]

Prepared according to Step D2 in General Procedure D using 5-fluoro-N-(2-(methylthio)phenyl)-2-nitroaniline (3.7956 g, 13.64 mmol) to give 5-fluoro-N1-(2-(methylthio)phenyl)benzene-1,2-diamine as a pale yellow syrup: $^{1}$H NMR (400 MHz, DMSO-$d_6$) δ ppm 7.35 (1H, dd, J=7.7, 1.5 Hz), 7.11 (1H, td, J=7.7, 1.5 Hz), 6.91 (1H, td, J=7.5, 1.2 Hz), 6.78 (1H, dd, J=8.0, 1.4 Hz), 6.71 (1H, dd, J=8.6, 5.9 Hz), 6.65 (1H, s), 6.52-6.62 (2H, m), 4.61 (2H, s), 2.40 (3H, s); LC-MS (ESI) m/z 249.0 [M+H]$^+$ at 2.275 min.

(S)-tert-Butyl 1-(4-fluoro-2-(2-(methylthio)phenylamino)phenylamino)-1-oxopropan-2-ylcarbamate

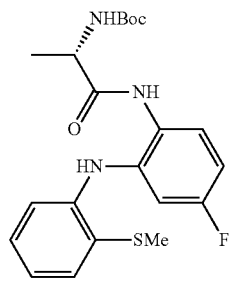 [SMILES: CSc1ccccc1Nc1cc(F)ccc1NC(=O)[C@H](C)NC(=O)OC(C)(C)C]

Prepared according to Step D3 in General Procedure D using 5-fluoro-N1-(2-(methylthio)phenyl)benzene-1,2-diamine (3.0658 g, 12.35 mmol) to give (S)-tert-butyl 1-(4-fluoro-2-(2-(methylthio)phenylamino)phenylamino)-1-oxopropan-2-ylcarbamate as a white solid: $^{1}$H NMR (400 MHz, DMSO-$d_6$) δ ppm 9.56 (1H, br. s.), 7.36 (1H, dd, J=7.8, 1.4 Hz), 7.26 (1H, dd, J=8.6, 6.3 Hz), 7.12-7.19 (1H, m), 7.10 (1H, d, J=6.8 Hz), 6.97-7.07 (3H, m), 6.70 (1H, td, J=8.2, 2.3 Hz), 6.61 (1H, d, J=11.0 Hz), 4.14 (1H, quin, J=6.8 Hz), 2.37 (3H, s), 1.34 (9H, s), 1.26 (3H, d, J=7.2 Hz); LC-MS (ESI) m/z 420.1 [M+H]$^+$ at 2.506 min.

N-(1-(6-Fluoro-1-(2-(methylthio)phenyl)-1H-benzo[d]imidazol-2-yl)ethyl)acetamide

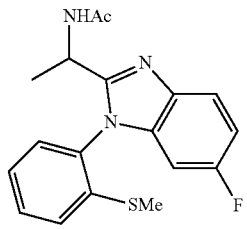 [SMILES: CSc1ccccc1-n1c(C(C)NC(C)=O)nc2ccc(F)cc21]

Prepared according to Step D4 in General Procedure D using (S)-tert-butyl 1-(4-fluoro-2-(2-(methylthio)phenylamino)phenylamino)-1-oxopropan-2-ylcarbamate (4.8685 g, 11.61 mmol) to give N-(1-(6-fluoro-1-(2-(methylthio)phenyl)-1H-benzo[d]imidazol-2-yl)ethyl)acetamide as a pink solid: LC-MS (ESI)] m/z 344.0 [M+H]$^+$.

N-(1-(6-Fluoro-1-(2-(methylsulfonyl)phenyl)-1H-benzo[d]imidazol-2-yl)-ethyl)acetamide

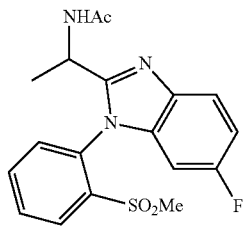 [SMILES: CC(=O)NC(C)c1nc2ccc(F)cc2n1-c1ccccc1S(C)(=O)=O]

To a mixture of N-(1-(6-fluoro-1-(2-(methylthio)phenyl)-1H-benzo[d]imidazol-2-yl)ethyl)acetamide (1.1697 g, 3.41 mmol) in THF (25.5 mL) and water (8.52 mL) was added oxone (5.23 g, 8.52 mmol) and the mixture was stirred at rt. After 48 h, to the mixture was added water (50 mL), extracted with DCM (50 mL×2). The combined organic layers were dried over Na$_2$SO$_4$, filtered, combined with the white solid, and concentrated under reduced pressure to give N-(1-(6-fluoro-1-(2-(methylsulfonyl)phenyl)-1H-benzo[d]imidazol-2-yl)ethyl)acetamide as an orange solid: LC-MS (ESI) m/z 376.0 [M+H]$^+$. The orange solid was carried on crude without purification.

1-(6-Fluoro-1-(2-(methylsulfonyl)phenyl)-1H-benzo[d]imidazol-2-yl)ethanamine

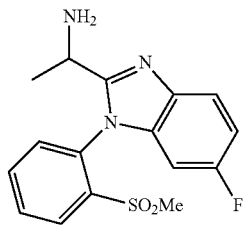 [SMILES: CC(N)c1nc2ccc(F)cc2n1-c1ccccc1S(C)(=O)=O]

Prepared according to Step D5a in General Procedure D using N-(1-(6-fluoro-1-(2-(methylsulfonyl)phenyl)-1H-benzo[d]imidazol-2-yl)ethyl)acetamide (1.2419 g, 3.31 mmol) to give 1-(6-fluoro-1-(2-(methylsulfonyl)phenyl)-1H-benzo[d]-imidazol-2-yl)ethanamine including its atropisomer as a tan solid: LC-MS (ESI) m/z 334.0 [M+H]$^+$.

4-Amino-6-((1-(6-fluoro-1-(2-(methylsulfonyl)phenyl)-1H-benzimidazol-2-yl)ethyl)amino)-5-pyrimidinecarbonitrile

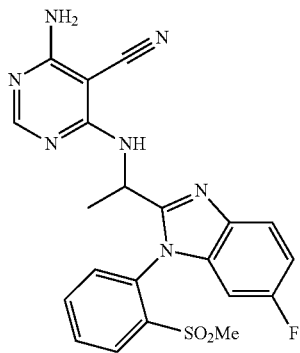 [SMILES: CC(Nc1ncnc(N)c1C#N)c1nc2ccc(F)cc2n1-c1ccccc1S(C)(=O)=O]

Prepared according to Step D6 in General Procedure D using 1-(6-fluoro-1-(2-(methylsulfonyl)phenyl)-1H-benzo[d]imidazol-2-yl)ethanamine (0.5316 g, 1.595 mmol) to give 4-amino-6-((1-(6-fluoro-1-(2-(methylsulfonyl)phenyl)-1H-benzimidazol-2-yl)ethyl)amino)-5-pyrimidinecarbonitrile as a yellow solid as a mixture of atropisomers and stereoisomers: $^1$H NMR (400 MHz, DMSO-d$_6$), $^1$H-NMR showed two sets of peaks due to the presence of two atropisomers; LC-MS (ESI) m/z 452.0 [M+H]$^+$.

4-Amino-6-(((1R)-1-(6-fluoro-1-(2-(methylsulfonyl)phenyl)-1H-benzimidazol-2-yl)ethyl)amino)-5-pyrimidinecarbonitrile and 4-amino-6-(((1R)-1-(6-fluoro-1-(2-(methylsulfonyl)phenyl)-1H-benzimidazol-2-yl)ethyl)amino)-5-pyrimidinecarbonitrile

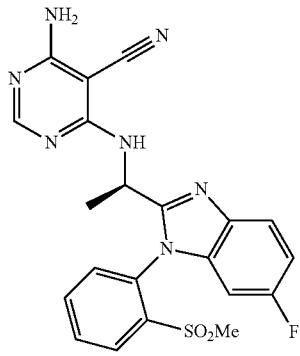

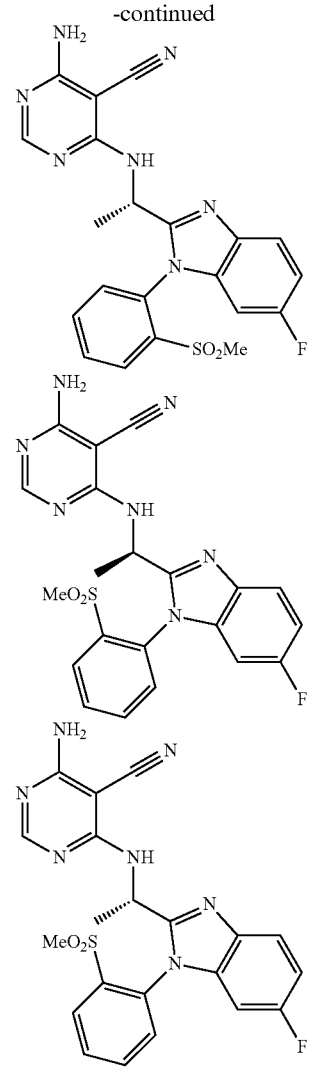

The mixture (403.9 mg) of atropisomers and stereoisomers was separated on AD-H column using preparative SFC to give four fractions:

First peak on SFC AD-H column: 4-amino-6-(((1R)-1-(6-fluoro-1-(2-(methylsulfonyl)phenyl)-1H-benzimidazol-2-yl)ethyl)amino)-5-pyrimidinecarbonitrile as a brown solid: $^1$H NMR (400 MHz, DMSO-d$_6$) δ ppm 8.05-8.11 (1H, m), 7.78 (1H, dd, J=8.8, 4.9 Hz), 7.66-7.73 (2H, m), 7.60-7.65 (2H, m), 7.44-7.52 (1H, m), 7.04-7.18 (3H, m), 6.89 (1H, dd, J=8.9, 2.4 Hz), 5.63-5.72 (1H, m), 2.85 (3H, s), 1.56 (3H, d, J=6.7 Hz); LC-MS (ESI) m/z 452.0 [M+H]$^+$.

Second peak on SFC AD-H column: 4-amino-6-(((1S)-1-(6-fluoro-1-(2-(methylsulfonyl)phenyl)-1H-benzimidazol-2-yl)ethyl)amino)-5-pyrimidinecarbonitrile as a brown solid: $^1$H NMR (400 MHz, DMSO-d$_6$) δ ppm 8.05-8.11 (1H, m), 7.78 (1H, dd, J=8.8, 4.9 Hz), 7.66-7.73 (2H, m), 7.60-7.66 (2H, m), 7.45-7.51 (1H, m), 7.13 (3H, ddd, J=9.8, 8.9, 2.4 Hz), 6.88 (1H, dd, J=8.8, 2.5 Hz), 5.62-5.72 (1H, m), 2.85 (3H, s), 1.56 (3H, d, J=6.8 Hz); LC-MS (ESI) m/z 452.0 [M+H]$^+$.

Third peak on SFC AD-H column: 4-amino-6-(((1R)-1-(6-fluoro-1-(2-(methylsulfonyl)phenyl)-1H-benzimidazol-2-yl)ethyl)amino)-5-pyrimidinecarbonitrile as a brown solid: $^1$H NMR] (400 MHz, DMSO-d$_6$) δ ppm 8.20 (1H, dd, J=7.7, 1.7 Hz), 7.87-7.99 (3H, m), 7.75-7.83 (2H, m), 7.32 (2H, br.

s.), 7.15 (1H, ddd, J=9.8, 8.9, 2.4 Hz), 6.92 (1H, dd, J=8.9, 2.4 Hz), 6.86 (1H, d, J=7.2 Hz), 5.36 (1H, quin, J=6.6 Hz), 2.88 (3H, s), 1.43 (3H, d, J=6.8 Hz); LC-MS (ESI) m/z 452.0 [M+H]⁺.

Fourth peak on SFC AD-H column: 4-amino-6-(((1S)-1-(6-fluoro-1-(2-(methylsulfonyl)phenyl)-1H-benzimidazol-2-yl)ethyl)amino)-5-pyrimidinecarbonitrile as a brown solid: ¹H NMR (400 MHz, DMSO-d₆) δ ppm 8.20 (1H, dd, J=7.7, 1.7 Hz), 7.86-8.00 (3H, m), 7.74-7.84 (2H, m), 7.32 (2H, br. s.), 7.10-7.20 (1H, m), 6.92 (1H, dd, J=9.0, 2.3 Hz), 6.86 (1H, d, J=5.5 Hz), 5.36 (1H, quin, J=6.1 Hz), 2.88 (3H, s), 1.43 (3H, d, J=6.7 Hz); LC-MS (ESI) m/z 452.0 [M+H]⁺.

Example 20

Preparation of 2-((1S)-1-((6-amino-5-cyano-4-pyrimidinyl)amino)ethyl)-1-cyclopropyl-N-methyl-1H-benzimidazole-7-carboxamide 2-(Cyclopropylamino)-N-methyl-3-nitrobenzamide

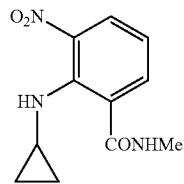

To a solution of 2-bromo-3-nitrobenzoic acid (0.974 g, 3.96 mmol) in DMF (3 mL) was added methylamine, 2.0 m solution in tetrahydrofuran (2.97 mL, 5.94 mmol), 1,1'-dimethyltriethylamine (1.38 mL, 7.92 mmol) and (1H-benzo[d]-[1,2,3]triazol-1-yloxy)tripyrrolidin-1-ylphosphonium hexafluorophosphate(V) (2.47 g, 4.75 mmol) and the resulting mixture was stirred at rt for 2 h. The reaction mixture was diluted with EtOAc, washed with water and brine, dried over MgSO₄, and concentrated under reduced pressure. The residue was purified by column chromatography on silica gel column using DCM/EtOAc-DCM (1:1) as eluent to give 2-bromo-N-methyl-3-nitrobenzamide: LC-MS (ESI) m/z 261.0 [M+H]⁺.

A mixture of 2-bromo-N-methyl-3-nitrobenzamide (830 mg, 3.20 mmol), cyclopropanamine (666 μL, 9.61 mmol) in THF (10 mL) under N₂ was heated at 60° C. for 18 h. The reaction mixture was diluted with EtOAc, washed with water and brine, dried over MgSO₄, and concentrated under reduced pressure. The residue was purified by column chromatography on a silica gel column using DCM-EtOAc (1:1) as eluent to give 2-(cyclopropylamino)-N-methyl-3-nitrobenzamide: ¹H NMR (400 MHz, DMSO-d₆) δ 8.54-8.47 (m, 2H), 7.95 (dd, J=8, 4 Hz, 1H), 7.64 (dd, J=8, 4 Hz, 1H), 6.77 (dd, J=8, 4 Hz, 1H), 2.76 (d, J=8 Hz, 3H), 2.68-2.62 (m, 1H), 0.67-0.60 (m, 2H), 0.44-0.40 (m, 2H); LC-MS (ESI) m/z 236.1 [M+H]⁺.

3-Amino-2-(cyclopropylamino)-N-methylbenzamide

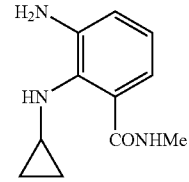

To a solution of 2-(cyclopropylamino)-N-methyl-3-nitrobenzamide (1.76 g, 7.48 mmol) in MeOH (25 mL) was added palladium 10 wt % on carbon (180 mg, 75 mmol) under N₂. After flushing the flask with N₂ for 2 min, the solution was stirred under a H₂ balloon for 3 h. LC-MS showed the reaction was complete. The reaction mixture was filtered and the filtrates collected, rinsed with MeOH and concentrated. The residue was purified by column chromatography on a silica gel column using EtOAc:DCM (1:1) as eluent to give 3-amino-2-(cyclopropylamino)-N-methylbenzamide: ¹H NMR (400 MHz, CDCl₃) δ 6.85-6.80 (m, 3H), 6.20 (br, 1H), 5.94 (br, 1H), 4.07 (br, 1H), 2.98 (d, J=4 Hz, 3H), 2.63-2.55 (m, 1H), 0.65-0.53 (m, 4H); LCMS (ESI) m/z 206.1 [M+H]⁺.

(S)-tert-Butyl 1-(2-(cyclopropylamino)-3-(methylcarbamoyl)phenylamino)-1-oxopropan-2-ylcarbamate

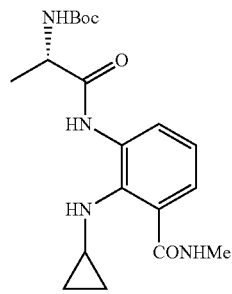

To a solution of 3-amino-2-(cyclopropylamino)-N-methylbenzamide (1.31 g, 6.38 mmol) in DMF (3 mL) was added Boc-L-Ala-OH (1.21 g, 6.38 mmol), 1,1'-dimethyltriethylamine (2.22 mL, 12.8 mmol) and (1H-benzo[d][1,2,3]triazol-1-yloxy)tripyrrolidin-1-ylphosphonium hexafluorophosphate(V) (3.99 g, 7.66 mmol) the resulting mixture was stirred at rt for 2 h. The reaction mixture was diluted with EtOAc, washed with water, brine and dried over magnesium sulfate. After being concentrated under reduced pressure, the residue was purified by column chromatography on a silica gel column using EtOAc:DCM (1:1) as eluent to give (S)-tert-butyl 1-(2-(cyclopropylamino)-3-(methylcarbamoyl) phenylamino)-1-oxopropan-2-ylcarbamate: ¹H NMR (400 MHz, CDCl₃) δ 8.56 (br, 1H), 8.14 (d, J=8 Hz, 1H), 7.18 (d, J=8 Hz, 1H), 6.99 (dd, J=8, 8 Hz, 1H), 6.24 (br, 1H), 6.01 (br, 1H), 4.38 (br, 1H), 3.00 (d, J=4 Hz, 3H), 2.58 (br, 1H), 1.60 (s, 3H), 1.48 (s, 9H), 0.64-0.59 (m, 2H), 0.54-0.49 (m, 2H); LC-MS (ESI) m/z 377.2 [M+H]⁺.

(S)-2-(1-Aminoethyl)-1-cyclopropyl-N-methyl-1H-benzo[d]imidazole-7-carboxamide

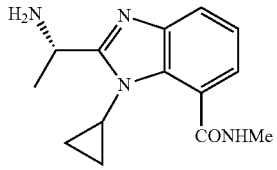

A stirred solution of (S)-tert-butyl 1-(2-(cyclopropylamino)-3-(methylcarbamoyl)phenylamino)-1-oxopropan-2-ylcarbamate (1.1 g, 2.9 mmol) in AcOH (30 mL) was heated at 65° C. for 2 h, and cooled to rt. After concentrating under reduced pressure, the residue was subjected to 4 M HCl in 1,4-dioxane (20 mL) and stirred at rt for 40 min. The mixture was concentrated under reduced pressure and dissolved in water (5 mL) basified with 1 N NaOH to pH 9.5. The mixture was concentrated and triturated with MeOH-CDM (1:1). The crude product was purified by column chromatography on a silica gel column using DCM-MeOH—NH$_4$OH (9:1:0.05) as eluent to give (S)-2-(1-aminoethyl)-1-cyclopropyl-N-methyl-1H-benzo[d]imidazole-7-carboxamide: $^1$H NMR (400 MHz, CDCl$_3$) δ 7.80 (d, J=8 Hz, 1H), 7.33 (d, J=8 Hz, 1H), 7.23 (dd, J=8, 8 Hz, 1H), 6.09 (br, 1H), 4.61 (t, J=8 Hz, 1H), 3.53-3.46 (m, 1H), 3.11 (d, J=4 Hz, 3H), 1.63 (d, J=8 Hz, 3H), 1.22-1.07 (m, 2H), 1.02-0.94 (m, 1H), 0.90-0.83 (m, 1H); LC-MS (ESI) m/z 259.1 [M+H]$^+$.

2-((1S)-1-((6-Amino-5-cyano-4-pyrimidinyl)amino)ethyl)-1-cyclopropyl-N-methyl-1H-benzimidazole-7-carboxamide

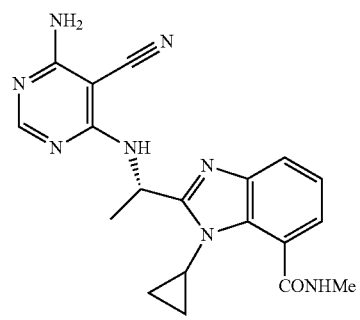

A mixture of (S)-2-(1-aminoethyl)-1-cyclopropyl-N-methyl-1H-benzo[d]imidazole-7-carboxamide (95 mg, 0.37 mmol), 4-amino-6-chloropyrimidine-5-carbonitrile (56.8 mg, 0.368 mmol) and 1,1'-dimethyltriethylamine (128 µL, 0.74 mmol) in n-butanol (2 mL) was stirred at 120° C. for 5 h. After cooling to rt, the mixture was concentrated under reduced pressure. The residue was purified by column chromatography on a silica gel column using 0 to 10% gradient of MeOH in DCM-EtOAc (1:1) as eluent to give 2-((1S)-1-((6-amino-5-cyano-4-pyrimidinyl)amino)ethyl)-1-cyclopropyl-N-methyl-1H-benzimidazole-7-carboxamide: $^1$H NMR (400 MHz, DMSO-d$_6$) δ 8.45-8.40 (m, 1H), 8.05 (s, 1H), 7.66 (d, J=8 Hz, 1H), 7.62 (d, J=4 Hz, 1H), 7.31 (br, 2H), 7.24 (d, J=8 Hz, 1H), 7.19 (dd, J=8, 8 Hz, 1H), 5.89-5.81 (m, 1H), 2.83 (d, J=4 Hz, 3H), 1.62 (d, J=8 Hz, 3H), 1.12-1.04 (m, 2H), 0.95-0.79 (m, 2H); LC-MS (ESI) m/z 377.2 [M+H]$^+$.

Example 21

Preparation of 2-((1S)-1-((6-amino-5-(4-(methylsulfonyl)phenyl)-4-pyrimidinyl)amino)ethyl)-1-cyclopropyl-N-methyl-1H-benzimidazole-7-carboxamide

6-Chloro-5-iodopyrimidin-4-amine

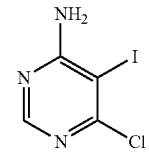

To a suspension of 6-chloropyrimidin-4-amine (5.29 g, 40.8 mmol) and trifluoro-methane sulfonic acid (40 mL, 452 mmol) was added N-iodosuccinimide (9.19 g, 40.8 mmol). The mixture was stirred for 3 h at rt. The mixture was poured into 50 mL of ice containing 15 g of NaOH with stirring for 10 min. The resulting precipitate was filtered washed with water, triturated in DCM and collected by filtration to give 6-chloro-5-iodopyrimidin-4-amine: $^1$H NMR (400 MHz, DMSO-d$_6$) δ 8.11 (s, 1H); LC-MS (ESI) m/z 255.9 [M+H]$^+$.

(S)-2-(1-(6-Amino-5-iodopyrimidin-4-ylamino)ethyl)-1-cyclopropyl-N-methyl-1H-benzo[d]imidazole-7-carboxamide

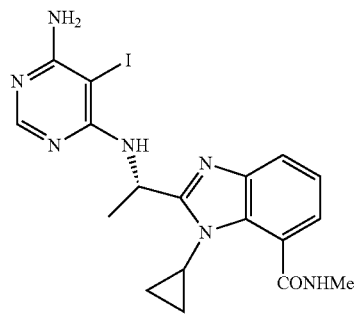

A mixture of (S)-2-(1-aminoethyl)-1-cyclopropyl-N-methyl-1H-benzo[d]imidazole-7-carboxamide (Prepared in Example 20, 190 mg, 0.74 mmol), 6-chloro-5-iodopyrimidin-4-amine (188 mg, 0.736 mmol) and 1,1'-dimethyltriethylamine (256 µL, 1.47 mmol) in n-butanol (2 mL) was stirred at 120° C. After 18 h, the mixture was cooled to rt and concentrated under reduced pressure. The residue was purified by column chromatography on a silica gel column using 0 to 10% gradient of MeOH in DCM-EtOAc (1:1) as eluent to give (S)-2-(1-(6-amino-5-iodopyrimidin-4-ylamino)ethyl)-1-cyclopropyl-N-methyl-1H-benzo-[d]imidazole-7-carboxamide: $^1$H NMR (400 MHz, DMSO-d$_6$) δ 8.46-8.40 (m, 1H), 7.87 (s, 1H), 7.67 (d, J=8 Hz, 1H), 7.24 (d, J=8 Hz, 1H), 7.20 (dd, J=8, 8 Hz, 1H), 6.46 (m, 1H), 6.37 (d, J=8 Hz, 1H), 5.82-5.75 (m, 1H), 2.84 (d, J=4 Hz, 3H), 1.60 (d, J=8 Hz, 3H), 1.14-1.04 (m, 2H), 0.93-0.90 (m, 1H), 0.85-0.76 (m, 1H); LC-MS (ESI) m/z 478.0 [M+H]$^+$.

2-((1S)-1-(((6-Amino-5-(4-(methylsulfonyl)phenyl)-4-pyrimidinyl)amino)ethyl)-1-cyclopropyl-N-methyl-1H-benzimidazole-7-carboxamide

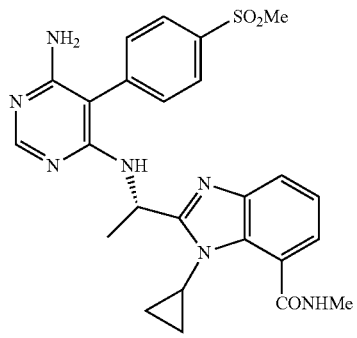

A mixture of (S)-2-(1-(6-amino-5-iodopyrimidin-4-ylamino)ethyl)-1-cyclopropyl-N-methyl-1H-benzo[d]imidazole-7-carboxamide (Prepared in Example 20, 50.4 mg, 0.106 mmol), 1,1'-bis(diphenylphosphino)ferrocene-palladium dichloride (17.25 mg, 0.021 mmol), Na$_2$CO$_3$ (0.026 ml, 0.634 mmol), 4-(methanesulfonyl)-benzeneboronic acid (52.8 mg, 0.264 mmol) in anhydrous 1,2-dimethoxyethane (5 mL) and water (1 mL) was heated to 80° C. under N$_2$. After 1 h, the mixture was cooled to rt and filtered. The filtrate was concentrated under reduced pressure, and purified by column chromatography on a silica gel column using 0 to 10% gradient of MeOH in DCM-EtOAc (1:1) as eluent to give 2-((1S)-1-(((6-amino-5-(4-(methylsulfonyl)phenyl)-4-pyrimidinyl)amino)ethyl)-1-cyclopropyl-N-methyl-1H-benzimidazole-7-carboxamide: $^1$H NMR (400 MHz, DMSO-d$_6$) δ 8.42-8.37 (m, 1H), 8.06 (d, J=8 Hz, 2H), 8.01 (s, 1H), 7.61 (d, J=8 Hz, 2H), 7.56 (d, J=8 Hz, 1H), 7.20 (d, J=8 Hz, 1H), 7.15 (dd, J=8, 8 Hz, 1H), 5.85-5.75 (m, 2H), 3.28 (s, 3H), 2.83 (d, J=4 Hz, 3H), 1.49 (d, J=8 Hz, 3H), 1.18-1.08 (m, 2H), 0.98-0.92 (m, 1H), 0.83-0.75 (m, 1H); LC-MS (ESI) m/z 506.0 [M+H]$^+$.

Example 22

Preparation of 4-amino-6-((1-(6-fluoro-1-(3-fluorophenyl)-1H-benzimidazol-2-yl)ethyl)amino)-5-pyrimidinecarbonitrile, 4-amino-6-(((1R)-1-(6-fluoro-1-(3-fluorophenyl)-1H-benzimidazol-2-yl)ethyl)amino)-5-pyrimidinecarbonitrile, and 4-amino-6-(((1S)-1-(6-fluoro-1-(3-fluorophenyl)-1H-benzimidazol-2-yl)ethyl)amino)-5-pyrimidinecarbonitrile 5-Fluoro-N-(3-fluorophenyl)-2-nitroaniline

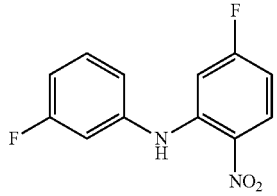 [SMILES: O=[N+]([O-])c1ccc(F)cc1Nc1cccc(F)c1]

To a solution of 3-fluoroaniline (1.813 mL, 18.86 mmol) and 2,4-difluoro-1-nitrobenzene (1.723 mL, 15.71 mmol) in DMF (26.2 mL) was added potassium tert-butoxide (3.53 g, 31.4 mmol) under argon gas. The solution was stirred overnight at rt poured into water and extracted with DCM. The combined organic extracts were purified by column chromatography on a silica gel column using 5 to 10% gradient of EtOAc in hexane as eluent to give an orange solid that was triturated in EtOAc:hexane (1:1) and filtered to give 5-fluoro-N-(3-fluorophenyl)-2-nitroaniline as an orange solid: LC-MS (ESI), m/z 251.1 [M+H]$^+$.

5-Fluoro-N1-(3-fluorophenyl)benzene-1,2-diamine

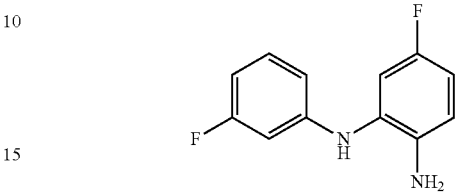

Prepared according to Step D2 in General Procedure D using 5-fluoro-N-(3-fluorophenyl)-2-nitroaniline (0.820 g, 3.28 mmol) to give 5-fluoro-N1-(3-fluorophenyl)benzene-1,2-diamine as an orange oil: LC-MS (ESI), m/z 221.1 [M+H]$^+$.

(S)-tert-Butyl-1-(4-fluoro-2-(3-fluorophenylamino)phenylamino)-1-oxopropan-2-ylcarbamate

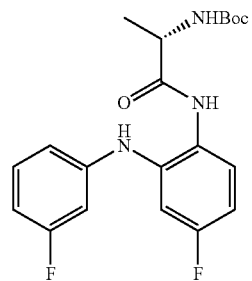 [SMILES: C[C@H](NC(=O)OC(C)(C)C)C(=O)Nc1ccc(F)cc1Nc1cccc(F)c1]

Prepared according to Step D3 in General Procedure D using 5-fluoro-N1-(3-fluorophenyl)benzene-1,2-diamine (0.501 g, 2.275 mmol) to give (S)-tert-butyl-1-(4-fluoro-2-(3-fluorophenylamino)phenylamino)-1-oxopropan-2-ylcarbamate as a white solid: LC-MS (ESI), m/z 390.1 [M+H]$^+$.

N-(1-(6-Fluoro-1-(3-fluorophenyl)-1H-benzo[d]imidazol-2-yl)ethyl)acetamide

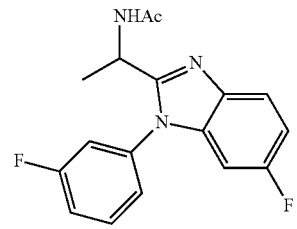 [SMILES: CC(=O)NC(C)c1nc2ccc(F)cc2n1-c1cccc(F)c1]

Prepared according to Step D4 in General Procedure D using (S)-tert-butyl-1-(4-fluoro-2-(3-fluorophenylamino)phenylamino)-1-oxopropan-2-ylcarbamate (0.830 g, 2.126 mmol) to give N-(1-(6-fluoro-1-(3-fluorophenyl)-1H-benzo[d]-imidazol-2-yl)ethyl)acetamide as a pink solid: LC-MS (ESI) m/z 316.1 [M+H]$^+$.

1-(6-Fluoro-1-(3-fluorophenyl)-1H-benzo[d]imidazol-2-yl)ethanamine

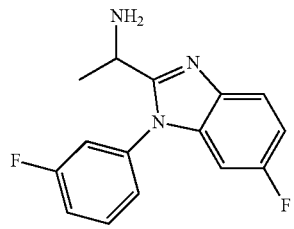 [SMILES: CC(N)c1nc2ccc(F)cc2n1-c1cccc(F)c1]

Prepared according to Step D5a in General Procedure D using N-(1-(6-fluoro-1-(3-fluorophenyl)-1H-benzo[d]imidazol-2-yl)ethyl)acetamide (0.670 g, 2.125 mmol) to give 1-(6-Fluoro-1-(3-fluorophenyl)-1H-benzo[d]imidazol-2-yl) ethanamine as an off-white solid (0.47 g, 81% yield over two steps): LC-MS (ESI), m/z 274.1 [M+H]$^+$.

4-Amino-6-(((1R)-1-(6-fluoro-1-(3-fluorophenyl)-1H-benzimidazol-2-yl)-ethyl)amino)-5-pyrimidinecarbonitrile and 4-amino-6-(((1S)-1-(6-fluoro-1-(3-fluorophenyl)-1H-benzimidazol-2-yl)ethyl)amino)-5-pyrimidinecarbonitrile

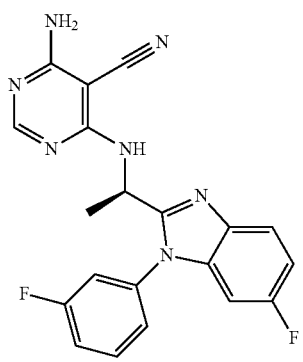

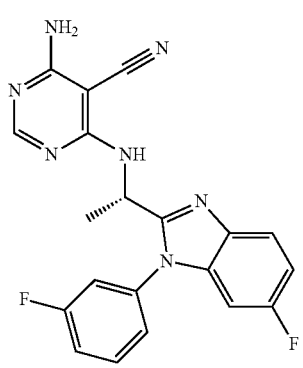

To a microwave vessel was added 4-amino-6-chloropyrimidine-5-carbonitrile (B) (0.057 g, 0.366 mmol), DIEA (0.192 mL, 1.098 mmol), and 1-(6-fluoro-1-(3-fluorophenyl)-1H-benzo[d]imidazol-2-yl)ethanamine (0.100 g, 0.366 mmol) in n-butanol (3.66 mL). The solution was stirred at 120° C. under microwave irradiation for 2 h and then purified by column chromatography on a silica gel column using 0 to 10% gradient of MeOH in DCM as eluent to give a racemic mixture 4-amino-6-((1-(6-fluoro-1-(3-fluorophenyl)-1H-benzimidazol-2-yl)ethyl)amino)-5-pyrimidinecarbonitrile as an off-white solid: $^1$H NMR (400 MHz, DMSO-d$_6$) δ ppm 1.54 (d, J=6.65 Hz, 3H) 5.56 (qd, J=6.91, 6.65 Hz, 1H) 6.93 (dd, J=9.00, 2.35 Hz, 1H) 7.08-7.15 (m, 1H) 7.17 (br. s., 2H) 7.31 (td, J=8.41, 2.15 Hz, 1H) 7.35-7.40 (m, 1H) 7.48 (d, J=9.59 Hz, 1H) 7.56 (td, J=8.12, 6.65 Hz, 1H) 7.69 (d, J=7.63 Hz, 1H) 7.73 (dd, J=8.80, 4.89 Hz, 1H) 7.86 (s, 1H); LC-MS (ESI) m/z 392.1 [M+H]$^+$. The racemic mixture (0.085 g) was separated by chiral separation using SFC to give two fractions:

First-eluting enantiomer on the AD-H column: 4-amino-6-(((1R)-1-(6-fluoro-1-(3-fluorophenyl)-1H-benzimidazol-2-yl)ethyl)amino)-5-pyrimidinecarbonitrile as a white solid (0.020 g, 47% yield): $^1$H NMR (400 MHz, DMSO-d$_6$) δ ppm 1.54 (d, J=6.85 Hz, 3H) 1.59-1.59 (m, 0H) 5.56 (quin, J=6.94 Hz, 1H) 6.94 (dd, J=8.90, 2.45 Hz, 1H) 7.13 (td, J=9.83, 8.95, 2.54 Hz, 1H) 7.18 (br. s., 2H) 7.31 (td, J=8.56, 2.45 Hz, 1H) 7.38 (dd, J=7.92, 0.88 Hz, 1H) 7.48 (d, J=9.59 Hz, 1H) 7.57 (td, J=8.12, 6.65 Hz, 1H) 7.70 (d, J=7.43 Hz, 1H) 7.74 (dd, J=8.80, 4.89 Hz, 1H) 7.86 (s, 1H); LC-MS (ESI) m/z 392.2 [M+H]$^+$.

Second-eluting enantiomer on the AD-H column: 4-Amino-6-(((1S)-1-(6-fluoro-1-(3-fluorophenyl)-1H-benzimidazol-2-yl)ethyl)amino)-5-pyrimidinecarbonitrile as a white solid (0.024 g, 57% yield): $^1$H NMR (400 MHz, DMSO-d$_6$) δ ppm 1.54 (d, J=6.85 Hz, 3H) 5.57 (quin, J=6.94 Hz, 1H) 6.94 (dd, J=8.90, 2.45 Hz, 1H) 7.13 (td, J=9.34, 2.45 Hz, 1H) 7.18 (br. s., 2H) 7.31 (td, J=8.51, 2.35 Hz, 1H) 7.38 (d, J=7.83 Hz, 1H) 7.49 (d, J=9.39 Hz, 1H) 7.53-7.62 (m, 1H) 7.70 (d, J=7.43 Hz, 1H) 7.74 (dd, J=8.80, 4.89 Hz, 1H) 7.87 (s, 1H); LC-MS (ESI) m/z 392.2 [M+H]$^+$.

Example 23

Preparation of N-((1R)-1-(6-fluoro-1-(3-fluorophenyl)-1H-benzimidazol-2-yl)ethyl)-9H-purin-6-amine and N-((1S)-1-(6-fluoro-1-(3-fluorophenyl)-1H-benzimidazol-2-yl)ethyl)-9H-purin-6-amine

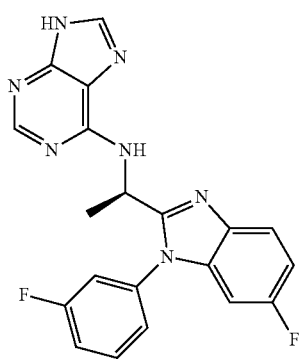

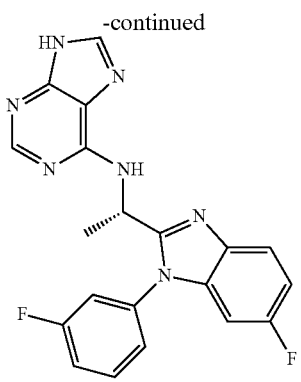

To a microwave vessel was added 6-chloropurine (0.113 g, 0.732 mmol), 1-(6-fluoro-1-(3-fluorophenyl)-1H-benzo[d]imidazol-2-yl)ethanamine (Prepared in Example 22, 0.200 g, 0.732 mmol), and DIEA (0.256 mL, 1.46 mmol) in n-butanol (3.66 mL). The solution was stirred at 120° C. for 3 h, filtered and the resulting precipitate was washed with EtOAc:hexane (1:4) to give an off-white solid. The solid was purified by column chromatography on a silica gel column using 10 to 90% gradient of DCM:MeOH:NH$_4$OH (90:10:1) in DCM as eluent to give an off-white solid. This material was triturated in EtOAc:hexane (1:3) and the suspension was filtered to give N-(1-(6-fluoro-1-(3-fluorophenyl)-1H-benzo[d]imidazol-2-yl)ethyl)-9H-purin-6-amine as an off-white solid: $^1$H NMR (400 MHz, DMSO-d$_6$) δ ppm 1.60 (d, J=6.65 Hz, 3H) 5.57 (br. s., 1H) 6.94 (dd, J=8.90, 2.25 Hz, 1H) 7.11 (td, J=9.39, 2.35 Hz, 1H) 7.29 (t, J=7.04 Hz, 1H) 7.40-7.47 (m, 1H) 7.47-7.63 (m, 2H) 7.70 (dd, J=8.80, 4.89 Hz, 1H) 7.94 (s, 1H) 8.07 (s, 1H) 8.12 (s, 1H) 12.78 (br. s., 1H); LC-MS (ESI) m/z 392.1 [M+H]$^+$.

The racemic mixture (0.090 g) was separated by chiral separation using SFC to give two fractions: First-eluting enantiomer on the AD-H column: N-((1R)-1-(6-fluoro-1-(3-fluorophenyl)-1H-benzimidazol-2-yl)ethyl)-9H-purin-6-amine as a white solid: $^1$H NMR (400 MHz, DMSO-d$_6$) δ ppm 1.59 (d, 3H) 5.56 (br. s., 1H) 6.93 (d, J=8.41 Hz, 1H) 7.10 (t, J=8.71 Hz, 1H) 7.28 (br. s., 1H) 7.43 (d, 1H) 7.47-7.60 (m, 2H) 7.69 (dd, J=8.51, 4.79 Hz, 1H) 7.94 (s, 1H) 8.01-8.21 (m, 2H) 12.88 (br. s., 1H); LC-MS (ESI) m/z 392.2 [M+H]$^+$.

Second-eluting enantiomer on the AD-H column: N-((1S)-1-(6-fluoro-1-(3-fluorophenyl)-1H-benzimidazol-2-yl)ethyl)-9H-purin-6-amine as a white solid: $^1$H NMR (400 MHz, DMSO-d$_6$) δ ppm 1.61 (d, J=6.85 Hz, 3H) 5.58 (br. s., 1H) 6.95 (dd, J=8.80, 2.35 Hz, 1H) 7.04-7.19 (m, 1H) 7.29 (t, J=6.26 Hz, 1H) 7.44 (d, J=8.00 Hz, 1H) 7.48-7.63 (m, 2H) 7.71 (dd, J=8.80, 4.89 Hz, 1H) 7.98 (br. s., 1H) 8.08 (s, 1H) 8.13 (br. s., 1H) 12.89 (br. s., 1H) Mass Spectrum (ESI) m/z 392.1 [M+H]$^+$.

Example 24

Preparation of 4-amino-6-(((1R)-1-(6-chloro-1-(3,5-difluorophenyl)-1H-benzimidazol-2-yl)ethyl)amino)-5-pyrimidinecarbonitrile and 4-amino-6-(((1S)-1-(6-chloro-1-(3,5-difluorophenyl)-1H-benzimidazol-2-yl)-ethyl)amino)-5-pyrimidinecarbonitrile 5-Chloro-N-(3,5-difluorophenyl)-2-nitroaniline

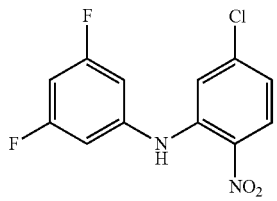 [SMILES: O=[N+]([O-])c1ccc(Cl)cc1Nc1cc(F)cc(F)c1]

To a solution of 4-chloro-2-fluoro-1-nitrobenzene (2.500 g, 14.24 mmol) and 3,5-difluoroaniline (2.206 g, 17.09 mmol) in DMF (22.61 mL) was added potassium tert-butoxide (3.20 g, 28.5 mmol) under argon and the solution was stirred at rt overnight. The solution was poured into water and extracted with DCM, and the organic extracts were purified by column chromatography on a silica gel column using 5 to 10% gradient of EtOAc in hexane as eluent to give 5-chloro-N-(3,5-difluorophenyl)-2-nitroaniline as an orange solid: $^1$H NMR (400 MHz, DMSO-d$_6$) δ ppm 6.98 (tt, J=9.34, 2.20 Hz, 1H) 7.02-7.11 (m, 3H) 7.35 (d, J=2.15 Hz, 1H) 8.14 (d, J=9.00 Hz, 1H) 9.40 (s, 1H).

5-Chloro-N1-(3,5-difluorophenyl)benzene-1,2-diamine

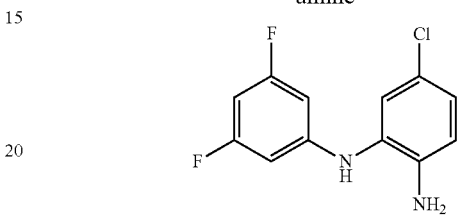

Prepared according to Step D2 in General Procedure D using 5-chloro-N-(3,5-difluorophenyl)-2-nitroaniline (0.890 g, 3.13 mmol) to give 5-chloro-N1-(3,5-difluorophenyl)benzene-1,2-diamine as a light purple solid: LC-MS (ESI) m/z 355.1.1 [M+H]$^+$.

(S)-tert-Butyl 1-(4-chloro-2-(3,5-difluorophenylamino)phenylamino)-1-oxopropan-2-ylcarbamate

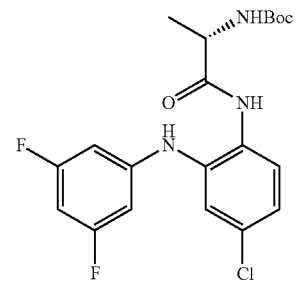

Prepared according to Step D3 in General Procedure D using 5-chloro-N1-(3,5-difluorophenyl)benzene-1,2-diamine (0.780 g, 3.06 mmol) to give (S)-tert-butyl 1-(4-chloro-2-(3,5-difluorophenylamino)phenylamino)-1-oxopropan-2-ylcarbamate as a white solid (1.12 g, 86% yield): LC-MS (ESI), m/z 424.0 [M+H]$^+$.

N-(1-(6-Chloro-1-(3,5-difluorophenyl)-1H-benzo[d]imidazol-2-yl)ethyl)acetamide

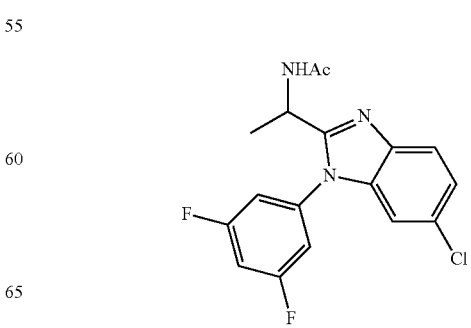

Prepared according to Step D4 in General Procedure D using (S)-tert-butyl 1-(4-chloro-2-(3,5-difluorophenylamino)phenylamino)-1-oxopropan-2-ylcarbamate (1.118 g, 2.63 mmol) to give N-(1-(6-chloro-1-(3,5-difluorophenyl)-1H-benzo[d]-imidazol-2-yl)ethyl)acetamide as a white solid: LC-MS (ESI) m/z 350.0 [M+H]$^+$.

1-(6-Chloro-1-(3,5-difluorophenyl)-1H-benzo[d]imidazol-2-yl)ethanamine

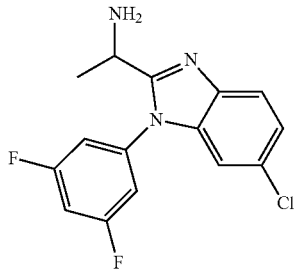 [SMILES: CC(N)c1nc2ccc(Cl)cc2n1-c1cc(F)cc(F)c1]

Prepared according to Step D5a in General Procedure D using N-(1-(6-chloro-1-(3,5-difluorophenyl)-1H-benzo[d]imidazol-2-yl)ethyl)acetamide (0.920 g, 2.63 mmol) to give 1-(6-chloro-1-(3,5-difluorophenyl)-1H-benzo[d]imidazol-2-yl)ethanamine as an off-white solid: LC-MS (ESI) m/z 308.0 [M+H]$^+$.

4-Amino-6-(((1R)-1-(6-chloro-1-(3,5-difluorophenyl)-1H-benzimidazol-2-yl)-ethyl)amino)-5-pyrimidinecarbonitrile and 4-amino-6-(((1S)-1-(6-chloro-1-(3,5-difluorophenyl)-1H-benzimidazol-2-yl)ethyl)amino)-5-pyrimidinecarbonitrile

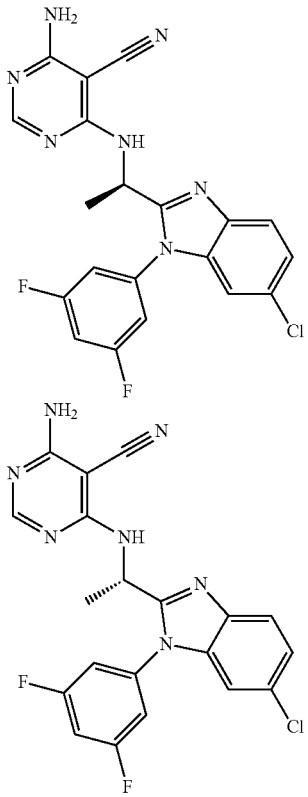

Prepared according to Step D6 in General Procedure D using 1-(6-chloro-1-(3,5-difluorophenyl)-1H-benzo[d]imidazol-2-yl)ethanamine (0.200 g, 0.650 mmol) to give 4-amino-6-((1-(6-chloro-1-(3,5-difluorophenyl)-1H-benzimidazol-2-yl)ethyl)amino)-5-pyrimidinecarbonitrile as an off-white solid: $^1$H NMR (400 MHz, DMSO-d$_6$) δ ppm 1.58 (d, 3H) 5.64 (qd, J=7.04, 6.85 Hz, 1H) 7.20 (br. s., 2H) 7.25-7.44 (m, 5H) 7.75 (t, J=7.83 Hz, 2H) 7.88 (s, 1H): LC-MS (ESI) m/z 426.0 [M+H]$^+$.

The racemic mixture (0.116 g) was separated by chiral separation using SFC to give two fractions:

First-eluting enantiomer on the AD-H column: 4-amino-6-(((1R)-1-(6-chloro-1-(3,5-difluorophenyl)-1H-benzimidazol-2-yl)ethyl)amino)-5-pyrimidinecarbonitrile (0.041 g, 71% yield) as an off-white solid: $^1$H NMR (400 MHz, DMSO-d$_6$) δ ppm 1.58 (d, J=6.85 Hz, 3H) 5.63 (q, J=6.90 Hz, 1H) 7.18 (br. s, 2H) 7.26-7.41 (m, 5H) 7.70-7.78 (m, 2H) 7.88 (s, 1H); LC-MS (ESI) m/z 426.2 [M+H]$^+$.

Second-eluting enantiomer on the AD-H column: 4-amino-6-(((1S)-1-(6-chloro-1-(3,5-difluorophenyl)-1H-benzimidazol-2-yl)ethyl)amino)-5-pyrimidinecarbonitrile as an off-white solid: $^1$H NMR (400 MHz, DMSO-d$_6$) δ ppm 1.56 (d, 3H) 5.63 (quin, J=6.90 Hz, 1H) 7.15 (br. s., 2H) 7.24-7.43 (m, 5H) 7.67-7.77 (m, 2H) 7.86 (s, 1H); LC-MS (ESI), m/z 426.2 [M+H]$^+$.

Example 25

Preparation of 4-amino-6-((1-(1-(3,5-difluorophenyl)-7-fluoro-1H-benzimidazol-2-yl)ethyl)amino)-5-pyrimidinecarbonitrile, 4-amino-6-(((1R)-1-(1-(3,5-difluorophenyl)-7-fluoro-1H-benzimidazol-2-yl)ethyl)amino)-5-pyrimidinecarbonitrile, and 4-amino-6-(((1S)-1-(1-(3,5-difluorophenyl)-7-fluoro-1H-benzimidazol-2-yl)ethyl)amino)-5-pyrimidinecarbonitrile 4-Amino-6-((1-(1-(3,5-difluorophenyl)-7-fluoro-1H-benzimidazol-2-yl)ethyl)amino)-5-pyrimidinecarbonitrile

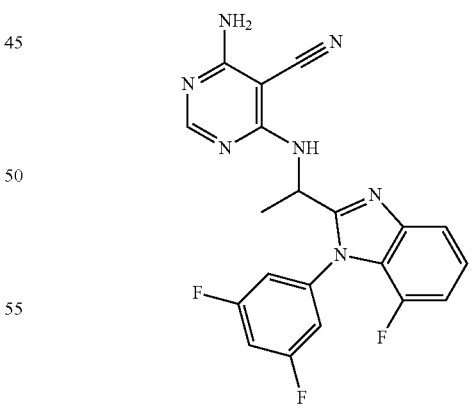

Prepared according to General Procedure D to give 4-amino-6-(1-(1-(3,5-difluorophenyl)-7-fluoro-1H-benzimidazol-2-yl)ethyl)amino)-5-pyrimidinecarbonitrile: $^1$H NMR (400 MHz, DMSO-d$_6$) δ ppm 7.86 (1H, s), 7.72 (1H, d, J=7.0 Hz), 7.58 (2H, dd, J=8.0, 0.6 Hz), 7.14-7.37 (5H, m), 7.04-7.12 (1H, m), 5.56 (1H, quin, J=6.5 Hz), 1.57 (3H, d, J=6.8 Hz); LC-MS (ESI)] m/z 410.25 [M+H]$^+$.

4-Amino-6-(((1R)-1-(1-(3,5-difluorophenyl)-7-fluoro-1H-benzimidazol-2-yl)-ethyl)amino)-5-pyrimidinecarbonitrile and 4-amino-6-(((1S)-1-(1-(3,5-difluorophenyl)-7-fluoro-1H-benzimidazol-2-yl)ethyl)amino)-5-pyrimidinecarbonitrile

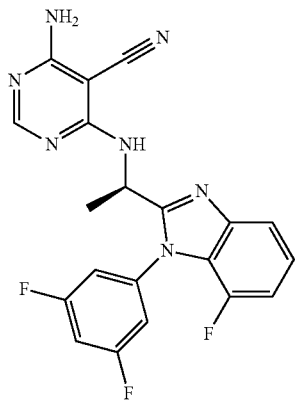

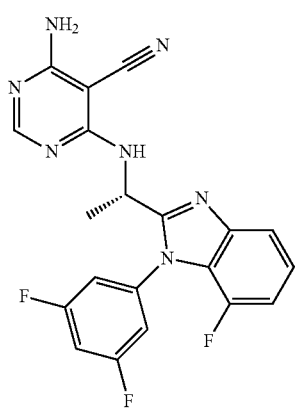

The racemic mixture (329 mg) was separated on AD-H column using preparative SFC to give two fractions:

First peak on SFC AD-H column: 4-amino-6-(((1R)-1-(1-(3,5-difluorophenyl)-7-fluoro-1H-benzimidazol-2-yl)ethyl)amino)-5-pyrimidinecarbonitrile as a tan solid: $^1$H NMR (400 MHz, DMSO-$d_6$) δ ppm 7.86 (1H, s), 7.72 (1H, d, J=7.2 Hz), 7.58 (2H, dd, J=8.1, 0.7 Hz), 7.14-7.38 (5H, m), 7.04-7.12 (1H, m), 5.56 (1H, quin, J=6.6 Hz), 1.57 (3H, d, J=6.8 Hz); LC-MS (ESI) m/z 410.0 [M+H]$^+$.

Second peak on SFC AD-H column: 4-amino-6-((1S)-1-(1-(3,5-difluorophenyl)-7-fluoro-1H-benzimidazol-2-yl)ethyl)amino)-5-pyrimidinecarbonitrile as a tan solid: $^1$H NMR (400 MHz, DMSO-$d_6$) δ ppm 7.86 (1H, s), 7.72 (1H, d, J=7.0 Hz), 7.58 (2H, dd, J=8.0, 0.6 Hz), 7.14-7.37 (5H, m), 7.04-7.12 (1H, m), 5.56 (1H, quin, J=6.5 Hz), 1.57 (3H, d, J=6.8 Hz); LC-MS (ESI)] m/z 410.0 [M+H]$^+$.

Example 26

Preparation of 4-amino-6-(((1S)-1-(1-(cyclopropylmethyl)-6-fluoro-1H-benzimidazol-2-yl)ethyl)amino)-5-pyrimidinecarbonitrile and 4-amino-6-(((1S)-1-(1-(cyclopropylmethyl)-5-fluoro-1H-benzimidazol-2-yl)-ethyl)amino)-5-pyrimidinecarbonitrile (S)-tert-Butyl 1-(1-(cyclopropylmethyl)-6-fluoro-1H-benzo[d]imidazol-2-yl)ethylcarbamate and (S)-tert-butyl 1-(1-(cyclopropylmethyl)-5-fluoro-1H-benzo[d]imidazol-2-yl)ethylcarbamate

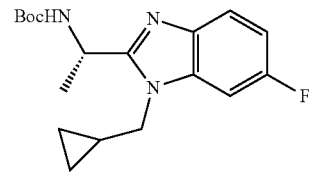

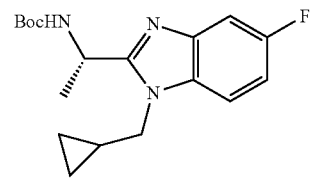

To a solution of (S)-tert-butyl 1-(6-fluoro-1H-benzo[d]imidazol-2-yl)ethylcarbamate (Prepared in Example 16, 0.500 g, 1.790 mmol) in anhydrous DMF (8.95 mL) was added cesium carbonate (1.167 g, 3.58 mmol). (Bromomethyl)-cyclopropane (0.208 mL, 2.148 mmol) was added and the solution was stirred at rt for two hours. The solution was poured into water and extracted with DCM. The organic layer was concentrated and purified by column chromatography on a silica gel column using 10 to 60% gradient of EtOAc in hexane as eluent to give mixed regioisomers (S)-tert-butyl 1-(1-(cyclopropylmethyl)-6-fluoro-1H-benzo-[d]imidazol-2-yl)ethylcarbamate and (S)-tert-butyl 1-(1-(cyclopropylmethyl)-5-fluoro-1H-benzo[d]imidazol-2-yl)ethylcarbamate as a white solid.

(S)-1-(1-(Cyclopropylmethyl)-6-fluoro-1H-benzo[d]imidazol-2-yl)ethanamine and (S)-1-(1-(cyclopropylmethyl)-5-fluoro-1H-benzo[d]imidazol-2-yl)ethanamine

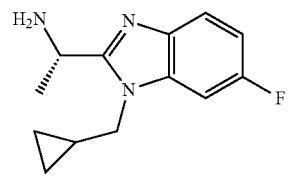

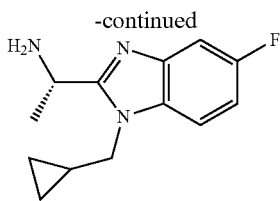

Prepared according to Step D5b in General Procedure D using mixed regioisomers (S)-tert-butyl 1-(1-(cyclopropylmethyl)-6-fluoro-1H-benzo[d]imidazol-2-yl)ethylcarbamate and (S)-tert-butyl 1-(1-(cyclopropylmethyl)-5-fluoro-1H-benzo[d]imidazol-2-yl)ethylcarbamate (0.514 g, 1.542 mmol) to give a mixture of (S)-1-(1-(cyclopropylmethyl)-6-fluoro-1H-benzo[d]imidazol-2-yl)ethanamine and (S)-1-(1-(cyclopropylmethyl)-5-fluoro-1H-benzo[d]imidazol-2-yl)ethanamine as a light yellow oil: LC-MS (ESI), m/z 234.2 [M+H]$^+$.

4-Amino-6-(((1S)-1-(1-(cyclopropylmethyl)-6-fluoro-1H-benzimidazol-2-yl)-ethyl)amino)-5-pyrimidinecarbonitrile and 4-amino-6-(((1S)-1-(1-(cyclopropylmethyl)-5-fluoro-1H-benzimidazol-2-yl)ethyl)amino)-5-pyrimidinecarbonitrile

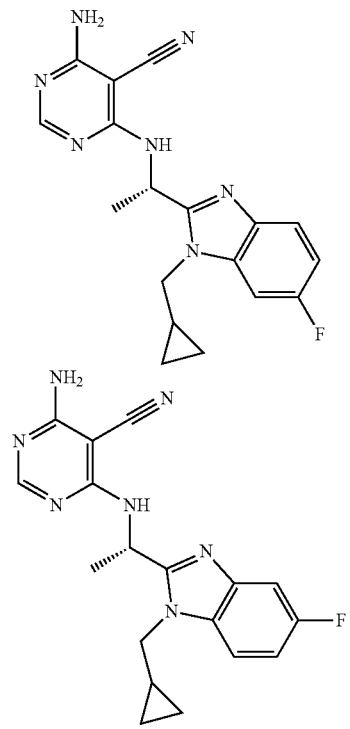

To a microwave vessel was added a mixture of (S)-1-(1-(cyclopropylmethyl)-6-fluoro-1H-benzo[d]imidazol-2-yl)ethanamine and (S)-1-(1-(cyclopropylmethyl)-5-fluoro-1H-benzo[d]imidazol-2-yl)ethanamine (0.280 g, 1.20 mmol) in butan-1-ol (6.0 mL), 4-amino-6-chloropyrimidine-5-carbonitrile (0.186 g, 1.200 mmol), and DIEA (0.252 mL, 1.44 mmol). The resulting solution was stirred at 120° C. under microwave irradiation for 3 h and the mixture purified by column chromatography on a silica gel column using 0 to 10% gradient of MeOH in DCM as eluent to give a mixture of the regioisomers 4-amino-6-(((1S)-1-(1-(cyclopropylmethyl)-6-fluoro-1H-benzimidazol-2-yl)ethyl)amino)-5-pyrimidinecarbonitrile and 4-amino-6-(((1S)-1-(1-(cyclopropylmethyl)-5-fluoro-1H-benzimidazol-2-yl)ethyl)amino)-5-pyrimidinecarbonitrile as a white solid: $^1$H NMR (400 MHz, DMSO-d$_6$) δ ppm 0.29-0.59 (m, 8H) 1.17-1.32 (m, 2H) 1.62 (d, J=6.85 Hz, 6H) 4.04-4.23 (m, 4H) 5.64-5.79 (m, 2H) 6.97-7.15 (m, 2H) 7.32 (br. s., 4H) 7.43 (dd, J=9.78, 2.54 Hz, 1H) 7.52 (dd, J=9.49, 2.45 Hz, 1H) 7.59-7.67 (m, 2H) 7.76 (d, J=2.74 Hz, 1H) 7.78 (d, J=2.54 Hz, 1H) 8.06 (s, 1H) 8.06 (s, 1H); LC-MS (ESI) m/z 352.2 [M+H]$^+$.

The racemic mixture (320 mg) was separated using preparative SFC to give two fractions:

First-eluting enantiomer on the column: 4-amino-6-(((1S)-1-(1-(cyclopropylmethyl)-6-fluoro-1H-benzimidazol-2-yl)ethyl)amino)-5-pyrimidinecarbonitrile (0.112 g, 81% yield) as a white solid: $^1$H NMR (400 MHz, DMSO-d$_6$) δ ppm 0.31-0.57 (m, 4H) 1.18-1.32 (m, 1H) 1.62 (d, J=6.65 Hz, 3H) 4.05-4.21 (m, 2H) 5.73 (quin, J=6.26 Hz, 1H) 7.04 (ddd, J=9.88, 8.90, 2.54 Hz, 1H) 7.32 (br. s., 2H) 7.52 (dd, J=9.49, 2.45 Hz, 1H) 7.62 (dd, J=8.80, 4.89 Hz, 1H) 7.76 (d, J=6.65 Hz, 1H) 8.06 (s, 1H); LC-MS (ESI), m/z 352.2 [M+H]$^+$.

Second eluting enantiomer on the column: 4-amino-6-(((1S)-1-(1-(cyclopropylmethyl)-5-fluoro-1H-benzimidazol-2-yl)ethyl)amino)-5-pyrimidinecarbonitrile (0.102 g, 73% yield): $^1$H NMR (400 MHz, DMSO-d$_6$) δ ppm 0.29-0.60 (m, 4H) 1.12-1.34 (m, 1H) 1.62 (d, J=6.85 Hz, 3H) 4.07-4.25 (m, 2H) 5.64-5.80 (m, 1H) 7.10 (td, J=9.29, 2.54 Hz, 1H) 7.31 (br. s., 2H) 7.43 (dd, J=9.78, 2.54 Hz, 1H) 7.63 (dd, J=8.80, 4.89 Hz, 1H) 7.77 (d, J=3.91 Hz, 1H) 8.06 (s, 1H); LC-MS (ESI) m/z 352.2 [M+H]$^+$.

Example 27

Preparation of 2-((1S)-1-((6-amino-5-(trifluoromethyl)-4-pyrimidinyl)amino)ethyl)-1-cyclopropyl-N-methyl-1H-benzimidazole-7-carboxamide

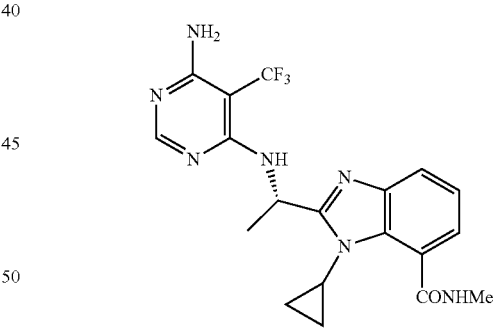

A mixture of (S)-2-(1-aminoethyl)-1-cyclopropyl-N-methyl-1H-benzo[d]-imidazole-7-carboxamide (Prepared in Example 20, 150 mg, 0.581 mmol), 6-chloro-5-(trifluoromethyl)pyrimidin-4-amine (172 mg, 0.871 mmol) and 1,1'-dimethyltriethylamine (202 µL, 1.161 mmol) in n-butanol (2 mL) was stirred at 120° C. After 42 h, the mixture was cooled to rt and concentrated under reduced pressure. The residue was purified by column chromatography on a silica gel column using 0 to 10% gradient of MeOH in DCM-EtOAc (1:1) with 0.2% NH$_4$OH as eluent to give 2-((1S)-1-((6-amino-5-(trifluoromethyl)-4-pyrimidinyl)amino)ethyl)-1-cyclopropyl-N-methyl-1H-benzimidazole-7-carboxamide: $^1$H NMR (400 MHz, DMSO-d$_6$) δ 8.50-8.41 (m, 1H), 8.05 (s, 1H), 7.66 (d, J=8 Hz, 1H), 7.28-7.18 (m, 2H), 6.90-6.78 (m, 2H), 5.89-

5.81 (m, 1H), 3.40-3.33 (m, 1H), 2.82 (d, J=4 Hz, 3H), 1.60 (d, J=8 Hz, 3H), 1.16-1.03 (m, 2H), 0.95-0.75 (m, 2H); LC-MS (ESI) m/z 420.1 [M+H]+.

Example 28

Preparation of N-((1R)-1-(6-chloro-1-(3,5-difluorophenyl)-1H-benzimidazol-2-yl)ethyl)-9H-purin-6-amine and N-((1S)-1-(6-chloro-1-(3,5-difluorophenyl)-1H-benzimidazol-2-yl)ethyl)-9H-purin-6-amine

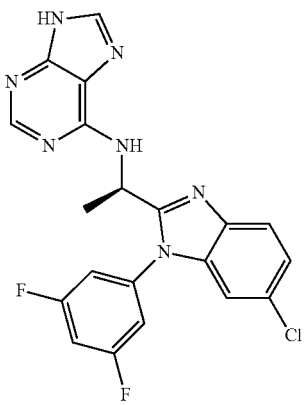

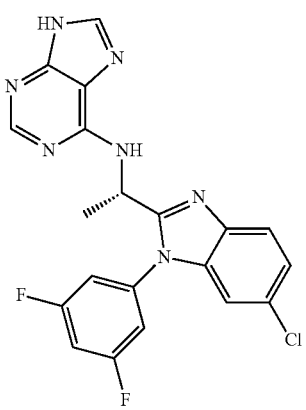

Prepared according to Procedure in Example 23 using 1-(6-chloro-1-(3,5-difluorophenyl)-1H-benzo[d]imidazol-2-yl)ethanamine (Prepared in Example 24, 0.143 g, 0.465 mmol) to give N-(1-(6-chloro-1-(3,5-difluorophenyl)-1H-benzo[d]imidazol-2-yl)ethyl)-9H-purin-6-amine (mixed enantiomers) as a light pink solid (0.083 g, 42% yield): 1H NMR (400 MHz, DMSO-d6) δ ppm 1.64 (d, 3H) 5.65 (br. s., 1H) 7.18-7.34 (m, 3H) 7.41 (d, J=6.26 Hz, 2H) 7.72 (d, J=8.61 Hz, 1H) 8.01 (br. s., 1H) 8.06 (s, 1H) 8.08 (s 1H) 12.89 (s, 1H): LC-MS (ESI) m/z 426.2 [M+H]+.

The racemic mixture (0.083 g) was separated by chiral separation using SFC to give two fractions:

First-eluting enantiomer on the AD-H column: N-((1R)-1-(6-chloro-1-(3,5-difluorophenyl)-1H-benzimidazol-2-yl)ethyl)-9H-purin-6-amine as a white solid: 1H NMR (400 MHz, DMSO-d6) δ ppm 1.64 (d, J=6.85 Hz, 3H) 5.65 (br. s., 1H) 7.20-7.33 (m, 3H) 7.41 (d, J=6.85 Hz, 2H) 7.71 (d, J=8.61 Hz, 1H) 7.97 (br. s., 1H) 8.06 (s, 1H) 8.10 (s, 1H) 12.75 (br. s., 1H); LC-MS (ESI) m/z 426.1 [M+H]+.

Second-eluting enantiomer on the AD-H column: N-((1S)-1-(6-chloro-1-(3,5-difluorophenyl)-1H-benzimidazol-2-yl)ethyl)-9H-purin-6-amine as a white solid: 1H NMR (500 MHz, DMSO-d6) δ ppm 1.64 (d, J=6.60 Hz, 3H) 5.65 (br. s., 1H) 7.17-7.35 (m, 3H) 7.41 (d, J=6.11 Hz, 2H) 7.71 (d, J=8.56 Hz, 1H) 7.97 (br. s., 1H) 8.06 (s, 1H) 8.11 (s, 1H) 12.87 (br. s., 1H). Mass Spectrum (ESI), m/e=426.2 [M+H]+.

Example 29

Preparation of 2-((1S)-1-((6-amino-5-(methylsulfonyl)-4-pyrimidinyl)amino)ethyl)-1-cyclopropyl-N-methyl-1H-benzimidazole-7-carboxamide

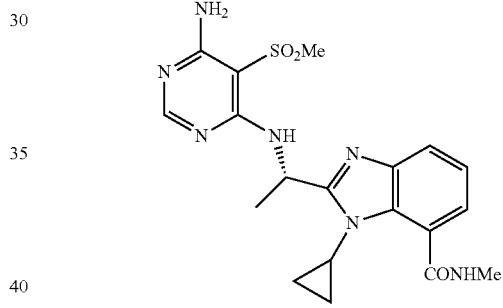

To a mixture of copper(II) triflate (7.6 mg, 0.021 mmol), sodium methanesulfinate (25.7 mg, 0.251 mmol), (S)-2-(1-(6-amino-5-iodopyrimidin-4-ylamino)ethyl)-1-cyclopropyl-N-methyl-1H-benzo[d]imidazole-7-carboxamide (prepared in Example 21, 100 mg, 0.210 mmol) under N2, N,N'-dimethylethylenediamine (4.52 µL, 0.042 mmol) and DMSO (1 mL) were added. The mixture was placed in a 110° C. oil bath. After stirring for 18 h at 110° C., the mixture was cooled to rt, diluted with EtOAc, and filtered through a pad of silica gel. The filtrate was washed with water, brine, dried and concentrated under reduced pressure. The residue was purified by column chromatography on a silica gel column using 0 to 10% gradient of MeOH in DCM-EtOAc (1:1) 0.2% NH4OH as eluent to give 2-((1S)-1-((6-amino-5-(methylsulfonyl)-4-pyrimidinyl)amino)ethyl)-1-cyclopropyl-N-methyl-1H-benzimidazole-7-carboxamide: 1H NMR (400 MHz, CDCl3) 8.02-7.97 (m, 2H), 7.65 (d, J=8 Hz, 1H), 7.22 (d, J=8 Hz, 1H), 7.12 (dd, J=8, 8 Hz, 1H), 6.01-5.92 (m, 2H), 3.45-3.40 (m, 2H), 3.16 (s, 3H), 3.01 (d, J=4 Hz, 3H), 1.61 (d, J=4 Hz, 3H), 1.22-1.10 (m, 2H), 1.04-0.96 (m, 1H), 0.80-0.73 (m, 1H); LC-MS (ESI) m/z 430.1 [M+H]+.

Example 30

Preparation of 4-amino-6-(((1S)-1-(1-cyclopropyl-6-fluoro-1H-benzimidazol-2-yl)ethyl)amino)-5-pyrimidinecarbonitrile and 4-amino-6-(((1S)-1-(1-cyclopropyl-5-fluoro-1H-benzimidazol-2-yl)ethyl)amino)-5-pyrimidinecarbonitrile (S)-tert-Butyl 1-(1-cyclopropyl-6-fluoro-1H-benzo[d]imidazol-2-yl)ethylcarbamate and (S)-tert-butyl 1-(1-cyclopropyl-5-fluoro-1H-benzo[d]imidazol-2-yl)ethylcarbamate

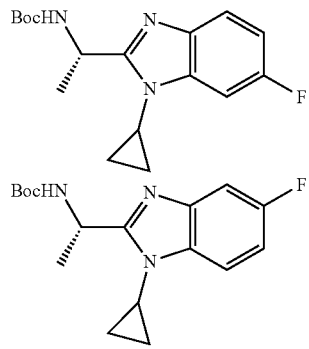

To a solution of (S)-tert-butyl 1-(6-fluoro-1H-benzo[d]imidazol-2-yl)ethylcarbamate (0.500 g, 1.790 mmol), cyclopropylboronic acid (0.308 g, 3.58 mmol), and cesium carbonate (1.167 g, 3.58 mmol) in dichloroethane (5.97 mL) was added 2,2'-bipyridyl (0.280 g, 1.790 mmol) and copper (II) acetate (0.173 mL, 1.790 mmol). The solution was stirred at 70° C. for 90 min then at rt overnight. The solution was poured into 10% aq. NH₄Cl and was extracted with DCM. The combined organic extracts were purified by column chromatography on a silica gel column using 0 to 10% gradient of MeOH in DCM as eluent to give a mixture of (S)-tert-butyl 1-(1-cyclopropyl-5-fluoro-1H-benzo[d]imidazol-2-yl)ethylcarbamate and (S)-tert-butyl 1-(1-cyclopropyl-6-fluoro-1H-benzo[d]imidazol-2-yl)ethylcarbamate as a tan solid.

(S)-1-(1-Cyclopropyl-6-fluoro-1H-benzo[d]imidazol-2-yl)ethanamine and (S)-1-(1-Cyclopropyl-5-fluoro-1H-benzo[d]imidazol-2-yl)ethanamine

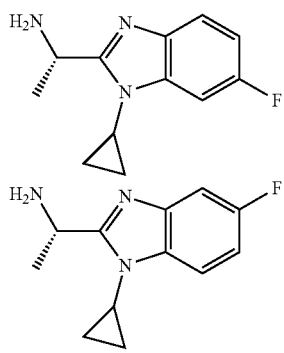

Prepared according to Step D5b in General Procedure D using (S)-tert-butyl 1-(1-cyclopropyl-6-fluoro-1H-benzo[d]imidazol-2-yl)ethylcarbamate and (S)-tert-butyl 1-(1-cyclopropyl-5-fluoro-1H-benzo[d]imidazol-2-yl)ethylcarbamate (mixed regioisomers, 0.220 g, 0.688 mmol) to give a mixture of (S)-1-(1-cyclopropyl-6-fluoro-1H-benzo[d]imidazol-2-yl)ethanamine and (S)-1-(1-cyclopropyl-5-fluoro-1H-benzo[d]imidazol-2-yl)ethanamine as a tan solid: LC-MS (ESI) m/z 220.1 [M+H]⁺.

4-Amino-6-(((1S)-1-(1-cyclopropyl-6-fluoro-1H-benzimidazol-2-yl)ethyl)amino)-5-pyrimidinecarbonitrile and 4-amino-6-(((1S)-1-(1-cyclopropyl-5-fluoro-1H-benzimidazol-2-yl)ethyl)amino)-5-pyrimidinecarbonitrile

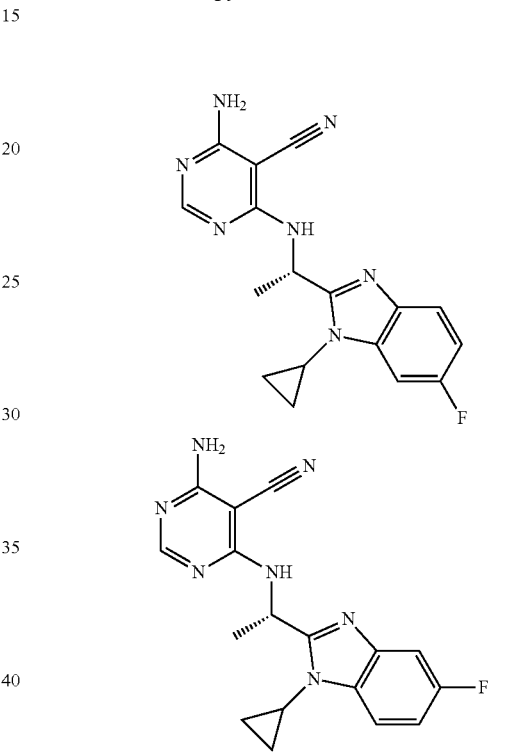

To a microwave vessel was added a mixture of (S)-1-(1-cyclopropyl-6-fluoro-1H-benzo[d]imidazol-2-yl)ethanamine and (S)-1-(1-cyclopropyl-5-fluoro-1H-benzo[d]imidazol-2-yl)ethanamine (mixed regioisomers, 0.142 g, 0.648 mmol) in n-butanol (2.159 mL) followed by DIEA (0.136 mL, 0.777 mmol) and 4-amino-6-chloropyrimidine-5-carbonitrile (0.100 g, 0.648 mmol). The suspension was stirred at 120° C. for 3 h under microwave irradiation and purified by column chromatography on a silica gel column using 0 to 8% gradient of MeOH in DCM as eluent to give a mixture of 4-amino-6-(((1S)-1-(1-cyclopropyl-6-fluoro-1H-benzimidazol-2-yl)ethyl)amino)-5-pyrimidinecarbonitrile and 4-amino-6-(((1S)-1-(1-cyclopropyl-5-fluoro-1H-benzimidazol-2-yl)ethyl)amino)-5-pyrimidinecarbonitrile as a white solid: ¹H NMR (400 MHz, DMSO-d₆) δ ppm 0.96-1.28 (m, 8H) 1.62 (d, J=6.85 Hz, 6H) 3.34-3.40 (m, 2H) 5.73-5.87 (m, 2H) 6.99-7.15 (m, 2H) 7.30 (br. s., 4H) 7.37 (dd, J=9.39, 2.54 Hz, 1H) 7.42 (dd, J=9.68, 2.45 Hz, 1H) 7.53-7.64 (m, 2H) 7.70 (d, J=7.24 Hz, 2H) 8.05 (s, 1H) 8.05 (s, 1H); LC-MS (ESI) m/z 338.2 [M+H]⁺.

Example 31

Preparation of 4-amino-6-((1-(6-fluoro-1-(2-pyridinyl)-1H-benzimidazol-2-yl)ethyl)amino)-5-pyrimidinecarbonitrile and 4-amino-6-((1-(5-fluoro-1-(2-pyridinyl)-1H-benzimidazol-2-yl)ethyl)amino)-5-pyrimidinecarbonitrile, 4-amino-6-(((1R)-1-(6-fluoro-1-(2-pyridinyl)-1H-benzimidazol-2-yl)ethyl)amino)-5-pyrimidinecarbonitrile, 4-amino-6-(((1R)-1-(5-fluoro-1-(2-pyridinyl)-1H-benzimidazol-2-yl)ethyl)amino)-5-pyrimidinecarbonitrile, 4-amino-6-(((1S)-1-(6-fluoro-1-(2-pyridinyl)-1H-benzimidazol-2-yl)ethyl)amino)-5-pyrimidinecarbonitrile, and 4-amino-6-(((1S)-1-(5-fluoro-1-(2-pyridinyl)-1H-benzimidazol-2-yl)ethyl)amino)-5-pyrimidinecarbonitrile

1-(6-Fluoro-1-(pyridin-2-yl)-1H-benzo[d]imidazol-2-yl)ethanamine and 1-(5-fluoro-1-(pyridin-2-yl)-1H-benzo[d]imidazol-2-yl)ethanamine

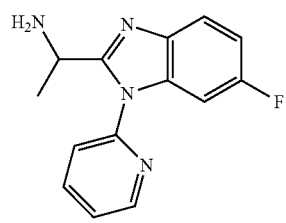

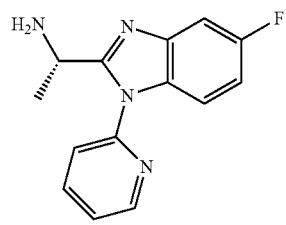

To a microwave vial was added (S)-tert-butyl 1-(6-fluoro-1H-benzo[d]imidazol-2-yl)ethylcarbamate (Prepared in Example 16, 0.5126 g, 1.835 mmol), N,N-Dimethylacetamide (4.08 mL), 2-fluoropyridine (0.189 mL, 2.202 mmol), and cesium carbonate (1.196 g, 3.67 mmol). The mixture was heated for 40 min in the microwave reactor (Temperature: 150° C. Pressure: 92~94 psi, Power: 8~10 W). At this time, the mixture was poured into EtOAc (100 mL), filtered and then concentrated on the high vacuum to remove most of the DMA. The residue was purified by silica gel column chromatography on a 40 g of Redi-Sep™ column using 0 to 20% gradient of EtOAc in hexane over 14 min, then 20% EtOAc in hexane for 14 min, then 20 to 50% gradient of EtOAc in hexane over 14 min, and then 50% EtOAc in hexane for 14 min as eluent to give a mixture of four isomer of two regioisomers and two stereoisomer of each regioisomer, 1-(6-fluoro-1-(pyridin-2-yl)-1H-benzo[d]imidazol-2-yl)ethanamine and 1-(5-fluoro-1-(pyridin-2-yl)-1H-benzo[d]imidazol-2-yl)ethanamine (0.1486 g, 0.580 mmol, 31.6% yield) as a yellow syrup: LC-MS (ESI) m/z 257.0 [M+H]$^+$.

4-Amino-6-((1-(6-fluoro-1-(2-pyridinyl)-1H-benzimidazol-2-yl)ethyl)amino)-5-pyrimidinecarbonitrile and 4-amino-6-((1-(5-fluoro-1-(2-pyridinyl)-1H-benzimidazol-2-yl)ethyl)amino)-5-pyrimidinecarbonitrile

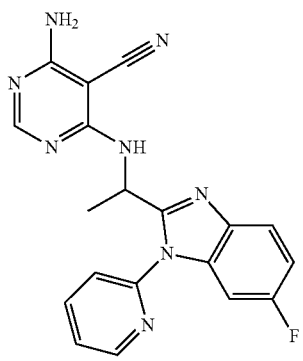

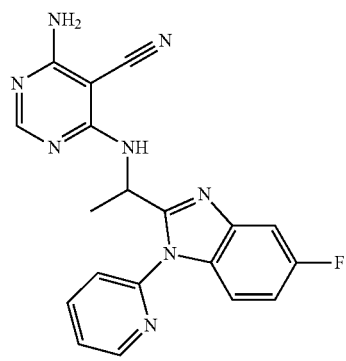

Prepared according to Step D6 in General Procedure D using a mixture of 1-(6-fluoro-1-(pyridin-2-yl)-1H-benzo[d]imidazol-2-yl)ethanamine and 1-(5-fluoro-1-(pyridin-2-yl)-1H-benzo[d]imidazol-2-yl)ethanamine (0.1428 g, 0.557 mmol) to give a mixture of four isomer 4-amino-6-((1-(6-fluoro-1-(2-pyridinyl)-1H-benzimidazol-2-yl)ethyl)amino)-5-pyrimidinecarbonitrile and 4-amino-6-((1-(5-fluoro-1-(2-pyridinyl)-1H-benzimidazol-2-yl)ethyl)amino)-5-pyrimidinecarbonitrile (0.1038 g, 0.277 mmol, 49.8% yield) as a light yellow solid: $^1$H NMR (400 MHz, DMSO-d$_6$) δ ppm 8.58-8.63 (2H, m), 8.06 (2H, tdd, J=7.7, 7.7, 4.5, 2.0 Hz), 7.86 (2H, d, J=3.3 Hz), 7.67-7.78 (5H, m), 7.57 (1H, dd, J=9.5, 2.4 Hz), 7.48-7.54 (2H, m), 7.35 (1H, dd, J=8.9, 4.8 Hz), 7.08-7.24 (7H, m), 5.76-5.87 (2H, m), 1.53 (6H, dd, J=6.7, 4.6 Hz), ~1:1 ratio of two regioisomers; LC-MS (ESI)] m/z 375.1 [M+H]$^+$. The retention times of two regioisomers were same on LC-MS and HPLC.

4-Amino-6-(((1R)-1-(6-fluoro-1-(2-pyridinyl)-1H-benzimidazol-2-yl)ethyl)amino)-5-pyrimidinecarbonitrile, 4-amino-6-(((1R)-1-(5-fluoro-1-(2-pyridinyl)-1H-benzimidazol-2-yl)ethyl)amino)-5-pyrimidinecarbonitrile, 4-amino-6-(((1S)-1-(6-fluoro-1-(2-pyridinyl)-1H-benzimidazol-2-yl)ethyl)amino)-5-pyrimidinecarbonitrile, and 4-amino-6-(((1S)-1-(5-fluoro-1-(2-pyridinyl)-1H-benzimidazol-2-yl)ethyl)amino)-5-pyrimidinecarbonitrile

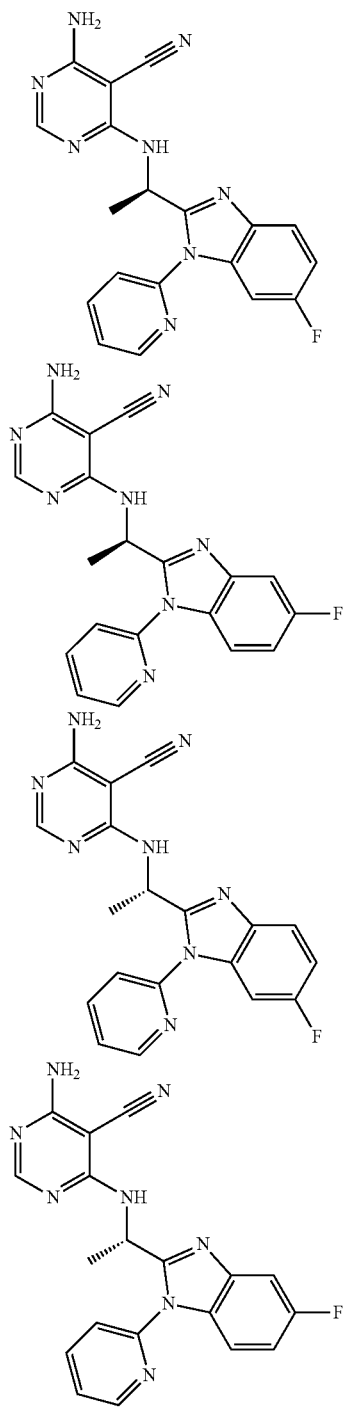

The racemic mixture (94 mg) was separated using Preparative SFC on AD-H column to give three fractions: 1a, 2a, and 3a and then the fraction 1a which contained two isomers was further separated on OJ column to give two fractions 1c and 2c.

Fraction 1c (from 1a): First peak on SFC AD-H column and first peak on SFC OJ-H column: (R)-4-amino-6-(1-(6-fluoro-1-(pyridin-2-yl)-1H-benzo[d]imidazol-2-yl)ethylamino)pyrimidine-5-carbonitrile as a tan solid: $^1$H NMR] (400 MHz, DMSO-$d_6$) δ ppm 8.58-8.62 (1H, m), 8.06 (1H, td, J=7.8, 1.9 Hz), 7.86 (1H, s), 7.75 (1H, dd, J=8.7, 4.8 Hz), 7.70 (2H, d, J=8.0 Hz), 7.50 (1H, ddd, J=7.5, 4.9, 0.9 Hz), 7.11-7.22 (4H, m), 5.82 (1H, quin, J=7.0 Hz), 1.53 (3H, d, J=6.8 Hz); LC-MS (ESI)] m/z 375.1 [M+H]$^+$;

Fraction 2c (from 1a): First peak on SFC AD-H column and Second peak on SFC OJ-H column: (R)-4-amino-6-(1-(5-fluoro-1-(pyridin-2-yl)-1H-benzo[d]imidazol-2-yl)ethylamino)pyrimidine-5-carbonitrile (0.01796 g, 0.048 mmol, 19.11% yield) as a tan solid: $^1$H NMR (400 MHz, DMSO-$d_6$) δ ppm 8.59-8.63 (1H, m), 8.07 (1H, td, J=7.7, 2.0 Hz), 7.85 (1H, s), 7.70 (2H, dd, J=7.8, 2.3 Hz), 7.57 (1H, dd, J=9.6, 2.3 Hz), 7.51 (1H, ddd, J=7.5, 4.9, 0.9 Hz), 7.35 (1H, dd, J=8.8, 4.7 Hz), 7.10-7.21 (3H, m), 5.80 (1H, quin, J=7.0 Hz), 1.54 (3H, d, J=6.8 Hz); LC-MS (ESI) m/z 375.1 [M+H]$^+$;

Fraction 2a: Second peak on SFC AD-H column: (S)-4-amino-6-(1-(6-fluoro-1-(pyridin-2-yl)-1H-benzo[d]imidazol-2-yl)ethylamino)pyrimidine-5-carbonitrile (0.0217 g, 0.058 mmol, 23.09% yield) as a tan solid: $^1$H NMR (400 MHz, DMSO-$d_6$) δ ppm 8.60 (1H, dt, J=3.8, 1.0 Hz), 8.06 (1H, td, J=7.7, 2.0 Hz), 7.86 (1H, s), 7.75 (1H, dd, J=8.7, 4.8 Hz), 7.70 (2H, d, J=8.0 Hz), 7.50 (1H, ddd, J=7.5, 4.9, 0.9 Hz), 7.10-7.25 (4H, m), 5.82 (1H, quin, J=7.0 Hz), 1.53 (3H, d, J=6.8 Hz); LC-MS (ESI)] m/z 375.1 [M+H]$^+$;

Fraction 3a: Third peak on SFC AD-H column: (S)-4-amino-6-(1-(5-fluoro-1-(pyridin-2-yl)-1H-benzo[d]imidazol-2-yl)ethylamino)pyrimidine-5-carbonitrile (0.01998 g, 0.053 mmol, 21.26% yield) as a tan solid: $^1$H NMR (400 MHz, DMSO-$d_6$) δ ppm 8.61 (1H, dd, J=4.8, 1.3 Hz), 8.07 (1H, td, J=7.7, 1.8 Hz), 7.85 (1H, s), 7.67-7.74 (2H, m), 7.57 (1H, dd, J=9.6, 2.3 Hz), 7.51 (1H, ddd, J=7.5, 4.9, 0.9 Hz), 7.35 (1H, dd, J=8.9, 4.8 Hz), 7.08-7.26 (3H, m), 5.80 (1H, quin, J=7.0 Hz), 1.54 (3H, d, J=6.8 Hz); LC-MS (ESI) m/z 375.1 [M+H]$^+$;

[NOTE]: The regiochemistry of each isomer was confirmed by HSQC, NOESY, and COSY NMR Example 32

Preparation of 1-cyclopropyl-N-methyl-2-((1S)-1-(9H-purin-6-ylamino)ethyl)-1H-benzimidazole-7-carboxamide

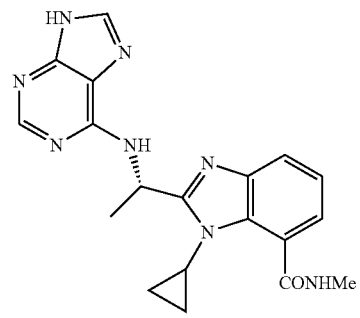

Prepared according to Procedure in Example 23 using (S)-2-(1-aminoethyl)-1-cyclopropyl-N-methyl-1H-benzo[d]imidazole-7-carboxamide (Prepared in Example 20, 91.8 mg, 0.355 mmol) to give 1-cyclopropyl-N-methyl-2-((1S)-1-(9H-purin-6-ylamino)ethyl)-1H-benzimidazole-7-carboxamide (45 mg, 0.120 mmol, 33.6% yield): $^1$H NMR (400 MHz, MeOH-$d_4$) δ 8.13 (s, 1H), 8.01 (s, 1H), 7.56 (d, J=8 Hz, 1H), 7.24 (d, J=8 Hz, 1H), 7.15 (dd, J=8.8 Hz, 1H), 3.43-3.35 (m, 1H), 2.88 (s, 3H), 1.70 (d, J=8 Hz, 3H), 1.38-1.30 (m, 1H), 1.16-0.98 (m, 2H), 0.92-0.83 (m, 1H); LC-MS (ESI) m/z 377.0 [M+H]$^+$.

Example 33

Preparation of 4-amino-6-((1-(6-fluoro-1-(5-fluoro-3-pyridinyl)-1H-benzimidazol-2-yl)ethyl)amino)-5-pyrimidinecarbonitrile 5-Fluoro-N-(4-fluoro-2-nitrophenyl)pyridin-3-amine

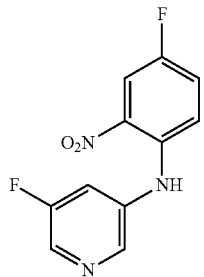

To a solution of 2,4-difluoro-1-nitrobenzene (1.723 mL, 15.71 mmol) and 3-amino-5-fluoropyridine (1.468 g, 13.10 mmol) in DMF (21.83 mL) was added potassium tert-butoxide (2.94 g, 26.2 mmol). The solution was stirred under argon at rt overnight. The solution was poured into water and extracted with EtOAc, organic extracts were dried over magnesium sulfate and concentrated to a brown solid. The brown solid was purified by column chromatography on a silica gel column using 5 to 30% gradient of EtOAc in hexane as eluent to give 5-fluoro-N-(4-fluoro-2-nitrophenyl)pyridin-3-amine as an orange solid: LC-MS (ESI) m/z 252.2 [M+H]$^+$.

4-Fluoro-N1-(5-fluoropyridin-3-yl)benzene-1,2-diamine

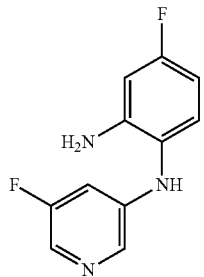 [SMILES: Nc1cc(F)ccc1Nc1cncc(F)c1]

Prepared according to Step D2 in General Procedure D using 5-fluoro-N-(4-fluoro-2-nitrophenyl)pyridin-3-amine (1.17 g, 4.66 mmol) to give 4-fluoro-N1-(5-fluoropyridin-3-yl)benzene-1,2-diamine as a yellow solid.

(S)-tert-Butyl 1-(4-fluoro-2-(5-fluoropyridin-3-ylamino)phenylamino)-1-oxopropan-2-ylcarbamate

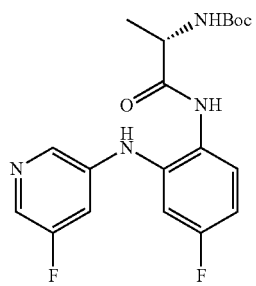 [SMILES: C[C@H](NC(=O)OC(C)(C)C)C(=O)Nc1ccc(F)cc1Nc1cncc(F)c1]

Prepared according to Step D3 in General Procedure D using 4-fluoro-N1-(5-fluoropyridin-3-yl)benzene-1,2-diamine (0.752 g, 3.40 mmol) to give (S)-tert-butyl 1-(4-fluoro-2-(5-fluoropyridin-3-ylamino)phenylamino)-1-oxopropan-2-ylcarbamate (1.274 g, 98% yield) as an orange solid: LC-MS (ESI) m/z 393.2 [M+H]$^+$.

N-(1-(6-Fluoro-1-(5-fluoropyridin-3-yl)-1H-benzo[d]imidazol-2-yl)ethyl)acetamide

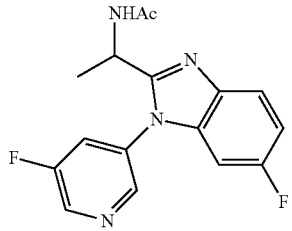 [SMILES: CC(=O)NC(C)c1nc2ccc(F)cc2n1-c1cncc(F)c1]

Prepared according to Step D4 in General Procedure D using (S)-tert-butyl 1-(4-fluoro-2-(5-fluoropyridin-3-ylamino)phenylamino)-1-oxopropan-2-ylcarbamate (1.27 g, 3.24 mmol) to give N-(1-(6-fluoro-1-(5-fluoropyridin-3-yl)-1H-benzo[d]imidazol-2-yl)ethyl)acetamide as a pink solid: LC-MS (ESI) m/z 317.2 [M+H]$^+$.

1-(6-Fluoro-1-(5-fluoropyridin-3-yl)-1H-benzo[d]imidazol-2-yl)ethanamine

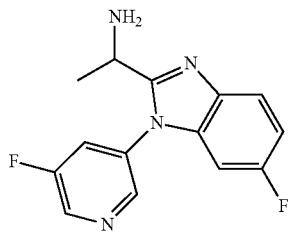 [SMILES: CC(N)c1nc2ccc(F)cc2n1-c1cncc(F)c1]

Prepared according to Step D5a in General Procedure D using N-(1-(6-fluoro-1-(5-fluoropyridin-3-yl)-1H-benzo[d]imidazol-2-yl)ethyl)acetamide (0.520 g, 1.644 mmol) to give 1-(6-fluoro-1-(5-fluoropyridin-3-yl)-1H-benzo[d]imidazol-2-yl)ethanamine as a pink foam: LC-MS (ESI) m/z 275.2 [M+H]$^+$.

4-Amino-6-((1-(6-fluoro-1-(5-fluoro-3-pyridinyl)-1H-benzimidazol-2-yl)-ethyl)amino)-5-pyrimidinecarbonitrile

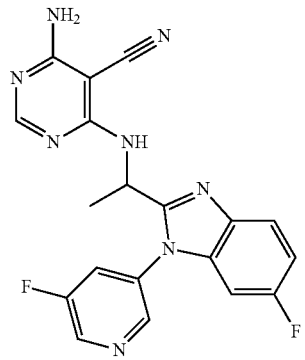 [SMILES: CC(Nc1ncnc(N)c1C#N)c1nc2ccc(F)cc2n1-c1cncc(F)c1]

To a microwave vessel was added 4-amino-6-chloropyrimidine-5-carbonitrile (0.075 g, 0.486 mmol), DIEA (0.162 mL, 0.926 mmol), and 1-(6-fluoro-1-(5-fluoropyridin-3-yl)-1H-benzo[d]imidazol-2-yl)ethanamine (0.127 g, 0.463 mmol) in n-butanol (2.315 mL). The solution was stirred at 120° C. for 4 h under microwave irradiation and then purified by column chromatography on a silica gel column using 0 to 10% gradient of MeOH in DCM as eluent to give 4-amino-6-((1-(6-fluoro-1-(5-fluoro-3-pyridinyl)-1H-benzimidazol-2-yl)ethyl)amino)-5-pyrimidinecarbonitrile: $^1$H NMR (400 MHz, DMSO-$d_6$) δ ppm 1.59 (d, J=6.85 Hz, 3H) 5.60 (qd, J=7.04, 6.85 Hz, 1H) 7.08 (dd, J=9.00, 2.35 Hz, 1H) 7.15 (td, J=9.78, 8.90, 2.45 Hz, 1H) 7.25 (br. s., 2H) 7.69-7.81 (m, 2H) 7.84 (s, 1H) 8.08 (d, J=9.00 Hz, 1H) 8.63 (s, 1H) 8.67 (d, J=2.54 Hz, 1H); LC-MS (ESI) m/z 393.0 [M+H]$^+$.

Example 34

Preparation of N-(1-(6-fluoro-1-(5-fluoropyridin-3-yl)-1H-benzo[d]imidazol-2-yl)ethyl)-9H-purin-6-amine

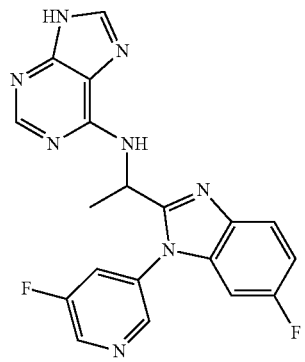 [SMILES: CC(Nc1ncnc2[nH]cnc12)c1nc2ccc(F)cc2n1-c1cncc(F)c1]

Prepared according to Procedure in Example 23 using 1-(6-fluoro-1-(5-fluoropyridin-3-yl)-1H-benzo[d]imidazol-2-yl)ethanamine (Prepared in Example 33, 0.160 g, 0.583 mmol) to give N-(1-(6-fluoro-1-(5-fluoropyridin-3-yl)-1H-benzo[d]imidazol-2-yl)ethyl)-9H-purin-6-amine as a white solid: $^1$H NMR (400 MHz, DMSO-$d_6$) δ ppm 1.66 (d, 3H) 5.61 (br. s., 1H) 7.05 (d, J=9.00 Hz, 1H) 7.14 (t, J=9.19 Hz, 1H) 7.73 (dd, J=8.71, 4.79 Hz, 1H) 7.98-8.16 (m, 4H) 8.56 (br. s., 1H) 8.64 (s, 1H) 12.89 (br. s., 1H); LC-MS (ESI) m/z 393.1 [M+H]$^+$.

Example 35

Preparation of N-((1S)-1-(7-fluoro-1H-benzimidazol-2-yl)ethyl)-9H-purin-6-amine

3-Fluorobenzene-1,2-diamine

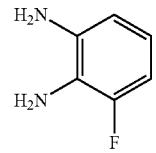

To a solution of 2-fluoro-6-nitroaniline (2 g, 12.8 mmol) in MeOH (15 mL) palladium 10 wt % on carbon (180 mg, 75 μmol) was added under $N_2$. After flushing the flask with $N_2$ for 2 min, the solution was stirred under a $H_2$ balloon. After 6 h, the mixture was filtered through a celite pad rinsed with MeOH, and concentrated under reduced pressure. The residue was purified by column chromatography on a silica gel column using EtOAc:DCM (1:1) as eluent to give 3-fluorobenzene-1,2-diamine: LC-MS (ESI) m/z 127.2 [M+H]$^+$.

N-((1S)-1-(7-Fluoro-1H-benzimidazol-2-yl)ethyl)-9H-purin-6-amine

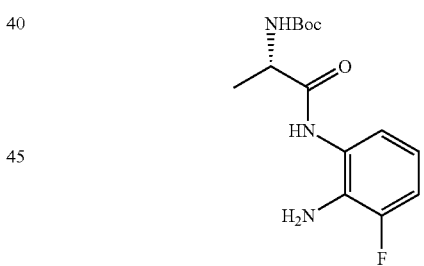

To a solution of 3-fluorobenzene-1,2-diamine (1.53 g, 12.1 mmol) in DMF (3 mL) was added Boc-L-Ala-OH (2.29 g, 12.1 mmol), 1,1'-dimethyltriethylamine (4.22 mL, 24.3 mmol) and (1H-benzo[d][1,2,3]triazol-1-yloxy)tripyrrolidin-1-yl-phosphonium hexafluorophosphate(V) (6.31 g, 12.1 mmol) and the resulting mixture was stirred at rt for 2 h. The reaction mixture was diluted with EtOAc, washed with water and brine, dried over $MgSO_4$, and concentrated under reduced pressure. The residue was purified by column chromatography on a silica gel column using EtOAC:DCM (1:1) as eluent to give N-((1S)-1-(7-fluoro-1H-benzimidazol-2-yl)ethyl)-9H-purin-6-amine: $^1$H NMR (400 MHz, DMSO-$d_6$) δ 9.31 (br, 1H), 7.12 (d, J=8 Hz, 1H), 7.00 (d, J=8 Hz, 1H), 6.94-6.87 (m, 1H), 6.58-6.52 (m, 1H), 4.83 (br, 1H), 4.17-4.05 (m, 1H), 1.40 (s, 9H), 1.28 (d, J=8 Hz, 3H).

(S)-1-(7-Fluoro-1H-benzo[d]imidazol-2-yl)ethanamine

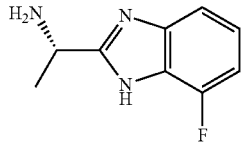

A stirred solution of (S)-tert-butyl 1-(2-amino-3-fluorophenylamino)-1-oxopropan-2-ylcarbamate (2.08 g, 7.00 mmol) in AcOH (30 mL) was heated at 65° C. for 2 h, cooled to rt. After being concentrated under reduced pressure, the residue was subjected to 4 M HCl in 1,4-Dioxane (20 mL). The resultant mixture was stirred at rt for 40 min. The mixture was concentrated under reduced pressure and dissolved in water (10 mL) and then basified with 1 N NaOH to pH 9.5. The mixture was concentrated under reduced pressure. The residue was triturated with MeOH-DCM (1:1). The crude product was purified by column chromatography on a silica gel column using DCM-MeOH—NH$_4$OH (9:1:0.05) as eluent to give (S)-1-(7-fluoro-1H-benzo[d]imidazol-2-yl)ethanamine: LC-MS (ESI) m/z 180.1 [M+H]$^+$.

N-((1S)-1-(7-Fluoro-1H-benzimidazol-2-yl)ethyl)-9H-purin-6-amine

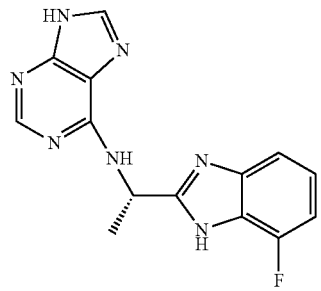 [SMILES: C[C@H](Nc1ncnc2[nH]cnc12)c1nc2cccc(F)c2[nH]1]

Prepared according to Procedure in Example 23 using (S)-1-(7-fluoro-1H-benzo[d]imidazol-2-yl)ethanamine (113.0 mg, 0.631 mmol) to give N-((1S)-1-(7-fluoro-1H-benzimidazol-2-yl)ethyl)-9H-purin-6-amine: $^1$H NMR (400 MHz, CD$_3$OD) δ 8.26 (s, 1H), 8.15 (s, 1H), 7.30 (d, J=8 Hz, 1H), 7.20-7.14 (m, 1H), 6.92-6.80 (m, 1H), 1.84 (d, J=8 Hz, 3H); LC-MS (ESI) m/z 298.0 [M+H]$^+$.

Example 36

Preparation of 4-amino-6-(((1S)-1-(7-fluoro-1H-benzimidazol-2-yl)ethyl)amino)-5-pyrimidinecarbonitrile

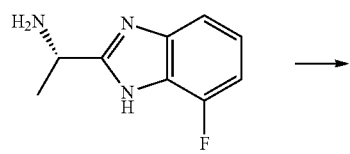 →

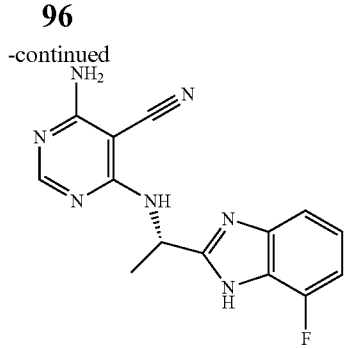

Prepared according to Step D6 in General Procedure D using (S)-1-(7-fluoro-1H-benzo[d]imidazol-2-yl)ethanamine (Prepared in Example 35, 178.8 mg, 0.998 mmol) to give 4-amino-6-(((1S)-1-(7-fluoro-1H-benzimidazol-2-yl)ethyl)amino)-5-pyrimidinecarbonitrile: $^1$H NMR (400 MHz, DMSO-d$_6$) δ 12.5 (br, 1H), 8.03 (s, 1H), 7.74 (d, J=8 Hz, 1H), 7.28 (d, J=8 Hz, 1H), 7.16-7.10 (m, 1H), 6.97-6.92 (m, 1H), 5.65-5.57 (m, 1H). 1.64 (d, J=8 Hz, 3H); LC-MS (ESI) m/z 298.1 [M+H]$^+$.

Example 37

Preparation of 4-amino-6-(((1S)-1-(1-cyclopropyl-7-fluoro-1H-benzimidazol-2-yl)ethyl)amino)-5-pyrimidinecarbonitrile N-Cyclopropyl-2-fluoro-6-nitroaniline

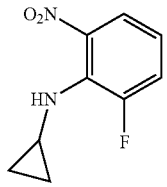 [SMILES: O=[N+]([O-])c1cccc(F)c1NC1CC1]

A mixture of 2-bromo-1-fluoro-3-nitrobenzene (2.0 g, 9.1 mmol), cyclopropanamine (1.26 mL, 18.2 mmol) in THF (10 mL) under N$_2$ was heated at 60° C. for 4 days. The reaction mixture was diluted with EtOAc, washed with water and brine, dried over MgSO$_4$, and concentrated under reduced pressure. The residue was purified by column chromatography on a silica gel column using hexane-EtOAc (8.5:1.5) as eluent to give N-cyclopropyl-2-fluoro-6-nitroaniline.

N1-Cyclopropyl-6-fluorobenzene-1,2-diamine

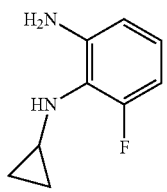

To a solution of N-cyclopropyl-2-fluoro-6-nitroaniline (650 mg, 3.31 mmol) in MeOH (15 mL) palladium 10 wt % on carbon (176 mg, 0.166 mmol) was added under N$_2$. After flushing the flask with N$_2$ for two minutes, the solution was stirred under a H₂ balloon. After 6 h, the mixture was filtered through a celite pad rinsed with MeOH, and concentrated under reduced pressure. The residue was purified by column chromatography on a silica gel column using EtOAc:DCM (1:1) as eluent to give N1-cyclopropyl-6-fluorobenzene-1,2-diamine: LC-MS (ESI) m/z 167.1 [M+H]⁺.

(S)-tert-Butyl 1-(2-(cyclopropylamino)-3-fluorophenylamino)-1-oxopropan-2-ylcarbamate

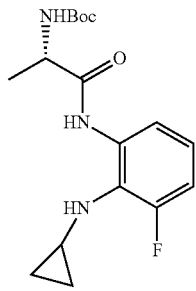 [SMILES: C[C@H](NC(=O)OC(C)(C)C)C(=O)Nc1cccc(F)c1NC1CC1]

To a solution of N1-cyclopropyl-6-fluorobenzene-1,2-diamine (392.7 mg, 2.363 mmol) in DMF (3 mL) was added Boc-L-Ala-OH (447 mg, 2.363 mmol), 1,1'-dimethyltriethylamine (822 µL, 4.73 mmol) and (1H-benzo[d][1,2,3]triazol-1-yloxy)tripyrrolidin-1-ylphosphonium hexafluorophosphate(V) (1.23 mg, 2.36 mmol) and the resulting mixture was stirred at rt for 4 h. The reaction mixture was diluted with EtOAc, washed with water and brine, dried over MgSO₄, and concentrated under reduced pressure. The residue was purified by column chromatography on a silica gel column using EtOAc:DCM (1:1) as eluent to give (S)-tert-butyl 1-(2-(cyclopropylamino)-3-fluorophenylamino)-1-oxopropan-2-ylcarbamate: LC-MS (ESI) m/z 338.2 [M+H]⁺.

(S)-1-(1-Cyclopropyl-7-fluoro-1H-benzo[d]imidazol-2-yl)ethanamine

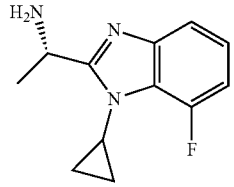 [SMILES: C[C@H](N)c1nc2cccc(F)c2n1C1CC1]

A stirred solution of (S)-tert-butyl 1-(2-(cyclopropylamino)-3-fluorophenylamino)-1-oxopropan-2-ylcarbamate (651.7 mg, 1.932 mmol) in AcOH (20 mL) was heated at 60° C. for 30 min, after being concentrated under reduced pressure, the residue was subjected to 4 M HCl in 1,4-Dioxane (20 mL). The resultant mixture was stirred at rt for 40 min. The mixture was concentrated under reduced pressure and dissolved in water (5 mL) and then basified with 1 N NaOH to pH 9.5. The mixture was concentrated under reduced pressure and triturated with MeOH-CDM (1:1). The crude product was purified by column chromatography on a silica gel column using DCM-MeOH—NH₄OH (9:1:0.05) as eluent to give (S)-1-(1-cyclopropyl-7-fluoro-1H-benzo[d]imidazol-2-yl)ethanamine: LC-MS (ESI) m/z 220.0 [M+H]⁺.

4-Amino-6-(((1S)-1-(1-cyclopropyl-7-fluoro-1H-benzimidazol-2-yl)ethyl)amino)-5-pyrimidinecarbonitrile

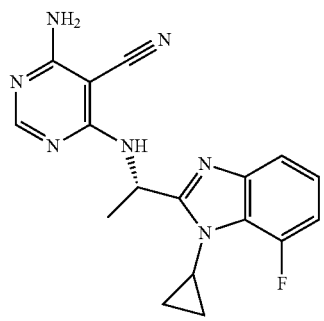 [SMILES: C[C@H](Nc1ncnc(N)c1C#N)c1nc2cccc(F)c2n1C1CC1]

Prepared according to Step D6 in General Procedure D using (S)-1-(1-cyclopropyl-7-fluoro-1H-benzo[d]imidazol-2-yl)ethanamine (176.5 mg, 0.805 mmol) to give 4-amino-6-(((1S)-1-(1-cyclopropyl-7-fluoro-1H-benzimidazol-2-yl)ethyl)amino)-5-pyrimidinecarbonitrile: ¹H NMR (400 MHz, MeOH-d₄) δ 8.03 (s, 1H), 7.41 (d, J=8 Hz, 1H), 7.22-7.16 (m, 1H), 7.05-7.00 (m, 1H), 6.00-5.95 (m, 1H), 3.60-3.55 (m, 1H), 1.73 (d, J=8 Hz, 3H), 1.52-1.45 (m, 1H), 1.35-1.15 (m, 3H); LC-MS (ESI) m/z 338.2 [M+H]⁺.

Example 38

Preparation of 4-amino-6-(((1S)-1-(4-fluoro-1-methyl-1H-benzimidazol-2-yl)ethyl)amino)-5-pyrimidinecarbonitrile and 4-amino-6-(((1S)-1-(7-fluoro-1-methyl-1H-benzimidazol-2-yl)ethyl)amino)-5-pyrimidinecarbonitrile

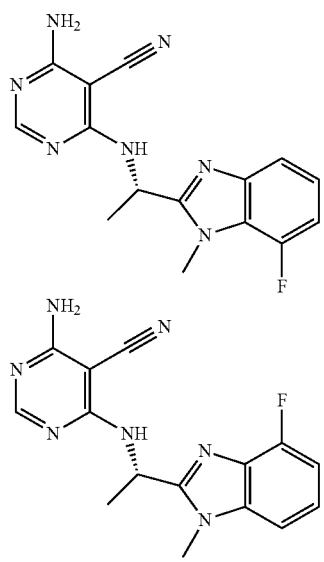

A mixture of 4-amino-6-(((1S)-1-(7-fluoro-1H-benzimidazol-2-yl)ethyl)amino)-5-pyrimidinecarbonitrile (Prepared in Example 36, 110 mg, 0.370 mmol), iodomethane (0.023 mL, 0.370 mmol) and potassium carbonate (51.1 mg, 0.370 mmol) in DMF (2 mL) was stirred at rt in a stoppered flask for 24 h. The reaction mixture was diluted with EtOAc, washed with water, brine, dried over MgSO₄, and concentrated under reduced pressure. The residue was purified by column chromatography on a silica gel column using 0 to 10% gradient of MeOH in DCM-EtOAc (1:1) with 0.2% NH₄OH as eluent to give a mixture of 4-amino-6-(((1S)-1-(4-fluoro-1-methyl-1H-benzimidazol-2-yl)ethyl)amino)-5-pyrimidinecarbonitrile and 4-amino-6-(((1S)-1-(7-fluoro-1-methyl-1H-benzimidazol-2-yl)ethyl)amino)-5-pyrimidinecarbonitrile: ¹H NMR (400 MHz, CD₃OD) δ 8.05 (d, J=8 Hz, 2H), 7.43 (d, J=8 Hz, 1H), 7.34 (d, J=8 Hz, 1H), 7.29-7.23 (m, 1H), 7.22-7.16 (m, 1H), 7.04-6.95 (m, 2H), 5.84-5.74 (m, 2H). 4.09 (s, 3H), 3.93 (s, 3H), 1.72 (d, J=8 Hz, 6H); LC-MS (ESI) m/z 312.1 [M+H]⁺.

Example 39

Preparation of 4-amino-6-(((1S)-1-(4-fluoro-1-(2-methoxyethyl)-1H-benzimidazol-2-yl)ethyl)amino)-5-pyrimidinecarbonitrile and 4-amino-6-(((1S)-1-(7-fluoro-1-(2-methoxyethyl)-1H-benzimidazol-2-yl)ethyl)amino)-5-pyrimidinecarbonitrile

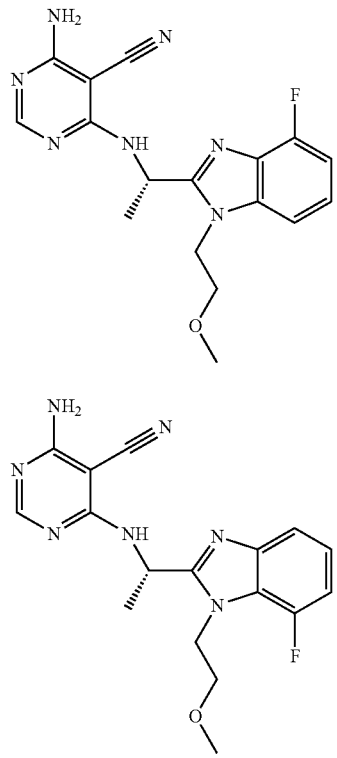

Prepared according to Procedure in Example 38 using 4-amino-6-(((1S)-1-(7-fluoro-1H-benzimidazol-2-yl)ethyl)amino)-5-pyrimidinecarbonitrile (Prepared in Example 36, 104 mg, 0.350 mmol) and 2-bromoethyl methyl ether (0.033 ml, 0.351 mmol) to give a mixture of 4-amino-6-(((1S)-1-(4-fluoro-1-(2-methoxyethyl)-1H-benzimidazol-2-yl)ethyl)amino)-5-pyrimidinecarbonitrile and 4-amino-6-(((1S)-1-(7-fluoro-1-(2-methoxyethyl)-1H-benzimidazol-2-yl)ethyl)amino)-5-pyrimidinecarbonitrile: ¹H NMR (400 MHz, CD₃OD) δ 8.07 (d, J=8 Hz, 2H), 7.46 (d, J=8 Hz, 1H), 7.37 (d, J=8 Hz, 1H), 7.29-7.19 (m, 2H), 7.06-6.95 (m, 2H), 5.86-5.78 (m, 2H), 4.88-4.78 (m, 2H), 4.62-4.53 (m, 1H), 4.52-4.33 (m, 1H), 3.82-3.73 (m, 4H), 3.30 (s, 6H), 1.73 (d, J=8 Hz, 6H); LC-MS (ESI) m/z 356.0 [M+H]⁺.

Example 40

Preparation of 4-amino-6-((1-(1-(3,5-difluorophenyl)-4,6-difluoro-1H-benzimidazol-2-yl)ethyl)amino)-5-pyrimidinecarbonitrile

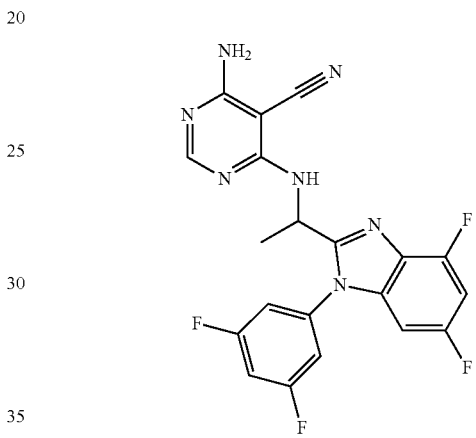

Prepared according to General Procedure D to give 4-amino-6-((1-(1-(3,5-difluorophenyl)-7-fluoro-1H-benzimidazol-2-yl)ethyl)amino)-5-pyrimidinecarbonitrile: ¹H NMR (400 MHz, DMSO-d₆) δ ppm 7.86 (1H, s), 7.75 (1H, d, J=7.0 Hz), 7.29-7.43 (3H, m), 7.17 (3H, td, J=10.6, 2.2 Hz), 6.97 (1H, dd, J=8.4, 2.2 Hz), 5.63 (1H, quin, J=6.6 Hz), 1.57 (3H, d, J=6.8 Hz); LC-MS (ESI)] m/z 427.84 [M+H]⁺.

Example 41

Preparation of 4-amino-6-((1-(3-phenyl-1-benzothiophen-2-yl)-ethyl)amino)-5-pyrimidinecarbonitrile

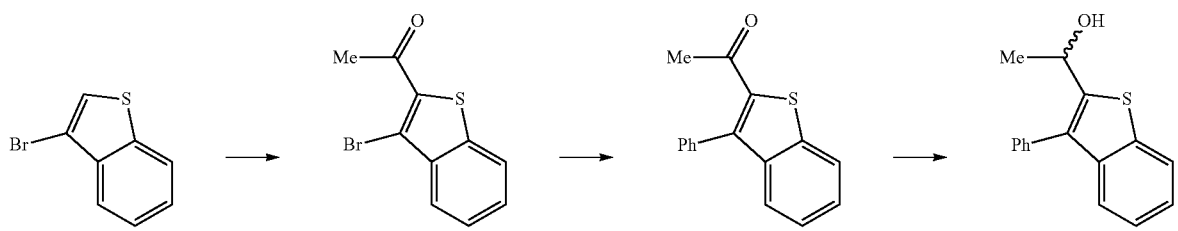

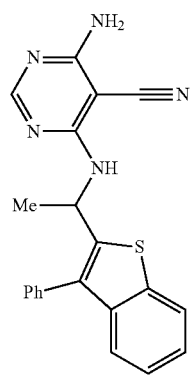

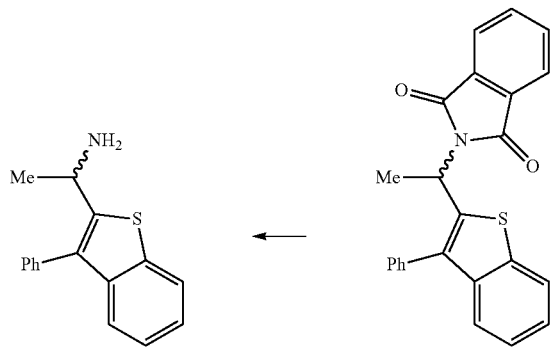

1-(3-Bromobenzo[b]thiophen-2-yl)ethanone

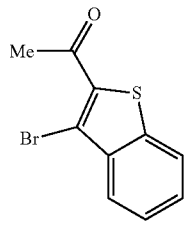

To a mixture of 3-bromothianaphthene (Sigma-Aldrich Chemical Company, 2.000 mL, 9.39 mmol) and aluminum chloride (1.002 mL, 9.39 mmol) in DCM (50 mL) cooled with an ice bath was added acetyl chloride (0.667 mL, 9.39 mmol) via syringe, in one minute. The resulting intense orange reaction solution was stirred at rt for 1 h. The reaction was poured into ice and partitioned between water and DCM. The aqueous layer was extracted with DCM, and the combined extracts were washed with 50 mL 5% aqueous sodium hydroxide, 50 mL brine, and stirred over anhydrous magnesium sulfate, filtered and concentrated under reduced pressure to give 1-(3-bromobenzo[b]thiophen-2-yl)ethanone as a pale yellow solid. $^1$H NMR (400 MHz, DMSO-$d_6$) δ 2.77 (s, 3H), 7.57-7.65 (m, 2H), 7.95 (dd, J=7.7, 1.1 Hz, 1H), 8.10 (dd, J=7.1, 1.3 Hz, 1H); LC-MS (ESI)] m/z 254.9 [M+H]$^+$.

1-(3-Phenylbenzo[b]thiophen-2-yl)ethanone

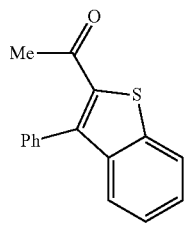 [SMILES: CC(=O)c1sc2ccccc2c1-c1ccccc1]

A mixture of trans-dichlorobis(triphenyl-phosphine)palladium (ii) (0.138 g, 0.196 mmol), phenylboronic acid (0.717 g, 5.88 mmol), 1-(3-bromobenzo[b]thiophen-2-yl)ethanone (0.50 g, 1.960 mmol) and 2.0 N aqueous sodium carbonate (2.94 mL, 5.88 mmol) in Toluene (10 mL) was purged with nitrogen and heated to 110° C. overnight. After 16 h, the reaction mixture was partitioned between EtOAc and water. The organic layer was stirred over MgSO$_4$, filtered and concentrated under reduced pressure to give a red oil. The product was purified by column chromatography on a silica gel column using 20 to 40% gradient of EtOAc in hexane as eluent to give 1-(3-phenylbenzo[b]thiophen-2-yl)ethanone a colorless oil: $^1$H NMR (400 MHz, CDCl$_3$) δ 2.12 (s, 3H) 7.30-7.35 (m, 1H) 7.38-7.42 (m, 2H) 7.42-7.49 (m, 2H) 7.52-7.58 (m, 3H) 7.87 (d, J=8.2 Hz, 1H); LC-MS (ESI)] m/z 253.1 [M+H]$^+$.

1-(3-Phenylbenzo[b]thiophen-2-yl)ethanol

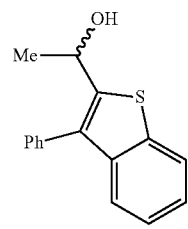 [SMILES: CC(O)c1sc2ccccc2c1-c1ccccc1]

To a stirred solution of 1-(3-phenylbenzo[b]thiophen-2-yl)ethanone (430 mg, 1.704 mmol) dissolved in MeOH (5 mL) at rt was added sodium borohydride (0.093 mL, 2.64 mmol). After 5 min, no starting material remained. The reaction was partitioned between water and EtOAc, and the aqueous layer was extracted with EtOAc. The combined organic layers were washed with brine then stirred over MgSO$_4$, filtered, and concentrated under reduced pressure to give 1-(3-phenylbenzo[b]thiophen-2-yl)ethanol as a colorless, crystalline solid: $^1$H NMR (400 MHz, CDCl$_3$) δ 1.46 (d, J=6.3 Hz, 3H), 2.19 (br. s., 1H), 5.09 (q, J=6.5 Hz, 1H), 7.16-7.40 (m, 8H), 7.70-7.77 (m, 1H).

2-(1-(3-Phenylbenzo[b]thiophen-2-yl)ethyl)isoindoline-1,3-dione

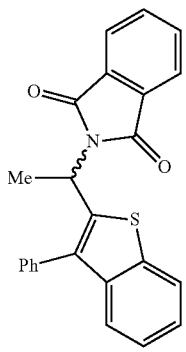 [SMILES: CC(c1sc2ccccc2c1-c1ccccc1)N1C(=O)c2ccccc2C1=O]

To a solution of triphenyl phosphorus (0.401 mL, 1.730 mmol) dissolved in THF (12 mL) cooled with an ice bath was added diisopropyl azodicarboxylate (0.340 mL, 1.730 mmol) via syringe in 1 min. The solution was equilibrated to rt and a colorless precipitate developed. After 20 min, the reaction mixture was cooled again to ice-bath temperature and 1-(3-phenylbenzo[b]thiophen-2-yl)ethanol (400 mg, 1.573 mmol) and phthalimide (255 mg, 1.730 mmol) were added sequentially. The cold bath was removed and the reaction equilibrated to rt.

The reaction was left to stir overnight then concentrated under reduced pressure. The desired product 2-(1-(3-phenylbenzo[b]thiophen-2-yl)ethyl)isoindoline-1,3-dione was isolated by column chromatography on a silica gel column using 2 to 5% gradient of MeOH in DCM as eluent to give 2-(1-(3-phenylbenzo[b]thiophen-2-yl)ethyl)isoindoline-1,3-dione: $^1$H NMR (400 MHz, CDCl$_3$) δ 1.94 (d, J=7.2 Hz, 3H), 5.92 (d, J=7.2 Hz, 1H), 7.27-7.53 (m, 8H), 7.67 (dd, J=5.6, 3.03 Hz, 2H), 7.73-7.79 (m, 2H), 7.84 (d, J=8.0 Hz, 1H); LC-MS (ESI)] m/z 406.1 [M+Na]$^+$.

1-(3-Phenylbenzo[b]thiophen-2-yl)ethanamine

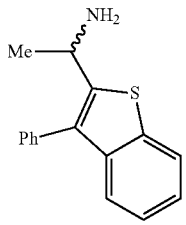 [SMILES: CC(N)c1sc2ccccc2c1-c1ccccc1]

A mixture of 2-(1-(3-phenylbenzo[b]thiophen-2-yl)ethyl)isoindoline-1,3-dione (170 mg, 0.443 mmol) and hydrazine, monohydrate (0.215 mL, 4.43 mmol) in EtOH (5 mL) was heated to 50° C. overnight. After 18 h, a precipitate had developed. The precipitate was removed by filtration, rinsed with EtOH, and concentrated under reduced pressure. The concentrate was dissolved in DCM, adsorbed onto silica gel and purified by column chromatography using 10% of MeOH in DCM as eluent to give 1-(3-phenylbenzo[b]thiophen-2-yl)ethanamine as a colorless, crystalline solid: $^1$H NMR (400 MHz, CDCl$_3$) δ 1.51 (d, J=6.5 Hz, 3H), 1.74 (br. s., 2H), 4.55 (q, J=6.5 Hz, 1H), 7.30-7.38 (m, 2H), 7.41-7.57 (m, 6H), 7.87-7.91 (m, 1H); LC-MS (ESI)] m/z 237.1 [M-16]$^-$.

4-Amino-6-((1-(3-phenyl-1-benzothiophen-2-yl)ethyl)amino)-5-pyrimidinecarbonitrile

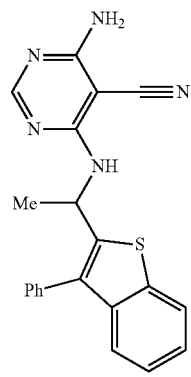 [SMILES: CC(Nc1ncnc(N)c1C#N)c1sc2ccccc2c1-c1ccccc1]

Prepared according to Step D6 in General Procedure D using 1-(3-phenylbenzo[b]thiophen-2-yl)ethanamine (56 mg, 0.221 mmol) to give 4-amino-6-((1-(3-phenyl-1-benzothiophen-2-yl)ethyl)amino)-5-pyrimidinecarbonitrile: $^1$H NMR (400 MHz, DMSO-d$_6$) δ 1.47 (d, J=7.0 Hz, 3H), 5.63 (t, J=6.9 Hz, 1H), 7.24 (br. s., 2H), 7.32-7.37 (m, 3H), 7.43-7.48 (m, 1H), 7.50-7.58 (m, 4H), 7.84 (d, J=6.8 Hz, 1H), 7.93 (s, 1H), 7.94-7.98 (m, 1H); LC-MS (ESI)] m/z 372.0 [M+H]$^+$.

Example 42

Preparation of 4-amino-6-((1-(3-(3,5-difluorophenyl)-1-benzothiophen-2-yl)ethyl)amino)-5-pyrimidinecarbonitrile

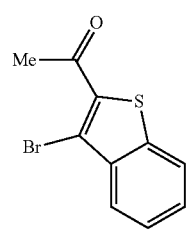

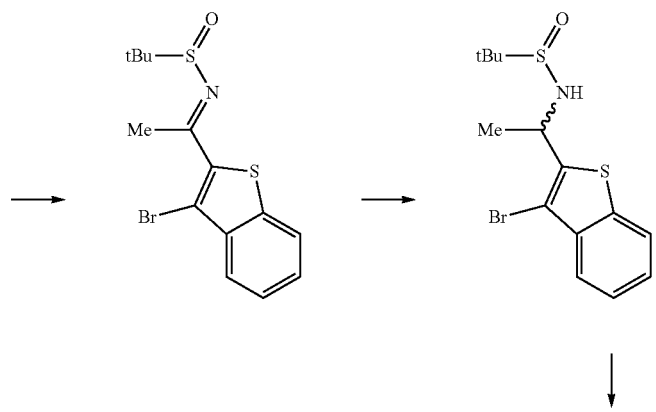

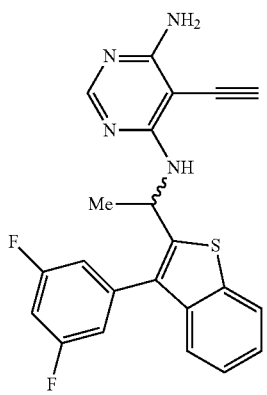
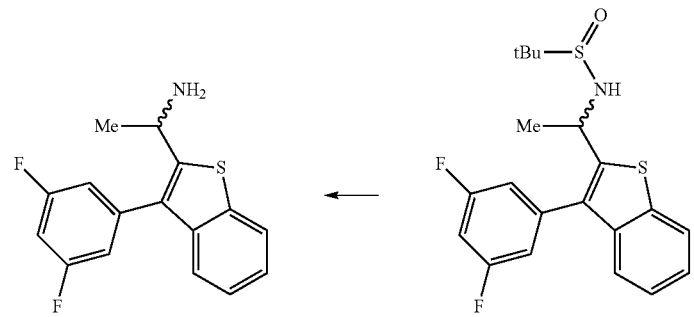

(E)-N-(1-(3-Bromobenzo[b]thiophen-2-yl)eth-ylidene)-2-methylpropane-2-sulfinamide

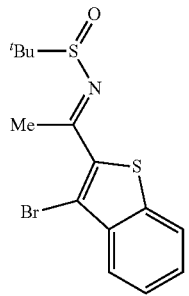 [SMILES: C/C(=N\S(=O)C(C)(C)C)c1sc2ccccc2c1Br]

A mixture of titanium (IV) ethoxide (2.272 mL, 10.97 mmol), 2-methyl-2-propane-sulfinamide (0.665 g, 5.49 mmol) and 1-(3-bromobenzo[b]thiophen-2-yl)ethanone (1.40 g, 5.49 mmol) in THF (15 mL) was heated to reflux overnight. After 24 h, the reaction was equilibrated to rt and poured into 100 mL of brine. The solid was removed by filtration through celite and the pad was rinsed with 100 mL of EtOAc. The organic layer was stirred over MgSO$_4$, filtered and concentrated under reduced pressure to give an orange oil. The product was purified by column chromatography on a silica column using 20 to 40% gradient of EtOAc-hexane as eluent to give (E)-N-(1-(3-bromobenzo[b]thiophen-2-yl)eth-ylidene)-2-methylpropane-2-sulfinamide as an orange oil: $^1$H NMR (400 MHz, CDCl$_3$) δ 1.34 (s, 9H), 2.98 (s, 3H), 7.35-7.45 (m, 2H), 7.65-7.73 (m, 1H), 7.83 (dd, J=7.3, 2.1 Hz, 1H).

N-(1-(3-Bromobenzo[b]thiophen-2-yl)ethyl)-2-methylpropane-2-sulfinamide

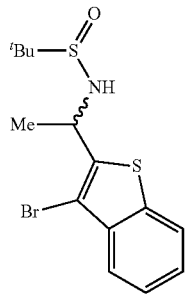 [SMILES: CC(NS(=O)C(C)(C)C)c1sc2ccccc2c1Br]

To a solution of (E)-N-(1-(3-bromobenzo[b]thiophen-2-yl)ethylidene)-2-methylpropane-2-sulfinamide (1.35 g, 3.77 mmol) dissolved in THF (30 mL) and water (0.612 mL) cooled by a water-ice bath was added sodium borohydride (0.265 mL, 7.54 mmol) all in one portion. The reaction was stirred at low temperature for 30 min, and judged complete. To the reaction solution was added satd. aq. NaHCO$_3$ and the resulting mixture stirred vigorously until gas evolution ceased. The aqueous layer was extracted with EtOAc, washed with brine, stirred over MgSO$_4$, filtered and concentrated under reduced pressure to give a red oil. The product was isolated by column chromatography on a silica gel column using 30 to 70% gradient of EtOAc in hexane as eluent to give N-(1-(3-bromobenzo[b]thiophen-2-yl)ethyl)-2-methylpropane-2-sulfinamide as a pale yellow oil: $^1$H NMR (400 MHz, CDCl$_3$) δ 1.24 (s, 10H), 1.63 (d, J=6.5 Hz, 3H), 3.85 (d, J=2.9 Hz, 1H), 5.16 (dd, J=6.7, 3.5 Hz, 1H), 7.35 (t, J=7.7 Hz, 1H), 7.41 (t, J=7.7 Hz, 1H), 7.76 (t, J=7.0 Hz, 2H). N-(1-(3-(3,5-Difluorophenyl)benzo[b]thiophen-2-yl)ethyl)-2-methylpropane-2-sulfinamide

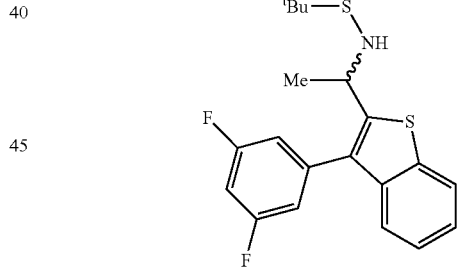

A mixture of 3,5-difluorophenylboronic acid (292 mg, 1.848 mmol), potassium phosphate (0.204 mL, 2.464 mmol), 2-dicyclohexylphosphino-2',6'-dimethoxy-1,1'-biphenyl (126 mg, 0.308 mmol), palladium (II) acetate (27.7 mg, 0.123 mmol) and N-(1-(3-bromobenzo[b]thiophen-2-yl)ethyl)-2-methylpropane-2-sulfinamide (444 mg, 1.232 mmol) in Toluene (10 mL) was purged with N$_2$ for 2 min, then heated to 110° C. overnight. After 19 h, the reaction was partitioned between water and EtOAc. The organic layer was stirred over MgSO$_4$, filtered and concentrated under reduced pressure to give amber oil. The product was purified by column chromatography on a silica gel column using 20 to 40% gradient of EtOAc in hexane as eluent to give N-(1-(3-(3,5-difluorophenyl)benzo[b]thiophen-2-yl)ethyl)-2-methylpropane-2-sulfinamide as a colorless glassy solid: $^1$H NMR (400 MHz, DMSO-d$_6$) δ 1.13 (s, 9H), 1.50 (d, J=6.7 Hz, 3H), 4.64-4.73

(m, 1H), 5.91 (d, J=4.7 Hz, 1H), 7.21 (dd, J=8.4, 2.3 Hz, 2H), 7.34-7.45 (m, 4H), 8.02 (ddd, J=7.5, 1.4, 1.1 Hz, 1H); LC-MS (ESI)] m/z 394.0 [M+H]$^+$.

1-(3-(3,5-Difluorophenyl)benzo[b]thiophen-2-yl)ethanamine

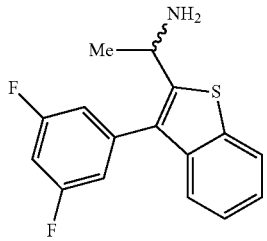 [SMILES: CC(N)c1sc2ccccc2c1-c1cc(F)cc(F)c1]

To a solution of N-(1-(3-(3,5-difluorophenyl)benzo[b]thiophen-2-yl)ethyl)-2-methylpropane-2-sulfinamide (392 mg, 0.996 mmol) in THF (7 mL) at rt was added HCl (1.0 mL, 11.85 mmol). The reaction was stirred at ambient temperature for 10 min, after which time LC-MS indicated no starting material remained. The reaction was poured into satd. aq. NaHCO$_3$ and extracted two times with EtOAc. The combined organic extracts were stirred over MgSO$_4$, filtered and concentrated under reduced pressure to give 1-(3-(3,5-difluorophenyl)benzo[b]thiophen-2-yl)ethanamine as a colorless oil: $^1$H NMR (500 MHz, CDCl$_3$) δ 1.35 (d, J=6.7 Hz, 3H), 1.60 (br. s., 2H), 4.39 (q, J=6.6 Hz, 1H), 6.73-6.86 (m, 3H), 7.19-7.24 (m, 2H), 7.30-7.36 (m, 1H), 7.71-7.77 (m, 1H); LC-MS (ESI)] m/z 273.0 [M+H]$^+$.

4-Amino-6-((1-(3-(3,5-difluorophenyl)-1-benzothiophen-2-yl)ethyl)amino)-5-pyrimidinecarbonitrile

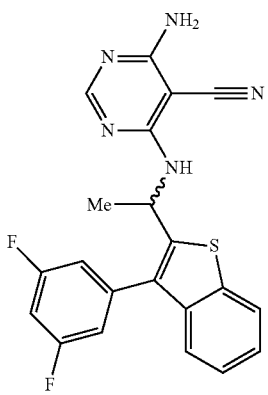 [SMILES: CC(Nc1ncnc(N)c1C#N)c1sc2ccccc2c1-c1cc(F)cc(F)c1]

Prepared according to Step D6 in General Procedure D using 1-(3-(3,5-difluorophenyl)benzo[b]thiophen-2-yl)ethanamine (280 mg, 0.968 mmol) to give 4-amino-6-((1-(3-(3,5-difluorophenyl)-1-benzothiophen-2-yl)ethyl)amino)-5-pyrimidinecarbonitrile: $^1$H NMR (400 MHz, DMSO-d$_6$) δ 1.52 (d, J=7.0 Hz, 3H), 5.62 (quin, J=6.9 Hz, 1H), 7.17-7.42 (m, 8H), 7.88-7.94 (m, 2H), 7.95-8.01 (m, 1H); LC-MS (ESI)] m/z 408.0 [M+H]$^+$.

Example 43

Preparation of 4-amino-6-((1-(3-(3,5-difluorophenyl)-3H-imidazo[4,5-b]pyridin-2-yl)ethyl)amino)-5-pyrimidinecarbonitrile

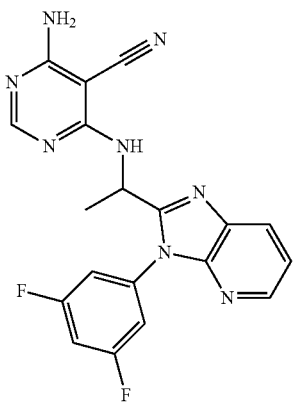 [SMILES: CC(Nc1ncnc(N)c1C#N)c1nc2cccnc2n1-c1cc(F)cc(F)c1]

Prepared according to General Procedure D to give 4-amino-6-((1-(1-(3,5-difluorophenyl)-7-fluoro-1H-benzimidazol-2-yl)ethyl)amino)-5-pyrimidinecarbonitrile: $^1$H NMR (400 MHz, DMSO-d$_6$) δ ppm 8.28 (1H, dd, J=4.7, 1.4 Hz), 8.16 (1H, dd, J=8.0, 1.4 Hz), 7.89 (1H, s), 7.75 (1H, d, J=7.8 Hz), 7.28-7.39 (4H, m), 7.19 (2H, br. s.), 5.72 (1H, quin, J=7.0 Hz), 1.58 (3H, d, J=6.8 Hz); LC-MS (ESI) m/z 393.1 [M+H]+.

Example 44

4-Amino-6-(((1S)-1-(1-cyclopropyl-6-fluoro-1H-benzimidazol-2-yl)ethyl)amino)-5-pyrimidinecarbonitrile and 4-amino-6-(((1S)-1-(1-cyclopropyl-5-fluoro-1H-1-benzimidazol-2-yl)ethyl)amino)-5-pyrimidinecarbonitrile

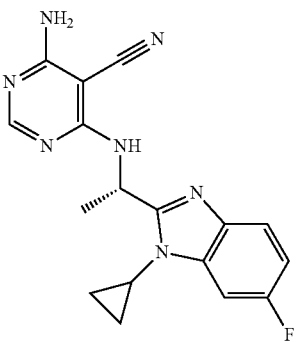

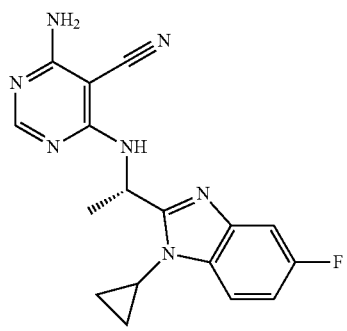

Mixed regioisomers (104 mg) were purified by SFC to give two fractions. First eluting peak: Repurified by reverse phase analytical HPLC (eluted with a gradient of 10-60% MeCN in water with 0.1% TFA) to give 4-amino-6-(((1S)-1-(1-cyclopropyl-6-fluoro-1H-benzimidazol-2-yl)ethyl)amino)-5-pyrimidinecarbonitrile as a white solid. $^1$H NMR (400 MHz, DMSO-$d_6$) δ ppm 0.97-1.29 (m, 4H) 1.62 (d, J=6.65 Hz, 3H) 3.34-3.40 (m, 1H) 5.81 (quin, J=6.94 Hz, 1H) 7.06-7.16 (m, 1H) 7.30 (br. s., 2H) 7.40-7.45 (m, 1H) 7.57 (dd, J=8.80, 4.70 Hz, 1H) 7.70 (d, J=7.24 Hz, 1H) 8.05 (s, 1H). LC-MS (ESI) m/z 336.1 [M–H]$^-$.

Second eluting peak: 4-amino-6-(((1S)-1-(1-cyclopropyl-5-fluoro-1H-benzimidazol-2-yl)ethyl)amino)-5-pyrimidinecarbonitrile as an off-white solid. $^1$H NMR (500 MHz, DMSO-$d_6$) δ ppm 1.04-1.34 (m, 4H) 1.68 (d, J=6.85 Hz, 3H) 3.41-3.44 (m, 1H) 5.87 (quin, J=6.91 Hz, 1H) 7.11 (ddd, J=9.90, 8.80, 2.57 Hz, 1H) 7.37 (br. s., 2H) 7.44 (dd, J=9.29, 2.45 Hz, 1H) 7.67 (dd, J=8.80, 4.89 Hz, 1H) 7.77 (d, J=7.09 Hz, 1H) 8.12 (s, 1H). LC-MS (ESI) m/z 338.2 [M+H]$^+$.

Example 45

4-amino-6-(((1S)-1-(6-fluoro-1-(5-fluoro-3-pyridinyl)-1H-benzimidazol-2-yl)ethyl)amino)-5-pyrimidinecarbonitrile and 4-amino-6-(((1R)-1-(6-fluoro-1-(5-fluoro-3-pyridinyl)-1H-benzimidazol-2-yl)ethyl)amino)-5-pyrimidinecarbonitrile

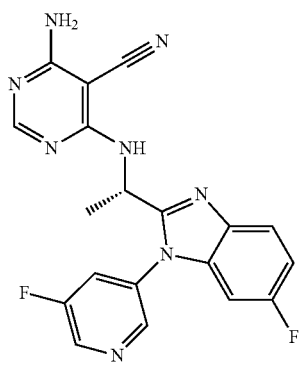

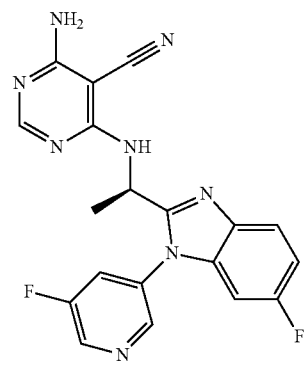

For synthesis see Example 33. The racemic mixture (100 mg) was separated on AD-H column using preparative SFC to give two fractions: First peak on OD-H column: Afforded a white solid that was triturated in water and filtered to give 4-amino-6-(((1S)-1-(6-fluoro-1-(5-fluoro-3-pyridinyl)-1H-benzimidazol-2-yl)ethyl)amino)-5-pyrimidinecarbonitrile as a white solid. $^1$H NMR (400 MHz, DMSO-$d_6$) δ ppm 1.59 (d, J=6.65 Hz, 3H) 5.60 (quin, J=6.99 Hz, 1H) 7.08 (dd, J=9.00, 2.54 Hz, 1H) 7.15 (ddd, J=9.78, 8.80, 2.54 Hz, 1H) 7.20 (br. s., 2H) 7.71-7.81 (m, 2H) 7.84 (s, 1H) 8.08 (d, J=8.61 Hz, 1H) 8.63 (s, 1H) 8.67 (d, J=2.54 Hz, 1H); LC-MS (ESI) m/z 393.0 [M+H]$^+$. Second peak on OD-H column: 4-amino-6-(((1R)-1-(6-fluoro-1-(5-fluoro-3-pyridinyl)-1H-benzimidazol-2-yl)ethyl)amino)-5-pyrimidinecarbonitrile as a white solid: $^1$H NMR (400 MHz, DMSO-$d_6$) δ ppm 1.59 (d, J=6.65 Hz, 3H) 5.60 (quin, J=6.94 Hz, 1H) 7.08 (dd, J=9.00, 2.35 Hz, 1H) 7.15 (td, J=9.29, 2.54 Hz, 1H) 7.21 (br. s., 2H) 7.72-7.80 (m, 2H) 7.83 (s, 1H) 8.08 (d, J=7.63 Hz, 1H) 8.62 (s, 1H) 8.67 (d, J=2.74 Hz, 1H); LC-MS (ESI) m/z 383.1 [M+H]$^+$.

Example 46

N-((1R)-1-(6-Fluoro-1-(5-fluoro-3-pyridinyl)-1H-benzimidazol-2-yl)ethyl)-9H-purin-6-amine and N-((1S)-1-(6-fluoro-1-(5-fluoro-3-pyridinyl)-1H-benzimidazol-2-yl)ethyl)-9H-purin-6-amine

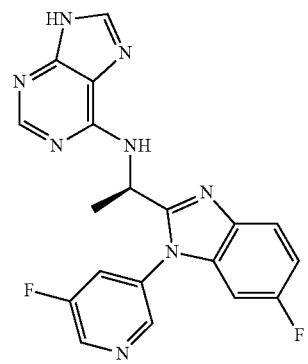

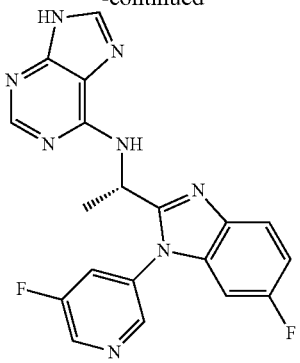

For synthesis see Example 34. The racemic mixture (78 mg) was separated on AD-H column using preparative SFC to give two fractions: First peak on OD-H column: N-((1R)-1-(6-fluoro-1-(5-fluoro-3-pyridinyl)-1H-benzimidazol-2-yl)ethyl)-9H-purin-6-amine as an off-white solid. $^1$H NMR (500 MHz, DMSO-$d_6$) δ ppm 1.66 (d, J=6.85 Hz, 3H) 5.61 (br. s., 1H) 7.06 (dd, J=9.05, 2.45 Hz, 1H) 7.13 (td, J=9.29, 2.45 Hz, 1H) 7.73 (dd, J=8.80, 4.89 Hz, 1H) 7.93-8.05 (m, 2H) 8.09 (br. s., 2H) 8.58 (br. s., 1H) 8.64 (s, 1H) 12.77 (br. s., 1H). MS (ESI) m/z 393.1 [M+H]$^+$. Second peak on OD-H column: N-((1S)-1-(6-fluoro-1-(5-fluoro-3-pyridinyl)-1H-benzimidazol-2-yl)ethyl)-9H-purin-6-amine as an off-white solid. $^1$H NMR (400 MHz, DMSO-$d_6$) δ ppm 1.66 (d, J=6.65 Hz, 3H) 5.61 (br. s., 1H) 7.06 (dd, J=9.00, 2.54 Hz, 1H) 7.14 (ddd, J=9.78, 8.80, 2.54 Hz, 1H) 7.74 (dd, J=8.90, 4.79 Hz, 1H) 7.99 (br. s., 1H) 8.02 (s, 1H) 8.05-8.17 (m, 2H) 8.58 (d, J=1.57 Hz, 1H) 8.64 (s, 1H) 12.75 (br. s., 1H). LC-MS (ESI) m/z 393.1 [M+H]$^+$.

Example 47

Preparation of 2-((1S)-1-((6-amino-5-cyano-4-pyrimidinyl)amino)ethyl)-N-cyclopentyl-1-cyclopropyl-1H-benzimidazole-7-carboxamide 2-(Cyclopropylamino)-3-nitrobenzoic acid

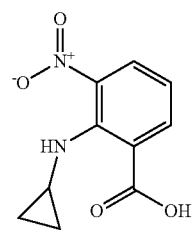

A mixture of 2-bromo-3-nitrobenzoic acid (1.0 g, 4.1 mmol), cyclopropanamine (0.85 mL, 12.2 mmol) in THF (10 mL) under N$_2$ was heated at 60° C. for 1 day. The reaction mixture was diluted with EtOAc, washed with water, brine, and dried over magnesium sulfate. The organic phase was concentrated in vacuo. The residue, as a crude 2-(cyclopropylamino)-3-nitrobenzoic acid: LC-MS (ESI) m/z 223.0 [M+H]$^+$. The crude product was subjected to the next reaction without further purification.

Methyl 2-(cyclopropylamino)-3-nitrobenzoate

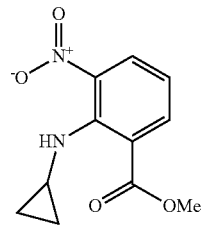

The crude 2-(cyclopropylamino)-3-nitrobenzoic acid (0.90 g, 4.1 mmol) was dissolved in MeOH (15 mL), and 2 mL H$_2$SO$_4$ (98%) was added. The mixture was heated to reflux for 18 h. The mixture was cooled, concentrated in vacuo, and purified by column chromatography on a silica gel column using DCM as eluent to give methyl 2-(cyclopropylamino)-3-nitrobenzoate: LC-MS (ESI) m/z 237.1 [M+H]$^+$.

Methyl 3-amino-2-(cyclopropylamino)benzoate

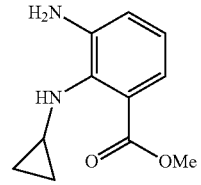 [SMILES: COC(=O)c1cccc(N)c1NC1CC1]

To a solution of methyl 2-(cyclopropylamino)-3-nitrobenzoate (1.1 g, 4.5 mmol) in MeOH (4 mL) was added palladium 10 wt % on carbon (0.24 g, 0.23 mmol) under N$_2$. After flushing the flask with N$_2$ several times, the solution was stirred under a H$_2$ balloon for 6 h. LCMS showed the reaction was complete. After filtration of the reaction mixture and rinsing with MeOH, the filtrate was collected and concentrated in vacuo. Purification of the residue by flash chromatography over silica gel column using 0-20% gradient of DCM-MeOH—NH$_4$OH (9:1:0.05) in DCM as eluent gave methyl 3-amino-2-(cyclopropylamino)benzoate: LC-MS (ESI) m/z 207.1 [M+H]$^+$.

(S)-Methyl 3-(2-(tert-butoxycarbonylamino)propanamido)-2-(cyclopropylamino)benzoate

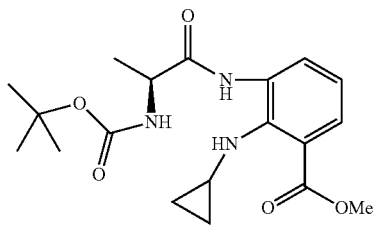 [SMILES: COC(=O)c1cccc(NC(=O)[C@H](C)NC(=O)OC(C)(C)C)c1NC1CC1]

To a solution of methyl 3-amino-2-(cyclopropylamino)benzoate (510 mg, 2.5 mmol) in DMF (3 mL) was added boc-1-alanine (470 mg, 2.5 mmol), 1,1'-dimethyltriethylamine (0.87 mL, 5.0 mmol) and PYBOP (1.3 g, 2.5 mmol). The resulting mixture was stirred at rt for 2 h. The mixture was diluted with EtOAc, washed with water, brine, dried over magnesium sulfate, and concentrated in vacuo. Purification of the residue by column chromatography on a silica gel column using 0 to 50% gradient of EtOAc:DCM (1:1) in DCM as eluent gave (S)-methyl 3-(2-(tert-butoxycarbonylamino)propanamido)-2-(cyclopropylamino)benzoate: $^1$H NMR (400 MHz, CDCl$_3$) δ ppm 8.43 (1H, s), 8.15 (1H, d, J=8.0 Hz), 7.74 (1H, d, J=8.0 Hz), 7.09 (1H, s), 6.91 (1H, t, J=8.0 Hz), 5.03 (1H, br), 4.39 (1H, br), 3.88 (3H, s), 2.71 (1H, m), 1.50 (3H, d, J=8.0 Hz), 1.48 (9H, s), 0.74-0.68 (2H, m), 0.63-0.55 (2H, m); LC-MS (ESI) m/z 378.1 [M+H]$^+$.

(S)-Methyl 2-(1-aminoethyl)-1-cyclopropyl-1H-benzo[d]imidazole-7-carboxylate

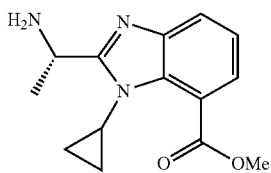 [SMILES: COC(=O)c1cccc2nc([C@H](C)N)n(C3CC3)c12]

A stirred solution of (S)-methyl 3-(2-(tert-butoxycarbonylamino)propanamido)-2-(cyclopropylamino)benzoate (600 mg, 1.6 mmol) in HOAc (20 mL) was heated at 60° C. for 1.5 h, and cooled to rt. After concentration of the mixture in vacuo, the residue was subjected to 4M HCl in dioxane (10 mL), and stirred at rt for 40 min. The mixture was concentrated in vacuo, dissolved in water (5 mL) and basified with 1N NaOH to pH 9.5. The mixture was concentrated and MeOH-DCM (1:1) was added to the residue to get the desired product into solution. The solution was concentrated in vacuo and the residue was purified by column chromatography on a silica gel column using DCM-MeOH—NH$_4$OH (9:1:0.05) as eluent to give (S)-methyl 2-(1-aminoethyl)-1-cyclopropyl-1H-benzo[d]imidazole-7-carboxylate: $^1$H NMR (400 MHz, CDCl$_3$) δ 7.86 (1H, d, J=8.0 Hz), 7.63 (1H, d, J=8.0 Hz), 7.27 (1H, t, J=8.0 Hz), 4.62 (1H, q, J=8.0 Hz), 4.01 (3H, s), 3.58-3.50 (3H, m), 1.65 (3H, d, J=8.0 Hz), 1.22-1.06 (2H, m), 0.95-0.65 (2H, m); LC-MS (ESI) m/z 260.0 [M+H]$^+$.

(S)-Methyl 2-(1-(6-amino-5-cyanopyrimidin-4-ylamino)ethyl)-1-cyclopropyl-1H-benzo[d]imidazole-7-carboxylate

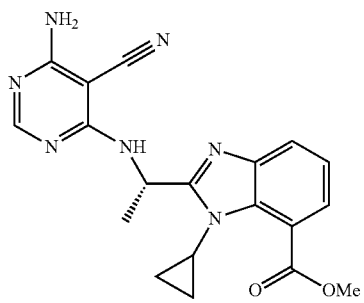 [SMILES: COC(=O)c1cccc2nc([C@H](C)Nc3ncnc(N)c3C#N)n(C3CC3)c12]

A mixture of (S)-methyl 2-(1-aminoethyl)-1-cyclopropyl-1H-benzo[d]imidazole-7-carboxylate (140 mg, 0.54 mmol), 4-amino-6-chloropyrimidine-5-carbonitrile (83 mg, 0.54 mmol) and 1,1'-dimethyltriethylamine (190 µL, 1.1 mmol) in n-butanol (3 mL) was stirred at 120° C. After 18 h, the mixture was cooled to rt and concentrated in vacuo. The residue was purified by column chromatography on silica gel using 0 to 10% gradient of MeOH in DCM-EtOAc (1:1) with 0.2% NH$_4$OH as eluent to give (S)-methyl 2-(1-(6-amino-5-cyanopyrimidin-4-ylamino)ethyl)-1-cyclopropyl-1H-benzo[d]imidazole-7-carboxylate: LC-MS (ESI) m/z 378.1 [M+H]$^+$.

(S)-2-(1-(6-Amino-5-cyanopyrimidin-4-ylamino)ethyl)-1-cyclopropyl-1H-benzo[d]imidazole-7-carboxylic acid

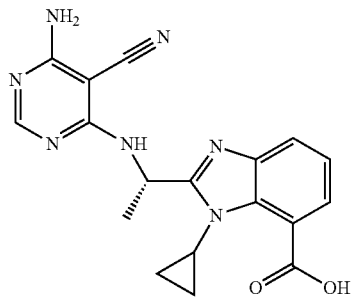 [SMILES: C[C@H](Nc1ncnc(N)c1C#N)c1nc2cccc(C(=O)O)c2n1C1CC1]

A solution of (S)-methyl 2-(1-(6-amino-5-cyanopyrimidin-4-ylamino)ethyl)-1-cyclopropyl-1H-benzo[d]imidazole-7-carboxylate (137 mg, 0.36 mmol) and lithium iodide (146 mg, 1.1 mmol) in pyridine (5 mL) was heated to reflux at 100° C. for 48 h. Another portion of lithium iodide (146 mg, 1.1 mmol) was added and the mixture was heated at 100° C. for another 48 h. The mixture was concentrated in vacuo, and subjected to the next reaction without further purification: LC-MS (ESI) m/z 364.1 [M+H]$^+$.

2-((1S)-1-((6-Amino-5-cyano-4-pyrimidinyl)amino)ethyl)-N-cyclopentyl-1-cyclopropyl-1H-benzimidazole-7-carboxamide

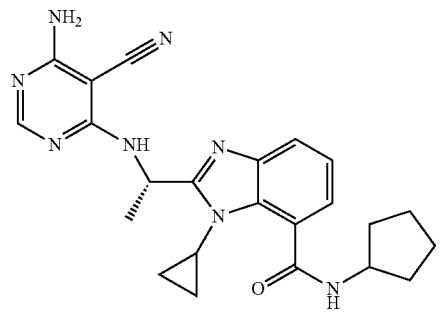 [SMILES: C[C@H](Nc1ncnc(N)c1C#N)c1nc2cccc(C(=O)NC3CCCC3)c2n1C1CC1]

To a solution of crude (S)-2-(1-(6-amino-5-cyanopyrimidin-4-ylamino)ethyl)-1-cyclopropyl-1H-benzo[d]imidazole-7-carboxylic acid (132 mg, 0.36 mmol) in DMF (3 mL) was added cyclopentanamine (0.10 mL, 1.0 mmol), N-ethyl-N-isopropylpropan-2-amine (0.060 mL, 0.36 mmol) and 1 h-benzotriazol-1-yl-oxytripyrrolidinophosphonium (190 mg, 0.36 mmol). The resulting mixture was stirred at rt for 2 h. The reaction mixture was diluted with EtOAc, washed with water, brine, dried over magnesium sulfate, and concentrated in vacuo. Purification of the residue by flash chromatography over silica gel, using 0 to 10% gradient of MeOH in DCM-EtOAc (1:1) with 0.2% NH$_4$OH as eluent gave 2-((1S)-1-((6- amino-5-cyano-4-pyrimidinyl)amino)ethyl)-N-cyclopentyl-1-cyclopropyl-1H-benzimidazole-7-carboxamide: ¹H NMR (400 MHz, MeOH-d₄) δ 8.03 (1H, s), 7.70 (1H, d, J=8.0 Hz), 7.37 (1H, d, J=8.0 Hz), 7.28 (1H, t, J=8.0 Hz), 6.03 (1H, q, J=8.0 Hz), 4.45-4.38 (1H, m), 4.11 (1H, dd, J=8.0, 4.0 Hz), 3.53-3.44 (1H, m), 2.15-2.05 (2H, m), 1.88-1.78 (2H, m), 1.75-1.60 (4H, m), 1.38-1.10 (3H, m), 1.00-0.92 (1H, m); LC-MS (ESI) m/z 431.2 [M+H]⁺.

Example 48

Preparation of 2-((1S)-1-((6-amino-5-cyano-4-pyrimidinyl)amino)ethyl)-N,1-dicyclopropyl-1H-benzimidazole-7-carboxamide N-Cyclopropyl-2-(cyclopropylamino)-3-nitrobenzamide

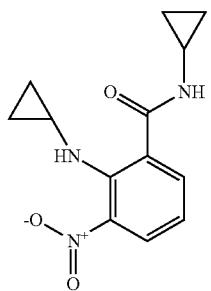

To a solution of 2-bromo-3-nitrobenzoic acid (500 mg, 2.03 mmol) in DMF (3 mL) was added cyclopropylamine (0.14 mL, 2.03 mmol), N-ethyl-N-isopropyl-propan-2-amine (0.34 mL, 2.03 mmol) and (1H-benzo[d][1,2,3]triazol-1-yloxy)-tripyrrolidin-1-ylphosphonium hexafluorophosphate (V) (1.27 g, 2.44 mmol). The resulting mixture was stirred at rt for 24 h. The reaction mixture was diluted with EtOAc, washed with water, brine, dried over magnesium sulfate, and concentrated in vacuo. The residue was subjected to flash chromatography on a silica gel column using 0 to 100% gradient of EtOAC:DCM (1:1) in DCM as eluent to give a crude product mixture. To the crude mixture in THF (10 mL) was added cyclopropylamine (0.141 mL, 2.03 mmol) and the resulting mixture was heated under N₂ at 60° C. for 18 h. The reaction mixture was diluted with EtOAc, washed with water, brine and dried over magnesium sulfate. After being concentrated in vacuo, the residue was purified by flash chromatography on silica gel using 0 to 100% gradient of EtOAC:DCM (1:1) in DCM as eluent to give N-cyclopropyl-2-(cyclopropylamino)-3-nitrobenzamide: ¹H NMR (400 MHz, CDCl₃) δ 8.27 (1H, s), 8.01 (1H, d, J=8.0 Hz), 7.45 (1H, d, J=8.0 Hz), 6.62 (1H, t, J=8.0 Hz), 5.98 (1H, s), 2.90-2.65 (2H, m), 0.90-0.78 (2H, m), 0.75-0.65 (2H, m), 0.58-0.50 (2H, m), 0.48-0.40 (2H, m); LC-MS (ESI) m/z 262.1 [M+H]⁺.

3-Amino-N-cyclopropyl-2-(cyclopropylamino)benzamide

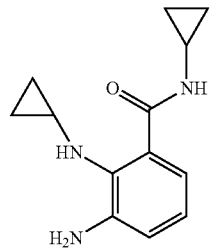 [SMILES: Nc1cccc(C(=O)NC2CC2)c1NC1CC1]

Using the general synthetic procedure for methyl 3-amino-2-(cyclopropylamino)benzoate in example 47, 3-amino-N-cyclopropyl-2-(cyclopropylamino)benzamide was prepared using N-cyclopropyl-2-(cyclopropylamino)-3-nitrobenzamide: ¹H NMR (400 MHz, CDCl₃) δ 6.85-6.77 (3H, m), 6.31 (1H, br), 5.97 (1H, br), 4.07 (2H, br), 2.93-2.85 (1H, m), 2.65-2.57 (1H, m), 0.92-0.85 (2H, m), 0.86-0.54 (6H, m); LC-MS (ESI) m/z 232.1 [M+H]⁺.

(S)-tert-Butyl 1-(2-(cyclopropylamino)-3-(cyclopropylcarbamoyl)phenylamino)-1-oxopropan-2-ylcarbamate

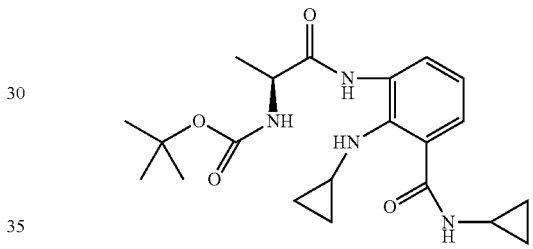

Using the general synthetic procedure for (S)-methyl 3-(2-(tert-butoxycarbonylamino)propanamido)-2-(cyclopropylamino)benzoate in example 47, (S)-tert-butyl 1-(2-(cyclopropylamino)-3-(cyclopropylcarbamoyl)phenylamino)-1-oxopropan-2-ylcarbamate was prepared using 3-amino-N-cyclopropyl-2-(cyclopropylamino)benzamide: ¹H NMR (400 MHz, MeOH-d₄) δ 7.39 (1H, d, J=8.0 Hz), 7.24 (1H, d, J=8.0 Hz), 6.82 (1H, t, J=8.0 Hz), 4.18 (1H, q, J=4.0 Hz), 2.88-2.82 (1H, m), 2.74-2.67 (1H, m), 1.50 (9H, s), 1.43 (3H, d, J=8.0 Hz), 0.84-0.79 (2H, m), 0.64-0.42 (6H, m); LC-MS (ESI) m/z 403.1 [M+H]⁺.

(S)-2-(1-Aminoethyl)-N,1-dicyclopropyl-1H-benzo[d]imidazole-7-carboxamide

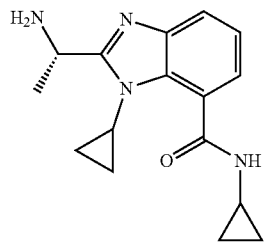 [SMILES: C[C@H](N)c1nc2cccc(C(=O)NC3CC3)c2n1C1CC1]

Using the general synthetic procedure for (S)-methyl 2-(1-aminoethyl)-1-cyclopropyl-1H-benzo[d]imidazole-7-carboxylate in example 47, (S)-2-(1-aminoethyl)-N,1-dicyclopropyl-1H-benzo[d]imidazole-7-carboxamide as was prepared using (S)-tert-butyl 1-(2-(cyclopropylamino)-3-(cyclopropylcarbamoyl)phenylamino)-1-oxopropan-2-yl-carbamate: ¹H NMR (400 MHz, MeOH-d₄) δ 7.72 (1H, d, J=8.0 Hz), 7.35 (1H, d, J=8.0 Hz), 7.29 (1H, t, J=8.0 Hz), 4.69 (1H, q, J=8.0 Hz), 3.49-3.43 (1H, m), 3.03-2.96 (1H, m), 1.60 (3H, d, J=4.0 Hz), 1.25-1.18 (2H, m), 1.08-1.02 (1H, m), 0.97-0.82 (3H, m), 0.74-0.67 (2H, m); LC-MS (ESI) m/z 285.1 [M+H]⁺.

2-((1S)-1-((6-Amino-5-cyano-4-pyrimidinyl)amino)ethyl)-N,1-dicyclopropyl-1H-benzimidazole-7-carboxamide

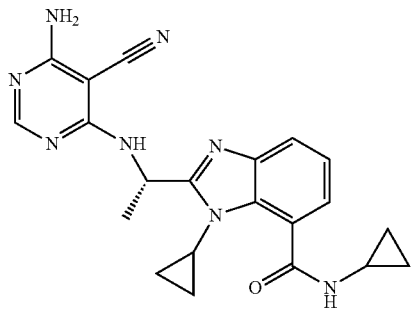 [SMILES: C[C@H](Nc1ncnc(N)c1C#N)c1nc2cccc(C(=O)NC3CC3)c2n1C1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate as in example 47, 2-((1S)-1-((6-amino-5-cyano-4-pyrimidinyl)amino)ethyl)-N,1-dicyclopropyl-1H-benzimidazole-7-carboxamide was prepared using (S)-2-(1-aminoethyl)-N,1-dicyclopropyl-1H-benzo[d]imidazole-7-carboxamide: ¹H NMR (400 MHz, MeOH-d₄) δ 8.03 (1H, s), 7.70 (1H, d, J=8.0 Hz), 7.35 (1H, d, J=8.0 Hz), 7.27 (1H, t, J=8.0 Hz), 6.03 (1H, q, J=8.0 Hz), 3.53-3.43 (1H, m), 3.03-2.96 (1H, m), 1.74 (3H, d, J=4.0 Hz), 1.40-1.30 (1H, m), 1.30-1.15 (2H, m), 1.00-0.93 (1H, m), 0.90-0.83 (2H, m), 0.74-0.67 (2H, m); LC-MS (ESI) m/z 403.1 [M+H]⁺.

Example 49

Preparation of 2-((1S)-1-((6-amino-5-cyano-4-pyrimidinyl)amino)ethyl)-N-tert-butyl-1-cyclopropyl-1H-benzimidazole-7-carboxamide 2-Bromo-N-tert-butyl-3-nitrobenzamide

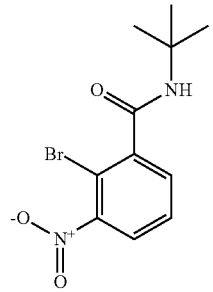

To a solution of 2-bromo-3-nitrobenzoic acid (500 mg, 2.03 mmol) in DMF (3 mL) was added tert-butylamine (0.22 mL, 2.04 mmol), 1,1'-dimethyltriethylamine (0.71 mL, 4.1 mmol) and (1H-benzo[d][1,2,3]triazol-1-yloxy)tripyrrolidin-1-ylphosphonium hexafluorophosphate(V) (1.27 g, 2.44 mmol). The resulting mixture was stirred at rt for 2 h. The reaction mixture was diluted with EtOAc, washed with water, brine, dried over magnesium sulfate and concentrated in vacuo. The residue was purified by flash chromatography on silica gel using 0 to 100% gradient of EtOAC:DCM (1:1) in DCM as eluent to give 2-bromo-N-tert-butyl-3-nitrobenzamide: ¹H NMR (400 MHz, CDCl₃) δ 7.74 (1H, dd, J=8.0, 4.0 Hz), 7.62 (1H, d, J=8.0 Hz), 7.51 (1H, t, J=8.0 Hz), 5.62 (1H, br), 1.52 (9H, s); LC-MS (ESI) m/z 301.0 [M+H]⁺.

N-tert-Butyl-2-(cyclopropylamino)-3-nitrobenzamide

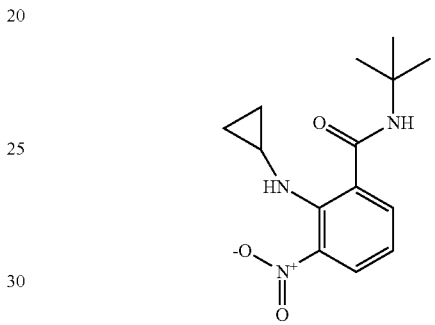

A mixture of 2-bromo-N-tert-butyl-3-nitrobenzamide (460 mg, 1.52 mmol) and cyclopropanamine (350 μL, 4.55 mmol) in THF (10 mL) was heated at 60° C. for 18 h. The reaction mixture was diluted with EtOAc, washed with water, brine, dried over magnesium sulfate, and concentrated in vacuo. The residue was purified by flash chromatography on silica gel using EtOAC:DCM (1:1) as eluent to give N-tert-butyl-2-(cyclopropylamino)-3-nitrobenzamide: ¹H NMR (400 MHz, CDCl₃) δ 8.26 (1H, br), 8.09 (1H, dd, J=8.0, 4.0 Hz), 7.57 (1H, d, J=8.0 Hz), 6.72 (1H, t, J=8.0 Hz), 5.81 (1H, br), 2.98-2.92 (1H, m), 1.49 (9H, s), 0.82-0.76 (2H, m), 0.58-0.52 (2H, m); LC-MS (ESI) m/z 278.2 [M+H]⁺.

3-Amino-N-tert-butyl-2-(cyclopropylamino)benzamide

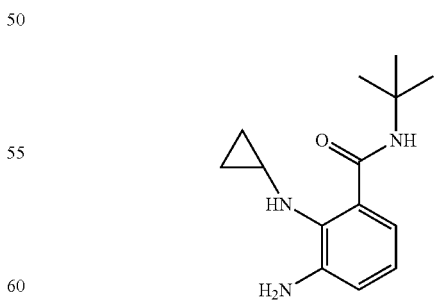

Using the general synthetic procedure for methyl 3-amino-2-(cyclopropylamino)benzoate in Example 47, 3-amino-N-tert-butyl-2-(cyclopropylamino)benzamide was prepared using N-tert-butyl-2-(cyclopropylamino)-3-nitrobenzamide: LC-MS (ESI) m/z 248.2 [M+H]⁺.

(S)-tert-Butyl 1-(3-(tert-butylcarbamoyl)-2-(cyclopropylamino)phenylamino)-1-oxopropan-2-ylcarbamate

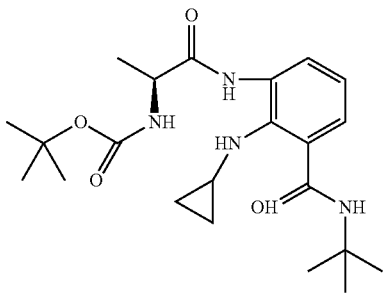 [SMILES: C[C@H](NC(=O)OC(C)(C)C)C(=O)Nc1cccc(C(=O)NC(C)(C)C)c1NC1CC1]

Using the general synthetic procedure for (S)-methyl 3-(2-(tert-butoxycarbonylamino)propanamido)-2-(cyclopropylamino)benzoate in example 47, (S)-tert-butyl 1-(3-(tert-butylcarbamoyl)-2-(cyclopropylamino)phenylamino)-1-oxopropan-2-ylcarbamate was prepared using 3-amino-N-tert-butyl-2-(cyclopropylamino)-benzamide: LC-MS (ESI) m/z 419.2 [M+H]$^+$.

(S)-2-(1-Aminoethyl)-N-tert-butyl-1-cyclopropyl-1H-benzo[d]imidazole-7-carboxamide

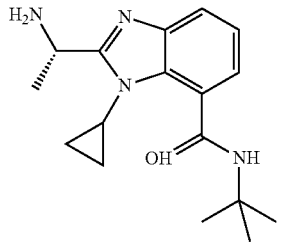 [SMILES: C[C@H](N)c1nc2cccc(C(=O)NC(C)(C)C)c2n1C1CC1]

Using the general synthetic procedure for (S)-methyl 2-(1-aminoethyl)-1-cyclopropyl-1H-benzo[d]imidazole-7-carboxylate in example 47, (S)-2-(1-aminoethyl)-N-tert-butyl-1-cyclopropyl-1H-benzo[d]imidazole-7-carboxamide was prepared using (S)-tert-butyl 1-(3-(tert-butylcarbamoyl)-2-(cyclopropylamino)phenylamino)-1-oxopropan-2-ylcarbamate: $^1$H NMR (400 MHz, MeOH-d$_4$) δ 7.70 (1H, d, J=8.0 Hz), 7.38 (1H, d, J=8.0 Hz), 7.28 (1H, t, J=8.0 Hz), 4.69 (1H, q, J=8.0 Hz), 3.49-3.43 (1H, m), 1.60 (3H, d, J=8.0 Hz), 1.53 (9H, s), 1.32-1.15 (2H, m), 1.10-1.02 (1H, m), 0.99-0.92 (1H, m); LC-MS (ESI) m/z 301.1 [M+H]$^+$.

2-((1S)-1-((6-Amino-5-cyano-4-pyrimidinyl)amino)ethyl)-N-tert-butyl-1-cyclopropyl-1H-benzimidazole-7-carboxamide

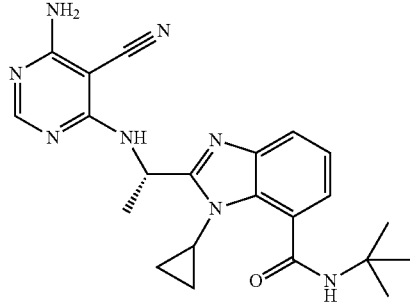 [SMILES: C[C@H](Nc1ncnc(N)c1C#N)c1nc2cccc(C(=O)NC(C)(C)C)c2n1C1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 2-((1S)-1-((6-amino-5-cyano-4-pyrimidinyl)amino)ethyl)-N-tert-butyl-1-cyclopropyl-1H-benzimidazole-7-carboxamide was prepared using (S)-2-(1-aminoethyl)-N-tert-butyl-1-cyclopropyl-1H-benzo[d]imidazole-7-carboxamide: $^1$H NMR (400 MHz, MeOH-d$_4$) δ 8.03 (1H, s), 7.68 (1H, d, J=8.0 Hz), 7.38 (1H, d, J=8.0 Hz), 7.27 (1H, t, J=8.0 Hz), 6.04 (1H, q, J=8.0 Hz), 3.55-3.43 (1H, m), 3.03-2.96 (1H, m), 1.73 (3H, d, J=4.0 Hz), 1.53 (9H, s), 1.40-1.30 (1H, m), 1.30-1.15 (2H, m), 1.10-0.93 (1H, m); LC-MS (ESI) m/z 419.2 [M+H]$^+$.

Example 50

Preparation of 4-amino-6-(((1S)-1-(1-(3,5-difluorophenyl)-4,6-difluoro-1H-benzimidazol-2-yl)ethyl)amino)-5-pyrimidinecarbonitrile and 4-amino-6-(((1R)-1-(1-(3,5-difluorophenyl)-4,6-difluoro-1H-benzimidazol-2-yl)ethyl)amino)-5-pyrimidinecarbonitrile N-(3,5-Difluorophenyl)-3,5-difluoro-2-nitroaniline

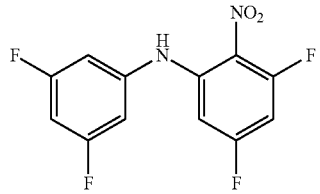

To a solution of 2,4,6-trifluoronitrobenzene (1.37 g, 7.74 mmol) and 3,5 difluoroaniline (1 g, 7.74 mmol) in THF (23 mL) was added potassium tert-butoxide (1.3 g, 11.6 mmol) and reaction mixture was stirred at rt for 4 h. After completion of the reaction, water (50 mL) was added and the organic phase extracted with EtOAc (200 mL), dried over sodium sulfate and purified by column chromatography using 100-200 mesh silica gel and 0-10% EtOAc in hexane to provide N-(3,5-difluorophenyl)-3,5-difluoro-2-nitroaniline: LC-MS (ESI) m/z 284.9 [M+H]$^+$.

N1-(3,5-Difluorophenyl)-3,5-difluoro-benzene-1,2-diamine

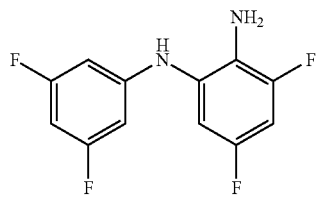 [SMILES: Nc1c(F)cc(F)cc1Nc1cc(F)cc(F)c1]

To a solution of N-(3,5-difluorophenyl)-3,5-difluoro-2-nitroaniline (1 g, 3.49 mmol) in AcOH (10.5 mL) was added iron powder (585 mg, 10.48 mmol) and the reaction mixture was heated to 100° C. for 1 h. The reaction mixture was cooled to rt and water was added. The organic layer was extracted with EtOAc and was basified by using satd. sodium bicarbonate solution. The organic phase was dried over sodium sulfate and concentrated in vacuo to provide N1-(3, 5-difluorophenyl)-3,5-difluoro-benzene-1,2-diamine. The crude product was carried without further purification.

(S)-tert-Butyl 1-(2-(3,5-difluorophenylamino)-4,6-difluorophenylamino-1-oxopropan-2-ylcarbamate

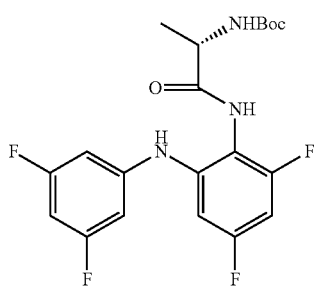 [SMILES: C[C@H](NC(=O)OC(C)(C)C)C(=O)Nc1c(F)cc(F)cc1Nc1cc(F)cc(F)c1]

Boc-L-Ala-OH (1 g, 5.46 mmol) and isobutyl chloroformate (0.745 g, 5.46 mmol) were suspended in DCM (5 mL) and N-methyl morpholine (0.58 g, 5.73 mmol) was added at −10° C. with stirring. After 30 min, to the mixture was added N1-(3,5-difluorophenyl)-3,5-difluoro-benzene-1,2-diamine (0.7 g, 2.73 mmol) in DCM (2 mL). The reaction mixture was stirred at −10° C. for 30 min and at rt overnight. After completion of the reaction, water was added and the organic layer was extracted with DCM, dried over sodium sulfate and concentrated in vacuo to provide the crude product. The crude product was purified by column chromatography using 100-200 mesh silica gel and 30% EtOAc in hexane to provide (S)-tert-butyl 1-(2-(3,5-difluorophenylamino)-4,6-difluorophenylamino-1-oxopropan-2-ylcarbamate: LC-MS (ESI) m/z 428.1 [M+H]$^+$.

tert-Butyl-1-(1-(3,5-difluorophenyl)-4,6-difluoro-1H-1-benzo[d]imidazol-2-yl)ethylcarbamate

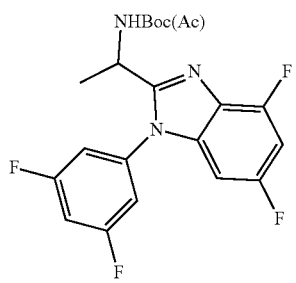

A solution of (S)-tert-butyl 1-(2-(3,5-difluorophenylamino)-4,6-difluorophenylamino-1-oxopropan-2-ylcarbamate (0.5 g, 1.16 mmol) in AcOH (3.5 mL) was stirred at 100° C. overnight. After completion of the reaction, the mixture was cooled to rt and was basified by using satd. sodium bicarbonate solution. The organic layer was extracted with EtOAc (75 mL), dried over sodium sulfate, concentrated to provide tert-butyl-1-(1-(3,5-difluorophenyl)-4,6-difluoro-1H-benzo[d]imidazol-2-yl)ethylcarbamate. The crude product was carried without further purification.

1-(1-(3,5-Difluorophenyl)-4,6-difluoro-1H-benzo[d]imidazol-2-yl]-ethanamine

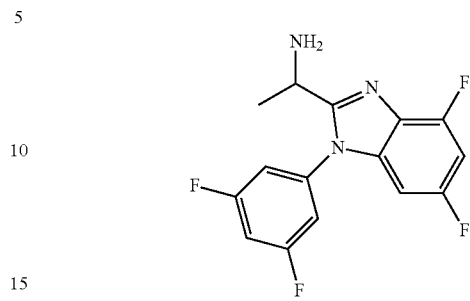

A solution of tert-butyl-1-(1-(3,5-difluorophenyl)-4,6-difluoro-1H-benzo[d]imidazol-2-yl)ethylcarbamate (0.4 g) was stirred in 2 N HCl (4 mL) at 120° C. for 4 h. The reaction mixture was cooled to rt and basified with satd. sodium bicarbonate solution (20 mL). The organic layer was extracted with EtOAc, dried over sodium sulfate and concentrated in vacuo to provide 1-(1-(3,5-difluorophenyl)-4,6-difluoro-1H-benzo[d]imidazol-2-yl]-ethanamine. The crude product was carried on without further purification.

4-Amino-6-(1-(1-(3,5-difluorophenyl)-4,6-difluoro-1H-benzo[d]imidazol-2-yl)ethylamino)pyrimidine-5-carbonitrile

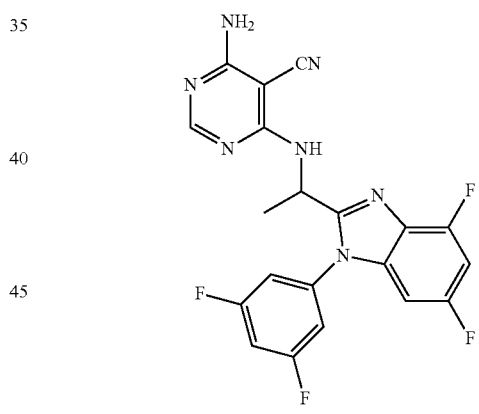

1-(1-(3,5-Difluorophenyl)-4,6-difluoro-1H-benzo[d]imidazol-2-yl]-ethanamine (0.25 g, 0.8 mmol) and 4-chloro-pyrimidine-5-carbonitrile (0.125 g, 0.8 mmol) were dissolved in n-butanol (8 mL) and to the mixture was added diisopropylethylamine (0.313 g, 2.42 mmol). The reaction mixture was heated at 120° C. overnight. The reaction mixture was cooled to rt and water was added. The mixture was extracted with EtOAc, dried over sodium sulfate and concentrated in vacuo. The crude product was purified by column chromatography using 100-200 mesh silica gel and 0-50% EtOAc in hexane to provide 4-amino-6-(1-(1-(3,5-difluorophenyl)-4,6-difluoro-M-benzo[d]imidazol-2-yl)ethylamino)pyrimidine-5-carbonitrile: $^1$H NMR (400 MHz, DMSO-d$_6$ with D$_2$O) δ 1.570 (d, J=6.8 Hz, 3H), 5.578-5.628 (m, 1H), 6.924 (dd, J=2 Hz, J=8 Hz, 1H), 7.109-7.166 (m, 1H), 7.275-7.316 (m, 3H), 7.838 (s, 1H); LC-MS (ESI) m/z 428.0 [M+H]$^+$.

4-Amino-6-(((1S)-1-(1-(3,5-difluorophenyl)-4,6-difluoro-1H-benzimidazol-2-yl)ethyl)amino)-5-pyrimidinecarbonitrile and 4-amino-6-(((1R)-1-(1-(3,5-difluorophenyl)-4,6-difluoro-1H-benzimidazol-2-yl)ethyl)amino)-5-pyrimidinecarbonitrile

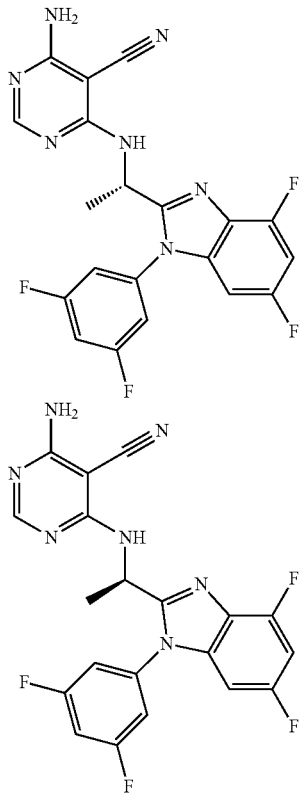

The racemic mixture 4-amino-6-(1-(1-(3,5-difluorophenyl)-4,6-difluoro-1H-benzo[d]imidazol-2-yl)ethylamino)pyrimidine-5-carbonitrile (0.185 g) was separated on an IC column using preparative SFC to give two fractions:

First peak on SFC IC column (first peak on Chiralcel OD-H column and second peak on Chiralpak AD-H column): 4-amino-6-4(1S)-1-(1-(3,5-difluorophenyl)-4,6-difluoro-1H-benzimidazol-2-yl)ethyl)amino)-5-pyrimidinecarbonitrile (0.083 g, 44.9% yield) as a white solid: $^1$H NMR (400 MHz, DMSO-d$_6$) δ ppm 7.86 (1H, s), 7.75 (1H, d, J=7.2 Hz), 7.30-7.42 (3H, m), 7.17 (3H, td, J=10.5, 2.2 Hz), 6.97 (1H, dd, J=8.6, 2.2 Hz), 5.63 (1H, quin, J=6.7 Hz), 1.57 (3H, d, J=6.8 Hz); LC-MS (ESI) m/z 428.0 [M+H]$^+$. Second peak on SFC IC column (second peak on Chiralcel OD-H column and first peak on Chiralpak AD-H column): 4-amino-6-(((1R)-1-(1-(3,5-difluorophenyl)-4,6-difluoro-1H-benzimidazol-2-yl)ethyl)amino)-5-pyrimidinecarbonitrile as a white solid: $^1$H NMR (400 MHz, DMSO-d$_6$) δ ppm 7.86 (1H, s), 7.75 (1H, d, J=7.0 Hz), 7.29-7.43 (3H, m), 7.17 (3H, td, J=10.6, 2.2 Hz), 6.97 (1H, dd, J=8.4, 2.2 Hz), 5.63 (1H, quin, J=6.6 Hz), 1.57 (3H, d, J=6.8 Hz); LC-MS (ESI) m/z 428.0 [M+H]$^+$. Using the general synthetic procedure for (S)-methyl 2-(1-aminoethyl)-1-cyclopropyl-1H-benzo[d]imidazole-7-carboxylate in example 47, (S)-2-(1-aminoethyl)-N-tert-butyl-1-cyclopropyl-1H-benzo[d]imidazole-7-carboxamide was prepared using (S)-tert-butyl 1-(3-(tert-butylcarbamoyl)-2-(cyclopropylamino)phenylamino)-1-oxopropan-2-ylcarbamate: $^1$H NMR (400 MHz, MeOH-d$_4$) δ 7.70 (1H, d, J=8.0 Hz), 7.38 (1H, d, J=8.0 Hz), 7.28 (1H, t, J=8.0 Hz), 4.69 (1H, q, J=8.0 Hz), 3.49-3.43 (1H, m), 1.60 (3H, d, J=8.0 Hz), 1.53 (9H, s), 1.32-1.15 (2H, m), 1.10-1.02 (1H, m), 0.99-0.92 (1H, m); LC-MS (ESI) m/z 301.1 [M+H]$^+$.

2-((1S)-1-((6-Amino-5-cyano-4-pyrimidinyl)amino)ethyl)-N-tert-butyl-1-cyclopropyl-1H-benzimidazole-7-carboxamide

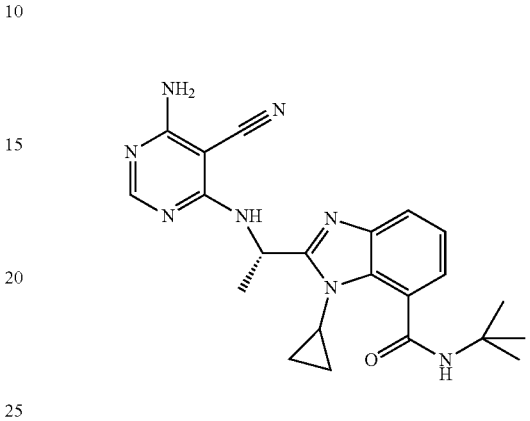

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 2-((1S)-1-((6-amino-5-cyano-4-pyrimidinyl)amino)ethyl)-N-tert-butyl-1-cyclopropyl-1H-benzimidazole-7-carboxamidewas prepared using (S)-2-(1-amino ethyl)-N-tert-butyl-1-cyclopropyl-1H-benzo[d]imidazole-7-carboxamide: $^1$H NMR (400 MHz, MeOH-d$_4$) δ 8.03 (1H, s), 7.68 (1H, d, J=8.0 Hz), 7.38 (1H, d, J=8.0 Hz), 7.27 (1H, t, J=8.0 Hz), 6.04 (1H, q, J=8.0 Hz), 3.55-3.43 (1H, m), 3.03-2.96 (1H, m), 1.73 (3H, d, J=4.0 Hz), 1.53 (9H, s), 1.40-1.30 (1H, m), 1.30-1.15 (2H, m), 1.10-0.93 (1H, m); LC-MS (ESI) m/z 419.2 [M+H]$^+$.

Example 51

Preparation of 4-amino-6-(((1S)-1-(7-(methylsulfonyl)-1H-benzimidazol-2-yl)ethyl)amino)-5-pyrimidinecarbonitrile

3-(Methylsulfonyl)-2-nitroaniline

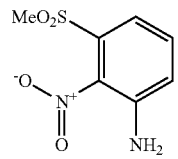

To a mixture of copper(II) triflate (0.83 g, 2.3 mmol), sodium methanesulfinate (2.8 g, 27.6 mmol), 3-bromo-2-nitroaniline (5.0 g, 23 mmol) under N$_2$, was added DIEA (0.50 mL, 4.6 mmol) and DMSO (10 mL). The stirred mixture was heated in a pre-heated 110° C. oil bath for 18 h. The mixture was cooled to rt, diluted with EtOAc, and filtered through a pad of Celite™. The filtrate was washed with water, brine, dried and concentrated in vacuo. Purification of the residue by flash chromatography over silica gel, using 0 to 10% gradient of MeOH in DCM with 0.2% NH$_4$OH as eluent gave 3-(methylsulfonyl)-2-nitroaniline: $^1$H NMR (400 MHz, CDCl$_3$) δ 7.44 (1H, dd, J=8.0, 4.0 Hz), 7.35 (1H, t, J=8.0 Hz), 7.02 (1H, dd, J=8.0, 4.0 Hz), 5.04 (2H, br), 3.36 (3H, s); LC-MS (ESI) m/z 217.0 [M+H]⁺.

3-(Methylsulfonyl)benzene-1,2-diamine

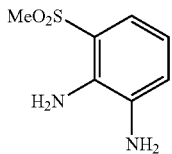

Using the general synthetic procedure for methyl 3-amino-2-(cyclopropylamino)benzoate in example 47, 3-(methylsulfonyl)benzene-1,2-diamine was prepared using 3-(methylsulfonyl)-2-nitroaniline: LC-MS (ESI) m/z 187.0 [M+H]⁺.

(S)-tert-Butyl 1-(2-amino-3-(methylsulfonyl)phenylamino)-1-oxopropan-2-ylcarbamate

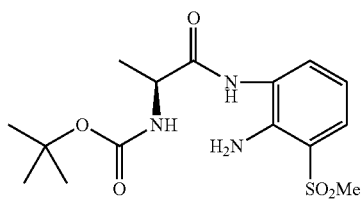

Using the general synthetic procedure for (S)-methyl 3-(2-(tert-butoxycarbonylamino)propanamido)-2-(cyclopropylamino)benzoate in example 47, (S)-tert-butyl 1-(2-amino-3-(methylsulfonyl)phenylamino)-1-oxopropan-2-ylcarbamate was prepared using 3-(methylsulfonyl)benzene-1,2-diamine: ¹H NMR (400 MHz, CDCl₃) δ 7.90 (1H, s), 7.70 (1H, dd, J=8.0, 4.0 Hz), 7.51 (1H, d, J=8.0 Hz), 6.84 (1H, t, J=8.0 Hz), 5.46 (2H, br), 5.06 (1H, d, J=8.0 Hz), 4.29-4.21 (2H, m), 3.08 (3H, s), 1.50 (9H, s), 1.48 (3H, d, J=8.0 Hz); LC-MS (ESI) m/z 358.1 [M+H]⁺.

(S)-1-(7-(Methylsulfonyl)-1H-benzo[d]imidazol-2-yl)ethanamine

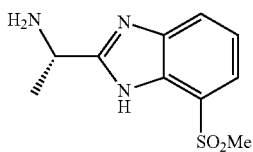 [SMILES: C[C@H](N)c1nc2cccc(S(C)(=O)=O)c2[nH]1]

Using the general synthetic procedure for (S)-methyl 2-(1-aminoethyl)-1-cyclopropyl-1H-benzo[d]imidazole-7-carboxylate in example 47, (S)-1-(7-(methyl-sulfonyl)-1H-benzo[d]imidazol-2-yl)ethanamine was prepared using (S)-tert-butyl 1-(2-amino-3-(methylsulfonyl)phenylamino)-1-oxopropan-2-ylcarbamate: LC-MS (ESI) m/z 240.1 [M+H]⁺.

4-Amino-6-(((1S)-1-(7-(methylsulfonyl)-1H-benzimidazol-2-yl)ethyl)amino)-5-pyrimidinecarbonitrile

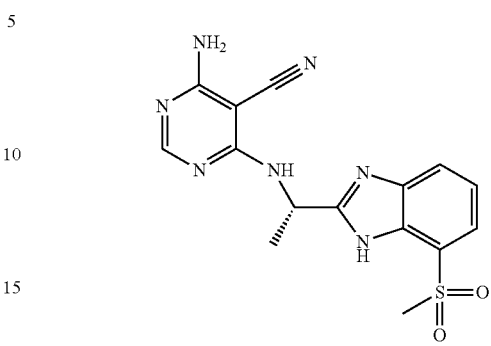

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(7-(methylsulfonyl)-1H-benzimidazol-2-yl)ethyl)amino)-5-pyrimidinecarbonitrile was prepared using (S)-1-(7-(methyl-sulfonyl)-1H-benzo[d]imidazol-2-yl)ethanamine: ¹H NMR (400 MHz, DMSO-d₆) δ 12.79 (0.8H, s), 12.60 (0.2H, s), 8.03 (0.8H, d, J=8.0 Hz), 7.97 (0.2H, d, J=8.0 Hz), 7.81 (1H, t, J=8.0 Hz), 7.73-7.65 (1H, m), 7.45-7.25 (3H, m), 5.78-5.60 (1H, m), 3.50 (3H, s), 1.69 (3H, d, J=8.0 Hz), 1.62 (1H, d, J=8.0 Hz); LC-MS (ESI) m/z 358.0 [M+H]

Example 52

Preparation of 4-amino-6-(((1R)-1-(3-(3,5-difluorophenyl)-3H-imidazo[4,5-b]pyridin-2-yl)ethyl)amino)-5-pyrimidinecarbonitrile and 4-amino-6-(((1S)-1-(3-(3,5-difluorophenyl)-3H-imidazo[4,5-b]pyridin-2-yl)ethyl)amino)-5-pyrimidinecarbonitrile N-(3,5-Difluorophenyl)-3-nitro-pyridin-2-amine

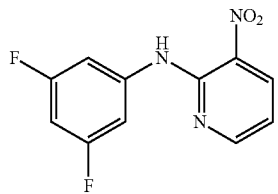

To a degassed solution of 2-chloro-3-nitro-pyridine (2.7 g, 17.03 mmol) and 3,5-difluoro aniline (2.0 g, 15.5 mmol) in dimethylacetamide (50 mL) was added cesium carbonate (10 g, 30.98 mmol) and was further degassed with nitrogen for 10 min. To the mixture was added xanthophos (448 mg, 0.77 mmol) and Pd₂(dba)₃ (851 mg, 0.92 mmol) and stirred at 100° C. for 16 h. After completion of the reaction, water (100 mL) was added and the mixture extracted with EtOAc (500 mL). The organic phase was dried over sodium sulfate and concentrated to provide the crude material, which was purified by column chromatography using 0-5% EtOAc in hexane to yield N-(3,5-difluorophenyl)-3-nitro-pyridin-2-amine: LC-MS (ESI) m/z 250.1 [M−H]⁻.

127

N1-(3,5-Difluorophenyl)-pyridine-2,3-diamine

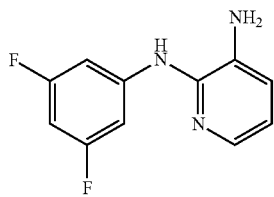 [SMILES: O=[N+]([O-])c1cccnc1Nc1cc(F)cc(F)c1]

To a solution of N-(3,5-difluorophenyl)-3-nitro-pyridin-2-amine (2.0 g, 7.96 mmol) in AcOH (24 mL) was added iron powder (1.33 g, 23.8 mmol) and the reaction mixture was heated to 100° C. for 1 h. The reaction mixture was cooled to rt and water (70 mL) was added. The organic layer was extracted with EtOAc (350 mL) and was basified by using satd. sodium bicarbonate solution (150 mL), dried over sodium sulfate and concentrated in vacuo to provide N1-(3,5-Difluorophenyl)-pyridine-2,3-diamine. The crude product was used without further purification.

(S)-tert-Butyl-1-(2-(3,5-difluorophenylamino)pyridine-3-ylamino)-1-oxopropan-2-ylcarbamate

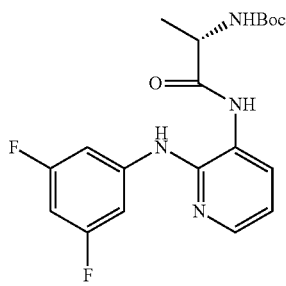 [SMILES: C[C@H](NC(=O)OC(C)(C)C)C(=O)Nc1cccnc1Nc1cc(F)cc(F)c1]

Boc-L-Ala-OH (2.05 g, 10.8 mmol) and isobutyl chloroformate (1.4 g, 10.8 mmol) were dissolved in DCM (20 mL) and N-methyl morpholine (1.14 g, 11.3 mmol) was added to at −10° C. and stirred for 30 min. To the mixture was added N1-(3,5-difluorophenyl)-pyridine-2,3-diamine (1.2 g, 5.42 mmol) dissolved in DCM (10 mL). The reaction mixture was stirred at −10° C. for 30 min and then at rt overnight. After completion of the reaction, water (100 mL) was added and the organic layer was extracted with DCM (200 mL), dried over sodium sulfate and concentrated to provide a crude product, which was purified by column chromatography using 100-200 mesh silica gel and 35% EtOAc in hexane to provide (S)-tert-butyl-1-(2-(3,5-difluorophenylamino)pyridine-3-ylamino)-1-oxopropan-2-ylcarbamate: LC-MS (ESI) m/z 393.2 [M+H]$^+$.

tert-Butyl 1-(3-(3,5-Difluorophenyl)-3H-imidazo[4,5-b]pyridin-2-yl)-ethylcarbamate

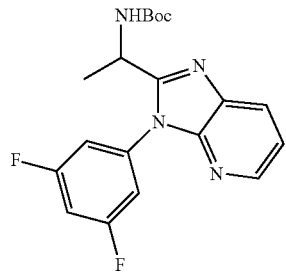 [SMILES: CC(NC(=O)OC(C)(C)C)c1nc2cccnc2n1-c1cc(F)cc(F)c1]

128

A solution of (S)-tert-butyl-1-(2-(3,5-difluorophenylamino)pyridine-3-ylamino)-1-oxopropan-2-ylcarbamate (1.7 g, 4.33 mmol) in AcOH (12 mL) was stirred at 100° C. overnight. After completion of the reaction the mixture was cooled to rt and basified with satd. sodium bicarbonate solution (60 mL). The organic layer was then extracted with EtOAc (150 mL), dried over sodium sulfate an concentrated in vacuo to provide tert-butyl 1-(3-(3,5-Difluorophenyl)-3H-imidazo[4,5-b]pyridin-2-yl)-ethylcarbamate. The crude product was used without further purification.

1-(-(3,5-Difluorophenyl)-3H-imidazo[4,5-b]pyridin-2-yl)ethylamine

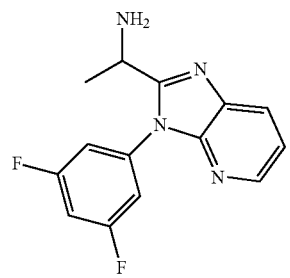 [SMILES: CC(N)c1nc2cccnc2n1-c1cc(F)cc(F)c1]

A solution of tert-butyl 1-(3-(3,5-difluorophenyl)-3H-imidazo[4,5-b]pyridin-2-yl)-ethylcarbamate (1.10 g, 2.94 mmol) was stirred in methanolic HCl (100 mL) at rt for 5 h. After completion of the reaction, the solvent was removed in vacuo and the resulting solid was dissolved in water. The solution was extracted with EtOAc (100 mL), washed with satd. sodium bicarbonate solution, brine, dried over sodium sulfate and concentrated in vacuo to provide 14-(3,5-difluorophenyl)-3H-imidazo[4,5-b]pyridin-2-yl)ethylamine:
LC-MS (ESI) m/z 275.1 [M+H]$^+$. The crude product was used without further purification.

4-Amino-6-(1-(3-(3,5-difluorophenyl)-3H-imidazo[4,5-b]pyridin-2-yl)ethylamino)pyrimidine-5-carbonitrile

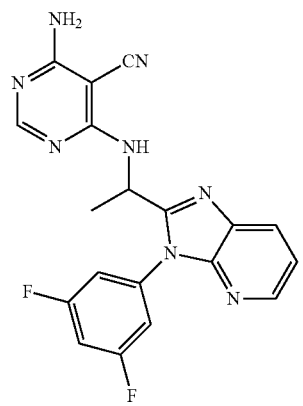 [SMILES: CC(Nc1ncnc(N)c1C#N)c1nc2cccnc2n1-c1cc(F)cc(F)c1]

1-(-(3,5-Difluorophenyl)-3H-imidazo[4,5-b]pyridin-2-yl) ethylamine (600 mg, 2.18 mmol) and 4-chloro-pyrimidine-5-carbonitrile (300 mg, 2.18 mmol) were dissolved in n-butanol (30 mL). After the addition of DIPEA (422 mg, 3.28 mmol) the reaction mixture was heated at 120° C. overnight. The mixture was cooled to rt and water (50 mL) was added. The mixture was extracted with EtOAc (300 mL), dried over sodium sulfate and concentrated in vacuo to provide a crude product. The crude product was purified by column chromatography using 100-200 mesh silica gel and 0-50% EtOAc in hexane to provide 4-amino-6-(1-(3-(3,5-difluorophenyl)-3H-imidazo[4,5-b]pyridin-2-yl)-ethylamino)pyrimidine-5-carbonitrile: ¹H NMR (400 MHz, DMSO-d₆) δ 1.580 (d, J=6.8 Hz, 3H), 5.683-5.753 (m, 1H), 7.205 (br s, 2H), 7.307-7.367 (m, 4H), 7.768 (d, J=8 Hz, 1H), 7.888 (s, 1H), 8.149-8.172 (m, 1H), 8.276-8.292 (m, 1H); LC-MS (ESI) m/z 393.0 [M+H]⁺.

4-Amino-6-(((1R)-1-(3-(3,5-difluorophenyl)-3H-imidazo[4,5-b]pyridin-2-yl)ethyl)amino)-5-pyrimidinecarbonitrile and 4-amino-6-(((1S)-1-(3-(3,5-difluorophenyl)-3H-imidazo[4,5-b]pyridin-2-yl)ethyl)amino)-5-pyrimidinecarbonitrile

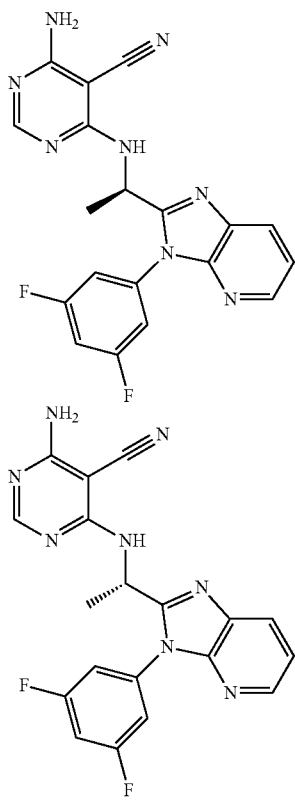

The racemic 4-amino-6-(1-(3-(3,5-difluorophenyl)-3H-imidazo[4,5-b]pyridin-2-yl)ethylamino)pyrimidine-5-carbonitrile (0.427 g, 1.09 mmol) was separated on AD-H column using preparative SFC to give two fractions: First peak on SFC AD-H column (second peak on Chiralcel OD-H column and second peak on Chiralpak AD-H column): 4-amino-6-(((1R)-1-(3-(3,5-difluorophenyl)-3H-imidazo[4,5-b]pyridin-2-yl)ethyl)amino)-5-pyrimidinecarbonitrile (0.1809 g, 42.4% yield) as a tan solid: ¹H NMR (400 MHz, DMSO-d₆) δ ppm 8.28 (1H, dd, J=4.7, 1.4 Hz), 8.16 (1H, dd, J=8.0, 1.4 Hz), 7.89 (1H, s), 7.75 (1H, d, J=7.8 Hz), 7.28-7.39 (4H, m), 7.19 (2H, br. s.), 5.72 (1H, quin, J=7.0 Hz), 1.58 (3H, d, J=6.8 Hz); LC-MS (ESI) m/z 393.1 [M+H]⁺. Second peak on SFC AD-H column (first peak on Chiralcel OD-H column and first peak on Chiralpak AD-H column): 4-amino-6-(((1S)-1-(3-(3,5-difluorophenyl)-3H-imidazo[4,5-b]pyridin-2-yl)ethyl) amino)-5-pyrimidinecarbonitril (0.144 g, 33.8% yield) as an off-white solid: ¹H NMR (400 MHz, DMSO-d₆) δ ppm 8.28 (1H, dd, J=4.8, 1.5 Hz), 8.16 (1H, dd, J=8.0, 1.4 Hz), 7.89 (1H, s), 7.75 (1H, d, J=7.6 Hz), 7.28-7.39 (4H, m), 7.19 (2H, br. s.), 5.66-5.77 (1H, m), 1.58 (3H, d, J=6.7 Hz); LC-MS (ESI) m/z 393.1 [M+H]⁺.

Example 53

6-Fluoro-N-(5-fluoro-2-nitrophenyl)pyridin-2-amine

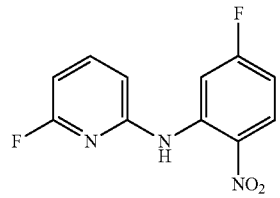 [SMILES: O=[N+]([O-])c1ccc(F)cc1Nc1cccc(F)n1]

Prepared according to Step D1 in General Procedure D using 6-fluoropyridin-2-amine (1.762 g, 15.71 mmol) to give 6-fluoro-N-(5-fluoro-2-nitrophenyl)pyridin-2-amine as an orange solid. LC-MS (ESI) m/z 251.9 [M+H]⁺.

5-Fluoro-N1-(6-fluoropyridin-2-yl)benzene-1,2-diamine

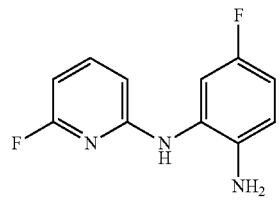

Prepared according to Step D2 in General Procedure D using 6-fluoro-N-(5-fluoro-2-nitrophenyl)pyridin-2-amine (3.95 g, 15.73 mmol) to give 5-fluoro-N1-(6-fluoropyridin-2-yl)benzene-1,2-diamine as a yellow solid. LC-MS (ESI) m/z 222.1 [M+H]⁺.

tert-Butyl-1-(4-fluoro-2-(6-fluoropyridin-2-ylamino)phenylamino)-1-oxopropan-2-ylcarbamate

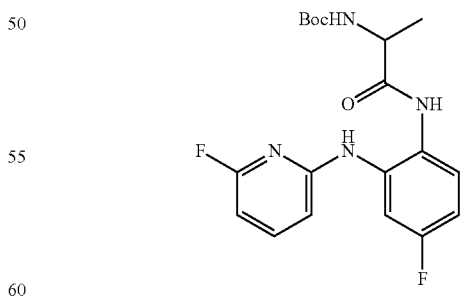

Prepared according to Step D3 in General Procedure D using 5-fluoro-N1-(6-fluoropyridin-2-yl)benzene-1,2-diamine (1.200 g, 5.42 mmol) to give tert-butyl 1-(4-fluoro-2-(6-fluoropyridin-2-ylamino)phenylamino)-1-oxopropan-2-ylcarbamate as an off-white solid. LC-MS (ESI) m/z 393.2 [M+H]⁺.

N-(1-(6-Fluoro-1-(6-fluoropyridin-2-yl)-1H-benzo[d]imidazol-2-yl)ethyl)acetamide

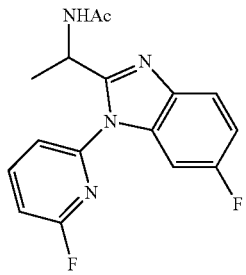 [SMILES: CC(=O)NC(C)c1nc2ccc(F)cc2n1-c1cccc(F)n1]

Prepared according to Step D4 in General Procedure D using tert-butyl 1-(4-fluoro-2-(6-fluoropyridin-2-ylamino)phenylamino)-1-oxopropan-2-ylcarbamate (2.10 g, 5.35 mmol) to give N-(1-(6-fluoro-1-(6-fluoropyridin-2-yl)-1H-benzo[d]imidazol-2-yl)ethyl)acetamide as a pink solid. LC-MS (ESI) m/z 317.1 [M+H]$^+$.

1-(6-Fluoro-1-(6-fluoropyridin-2-yl)-1H-benzo[d]imidazol-2-yl)ethanamine

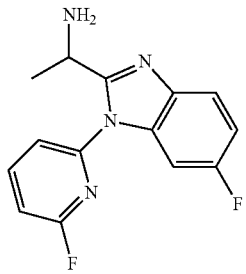 [SMILES: CC(N)c1nc2ccc(F)cc2n1-c1cccc(F)n1]

Prepared according to Step D5a in General Procedure D using N-(1-(6-fluoro-1-(6-fluoropyridin-2-yl)-1H-benzo[d]imidazol-2-yl)ethyl)acetamide (1.200 g, 3.79 mmol) to give 1-(6-fluoro-1-(6-fluoropyridin-2-yl)-1H-benzo[d]imidazol-2-yl)ethanamine as a pink solid. LC-MS (ESI) m/z 275.1 [M+H]$^+$.

4-Amino-6-(1-(6-fluoro-1-(6-fluoropyridin-2-yl)-1H-benzo[d]imidazol-2-yl)ethylamino)pyrimidine-5-carbonitrile

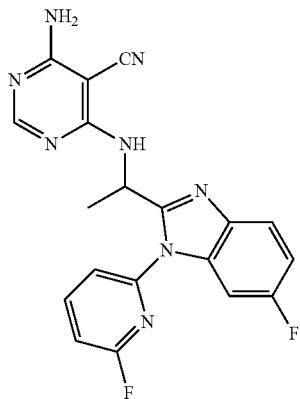 [SMILES: CC(Nc1ncnc(N)c1C#N)c1nc2ccc(F)cc2n1-c1cccc(F)n1]

Prepared according to Step D6 in General Procedure D using 1-(6-fluoro-1-(6-fluoropyridin-2-yl)-1H-benzo[d]imidazol-2-yl)ethanamine (0.300 g, 1.094 mmol) to give 4-amino-6-(1-(6-fluoro-1-(6-fluoropyridin-2-yl)-1H-benzo[d]imidazol-2-yl)ethylamino)pyrimidine-5-carbonitrile as a white solid: $^1$H NMR (500 MHz, DMSO-d$_6$) δ ppm 1.60 (d, J=6.85 Hz, 3H) 5.85 (quin, J=7.03 Hz, 1H) 7.17 (td, J=9.23, 2.57 Hz, 3H) 7.27 (ddd, J=11.43, 8.86, 2.20 Hz, 2H) 7.64 (dd, J=7.46, 1.10 Hz, 1H) 7.73 (d, J=7.83 Hz, 1H) 7.77 (dd, J=8.80, 4.89 Hz, 1H) 7.87 (s, 1H) 8.20 (q, J=8.23 Hz, 1H). LC-MS (ESI) m/z 393.1 [M+H]$^+$.

4-Amino-6-(((1S)-1-(6-fluoro-1-(6-fluoro-2-pyridinyl)-1H-benzimidazol-2-yl)ethyl)amino)-5-pyrimidinecarbonitrile and 4-amino-6-(((1R)-1-(6-fluoro-1-(6-fluoro-2-pyridinyl)-1H-benzimidazol-2-yl)ethyl)amino)-5-pyrimidinecarbonitrile

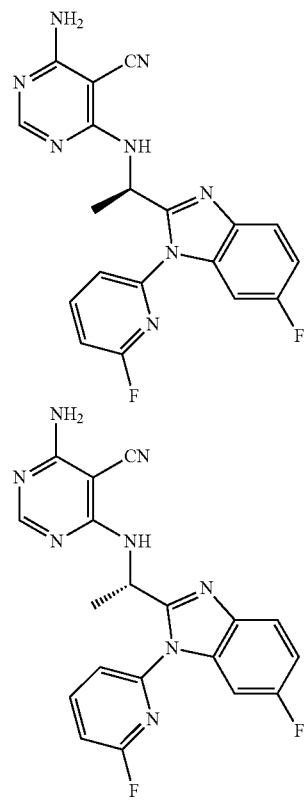

The racemic mixture (261 mg) was separated on AD-H column using preparative SFC to give two fractions: First peak on OD-H column: 4-amino-6-(((1R)-1-(6-fluoro-1-(6-fluoro-2-pyridinyl)-1H-benzimidazol-2-yl)ethyl)amino)-5-pyrimidinecarbonitrile as a white solid: $^1$H NMR (400 MHz, DMSO-d$_6$) δ ppm 1.60 (d, J=6.85 Hz, 3H) 5.86 (br. s., 1H) 7.17 (ddd, J=9.78, 8.80, 2.35 Hz, 3H) 7.23-7.32 (m, 2H) 7.65 (dd, J=7.53, 1.47 Hz, 1H) 7.73 (br. s., 1H) 7.77 (dd, J=8.90, 4.99 Hz, 1H) 7.87 (s, 1H) 8.21 (q, J=8.22 Hz, 1H). LC-MS (ESI) m/z 393.0 [M+H]$^+$. Second peak on OD-H column: 4-amino-6-4(1S)-1-(6-fluoro-1-(6-fluoro-2-pyridinyl)-1H-benzimidazol-2-yl)ethyl)amino)-5-pyrimidinecarbonitrile as a white solid: $^1$H NMR (400 MHz, DMSO-d$_6$) δ ppm 1.59 (d, J=6.85 Hz, 3H) 5.85 (quin, J=6.99 Hz, 1H) 7.17 (td, J=9.24, 2.45 Hz, 3H) 7.27 (td, J=8.95, 2.45 Hz, 2H) 7.64 (dd, J=7.53, 1.47 Hz, 1H) 7.71-7.81 (m, 2H) 7.86 (s, 1H) 8.20 (q, J=8.22 Hz, 1H). LC-MS (ESI) m/z 393.0 [M+H]$^+$.

Example 54

Preparation of 4-amino-6-(((1S)-1-(1-cyclopentyl-4-(methylsulfonyl)-1H-benzimidazol-2-yl)ethyl)amino)-5-pyrimidinecarbonitrile

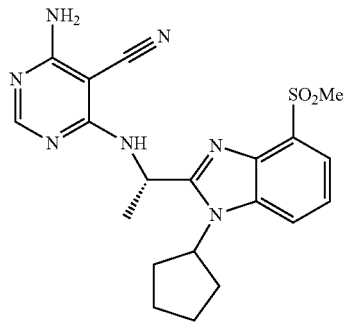 [SMILES: C[C@H](Nc1ncnc(N)c1C#N)c1nc2c(S(C)(=O)=O)cccc2n1C1CCCC1]

A mixture of 4-amino-6-(((1S)-1-(7-(methylsulfonyl)-1H-benzimidazol-2-yl)-ethyl)amino)-5-pyrimidinecarbonitrile (110 mg, 0.31 mmol) and cesium carbonate (100 mg, 0.31 mmol) was stirred at rt for 30 min in DMF (2 mL). At this time bromocyclopentane (92 µL, 0.62 mmol) was added. The mixture was stirred at 110° C. in a sealed flask for 18 h. The mixture was cooled to rt and concentrated under reduced pressure. Purification of the residue by flash chromatography over silica gel, using 0 to 10% gradient of MeOH in DCM-EtOAc (1:1) with 0.2% NH$_4$OH as eluent gave 4-amino-6-(((1S)-1-(1-cyclopentyl-4-(methylsulfonyl)-1H-benzimidazol-2-yl)ethyl)amino)-5-pyrimidinecarbonitrile: $^1$H NMR (400 MHz, DMSO-d$_6$) δ 8.09 (1H, s), 7.95 (1H, s), 7.94 (1H, d, J=8.0 Hz), 7.72 (1H, d, J=8.0 Hz), 7.43 (1H, t, J=8.0 Hz), 7.35 (2H, br), 5.93-5.85 (1H, m), 5.03-4.95 (1H, m), 3.54 (3H, s), 2.70-2.66 (1H, m), 2.35-2.32 (1H, m), 2.18-1.94 (6H, m), 1.67 (3H, d, J=8.0 Hz); LC-MS (ESI) m/z 426.1 [M+H]$^+$.

Example 55

N-(5-Fluoro-2-nitrophenyl)pyridin-3-amine

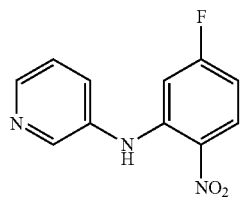 [SMILES: O=[N+]([O-])c1ccc(F)cc1Nc1cccnc1]

Prepared according to Step D1 in General Procedure D using pyridin-3-amine (1.479 g, 15.71 mmol) to give N-(5-fluoro-2-nitrophenyl)pyridin-3-amine as an orange solid. LC-MS (ESI) m/z 234.1 [M+H]$^+$.

5-Fluoro-N1-(pyridin-3-yl)benzene-1,2-diamine

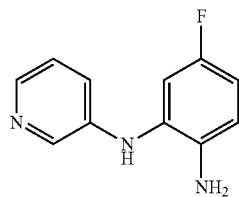 [SMILES: Nc1ccc(F)cc1Nc1cccnc1]

Prepared according to Step D2 in General Procedure D using N-(5-fluoro-2-nitrophenyl)pyridin-3-amine (1.24 g, 5.32 mmol) to give 5-fluoro-N1-(pyridin-3-yl)benzene-1,2-diamine as a dark oil. LC-MS (ESI) m/z 204.2 [M+H]$^+$.

tert-Butyl-1-(4-fluoro-2-(pyridin-3-ylamino)phenylamino)-1-oxopropan-2-ylcarbamate

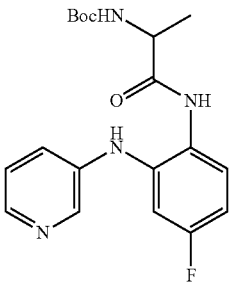 [SMILES: CC(NC(=O)OC(C)(C)C)C(=O)Nc1ccc(F)cc1Nc1cccnc1]

Prepared according to Step D1 in General Procedure D using 5-fluoro-N1-(pyridin-3-yl)benzene-1,2-diamine (0.810 g, 3.99 mmol) to give tert-butyl 1-(4-fluoro-2-(pyridin-3-ylamino)phenylamino)-1-oxopropan-2-ylcarbamate as a yellow solid. LC-MS (ESI) m/z 375.2 [M+H]$^+$.

N-(1-(6-Fluoro-1-(pyridin-3-yl)-1H-benzo[d]imidazol-2-yl)ethyl)acetamide

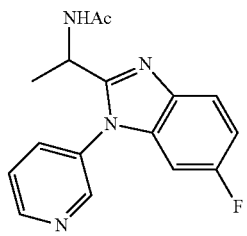 [SMILES: CC(=O)NC(C)c1nc2ccc(F)cc2n1-c1cccnc1]

Prepared according to Step D4 in General Procedure D using tert-butyl 1-(4-fluoro-2-(pyridin-3-ylamino)phenylamino)-1-oxopropan-2-ylcarbamate (0.610 g, 1.63 mmol) to give N-(1-(6-fluoro-1-(pyridin-3-yl)-1H-benzo[d]imidazol-2-yl)-ethyl)acetamide as a brown glass. LC-MS (ESI) m/z 299.1 [M+H]$^+$.

1-(6-Fluoro-1-(pyridin-3-yl)-1H-benzo[d]imidazol-2-yl)ethanamine

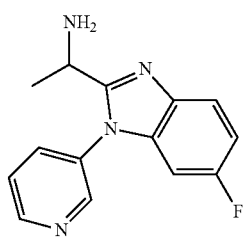 [SMILES: CC(N)c1nc2ccc(F)cc2n1-c1cccnc1]

Prepared according to Step D5a in General Procedure D using N-(1-(6-fluoro-1-(pyridin-3-yl)-1H-benzo[d]imidazol-2-yl)ethyl)acetamide (0.486 g, 1.63 mmol) to give 1-(6-fluoro-1-(pyridin-3-yl)-1H-benzo[d]imidazol-2-yl)ethanamine as a tan oil. LC-MS (ESI) m/z 257.1 [M+H]$^+$.

4-Amino-6-(1-(6-fluoro-1-(pyridin-3-yl)-1H-benzo[d]imidazol-2-yl)ethylamino)pyrimidine-5-carbonitrile

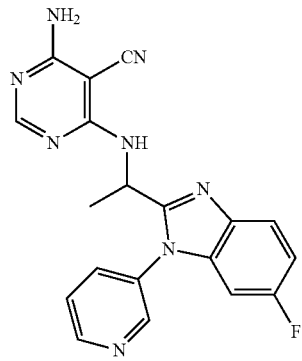 [SMILES: CC(Nc1ncnc(N)c1C#N)c1nc2ccc(F)cc2n1-c1cccnc1]

Prepared according to Step D6 in General Procedure D using 1-(6-fluoro-1-(pyridin-3-yl)-1H-benzo[d]imidazol-2-yl)ethanamine (0.160 g, 0.624 mmol) to give 4-amino-6-(1-(6-fluoro-1-(pyridin-3-yl)-1H-benzo[d]imidazol-2-yl)ethylamino)-pyrimidine-5-carbonitrile as a tan solid. $^1$H NMR (400 MHz, DMSO-d$_6$) δ ppm 1.57 (d, J=6.65 Hz, 3H) 5.49 (quin, J=6.94 Hz, 1H) 6.95 (dd, J=9.00, 2.35 Hz, 1H) 7.08-7.17 (m, 1H) 7.19 (br. s., 2H) 7.57 (dd, J=7.92, 4.60 Hz, 1H) 7.68-7.80 (m, 2H) 7.83 (s, 1H) 8.01 (d, J=8.22 Hz, 1H) 8.66 (dd, J=4.79, 1.47 Hz, 1H) 8.74 (d, J=2.35 Hz, 1H). LC-MS (ESI) m/z 375.1 [M+H]$^+$.

4-Amino-6-(((1R)-1-(6-fluoro-1-(3-pyridinyl)-1H-benzimidazol-2-yl)ethyl)amino)-5-pyrimidinecarbonitrile and 4-amino-6-(((1S)-1-(6-fluoro-1-(3-pyridinyl)-1H-benzimidazol-2-yl)ethyl)amino)-5-pyrimidinecarbonitrile

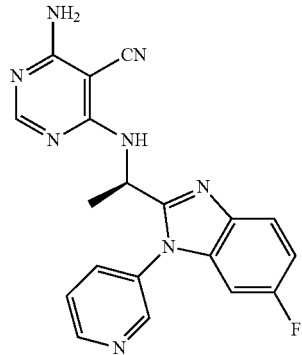

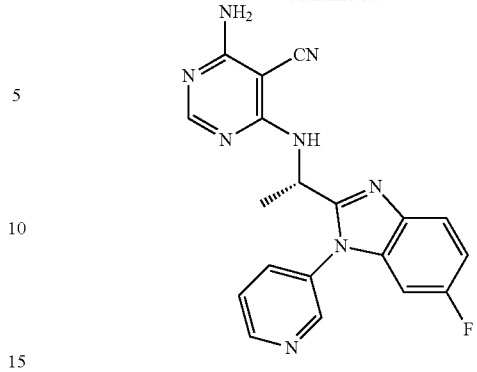

The racemic mixture (160 mg) was separated on AD-H column using preparative SFC to give two fractions. First peak on OD-H column: 4-amino-6-(((1R)-1-(6-fluoro-1-(3-pyridinyl)-1H-benzimidazol-2-yl)ethyl)amino)-5-pyrimidinecarbonitrile as an off-white solid: $^1$H NMR (400 MHz, DMSO-d$_6$) δ ppm 1.63 (d, J=6.85 Hz, 3H) 5.56 (quin, J=6.99 Hz, 1H) 7.01 (dd, J=8.90, 2.45 Hz, 1H) 7.21 (ddd, J=9.88, 8.90, 2.54 Hz, 1H) 7.25 (br. s., 2H) 7.63 (ddd, J=8.12, 4.79, 0.78 Hz, 1H) 7.75-7.86 (m, 2H) 7.89 (s, 1H) 8.08 (dt, J=8.31, 1.71 Hz, 1H) 8.72 (dd, J=4.79, 1.47 Hz, 1H) 8.81 (d, J=2.15 Hz, 1H). LC-MS (ESI) m/z 375.1 [M+H]$^+$. Second peak on OD-H column: 4-amino-6-(((1S)-1-(6-fluoro-1-(3-pyridinyl)-1H-benzimidazol-2-yl)ethyl)amino)-5-pyrimidinecarbonitrile as an off-white solid: $^1$H NMR (400 MHz, DMSO-d$_6$) δ ppm 1.57 (d, J=6.85 Hz, 3H) 5.50 (quin, J=6.94 Hz, 1H) 6.95 (dd, J=8.90, 2.45 Hz, 1H) 7.14 (ddd, J=9.78, 8.80, 2.54 Hz, 1H) 7.19 (br. s., 2H) 7.54-7.61 (m, 1H) 7.76 (dd, J=8.80, 5.09 Hz, 2H) 7.83 (s, 1H) 8.01 (dt, J=8.31, 1.71 Hz, 1H) 8.66 (dd, J=4.79, 1.47 Hz, 1H) 8.75 (d, J=2.15 Hz, 1H). LC-MS (ESI) m/z 375.1 [M+H]$^+$.

Example 56

Preparation of 4-amino-6-(((1R)-1-(1-(2-pyridinyl)-1H-imidazo-[4,5-b]pyridin-2-yl)ethyl)amino)-5-pyrimidinecarbonitrile and 4-amino-6-(((1S)-1-(1-(2-pyridinyl)-1H-imidazo[4,5-b]pyridin-2-yl)ethyl)amino)-5-pyrimidinecarbonitrile N-(2-Nitropyridin-3-yl)pyridin-2-amine

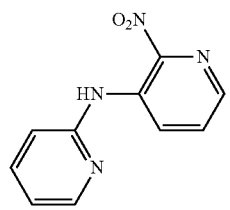

To a solution of 3-fluoro-2-nitropyridine (3.32 g, 23.38 mmol) and 2-aminopyridine (2.0 g, 21.25 mmol) in DMF (35.4 mL) was added potassium tert-butoxide (4.77 g, 42.5 mmol). The solution was stirred under nitrogen at rt overnight. After 22 h, the mixture was poured into water (100 mL) and extracted with EtOAc (2×100 mL). After drying with MgSO$_4$, the solution was filtered and concentrated in vacuo to provide the crude material as a orange solid. The orange solid was purified by chromatography through a Redi-Sep™ pre-packed silica gel column (80 g), eluting with a gradient of 0% to 50% EtOAc in hexane, to provide N-(2-nitropyridin-3-yl)pyridin-2-amine as an orange solid: $^1$H NMR (400 MHz, DMSO-$d_6$) δ ppm 9.53 (1H, s), 8.58 (1H, dd, J=8.4, 1.6 Hz), 8.15 (1H, dd, J=4.3, 1.4 Hz), 8.10-8.14 (1H, m), 7.66-7.76 (2H, m), 7.05 (1H, dt, J=8.4, 0.8 Hz), 6.93 (1H, ddd, J=7.2, 5.0, 0.9 Hz); LC-MS (ESI) m/z 217.0 [M+H]$^+$.

N3-(Pyridin-2-yl)pyridine-2,3-diamine

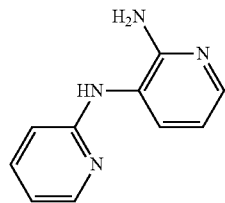 [SMILES: Nc1ncccc1Nc1ccccn1]

A heterogeneous mixture of N-(2-nitropyridin-3-yl)pyridin-2-amine (2.46 g, 11.38 mmol) and Tin(II) chloride dihydrate (12.84 g, 56.9 mmol) in EtOAc (76 mL) was heated under reflux with stirring. After 5 h, the mixture was cooled to rt. To the cooled mixture was added 10M aq. NaOH solution (100 mL). The mixture was extracted with EtOAc (3×50 mL). The organic extract was washed with water (1×100 mL), satd. NaCl (1×100 mL) and dried over MgSO$_4$. The solution was filtered and concentrated in vacuo to provide a brown solid. The residue was purified by silica gel column chromatography on a 80 g of Redi-Sep™ column using 0 to 50% gradient of DCM:MeOH:NH$_4$OH (89:9:1) in DCM over 25 min and then 50% isocratic of DCM:MeOH:NH$_4$OH (89:9:1) in DCM for 20 min as eluent to give N3-(pyridin-2-yl)pyridine-2,3-diamine as a brown solid: $^1$H NMR (400 MHz, DMSO-$d_6$) δ ppm 8.03-8.09 (1H, m), 7.92 (1H, s), 7.79 (1H, dd, J=7.6, 1.6 Hz), 7.69 (1H, dd, J=4.9, 1.6 Hz), 7.48-7.56 (1H, m), 6.66-6.74 (2H, m), 6.56 (1H, dd, J=7.7, 4.8 Hz), 5.67 (2H, s); LC-MS (ESI) m/z 187.1 [M+H]$^+$.

(S)-tert-Butyl 1-oxo-1-(3-(pyridin-2-ylamino)pyridin-2-ylamino)propan-2-ylcarbamate

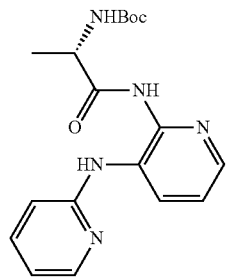 [SMILES: C[C@H](NC(=O)OC(C)(C)C)C(=O)Nc1ncccc1Nc1ccccn1]

To a −10° C. solution (NaCl-ice bath) of Boc-L-Ala-OH (1.214 g, 6.42 mmol) and N-methylmorpholine (0.741 mL, 6.74 mmol) in DCM (16.04 mL) was added isobutyl chloroformate (0.839 mL, 6.42 mmol). The resulting cloudy light yellow mixture was stirred at −10° C. After 15 min at −10° C., to the mixture was then added a solution of N3-(pyridin-2-yl)pyridine-2,3-diamine (0.5974 g, 3.21 mmol) in DCM (16 mL) at −10° C. with stirring. The resulting mixture was allowed to warm to rt with stirring. After 15.5 h at rt, to the mixture was added satd. NH$_4$Cl (50 mL). The organic layer was separated. The aqueous mixture was extracted with DCM (50 mL×1). The combined organic layers were dried over MgSO$_4$, filtered, and concentrated in vacuo. The residue was purified by silica gel column chromatography on a 40 g of Redi-Sep™ column using 0 to 50% gradient of EtOAc in hexane over 14 min, then 50% isocratic of EtOAC in hexane for 14 min, then 50 to 100% gradient of EtOAc in hexane over 14 min, and then 100% isocratic of EtOAC for 30 min as eluent to give (S)-tert-butyl 1-oxo-1-(3-(pyridin-2-ylamino)pyridin-2-ylamino)propan-2-ylcarbamate as a light pink foamy solid: LC-MS (ESI) m/z 358.1 [M+H]$^+$.

tert-Butyl 1-(1-(pyridin-2-yl)-1H-imidazo[4,5-b]pyridin-2-yl)ethylcarbamate

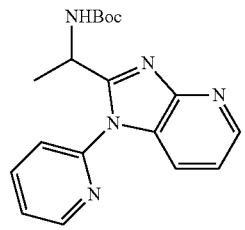 [SMILES: CC(NC(=O)OC(C)(C)C)c1nc2ncccc2n1-c1ccccn1]

A solution of (S)-tert-butyl 1-oxo-1-(3-(pyridin-2-ylamino)pyridin-2-ylamino)-propan-2-ylcarbamate (0.5432 g, 1.520 mmol) in AcOH (5.07 mL) was heated at 100° C. with stirring. After 3 days, the mixture was concentrated in vacuo to provide tert-butyl 1-(1-(pyridin-2-yl)-1H-imidazo[4,5-b]pyridin-2-yl)ethylcarbamate as a brown syrup: LC-MS (ESI) m/z 340.1 [M+H]$^+$. Epimerization occurred. The crude product was used without further purification.

1-(1-(Pyridin-2-yl)-1H-imidazo[4,5-b]pyridin-2-yl)ethanamine

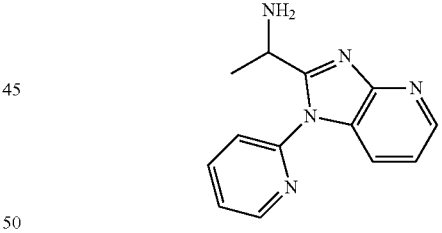

To a mixture of tert-butyl 1-(1-(pyridin-2-yl)-1H-imidazo[4,5-b]pyridin-2-yl)ethylcarbamate (0.516 g, 1.520 mmol) in DCM (10.14 mL) was added TFA (10.14 mL, 132 mmol) dropwise at rt with stirring. After 50 min, the mixture was concentrated in vacuo and co-evaporated with triethylamine and MeOH. The neutralized crude mixture was purified by chromatography through a Redi-Sep™ pre-packed silica gel column (40 g), eluting with a gradient of 0% to 100% DCM:MeOH:NH$_4$OH (89:9:1) in DCM, to provide 1-(1-(pyridin-2-yl)-1H-imidazo[4,5-b]pyridin-2-yl)ethanamine as brown syrup: $^1$H NMR (400 MHz, DMSO-$d_6$) δ ppm 8.68-8.76 (1H, m), 8.49 (1H, dd, J=4.7, 1.6 Hz), 8.19 (1H, td, J=7.7, 2.0 Hz), 7.79-7.92 (2H, m), 7.63 (1H, ddd, J=7.6, 4.8, 0.9 Hz), 7.32 (1H, dd, J=8.1, 4.8 Hz), 4.47 (1H, q, J=6.7 Hz), 1.45 (3H, d, J=6.8 Hz); LC-MS (ESI) m/z 240.1 [M+H]$^+$.

4-Amino-6-(1-(1-(pyridin-2-yl)-1H-imidazo[4,5-b]pyridin-2-yl)ethylamino)pyrimidine-5-carbonitrile

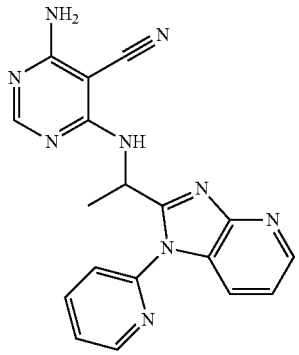 [SMILES: CC(Nc1ncnc(N)c1C#N)c1nc2ncccc2n1-c1ccccn1]

A mixture of 4-amino-6-chloropyrimidine-5-carbonitrile (0.235 g, 1.521 mmol), 1-(1-(pyridin-2-yl)-1H-imidazo[4,5-b]pyridin-2-yl)ethanamine (0.364 g, 1.521 mmol), and DIEA (1.325 mL, 7.61 mmol) in butan-1-ol (15.21 mL) was stirred at 120° C. After 17.5 h, the mixture was removed from the heat. The mixture was cooled and concentrated in vacuo to give a brown solid: The brown solid was suspended in water (50 mL) and extracted with DCM (50 mL). The organic phase was washed with water (30 mL), dried over MgSO$_4$, filtered, and concentrated in vacuo to give a brown solid. The residue was purified by column chromatography on a 40 g of Redi-Sep™ column using 0 to 100% gradient of DCM:MeOH:—NH$_4$OH (89:9:1) in DCM over 14 min and then 100% isocratic of DCM:MeOH:—NH$_4$OH (89:9:1) for 30 min as eluent to give a brown solid. The brown solid was suspended in EtOAc-hexane (1:1) and filtered to give 4-amino-6-(1-(1-(pyridin-2-yl)-1H-imidazo[4,5-b]pyridin-2-yl)ethylamino)pyrimidine-5-carbonitrile as a tan solid: $^1$H NMR (400 MHz, DMSO-d$_6$) δ ppm 8.63 (1H, dd, J=4.9, 1.2 Hz), 8.48 (1H, dd, J=4.7, 1.4 Hz), 8.09 (1H, td, J=7.8, 1.9 Hz), 7.85 (1H, s), 7.80 (1H, dd, J=8.1, 1.5 Hz), 7.77 (1H, d, J=7.6 Hz), 7.73 (1H, d, J=8.0 Hz), 7.50-7.57 (1H, m), 7.30 (1H, dd, J=8.1, 4.8 Hz), 7.20 (2H, br. s.), 5.84 (1H, quin, J=6.9 Hz), 1.58 (3H, d, J=6.8 Hz); LC-MS (ESI) m/z 358.1 [M+H]$^+$.

4-Amino-6-(((1R)-1-(1-(2-pyridinyl)-1H-imidazo[4,5-b]pyridin-2-yl)ethyl)amino)-5-pyrimidinecarbonitrile and 4-amino-6-(((1S)-1-(1-(2-pyridinyl)-1H-imidazo[4,5-b]pyridin-2-yl)ethyl)amino)-5-pyrimidinecarbonitrile

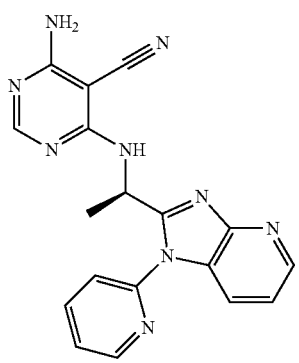

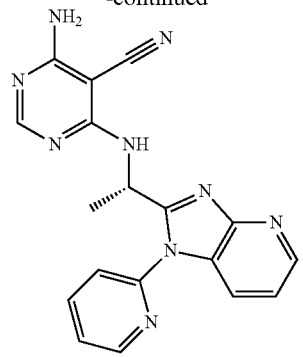

The above racemic mixture (227.63 mg) was separated on AD-H column using preparative SFC to give two fractions: First peak on SFC AD-H column (second peak on Chiralcel™ OD-H column and first peak on Chiralpak™ AD-H column): 4-amino-6-(((1R)-1-(1-(2-pyridinyl)-1H-imidazo[4,5-b]pyridin-2-yl)ethyl)amino)-5-pyrimidinecarbonitrile as a light-yellow solid: $^1$H NMR (400 MHz, DMSO-d$_6$) δ ppm 8.60-8.66 (1H, m), 8.48 (1H, dd, J=4.7, 1.6 Hz), 8.09 (1H, td, J=7.7, 2.0 Hz), 7.85 (1H, s), 7.80 (1H, dd, J=8.2, 1.6 Hz), 7.77 (1H, d, J=7.4 Hz), 7.73 (1H, d, J=8.0 Hz), 7.53 (1H, ddd, J=7.6, 4.8, 0.9 Hz), 7.30 (1H, dd, J=8.1, 4.8 Hz), 7.20 (2H, br. s.), 5.84 (1H, quin, J=7.0 Hz), 1.58 (3H, d, J=6.8 Hz); LC-MS (ESI)] m/z 358.1 [M+H]$^+$. Second peak on SFC AD-H column (first peak on Chiralcel™ OD-H column and second peak on Chiralpak™ AD-H column): 4-amino-6-(((1S)-1-(1-(2-pyridinyl)-1H-imidazo[4,5-b]pyridin-2-yl)ethyl)amino)-5-pyrimidinecarbonitrile as a light-yellow solid: $^1$H NMR (400 MHz, DMSO-d$_6$) δ ppm 8.60-8.65 (1H, m), 8.48 (1H, dd, J=4.7, 1.6 Hz), 8.09 (1H, td, J=7.7, 2.0 Hz), 7.85 (1H, s), 7.80 (1H, dd, J=8.2, 1.6 Hz), 7.76 (1H, d, J=7.6 Hz), 7.73 (1H, d, J=8.0 Hz), 7.53 (1H, ddd, J=7.6, 4.9, 1.0 Hz), 7.30 (1H, dd, J=8.1, 4.8 Hz), 7.20 (2H, br. s.), 5.84 (1H, quin, J=7.0 Hz), 1.58 (3H, d, J=6.8 Hz); LC-MS (ESI)] m/z 358.1 [M+H]$^+$.

Example 57

Preparation of 4-amino-6-(((1R)-1-(1-(3,5-difluorophenyl)-1H-imidazo[4,5-b]pyridin-2-yl)ethyl)amino)-5-pyrimidinecarbonitrile and 4-amino-6-(((1S)-1-(1-(3,5-difluorophenyl)-1H-imidazo[4,5-b]pyridin-2-yl)ethyl)amino)-5-pyrimidinecarbonitrile (3,5-Difluorophenyl)-(2-nitro-pyridin-3-yl)-amine

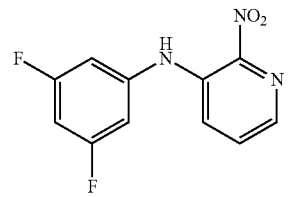 [SMILES: O=[N+]([O-])c1ncccc1Nc1cc(F)cc(F)c1]

To a degassed solution of 3-chloro-2-nitro-pyridine (1.35 g, 8.51 mmol) and 3,5 difluoroaniline (1.0 g, 7.74 mmol) in dimethyl acetamide (23.2 mL) was added cesium carbonate (6.34 g, 19.35 mmol) and the reaction mixture was further degassed with nitrogen for 15 min. xanthophos (267 mg, 0.46 mmol) and Pd$_2$ (dba)$_3$ (212 mg, 0.23 mmol) were added to the reaction mixture and stirred at 100° C. for 12 h. After completion, the reaction mixture was diluted with water (50 mL) and extracted with ethyl actate (2×25 mL). The organic layer was dried over sodium sulfate and concentrated in vacuo to get the crude material, which was purified by column chromatography using silica gel (100-200 mesh) and 0-30% EtOAc in hexane to provide (3,5-difluorophenyl)-(2-nitro-pyridin-3-yl)-amine: $^1$H NMR (DMSO-$d_6$, 400 MHz) δ 6.856-6.980 (m, 3H), 7.659-7.691 (m, 1H), 8.017 (dd, J=1.6 Hz, J=1.6 Hz, 1H), 8.126-8.140 (m, 1H), 9.094 (s, 1H); LC-MS (ESI) m/z 252.0 [M+H]$^+$.

N3-(3,5-Difluorophenyl)-pyridine-2,3-diamine

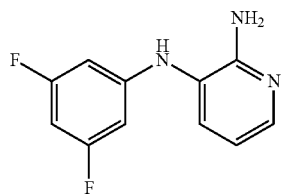 [SMILES: Nc1ncccc1Nc1cc(F)cc(F)c1]

To a solution of (3,5-difluorophenyl)-(2-nitro-pyridin-3-yl)-amine (900 mg, 3.58 mmol) in EtOH (10.7 mL) was added stannous chloride dihydrate (3.23 g, 14.33 mmol) and 35% HCl (0.5 mL). The reaction mixture was stirred at 75° C. for 2 h, when it was basified using aqueous ammonia and extracted with EtOAc. The organic layer was dried over sodium sulfate and concentrated in vacuo to provide N3-(3, 5-Difluorophenyl)-pyridine-2,3-diamine: $^1$H NMR (400 MHz, DMSO-$d_6$) δ 5.703 (br s, 2H), 6.227-6.289 (m, 2H), 6.383-6.442 (m, 1H), 6.564-6.595 (m, 1H), 7.333 (dd, J=1.6 Hz, J=1.6 Hz, 1H), 7.784-7.791 (m, 2H); LC-MS (ESI) m/z 222.0 [M+H]$^+$.

{1-[3-(3,5-Difluorophenylamino)-pyridin-2-ylcarbamoyl]-ethyl}-carbamic acid tert-butyl ester

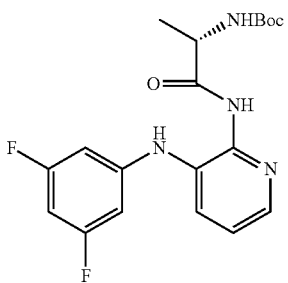 [SMILES: C[C@H](NC(=O)OC(C)(C)C)C(=O)Nc1ncccc1Nc1cc(F)cc(F)c1]

N3-(3,5-Difluorophenyl)-pyridine-2,3-diamine (750 mg, 3.39 mmol), Boc-L-Ala-OH (640 mg, 3.39 mmol) and HATU (2.57 g, 6.78 mmol) were suspended in DCM-DMF (1:1) (10.2 mL). DIEA (874.6 mg, 6.78 mmol) was added to reaction mixture and stirred at rt for 8 h. After completion, the reaction mixture was diluted with water and extracted with EtOAc. The organic layer was dried over sodium sulfate and concentrated in vacuo. The crude product was purified by column chromatography using silica gel (100-200 mesh) and 0-10% MeOH in DCM to provide {1-[3-(3,5-difluorophenylamino)-pyridin-2-ylcarbamoyl]-ethyl}-carbamic acid tert-butyl ester: LC-MS (ESI) m/z 393.2 [M+H]$^+$.

{1-[1-(3,5-Difluorophenyl)-1H-imidazo[4,5-b]pyridin-2-yl]ethyl}-carbamic acid tert-butyl ester

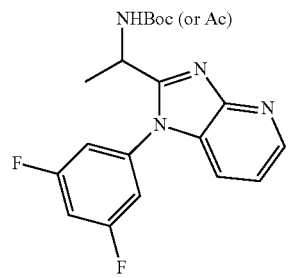

A solution of {1-[3-(3,5-difluorophenylamino)-pyridin-2-ylcarbamoyl]-ethyl}-carbamic acid tert-butyl ester (500 mg, 1.27 mmol) in AcOH (4.0 mL) was stirred at 100° C. overnight. After completion of the reaction the reaction mixture was cooled to rt, basified using satd. sodium bicarbonate solution (25 mL) and extracted with EtOAc. The organic layer was dried over sodium sulfate and concentrated in vacuo to provide a mixture of {1-[1-(3,5-difluorophenyl)-1H-imidazo[4,5-b]pyridin-2-yl]-ethyl}-carbamic acid tert-butyl ester and N-{1-[1-(3,5-difluorophenyl)-1H-imidazo[4,5-b]pyridin-2-yl]-ethyl}-acetamide.

1-[1-(3,5-Difluorophenyl)-1H-imidazo[4,5-b]pyridin-2-yl]ethylamine

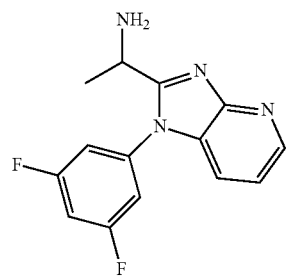 [SMILES: CC(N)c1nc2ncccc2n1-c1cc(F)cc(F)c1]

A crude mixture of {{1-[1-(3,5-difluorophenyl)-1H-imidazo[4,5-b]pyridin-2-yl]-ethyl}-carbamic acid tert-butyl ester and N-{1-[1-(3,5-difluorophenyl)-1H-imidazo[4,5-b]pyridin-2-yl]-ethyl}-acetamide (300 mg) was suspended in methanolic HCl (3 mL). The reaction mixture was stirred at 70° C. for 12 h. After completion of the reaction, the solvent was removed under vacuum. The residue was suspended in water and basified using satd sodium bicarbonate solution and extracted with EtOAc. The organic layer was dried over sodium sulfate and concentrated in vacuo to provide 1-[1-(3, 5-difluorophenyl)-1H-imidazo[4,5-b]pyridin-2-yl]-ethylamine: LC-MS (ESI) m/z 275.1 [M+H]$^+$. The crude product was used without further purification.

4-Amino-6-{1-[1-(3,5-difluorophenyl)-1H-imidazo[4,5-b]pyridin-2-yl]ethylamino}-pyrimidine-5-carbonitrile

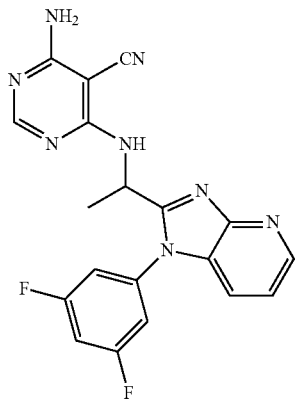 [SMILES: CC(Nc1ncnc(N)c1C#N)c1nc2ncccc2n1-c1cc(F)cc(F)c1]

To a solution of 1-[1-(3,5-difluorophenyl)-1H-imidazo[4,5-b]pyridin-2-yl]-ethylamine (200 mg, 0.729 mmol) and 4-chloro-pyrimidine 5-carbonitrile (112 mg, 0.729 mmol) in n-butanol (2.18 mL) was added DIEA (282 mg, 2.187 mmol) at rt. The reaction mixture was heated at 120° C. overnight. After completion, the reaction mixture was diluted with EtOAc and the resulting solid was collected by filtration to provide 4-amino-6-{1-[1-(3,5-difluorophenyl)-1H-imidazo[4,5-b]-pyridin-2-yl]ethylamino}-pyrimidine-5-carbonitrile: $^1$H NMR (400 MHz, DMSO-d$_6$) δ 1.597 (d, J=6.8 Hz, 3H), 5.631-5.698 (m, 1H), 7.201 (br s, 2H), 7.255-7.287 (m, 1H), 7.363-7.409 (m, 3H), 7.663 (d, J=7.6 Hz, 1H), 7.759 (d, J=7.6 Hz, 1H), 7.882 (s, 1H), 8.462 (d, J=3.6 Hz, 1H); LC-MS (ESI) m/z 393.1 [M+H]$^+$.

Example 58

Preparation of 4-amino-6-(((1R)-1-(1-(3,5-difluorophenyl)-1H-imidazo[4,5-c]pyridin-2-yl)ethyl)amino)-5-pyrimidinecarbonitrile and 4-amino-6-(((1S)-1-(1-(3,5-difluorophenyl)-1H-imidazo[4,5-c]pyridin-2-yl)ethyl)amino)-5-pyrimidinecarbonitrile

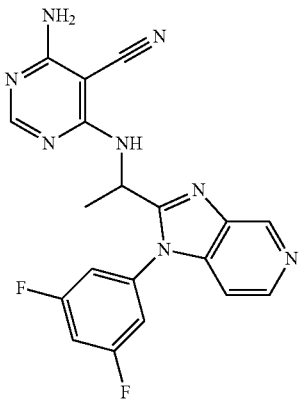 [SMILES: CC(Nc1ncnc(N)c1C#N)c1nc2cnccc2n1-c1cc(F)cc(F)c1]

Prepared according to example 57 to provide 4-amino-6-(1-(1-(3,5-difluorophenyl)-1H-imidazo[4,5-c]pyridin-2-yl)ethyl)amino)-5-pyrimidinecarbonitrile: $^1$H NMR (400 MHz, DMSO-d$_6$) δ 1.597 (d, J=6.8 Hz, 3H), 5.669-5.738 (m, 1H), 7.194 (br s, 2H), 7.274 (d, J=5.6 Hz, 1H), 7.344-7.389 (m, 3H), 7.752 (d, J=7.6 Hz, 1H), 7.874 (s, 1H), 8.347 (d, J=5.6 Hz, 1H), 9.022 (s, 1H).

Example 59

Preparation of 4-amino-6-(((1S)-1-(1-(4-fluorobenzyl)-4-(methylsulfonyl)-1H-benzimidazol-2-yl)ethyl)amino)-5-pyrimidinecarbonitrile

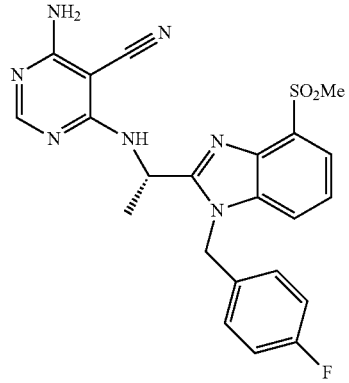 [SMILES: C[C@H](Nc1ncnc(N)c1C#N)c1nc2c(S(C)(=O)=O)cccc2n1Cc1ccc(F)cc1]

A mixture of 4-amino-6-(((1S)-1-(7-(methylsulfonyl)-1H-benzimidazol-2-yl)ethyl)amino)-5-pyrimidinecarbonitrile (36 mg, 0.10 mmol), potassium carbonate (21 mg, 0.15 mmol) and 4-fluorobenzyl bromide (15 μL, 0.12 mmol) in DMF (3 mL) was stirred at rt in a sealed flask for 18 h. The reaction mixture was diluted with EtOAc, washed with water, brine, dried over magnesium sulfate, and concentrated under reduced pressure. Purification of the residue by flash chromatography over silica gel, using 2.5% MeOH in DCM as eluent gave 4-amino-6-(((1S)-1-(1-(4-fluorobenzyl)-4-(methylsulfonyl)-1H-benzimidazol-2-yl)ethyl)amino)-5-pyrimidinecarbonitrile: $^1$H NMR (400 MHz, CDCl$_3$) δ 8.08 (1H, s), 7.88 (1H, d, J=8.0 Hz), 7.44 (1H, d, J=8.0 Hz), 7.31 (1H, t, J=8.0 Hz), 6.93 (4H, t, J=8.0 Hz), 6.19 (1H, t, J=8.0 Hz), 5.80-5.71 (1H, m), 5.52 (1H, d, J=16.0 Hz), 5.50 (1H, d, J=16.0 Hz), 5.31 (2H, br), 3.47 (3H, s), 1.62 (3H, d, J=8.0 Hz); LC-MS (ESI) m/z 466.0 [M+H]$^+$.

Example 60

Preparation of 4-amino-6-(((1S)-1-(1-(4-fluorobenzyl)-7-(methylsulfonyl)-1H-benzimidazol-2-yl)ethyl)amino)-5-pyrimidinecarbonitrile (S)-tert-Butyl 1-(2-(4-fluorobenzylamino)-3-(methylsulfonyl)phenylamino)-1-oxopropan-2-ylcarbamate

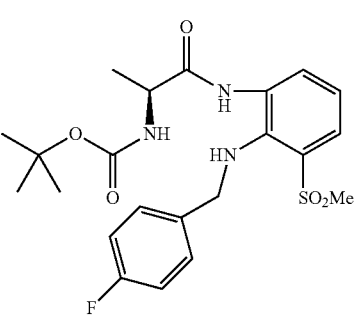 [SMILES: C[C@H](NC(=O)OC(C)(C)C)C(=O)Nc1cccc(S(C)(=O)=O)c1NCc1ccc(F)cc1]

Using the general synthetic procedure for 4-amino-6-(((1S)-1-(1-(4-fluorobenzyl)-4-(methylsulfonyl)-1H-benzimidazol-2-yl)ethyl)amino)-5-pyrimidinecarbonitrile in example 59, (S)-tert-butyl 1-(2-(4-fluorobenzylamino)-3-(methylsulfonyl)phenylamino)-1-oxopropan-2-ylcarbamate was prepared using (S)-tert-butyl 1-(2-amino-3-(methylsulfonyl)phenylamino)-1-oxopropan-2-ylcarbamate (prepared in example 51): LC-MS (ESI) m/z 466.1 [M+H]$^+$.

(S)-1-(1-(4-Fluorobenzyl)-7-(methylsulfonyl)-1H-benzo[d]imidazol-2-yl)ethanamine

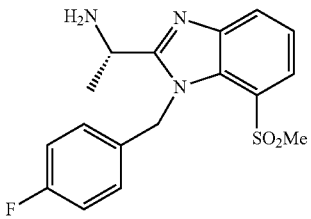 [SMILES: C[C@H](N)c1nc2cccc(S(C)(=O)=O)c2n1Cc1ccc(F)cc1]

Using the general synthetic procedure for (S)-methyl 2-(1-aminoethyl)-1-cyclopropyl-1H-benzo[d]imidazole-7-carboxylate in example 47, (S)-1-(1-(4-fluorobenzyl)-7-(methylsulfonyl)-1H-benzo[d]imidazol-2-yl)ethanamine was prepared using (S)-tert-butyl 1-(2-(4-fluorobenzylamino)-3-(methylsulfonyl)phenylamino)-1-oxopropan-2-ylcarbamate: LC-MS (ESI) m/z 348.1 [M+H]$^+$.

4-Amino-6-(((1S)-1-(1-(4-fluorobenzyl)-7-(methylsulfonyl)-1H-benzimidazol-2-yl)ethyl)amino)-5-pyrimidinecarbonitrile

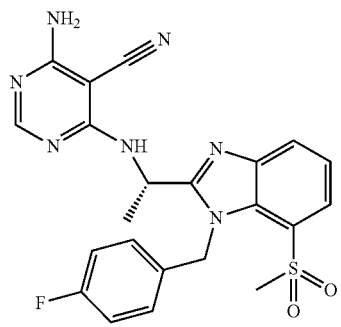 [SMILES: C[C@H](Nc1ncnc(N)c1C#N)c1nc2cccc(S(C)(=O)=O)c2n1Cc1ccc(F)cc1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(4-fluorobenzyl)-7-(methylsulfonyl)-1H-benzimidazol-2-yl)ethyl)amino)-5pyrimidinecarbonitrile was prepared using (S)-1-(1-(4-fluorobenzyl)-7-(methylsulfonyl)-1H-benzo[d]imidazol-2-yl)ethanamine:
$^1$H NMR (400 MHz, CDCl$_3$) δ 8.16 (1H, d, J=8.0 Hz), 8.15 (1H, s), 8.05 (1H, dd, J=8.0, 4.0 Hz), 7.50 (1H, t, J=8.0 Hz), 7.05-6.98 (2H, m), 6.88-6.81 (2H, m), 6.32 (1H, d, J=16.0 Hz), 6.20 (1H, br), 6.14 (1H, d, J=16.0 Hz), 5.80-5.71 (1H, m), 5.57 (2H, br), 2.70 (3H, s), 1.67 (3H, d, J=8.0 Hz); LC-MS (ESI) m/z 466.0 [M+H]$^+$.

Example 61

Preparation of 4-amino-6-(((1S)-1-(1-(3,5-difluorobenzyl)-7-(methylsulfonyl)-1H-benzimidazol-2-yl)ethyl)amino)-5-pyrimidinecarbonitrile (S)-tert-Butyl 1-(2-(3,5-difluorobenzylamino)-3-(methylsulfonyl)phenylamino)-1-oxopropan-2-ylcarbamate

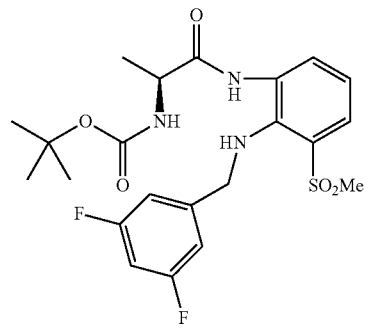 [SMILES: C[C@H](NC(=O)OC(C)(C)C)C(=O)Nc1cccc(S(C)(=O)=O)c1NCc1cc(F)cc(F)c1]

Using the general synthetic procedure for 4-amino-6-(((1S)-1-(1-(4-fluorobenzyl)-4-(methylsulfonyl)-1H-benzimidazol-2-yl)ethyl)amino)-5-pyrimidinecarbonitrile in example 59, (S)-tert-butyl 1-(2-(3,5-difluorobenzylamino)-3-(methylsulfonyl)phenylamino)-1-oxopropan-2-ylcarbamate was prepared using (S)-tert-butyl 1-(2-amino-3-(methylsulfonyl)phenylamino)-1-oxopropan-2-ylcarbamate (Prepared in Example 51): LC-MS (ESI) m/z 484.1 [M+H]$^+$.

(S)-1-(1-(3,5-Difluorobenzyl)-7-(methylsulfonyl)-1H-benzo[d]imidazol-2-yl)ethanamine

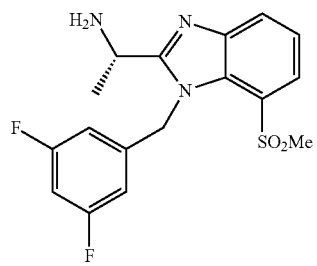 [SMILES: C[C@H](N)c1nc2cccc(S(C)(=O)=O)c2n1Cc1cc(F)cc(F)c1]

Using the general synthetic procedure for (S)-methyl 2-(1-aminoethyl)-1-cyclopropyl-1H-benzo[d]imidazole-7-carboxylate in example 47, (S)-1-(1-(3,5-di-fluorobenzyl)-7-(methylsulfonyl)-1H-benzo[d]imidazol-2-yl)ethanamine was prepared using (S)-tert-butyl 1-(2-(3,5-difluorobenzylamino)-3-(methylsulfonyl)phenylamino)-1-oxopropan-2-ylcarbamate: LC-MS (ESI) m/z 366.1 [M+H]$^+$.

4-Amino-6-(((1S)-1-(1-(3,5-difluorobenzyl)-7-(methylsulfonyl)-1H-benzimidazol-2-yl)ethyl)amino)-5-pyrimidinecarbonitrile

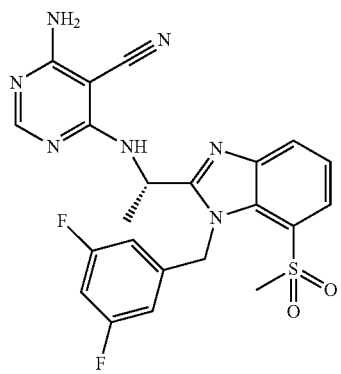 [SMILES: C[C@H](Nc1ncnc(N)c1C#N)c1nc2cccc(S(C)(=O)=O)c2n1Cc1cc(F)cc(F)c1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(3,5-difluorobenzyl)-7-(methylsulfonyl)-1H-benzimidazol-2-yl)ethyl)amino)-5-pyrimidinecarbonitrile was prepared using (S)-1-(1-(3,5-difluorobenzyl)-7-(methylsulfonyl)-1H-benzo[d]imidazol-2-yl)ethanamine: $^1$H NMR (400 MHz, CDCl$_3$) δ 8.16 (1H, d, J=8.0 Hz), 8.16 (1H, s), 8.05 (1H, dd, J=8.0, 4.0 Hz), 7.51 (1H, t, J=8.0 Hz), 6.79-6.71 (1H, m), 6.50-6.45 (2H, m), 6.37 (1H, d, J=16.0 Hz), 6.26 (1H, br), 6.11 (1H, d, J=16.0 Hz), 5.75 (2H, br), 5.72-5.62 (1H, m), 3.52 (3H, s), 1.70 (3H, d, J=8.0 Hz); LC-MS (ESI) m/z 484.0 [M+H]$^+$.

Example 62

5-Fluoro-N-(4-fluoro-2-nitrophenyl)pyridin-3-amine

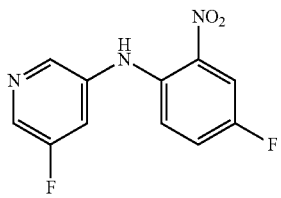 [SMILES: O=[N+]([O-])c1cc(F)ccc1Nc1cncc(F)c1]

Prepared according to Step D1 in General Procedure D using 5-fluoropyridin-3-amine (2.114 g, 18.86 mmol) to give 5-fluoro-N-(4-fluoro-2-nitrophenyl)pyridin-3-amine as an orange solid. LC-MS (ESI) m/z 252.1 [M+H]$^+$.

4-Fluoro-N1-(5-fluoropyridin-3-yl)benzene-1,2-diamine

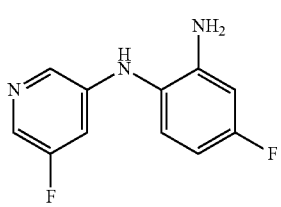 [SMILES: Nc1cc(F)ccc1Nc1cncc(F)c1]

Prepared according to Step D2 in General Procedure D using 5-fluoro-N-(4-fluoro-2-nitrophenyl)pyridin-3-amine (1.42 g, 5.64 mmol) to give 4-fluoro-N1-(5-fluoropyridin-3-yl)benzene-1,2-diamine as a red oil. LC-MS (ESI) m/z 222.1 [M+H]$^+$.

tert-Butyl 1-(5-fluoro-2-(5-fluoropyridin-3-ylamino)phenylamino)-1-oxopropan-2-ylcarbamate

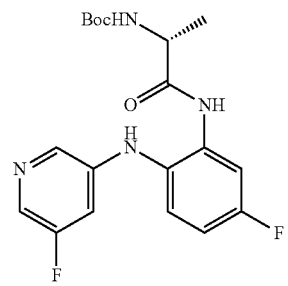 [SMILES: C[C@@H](NC(=O)OC(C)(C)C)C(=O)Nc1cc(F)ccc1Nc1cncc(F)c1]

Prepared according to Step D3 in General Procedure D using 4-fluoro-N1-(5-fluoropyridin-3-yl)benzene-1,2-diamine (0.890 g, 4.02 mmol) to give tert-butyl 1-(5-fluoro-2-(5-fluoropyridin-3-ylamino)phenylamino)-1-oxopropan-2-ylcarbamate as a white solid. LC-MS (ESI) m/z 393.2 [M+H]$^+$. N-(1-(5-Fluoro-1-(5-fluoropyridin-3-yl)-1H-benzo[d]imidazol-2-yl)ethyl)acetamide

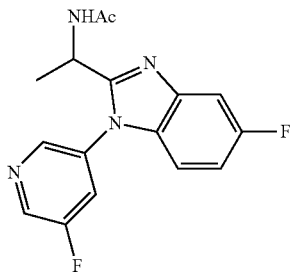 [SMILES: CC(=O)NC(C)c1nc2cc(F)ccc2n1-c1cncc(F)c1]

Prepared according to Step D4 in General Procedure D using tert-butyl 1-(5-fluoro-2-(5-fluoropyridin-3-ylamino)phenylamino)-1-oxopropan-2-ylcarbamate (0.500 g, 1.274 mmol) to give N-(1-(5-fluoro-1-(5-fluoropyridin-3-yl)-1H-benzo[d]imidazol-2-yl)ethyl)acetamide as a tan solid. LC-MS (ESI) m/z 317.1 [M+H]$^+$.

1-(5-Fluoro-1-(5-fluoropyridin-3-yl)-1H-benzo[d]imidazol-2-yl)ethanamine

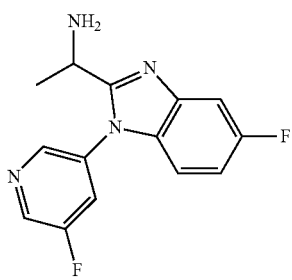 [SMILES: CC(N)c1nc2cc(F)ccc2n1-c1cncc(F)c1]

Prepared according to Step D5a in General Procedure D using N-(1-(5-fluoro-1-(5-fluoropyridin-3-yl)-1H-benzo[d]imidazol-2-yl)ethyl)acetamide (0.110 g, 0.348 mmol) to give 1-(5-fluoro-1-(5-fluoropyridin-3-yl)-1H-benzo[d]imidazol-2-yl)ethanamine as a tan foam. LC-MS (ESI) m/z 275.1 [M+H]+.

4-Amino-6-(1-(5-fluoro-1-(5-fluoropyridin-3-yl)-1H-benzo[d]imidazol-2-yl)ethylamino)pyrimidine-5-carbonitrile

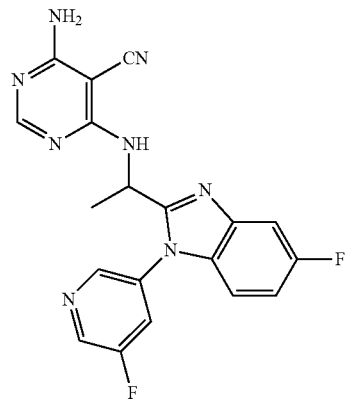 [SMILES: CC(Nc1ncnc(N)c1C#N)c1nc2cc(F)ccc2n1-c1cncc(F)c1]

Prepared according to Step D6 in General Procedure D using 1-(5-fluoro-1-(5-fluoropyridin-3-yl)-1H-benzo[d]imidazol-2-yl)ethanamine (0.095 g, 0.346 mmol) to give 4-amino-6-(1-(5-fluoro-1-(5-fluoropyridin-3-yl)-1H-benzo[d]imidazol-2-yl)ethylamino)pyrimidine-5-carbonitrile as a white solid. $^1$H NMR (400 MHz, DMSO-$d_6$) δ ppm 1.59 (d, J=6.85 Hz, 3H) 5.59 (quin, J=6.99 Hz, 1H) 7.02-7.39 (m, 4H) 7.60 (dd, J=9.59, 2.35 Hz, 1H) 7.77 (d, J=7.63 Hz, 1H) 7.84 (s, 1H) 8.10 (d, J=9.19 Hz, 1H) 8.63 (s, 1H) 8.68 (d, J=2.74 Hz, 1H). LC-MS (ESI) m/z 393.0 [M+H]+.

4-Amino-6-(((1R)-1-(5-fluoro-1-(5-fluoro-3-pyridinyl)-1H-benzimidazol-2-yl)ethyl)amino)-5-pyrimidinecarbonitrile and 4-amino-6-(((1S)-1-(5-fluoro-1-(5-fluoro-3-pyridinyl)-1H-benzimidazol-2-yl)ethyl)amino)-5-pyrimidinecarbonitrile

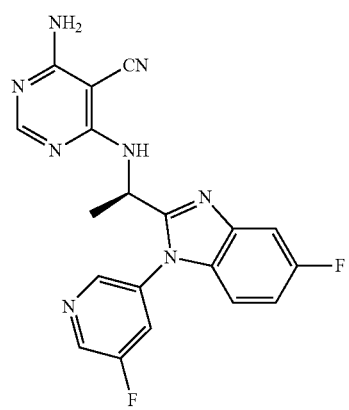

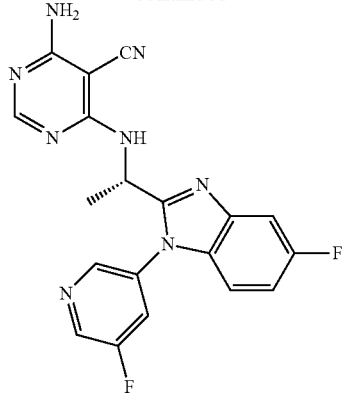

The racemic mixture (96 mg) was separated on AD-H column using preparative SFC to give two fractions. First peak on OD-H column: 4-Amino-6-(((1R)-1-(5-fluoro-1-(5-fluoro-3-pyridinyl)-1H-benzimidazol-2-yl)ethyl)amino)-5-pyrimidinecarbonitrile as a light yellow solid. $^1$H NMR (400 MHz, DMSO-$d_6$) δ ppm 1.60 (d, J=6.85 Hz, 3H) 5.59 (quin, J=6.99 Hz, 1H) 7.01-7.34 (m, 4H) 7.60 (dd, J=9.59, 2.35 Hz, 1H) 7.77 (d, J=7.63 Hz, 1H) 7.84 (s, 1H) 8.10 (d, J=9.00 Hz, 1H) 8.64 (s, 1H) 8.69 (d, J=2.54 Hz, 1H). LC-MS (ESI) m/z 393.0 [M+H]+. Second peak on OD-H column: 4-Amino-6-(((1S)-1-(5-fluoro-1-(5-fluoro-3-pyridinyl)-1H-benzimidazol-2-yl)ethyl)amino)-5-pyrimidinecarbonitrile as a light yellow solid. $^1$H NMR (400 MHz, DMSO-$d_6$) δ ppm 1.59 (d, J=6.65 Hz, 3H) 5.59 (quin, J=6.90 Hz, 1H) 7.01-7.35 (m, 4H) 7.60 (dd, J=9.59, 2.54 Hz, 1H) 7.77 (d, J=7.82 Hz, 1H) 7.84 (s, 1H) 8.10 (d, J=9.19 Hz, 1H) 8.63 (s, 1H) 8.68 (d, J=2.54 Hz, 1H). LC-MS (ESI) m/z 393.0 [M+H]+.

Example 63

(S)-Benzyl 1-(6-fluoro-3-(5-fluoropyridin-3-yl)imidazo[1,2-a]pyridin-2-yl)ethylcarbamate

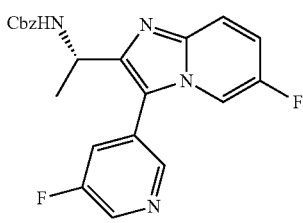 [SMILES: C[C@H](NC(=O)OCc1ccccc1)c1nc2ccc(F)cn2c1-c1cncc(F)c1]

A solution of 5-fluoropyridin-3-ylboronic acid (0.096 g, 0.68 mmol), (S)-benzyl 1-(6-fluoro-3-iodoimidazo[1,2-a]pyridin-2-yl)ethylcarbamate (0.200 g, 0.455 mmol), sodium carbonate (0.145 g, 1.366 mmol), and 1,1'-bis(diphenylphosphino)ferrocene palladium (II) chloride, 1:1 complex with DCM (0.019 g, 0.023 mmol) in dioxane (2.53 mL) and water (0.50 mL) was stirred at 110° C. under microwave irradiation for 2 h. Purification by MPLC (eluted with a gradient of 10-60% EtOAc in hexanes) afforded crude (S)-benzyl 1-(6-fluoro-3-(5-fluoropyridin-3-yl)imidazo[1,2-a]pyridin-2-yl)ethylcarbamate as an off-white foam. LC-MS (ESI) m/z 409.1 [M+H]

(S)-1-(6-Fluoro-3-(5-fluoropyridin-3-yl)imidazo[1,2-a]pyridin-2-yl)ethanamine

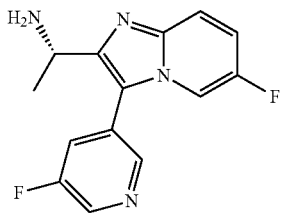 [SMILES: C[C@H](N)c1nc2ccc(F)cn2c1-c1cncc(F)c1]

Prepared according to Step C4 in General Procedure C using (S)-benzyl 1-(6-fluoro-3-(5-fluoropyridin-3-yl)imidazo[1,2-a]pyridin-2-yl)ethylcarbamate (0.142 g, 0.348 mmol) to give (S)-1-(6-fluoro-3-(5-fluoropyridin-3-yl)imidazo[1,2-a]-pyridin-2-yl)ethanamine as a tan solid. LC-MS (ESI) m/z 275.1 [M+H]$^+$.

4-Amino-6-(((1S)-1-(6-fluoro-3-(5-fluoro-3-pyridinyl)imidazo[1,2-a]pyridin-2-yl)ethyl)amino)-5-pyrimidinecarbonitrile

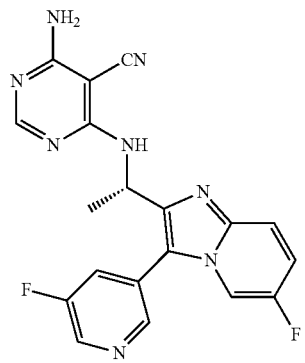 [SMILES: C[C@H](Nc1ncnc(N)c1C#N)c1nc2ccc(F)cn2c1-c1cncc(F)c1]

Prepared according to Step C5 in General Procedure C using (S)-1-(6-fluoro-3-(5-fluoropyridin-3-yl)imidazo[1,2-a]pyridin-2-yl)ethanamine (0.095 g, 0.346 mmol) to give (S)-4-amino-6-(1-(6-fluoro-3-(5-fluoropyridin-3-yl)imidazo[1,2-a]pyridin-2-yl)ethylamino)pyrimidine-5-carbonitrile as an off-white solid. $^1$H NMR (400 MHz, DMSO-$d_6$) δ ppm 1.54 (d, J=6.85 Hz, 3H) 5.47 (quin, J=6.90 Hz, 1H) 7.09 (d, J=7.24 Hz, 1H) 7.22 (br. s., 2H) 7.39-7.48 (m, 1H) 7.74 (dd, J=9.78, 5.28 Hz, 1H) 7.89 (s, 1H) 8.00 (dt, J=9.73, 1.98 Hz, 1H) 8.43 (dd, J=4.50, 2.15 Hz, 1H) 8.56 (s, 1H) 8.66 (d, J=2.74 Hz, 1H). LC-MS (ESI) m/z 393.0 [M+H]$^+$.

Example 64

(S)-Benzyl 1-(6-fluoro-3-phenylimidazo[1,2-a]pyridin-2-yl)ethylcarbamate

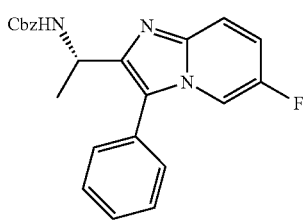 [SMILES: C[C@H](NC(=O)OCc1ccccc1)c1nc2ccc(F)cn2c1-c1ccccc1]

To a microwave vial was added phenylboronic acid (0.104 g, 0.852 mmol), (S)-benzyl 1-(6-fluoro-3-iodoimidazo[1,2-a]pyridin-2-yl)ethylcarbamate (0.250 g, 0.568 mmol), sodium carbonate (0.181 g, 1.74 mmol), and 1,1'-bis(diphenyl-phosphino)ferrocene palladium (II) chloride, 1:1 complex with DCM (0.023 g, 0.028 mmol) in dioxane (3.44 mL) and water (0.34 mL). The suspension was stirred at 110° C. under microwave irradiation for 2 h. Purification by MPLC (eluted with a gradient of 0-6% MeOH in DCM) afforded (S)-benzyl 1-(6-fluoro-3-phenylimidazo[1,2-a]pyridin-2-yl)ethylcarbamate as a brown oil. LC-MS (ESI) m/z 390.1 [M+H]$^+$.

(S)-1-(6-Fluoro-3-phenylimidazo[1,2-a]pyridin-2-yl)ethanamine

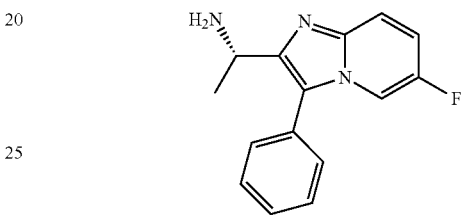

Prepared according to Step C4 in General Procedure C using (S)-benzyl 1-(6-fluoro-3-phenylimidazo[1,2-a]pyridin-2-yl)ethylcarbamate (0.142 g, 0.365 mmol) to give (S)-1-(6-fluoro-3-phenylimidazo[1,2-a]pyridin-2-yl)ethanamine as a yellow solid. LC-MS (ESI) m/z 256.1 [M+H]$^+$.

(S)-4-amino-6-(1-(6-fluoro-3-phenylimidazo[1,2-a]pyridin-2-yl)ethylamino)pyrimidine-5-carbonitrile

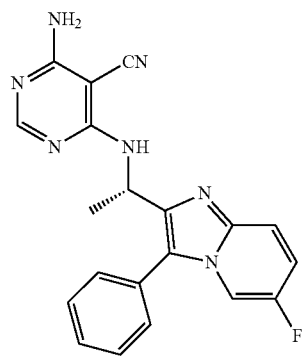 [SMILES: C[C@H](Nc1ncnc(N)c1C#N)c1nc2ccc(F)cn2c1-c1ccccc1]

Prepared according to Step C5 in General Procedure C using (S)-1-(6-fluoro-3-phenylimidazo[1,2-a]pyridin-2-yl)ethanamine (0.093 g, 0.364 mmol) to give (S)-4-amino-6-(1-(6-fluoro-3-phenylimidazo[1,2-a]pyridin-2-yl)ethylamino)pyrimidine-5-carbonitrile as a beige solid. $^1$H NMR (400 MHz, DMSO-$d_6$) δ ppm 1.50 (d, J=6.65 Hz, 3H) 5.47 (quin, J=6.85 Hz, 1H) 6.91 (d, J=7.43 Hz, 1H) 7.27 (br. s., 2H) 7.41 (ddd, J=10.03, 8.07, 2.45 Hz, 1H) 7.51 (dq, J=8.85, 4.22 Hz, 1H) 7.58 (d, J=4.30 Hz, 4H) 7.75 (dd, J=9.78, 5.28 Hz, 1H) 7.97 (s, 1H) 8.25 (dd, J=4.50, 2.35 Hz, 1H). LC-MS (ESI) m/z 374.1 [M+H]$^+$.

Example 65

Preparation of 2-((1R)-1-(((6-amino-5-cyano-4-pyrimidinyl)amino)ethyl)-1-(5-fluoro-3-pyridinyl)-N-methyl-1H-benzimidazole-7-carboxamide, and 2-((1S)-1-(((6-amino-5-cyano-4-pyrimidinyl)amino)ethyl)-1-(5-fluoro-3-pyridinyl)-N-methyl-1H-benzimidazole-7-carboxamide 2-(5-Fluoropyridin-3-ylamino)-N-methyl-3-nitrobenzamide

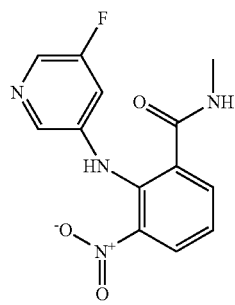

A mixture of cesium carbonate (1.55 g, 4.75 mmol), xantphos (550 mg, 0.950 mmol), 2-bromo-N-methyl-3-nitrobenzamide (820 mg, 3.17 mmol) (Prepared in Example 20), tris(dibenzylideneacetone)dipalladium (0) (580 mg, 0.63 mmol), 5-fluoropyridin-3-amine (532 mg, 4.75 mmol) in toluene (15 mL) under $N_2$ was heated at 100° C. for 18 h. The mixture was cooled to rt and diluted with EtOAc. The mixture was filtered and the filtrates were concentrated in vacuo. Purification of the residue by flash chromatography over silica gel, using EtOAc as eluent gave 2-(5-fluoropyridin-3-ylamino)-N-methyl-3-nitrobenzamide: $^1$H NMR (400 MHz, CDCl$_3$) δ 9.29 (1H, s), 8.23 (1H, s), 8.21 (1H, d, J=8.0 Hz), 8.16 (1H, s), 7.89 (1H, d, J=8.0 Hz), 7.26 (1H, t, J=8.0 Hz), 7.04 (1H, d, J=8.0 Hz), 6.41 (1H, br), 2.78 (3H, d, J=4.0 Hz); LC-MS (ESI) m/z 291.1 [M+H]$^+$.

3-Amino-2-(5-fluoropyridin-3-ylamino)-N-methylbenzamide

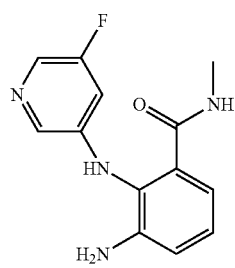 [SMILES: CNC(=O)c1cccc(N)c1Nc1cncc(F)c1]

Using the general synthetic procedure for methyl 3-amino-2-(cyclopropylamino)benzoate in example 47, 3-amino-2-(5-fluoropyridin-3-ylamino)-N-methylbenzamide was prepared using 2-(5-fluoropyridin-3-ylamino)-N-methyl-3-nitrobenzamide: LC-MS (ESI) m/z 261.1 [M+H]$^+$.

(S)-tert-Butyl 1-(2-(5-fluoropyridin-3-ylamino)-3-(methylcarbamoyl)phenylamino)-1-oxopropan-2-ylcarbamate

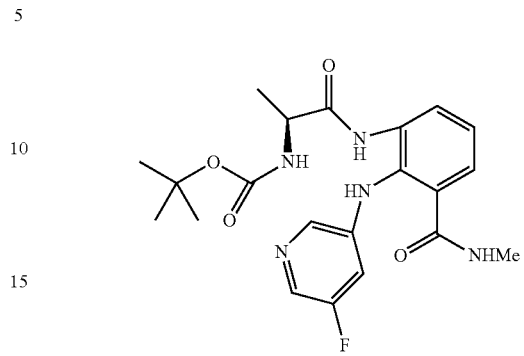

Using the general synthetic procedure for (S)-methyl 3-(2-(tert-butoxycarbonylamino)propanamido)-2-(cyclopropylamino)benzoate in example 47, (S)-tert-butyl 1-(2-(5-fluoropyridin-3-ylamino)-3-(methylcarbamoyl)phenylamino)-1-oxopropan-2-ylcarbamate was prepared using 3-amino-2-(5-fluoropyridin-3-yl-amino)-N-methylbenzamide: $^1$H NMR (400 MHz, CDCl$_3$) δ 8.60 (1H, br), 8.43 (1H, br), 8.34 (1H, d, J=8.0 Hz), 8.13 (1H, br), 8.00 (1H, s), 7.42-7.32 (2H, m), 6.73 (1H, d, J=8.0 Hz), 6.47 (1H, br), 4.84 (1H, br), 4.24 (1H, br), 2.94 (3H, d, J=4.0 Hz), 1.41 (9H, s), 1.28 (3H, d, J=4.0 Hz); LC-MS (ESI) m/z 432.1 [M+H]$^+$.

(S)-2-(1-Aminoethyl)-1-(5-fluoropyridin-3-yl)-N-methyl-1H-benzo[d]-imidazole-7-carboxamide and (R)-2-(1-aminoethyl)-1-(5-fluoropyridin-3-yl)-N-methyl-1H-benzo[d]imidazole-7-carboxamide

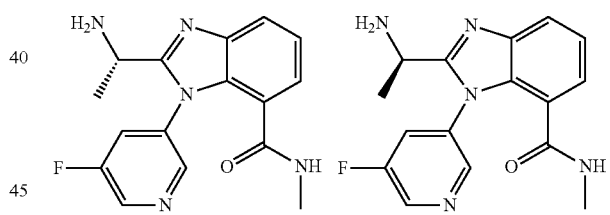

A stirred suspension of (S)-tert-butyl 1-(2-(5-fluoropyridin-3-ylamino)-3-(methylcarbamoyl)phenylamino)-1-oxopropan-2-ylcarbamate (260 mg, 0.60 mmol) and HOAc (3 mL) in a sealed Q-Tube was heated at 140° C. for 2 h. The mixture was cooled to rt and concentrated in vacuo. To the residue mixture 37% HCl (10 mL) was added. The mixture was refluxed for 3 h cooled to rt and concentrated in vacuo. The residue was dissolved in water (5 mL) and basified with 1N NaOH to pH 9.5. The mixture was concentrated in vacuo and triturated with MeOH-CDM (1:1). The crude product in the solution was concentrated in vacuo. Purification of the residue by flash chromatography over silica gel, using 6 to 15% gradient of MeOH in DCM-EtOAc (1:1) with 0.2% NH$_4$OH as eluent to give a racemic mixture of (S)-2-(1-aminoethyl)-1-(5-fluoropyridin-3-yl)-N-methyl-1H-benzo[d]imidazole-7-carboxamide and (R)-2-(1-aminoethyl)-1-(5-fluoropyridin-3-yl)-N-methyl-1H-benzo[d]imidazole-7-carboxamide: $^1$H NMR (400 MHz, MeOH-d$_4$) 8.72 (1H, d, J=4.0 Hz), 8.59 (0.5H, s), 8.49 (0.5H, s), 7.97-7.92 (0.5H, m), 7.88-7.82 (1.5H, m), 7.41 (0.5H, d, J=8.0 Hz), 7.39 (0.5H, d, J=8.0 Hz), 7.34 (1H, d, J=8.0 Hz), 4.05-3.98 (1H, m), 2.50 (3H, s), 1.48 (3H, dd, J=4.0, 4.0 Hz); LC-MS (ESI) m/z 314.2 [M+H]+.

2-((1R)-1-((6-Amino-5-cyano-4-pyrimidinyl)amino)ethyl)-1-(5-fluoro-3-pyridinyl)-N-methyl-1H-benzimidazole-7-carboxamide and 2-((1S)-1-((6-amino-5-cyano-4-pyrimidinyl)amino)ethyl)-1-(5-fluoro-3-pyridinyl)-N-methyl-1H-benzimidazole-7-carboxamide

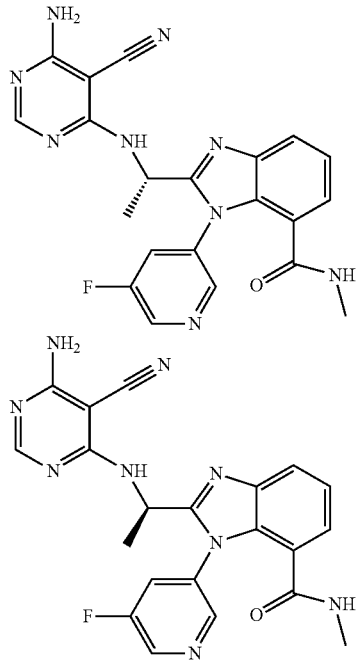

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, the racemic mixture of 2-((1R)-1-((6-amino-5-cyano-4-pyrimidinyl)amino)ethyl)-1-(5-fluoro-3-pyridinyl)-N-methyl-1H-benzimidazole-7-carboxamide, and 2-((1S)-1-((6-amino-5-cyano-4-pyrimidinyl)amino)ethyl)-1-(5-fluoro-3-pyridinyl)-N-methyl-1H-benzimidazole-7-carboxamide was prepared using a racemic mixture of (S)-2-(1-aminoethyl)-1-(5-fluoropyridin-3-yl)-N-methyl-1H-benzo[d]imidazole-7-carboxamide and (R)-2-(1-aminoethyl)-1-(5-fluoropyridin-3-yl)-N-methyl-1H-benzo[d]imidazole-7-carboxamide: 1H NMR (400 MHz, DMSO-d6) δ 8.60 (0.5H, br), 8.54 (1H, br), 8.33 (0.5H, br), 8.20-8.14 (1H, m), 8.04 (0.5H, d, J=8.0 Hz), 7.84-7.73 (3H, m), 7.64 (0.5H, d, J=8.0 Hz), 7.30 (1H, t, J=8.0 Hz), 7.25-7.15 (3H, m), 5.55-5.40 (1H, m), 2.24 (3H, d, J=4.0 Hz), 1.58 (3H, d, J=4.0 Hz); LC-MS (ESI) m/z 432.1 [M+H]+.

The racemic mixture was separated by chiral separation using SFC to give two fractions: First-eluting enantiomer on the AD-H column: 2-((1R)-1-((6-amino-5-cyano-4-pyrimidinyl)amino)ethyl)-1-(5-fluoro-3-pyridinyl)-N-methyl-1H-benzimidazole-7-carboxamide: 1H NMR (400 MHz, DMSO-d6) δ 8.60 (0.5H, br), 8.54 (1H, br), 8.33 (0.5H, br), 8.20-8.14 (1H, m), 8.04 (0.5H, d, J=8.0 Hz), 7.84-7.73 (3H, m), 7.64 (0.5H, d, J=8.0 Hz), 7.30 (1H, t, J=8.0 Hz), 7.25-7.15 (3H, m), 5.55-5.40 (1H, m), 2.24 (3H, d, J=4.0 Hz), 1.58 (3H, d, J=4.0 Hz); LC-MS (ESI) m/z 432.1 [M+H]+. Second-eluting enantiomer on the AD-H column: 2-((1S)-1-((6-amino-5-cyano-4-pyrimidinyl)amino)ethyl)-1-(5-fluoro-3-pyridinyl)-N-methyl-1H-benzimidazole-7-carboxamide: 1H NMR (400 MHz, DMSO-d6) δ 8.60 (0.5H, br), 8.54 (1H, br), 8.33 (0.5H, br), 8.20-8.14 (1H, m), 8.04 (0.5H, d, J=8.0 Hz), 7.84-7.73 (3H, m), 7.64 (0.5H, d, J=8.0 Hz), 7.30 (1H, t, J=8.0 Hz), 7.25-7.15 (3H, m), 5.55-5.40 (1H, m), 2.24 (3H, d, J=4.0 Hz), 1.58 (3H, d, J=4.0 Hz); LC-MS (ESI) m/z 432.1 [M+H]+.

Example 66

Preparation of 4-amino-6-(((1S)-1-(1-(cyclopropylmethyl)-7-(methylsulfonyl)-1H-benzimidazol-2-yl)ethyl)amino)-5-pyrimidinecarbonitrile (S)-tert-Butyl 1-(2-(cyclopropylmethylamino)-3-(methylsulfonyl)phenylamino)-1-oxopropan-2-ylcarbamate

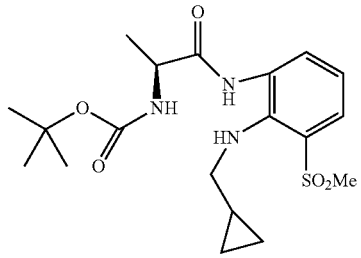 [SMILES: C[C@H](NC(=O)OC(C)(C)C)C(=O)Nc1cccc(S(C)(=O)=O)c1NCC1CC1]

To a mixture of (S)-tert-butyl 1-(2-amino-3-(methylsulfonyl)phenylamino)-1-oxopropan-2-ylcarbamate (prepared in example 51) (440 mg, 1.23 mmol), glacial AcOH (0.43 mL, 7.4 mmol) and cyclopropanecarbaldehyde (0.18 mL, 2.5 mmol) in 1,2-dichloroethane (5 mL) was added sodium triacetoxyborohydride (780 mg, 3.7 mmol) and stirred at rt under N2 for 18 h. The reaction mixture was diluted with EtOAc, washed with water, sat. aq sodium bicarbonate solution, brine, dried over magnesium sulfate, and concentrated in vacuo. Purification of the residue by flash chromatography on silica gel column using 10 to 20% gradient of EtOAC:DCM (1:1) in DCM as eluent to give (S)-tert-butyl 1-(2-(cyclopropylmethylamino)-3-(methylsulfonyl)phenylamino)-1-oxopropan-2-ylcarbamate: LC-MS (ESI) m/z 412.1 [M+H]+.

(S)-1-(1-(Cyclopropylmethyl)-7-(methylsulfonyl)-1H-benzo[d]imidazol-2-yl)ethanamine Using the general synthetic procedure for (S)-methyl 2-(1-aminoethyl)-1-cyclopropyl-1H-benzo[d]imidazole-7-carboxylate in example 47, (S)-1-(1-(cyclopropylmethyl)-7-(methylsulfonyl)-1H-benzo[d]imidazol-2-yl)ethanamine was prepared using (S)-tert-butyl 1-(2-(cyclopropylmethylamino)-3-(methylsulfonyl)phenylamino)-1-oxopropan-2-ylcarbamate: LC-MS (ESI) m/z 294.1 [M+H]+.

4-Amino-6-(((1S)-1-(1-(cyclopropylmethyl)-7-(methylsulfonyl)-1H-benzimidazol-2-yl)ethyl)amino)-5-pyrimidinecarbonitrile

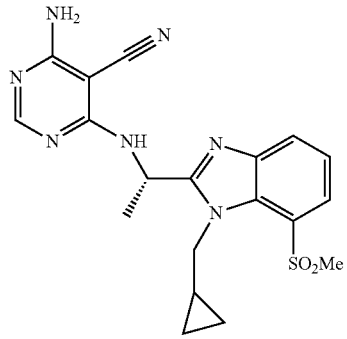 [SMILES: C[C@H](Nc1ncnc(N)c1C#N)c1nc2cccc(S(C)(=O)=O)c2n1CC1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(cyclopropylmethyl)-7-(methylsulfonyl)-1H-benzimidazol-2-yl)ethyl)amino)-5-pyrimidinecarbonitrile was prepared using (S)-1-(1-(cyclopropylmethyl)-7-(methylsulfonyl)-1H-benzo[d]imidazol-2-yl)ethanamine: $^1$H NMR (400 MHz, DMSO-$d_6$) δ 8.06 (1H, s), 8.03 (1H, d, J=8.0 Hz), 7.89 (1H, d, J=8.0 Hz), 7.76 (1H, t, J=8.0 Hz), 7.43 (1H, t, J=8.0 Hz), 7.34 (2H, br), 5.84-5.76 (1H, m), 4.82 (1H, dd, J=12.0, 4.0 Hz), 4.55 (1H, dd, J=12.0, 4.0 Hz), 3.44 (3H, s), 1.66 (3H, d, J=4.0 Hz), 1.34-1.26 (1H, m), 0.55-0.35 (4H, m); LC-MS (ESI) m/z 412.0 [M+H]$^+$.

Example 67

Preparation of 4-amino-6-(((1S)-1-(3-(2-pyridinyl)imidazo[1,2-a]pyrimidin-2-yl)ethyl)amino)-5-pyrimidinecarbonitrile (1-Imidazo[1,2-a]pyrimidin-2-yl-ethyl)-carbamic acid benzyl ester

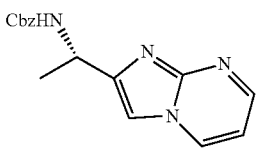 [SMILES: C[C@H](NC(=O)OCc1ccccc1)c1cn2cccnc2n1]

A mixture of pyrimidin-2-ylamine (3 gm, 31.5 mmol) and (3-bromo-1-methyl-2-oxopropyl)-carbamic acid benzyl ester (9.4 gm, 31.54 mmol) in EtOH (20 mL) was heated to reflux overnight. After completion, the reaction mixture was cooled to rt and EtOH was removed in vacuo. The residue was dissolved in EtOAc and washed with satd. sodium bicarbonate solution. The organic layer was dried over sodium sulfate, filtered and concentrated in vacuo. The crude product was purified by column chromatography using silica gel (100-200 mesh) and 0-5% MeOH in DCM to provide (1-imidazo[1,2-a]pyrimidin-2-yl-ethyl)-carbamic acid benzyl ester: LC-MS (ESI) m/z 297.1 [M+H]$^+$.

[1-(3-Iodo-imidazo[1,2-a]pyrimidin-2-yl)-ethyl]-carbamic acid benzyl ester

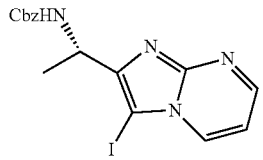 [SMILES: C[C@H](NC(=O)OCc1ccccc1)c1nc2ncccn2c1I]

To a solution of (1-imidazo[1,2-a]pyrimidin-2-yl-ethyl)-carbamic acid benzyl ester (5.3 g, 17.90 mmol) in acetonitrile (30 mL) was added n-iodosuccinimide (4.0 g, 17.90 mmol) and stirred at rt overnight. After completion of the reaction, the mixture was diluted with water and extracted with EtOAc. The organic layer was washed with satd. sodium bicarbonate solution, dried over sodium sulfate, filtered and concentrated in vacuo. The crude product was purified by column chromatography using silica gel (100-200 mesh) and 0-4% MeOH in DCM to provide [1-(3-iodo-imidazo[1,2-a]pyrimidin-2-yl)-ethyl]-carbamic acid benzyl ester: LC-MS (ESI) m/z 422.8 [M+H]$^+$.

[1-(3-Pyridin-2-yl-imidazo[1,2-a]pyrimidin-2-yl)-ethyl]-carbamic acid benzyl ester

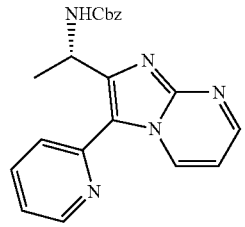 [SMILES: C[C@H](NC(=O)OCc1ccccc1)c1nc2ncccn2c1-c1ccccn1]

To a solution of [1-(3-iodo-imidazo[1,2-a]pyrimidin-2-yl)-ethyl]-carbamic acid benzyl ester (5.0 g, 14.21 mmol) and 2-tributylstannanyl-pyridine (15.6 g, 42.63 mmol) in 1,4-dioxane (30 mL) was added Pd(PPh$_3$)$_4$ (1.6 g, 1.4 mmol) at rt. The reaction mixture was stirred overnight at 110° C. After completion of the reaction, the mixture was concentrated in vacuo. The crude product was purified by column chromatography using silica gel (100-200 mesh) and 0-40% acetone in hexane to provide [1-(3-iodo-imidazo[1,2-a]pyrimidin-2-yl)-ethyl]-carbamic acid benzyl ester: LC-MS (ESI) m/z 374.1 [M+H]$^+$.

1-(3-Pyridin-2-yl-imidazo[1,2-a]pyrimidin-2-yl)-ethylamine

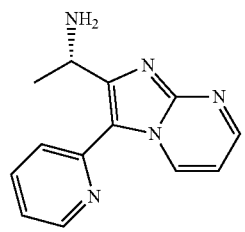 [SMILES: C[C@H](N)c1nc2ncccn2c1-c1ccccn1]

A mixture of [1-(3-iodo-imidazo[1,2-a]pyrimidin-2-yl)-ethyl]-carbamic acid benzyl ester (900 mg, 2.4 mmol) and dimethylsulfide (0.9 mL) in TFA (4.5 mL) was stirred at rt overnight. The mixture was concentrated in vacuo, dissolved in EtOAc washed with satd. sodium bicarbonate solution, dried over sodium sulfate, filtered and concentrated in vacuo to provide 1-(3-pyridin-2-yl-imidazo[1,2-a]pyrimidin-2-yl)-ethylamine: LC-MS (ESI) m/z 240.0 [M+H]+.

4-Amino-6-[1-(3-pyridin-2-yl-imidazo[1,2-a]pyrimidin-2-yl)-ethyl amino]-pyrimidine-5-carbonitrile

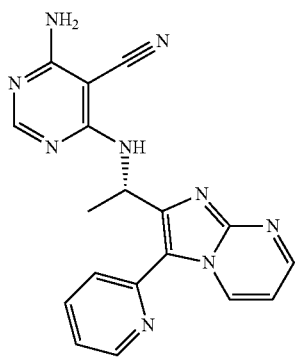 [SMILES: C[C@H](Nc1ncnc(N)c1C#N)c1nc2ncccn2c1-c1ccccn1]

To a mixture of 1-(3-pyridin-2-yl-imidazo[1,2-a]pyrimidin-2-yl)-ethylamine (800 mg, 3.34 mmol) and 4-amino-6-chloro-pyrimidine-5-carbonitrile (520 mg 3.34 mmol) in n-butanol (5 mL) was added DIEA (1.7 mL, 10.04 mmol) at rt. The reaction mixture was stirred at 100° C. overnight. The mixture was concentrated in vacuo. The residue was purified by column chromatography using silica gel (100-200 mesh) and 0-30% acetone in hexane to provide 4-amino-6-[1-(3-pyridin-2-yl-imidazo[1,2-a]pyrimidin-2-yl)-ethylamino]-pyrimidine-5-carbonitrile: 1H NMR: (DMSO-d6, 400 MHz) δ 1.547 (d, J=6.4 Hz, 3H), 5.807-5.841 (br s, 1H), 7.150-7.176 (m, 1H), 7.289 (br s, 2H), 7.429-7.466 (m, 2H), 7.847-7.867 (m, 1H), 7.998 (s, 2H), 8.653 (s, 1H), 8.789 (s, 1H), 9.419 (d, J=6.4 Hz, 1H); LC-MS (ESI) m/z 358.2 [M+H]+.

Example 68

(S)-Methyl 2-(1-(benzyloxycarbonylamino)ethyl)-3-(5-fluoropyridin-3-yl)-imidazo[1,2-a]pyridine-5-carboxylate

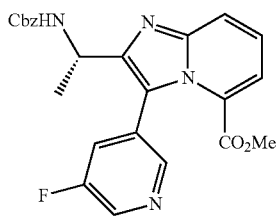 [SMILES: COC(=O)c1cccc2nc([C@H](C)NC(=O)OCc3ccccc3)c(-c3cncc(F)c3)n12]

Prepared according to Step C3b in General Procedure C using (S)-methyl 2-(1-(benzyloxycarbonylamino)ethyl)-3-iodoimidazo[1,2-a]pyridine-5-carboxylate (0.350 g, 0.730 mmol) and 5-fluoropyridin-3-ylboronic acid (0.154 g, 1.10 mmol) to give (S)-methyl 2-(1-(benzyloxycarbonylamino)ethyl)-3-(5-fluoropyridin-3-yl)imidazo[1,2-a]pyridine-5-carboxylate as a tan solid. LC-MS (ESI) m/z 449.1 [M+H]+.

(S)-Methyl 2-(1-aminoethyl)-3-(5-fluoropyridin-3-yl)imidazo[1,2-a]pyridine-5-carboxylate

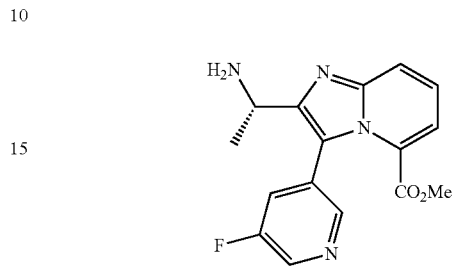

Prepared according to Step C4 in General Procedure C using (S)-methyl 2-(1-(benzyloxycarbonylamino)ethyl)-3-(5-fluoropyridin-3-yl)imidazo[1,2-a]pyridine-5-carboxylate (0.215 g, 0.479 mmol) to give (S)-methyl 2-(1-aminoethyl)-3-(5-fluoropyridin-3-yl)imidazo[1,2-a]pyridine-5-carboxylate. LC-MS (ESI) m/z 315.0 [M+H]+.

Methyl 2-((1S)-1-((6-amino-5-cyano-4-pyrimidinyl)amino)ethyl)-3-(5-fluoro-3-pyridinyl)imidazo[1,2-a]pyridine-5-carboxylate

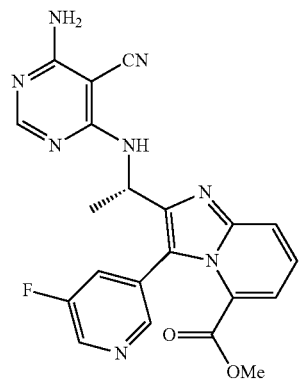 [SMILES: COC(=O)c1cccc2nc([C@H](C)Nc3ncnc(N)c3C#N)c(-c3cncc(F)c3)n12]

A solution of (S)-methyl 2-(1-aminoethyl)-3-(5-fluoropyridin-3-yl)imidazo[1,2-a]pyridine-5-carboxylate (0.151 g, 0.480 mmol), 4-amino-6-chloropyrimidine-5-carbonitrile (0.089 g, 0.576 mmol) and DIEA (0.252 mL, 1.441 mmol) in n-butanol (2.40 mL) was stirred at 110° C. for 2 h. The mixture was loaded onto silica gel and purified by MPLC (eluted with a gradient of 0-7% MeOH in DCM) to afford the methyl 2-((1S)-1-((6-amino-5-cyano-4-pyrimidinyl)amino)ethyl)-3-(5-fluoro-3-pyridinyl)imidazo[1,2-a]pyridine-5-carboxylate as a light yellow solid. 1H NMR (400 MHz, DMSO-d6) δ ppm 1.55 (d, J=6.65 Hz, 3H) 3.33 (s, 3H) 5.41 (quin, J=6.65 Hz, 1H) 7.16 (d, J=7.24 Hz, 1H) 7.23 (br. s., 2H) 7.38-7.50 (m, 2H) 7.75-7.90 (m, 2H) 7.95 (dd, J=8.61, 1.57 Hz, 1H) 8.42 (br. s., 1H) 8.62 (d, J=2.74 Hz, 1H). LC-MS (ESI) m/z 433.1 [M+H]+.

Example 69

Preparation of 4-amino-6-(((1S)-1-(1-cyclopropyl-7-(methylsulfonyl)-1H-benzimidazol-2-yl)ethyl)amino)-5-pyrimidinecarbonitrile and 4-amino-6-(((1R)-1-(1-cyclopropyl-7-(methylsulfonyl)-1H-benzimidazol-2-yl)-ethyl)amino)-5-pyrimidinecarbonitrile 2-Bromo-N-cyclopropyl-6-nitroaniline

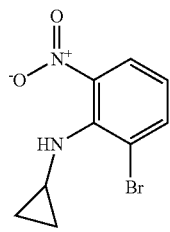

A mixture of 1-bromo-2-fluoro-3-nitrobenzene (4.1 g, 18.6 mmol) and cyclopropanamine (1.29 mL, 18.6 mmol) in THF (10 mL) was stirred under $N_2$ at 60° C. for 18 h. The reaction mixture was diluted with EtOAc, washed with water, filtered on a pad of Celite™, washed with brine and dried over magnesium sulfate. The solution was concentrated in vacuo. Purification of the residue by flash chromatography on a silica gel column using 30 to 50% gradient of DCM in hexane as eluent gave 2-bromo-N-cyclopropyl-6-nitroaniline: LC-MS (ESI) m/z 259.0 [M+H]$^+$.

N-Cyclopropyl-2-(methylsulfonyl)-6-nitroaniline

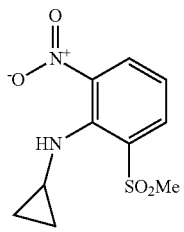

Using the general synthetic procedure for 3-(methylsulfonyl)-2-nitroaniline in example 51, N-cyclopropyl-2-(methylsulfonyl)-6-nitroaniline was prepared using 2-bromo-N-cyclopropyl-6-nitroaniline: LC-MS (ESI) m/z 257.0 [M+H]$^+$.

N1-Cyclopropyl-6-(methylsulfonyl)benzene-1,2-diamine

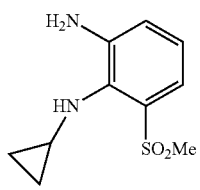 [SMILES: CS(=O)(=O)c1cccc(N)c1NC1CC1]

Using the general synthetic procedure for methyl 3-amino-2-(cyclopropylamino)benzoate in example 47, N1-cyclopropyl-6-(methylsulfonyl)benzene-1,2-diamine was prepared using N-cyclopropyl-2-(methylsulfonyl)-6-nitroaniline: LC-MS (ESI) m/z 227.1 [M+H]$^+$.

(S)-tert-Butyl 1-(2-(cyclopropylamino)-3-(methylsulfonyl)phenylamino)-1-oxopropan-2-ylcarbamate

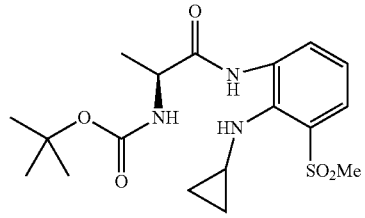 [SMILES: C[C@H](NC(=O)OC(C)(C)C)C(=O)Nc1cccc(S(C)(=O)=O)c1NC1CC1]

Using the general synthetic procedure for (S)-methyl 3-(2-(tert-butoxycarbonylamino)propanamido)-2-(cyclopropylamino)benzoate in example 47, (S)-tert-butyl 1-(2-(cyclopropylamino)-3-(methylsulfonyl)phenylamino)-1-oxopropan-2-ylcarbamate was prepared using N1-cyclopropyl-6-(methylsulfonyl)benzene-1,2-diamine: LC-MS (ESI) m/z 398.0 [M+H]$^+$.

(S)-1-(1-Cyclopropyl-7-(methylsulfonyl)-1H-benzo[d]imidazol-2-yl)ethanamine and (R)-1-(1-cyclopropyl-7-(methylsulfonyl)-1H-benzo[d]imidazol-2-yl)ethanamine

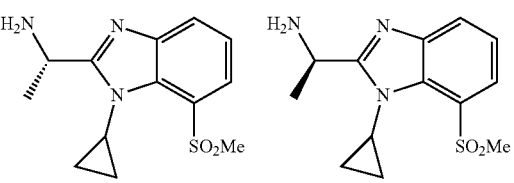 [SMILES: C[C@H](N)c1nc2cccc(S(C)(=O)=O)c2n1C1CC1 ; C[C@@H](N)c1nc2cccc(S(C)(=O)=O)c2n1C1CC1]

Using the general synthetic procedure for the synthesis of (S)-2-(1-aminoethyl)-1-(5-fluoropyridin-3-yl)-N-methyl-1H-benzo[d]imidazole-7-carboxamide and (R)-2-(1-aminoethyl)-1-(5-fluoropyridin-3-yl)-N-methyl-1H-benzo[d]imidazole-7-carboxamide in example 65, a racemic mixture of (S)-1-(1-cyclopropyl-7-(methylsulfonyl)-1H-benzo[d]imidazol-2-yl)ethanamine and (R)-1-(1-cyclopropyl-7-(methylsulfonyl)-1H-benzo[d]imidazol-2-yl)ethanamine was prepared using (S)-tert-butyl 1-(2-(cyclopropylamino)-3-(methylsulfonyl)phenylamino)-1-oxopropan-2-ylcarbamate: LC-MS (ESI) m/z 280.0 [M+H]$^+$.

4-Amino-6-(((1S)-1-(1-cyclopropyl-7-(methylsulfonyl)-1H-benzimidazol-2-yl)ethyl)amino)-5-pyrimidinecarbonitrile and 4-amino-6-(((1R)-1-(1-cyclopropyl-7-(methylsulfonyl)-1H-benzimidazol-2-yl)ethyl)amino)-5-pyrimidinecarbonitrile

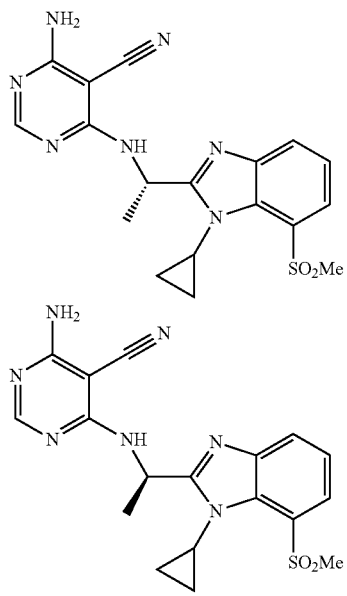

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, the racemic mixture of 4-amino-6-(((1S)-1-(1-cyclopropyl-7-(methylsulfonyl)-1H-benzimidazol-2-yl)ethyl)amino)-5-pyrimidinecarbonitrile and 4-amino-6-(((1R)-1-(1-cyclopropyl-7-(methylsulfonyl)-1H-benzimidazol-2-yl)ethyl)amino)-5-pyrimidinecarbonitrile was prepared using a racemic mixture of (S)-1-(1-cyclopropyl-7-(methylsulfonyl)-1H-benzo[d]imidazol-2-yl)ethanamine and (R)-1-(1-cyclopropyl-7-(methylsulfonyl)-1H-benzo[d]imidazol-2-yl)ethanamine: $^1$H NMR (400 MHz, DMSO-$d_6$) δ 8.05 (1H, s), 7.94 (1H, d, J=8.0 Hz), 7.90 (1H, d, J=8.0 Hz), 7.76 (1H, d, J=8.0 Hz), 7.39 (1H, t, J=8.0 Hz), 7.32 (2H, br), 5.97-5.90 (1H, m), 3.70-3.62 (1H, m), 3.52 (3H, s), 1.62 (3H, d, J=4.0 Hz), 1.28-0.97 (4H, m); LC-MS (ESI) m/z 398.0 [M+H]$^+$. The racemic mixture was separated by chiral separation using SFC to give two fractions:

First-eluting enantiomer on the AD-H column: 4-Amino-6-(((1R)-1-(1-cyclopropyl-7-(methylsulfonyl)-1H-benzimidazol-2-yl)ethyl)amino)-5-pyrimidinecarbonitrile: $^1$H NMR (400 MHz, DMSO-$d_6$) δ 8.05 (1H, s), 7.94 (1H, d, J=8.0 Hz), 7.90 (1H, d, J=8.0 Hz), 7.76 (1H, d, J=8.0 Hz), 7.39 (1H, t, J=8.0 Hz), 7.32 (2H, br), 5.97-5.90 (1H, m), 3.70-3.62 (1H, m), 3.52 (3H, s), 1.62 (3H, d, J=4.0 Hz), 1.28-0.97 (4H, m); LC-MS (ESI) m/z 398.0 [M+H]$^+$.

Second-eluting enantiomer on the AD-H column: 4-amino-6-((1S)-1-(1-cyclopropyl-7-(methylsulfonyl)-1H-benzimidazol-2-yl)ethyl)amino)-5-pyrimidinecarbonitrile: $^1$H NMR (400 MHz, DMSO-$d_6$) δ 8.05 (1H, s), 7.94 (1H, d, J=8.0 Hz), 7.90 (1H, d, J=8.0 Hz), 7.76 (1H, d, J=8.0 Hz), 7.39 (1H, t, J=8.0 Hz), 7.32 (2H, br), 5.97-5.90 (1H, m), 3.70-3.62 (1H, m), 3.52 (3H, s), 1.62 (3H, d, J=4.0 Hz), 1.28-0.97 (4H, m); LC-MS (ESI) m/z 398.0 [M+H]$^+$.

Example 70

(S)-2-(1-((3-Amino-2-cyanophenyl)amino)ethyl)-3-(5-fluoropyridin-3-yl)imidazo[1,2-a]pyridine-5-carboxylic acid

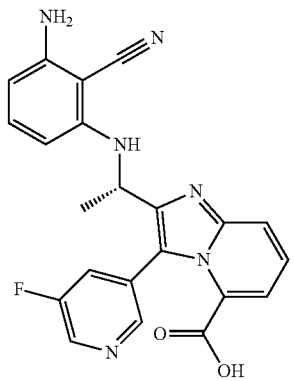 [SMILES: C[C@H](Nc1cccc(N)c1C#N)c1nc2cccc(C(=O)O)n2c1-c1cncc(F)c1]

A solution of methyl 2-((1S)-1-(6-amino-5-cyano-4-pyrimidinyl)amino)ethyl)-3-(5-fluoro-3-pyridinyl)imidazo[1,2-a]pyridine-5-carboxylate (0.060 g, 0.139 mmol) and lithium iodide (0.056 g, 0.416 mmol) in pyridine (0.73 mL) was stirred at 100° C. for 6 h. Volatiles were removed under reduced pressure to afford (S)-2-(1-((3-amino-2-cyanophenyl)amino)ethyl)-3-(5-fluoropyridin-3-yl)imidazo[1,2-a]pyridine-5-carboxylic acid as a dark residue. LC-MS (ESI) m/z 419.1 [M+H]$^+$.

2-((1S)-1-((6-Amino-5-cyano-4-pyrimidinyl)amino)ethyl)-3-(5-fluoro-3-pyridinyl)-N-methylimidazo[1,2-a]pyridine-5-carboxamide

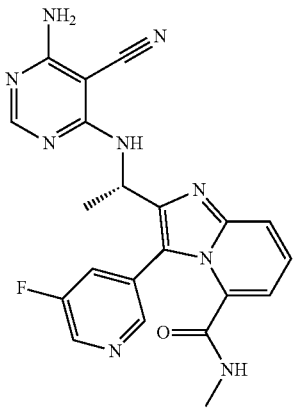 [SMILES: CNC(=O)c1cccc2nc([C@H](C)Nc3ncnc(N)c3C#N)c(-c3cncc(F)c3)n12]

To a solution of (S)-2-(1-((3-amino-2-cyanophenyl)amino)ethyl)-3-(5-fluoropyridin-3-yl)imidazo[1,2-a]pyridine-5-carboxylic acid (0.058 g, 0.139 mmol) in DMF (0.93 mL) was added benzotriazol-1-yl-oxytripyrrolidinophosphonium hexafluorophosphate (PyBOP) (181 mg, 0.348 mmol) followed by DIEA (0.049 mL, 0.278 mmol) and methylamine (2.0M solution in THF, 0.174 mL, 0.348 mmol). The solution was stirred at rt for 1 h then was loaded onto silica gel and purified by MPLC (eluted with a gradient of 0-8% MeOH in DCM) to afford a light yellow solid. Repurified by MPLC (eluted with a gradient of 0-90% (1:10:90 NH$_4$OH:MeOH:

DCM solution) in DCM to afford 2-((1S)-1-((6-amino-5-cyano-4-pyrimidinyl)amino)ethyl)-3-(5-fluoro-3-pyridinyl)-N-methylimidazo-[1,2-a]pyridine-5-carboxamide as a white solid. ¹H NMR (400 MHz, DMSO-$d_6$) δ ppm 1.55 (br. s., 3H) 2.28 (d, J=4.70 Hz, 3H) 5.35 (quin, J=6.94 Hz, 1H) 7.00 (dd, J=6.75, 0.88 Hz, 1H) 7.08 (d, J=7.43 Hz, 1H) 7.22 (br. s., 2H) 7.39 (dd, J=9.00, 6.85 Hz, 1H) 7.67 (br. s., 1H) 7.78 (dd, J=9.10, 0.88 Hz, 1H) 7.87 (s, 1H) 8.31 (br. s., 1H) 8.57 (d, J=2.74 Hz, 1H) 8.73 (q, J=4.30 Hz, 1H). LC-MS (ESI) m/z 432.0 [M+H]⁺.

Example 71

3-(5-Fluoro-2-nitrophenylamino)benzonitrile

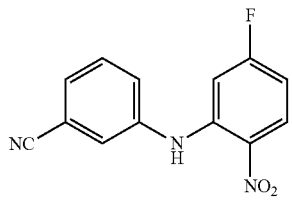

Prepared according to Step D1 in General Procedure D using 3-aminobenzonitrile (1.00 g, 8.46 mmol) to give 3-(5-fluoro-2-nitrophenylamino)benzonitrile as an orange solid. LC-MS (ESI) m/z 256.1 [M–H]⁻.

3-(2-Amino-5-fluorophenylamino)benzonitrile

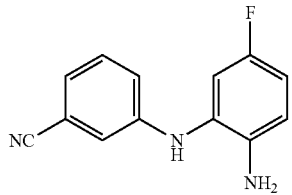 [SMILES: N#Cc1cccc(Nc2cc(F)ccc2[N+](=O)[O-])c1]

Prepared according to Step D2 in General Procedure D using 3-(5-fluoro-2-nitrophenylamino)benzonitrile (0.538 g, 2.09 mmol) to give 3-(2-amino-5-fluorophenylamino)benzonitrile as a yellow solid. LC-MS (ESI) m/z 228.1 [M+H]⁺.

tert-Butyl 1-(2-(3-cyanophenylamino)-4-fluorophenylamino)-1-oxopropan-2-ylcarbamate

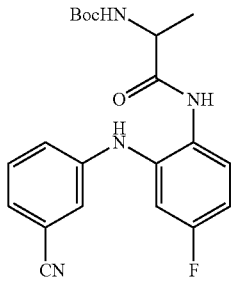 [SMILES: CC(NC(=O)OC(C)(C)C)C(=O)Nc1ccc(F)cc1Nc1cccc(C#N)c1]

Prepared according to Step D3 in General Procedure D using 3-(2-amino-5-fluorophenylamino)benzonitrile (0.451 g, 1.985 mmol) to give tert-butyl 1-(2-(3-cyanophenylamino)-4-fluorophenylamino)-1-oxopropan-2-ylcarbamate as a yellow solid. LC-MS (ESI) m/z 421.1 [M+Na]⁺.

N-(1-(1-(3-Cyanophenyl)-6-fluoro-1H-benzo[d]imidazol-2-yl)ethyl)acetamide

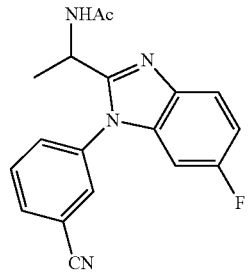 [SMILES: CC(=O)NC(C)c1nc2ccc(F)cc2n1-c1cccc(C#N)c1]

Prepared according to Step D4 in General Procedure D using tert-butyl 1-(2-(3-cyanophenylamino)-4-fluorophenylamino)-1-oxopropan-2-ylcarbamate (0.783 g, 1.97 mmol) to give N-(1-(1-(3-cyanophenyl)-6-fluoro-1H-benzo[d]imidazol-2-yl)ethyl)acetamide as a white solid. LC-MS (ESI) m/z 323.1 [M+H]⁺.

3-(2-(1-Aminoethyl)-6-fluoro-1H-benzo[d]imidazol-1-yl)benzonitrile

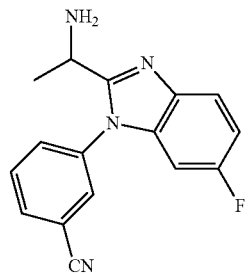 [SMILES: CC(N)c1nc2ccc(F)cc2n1-c1cccc(C#N)c1]

Prepared according to Step D5a in General Procedure D using N-(1-(1-(3-cyanophenyl)-6-fluoro-1H-benzo[d]imidazol-2-yl)ethyl)acetamide (0.247 g, 0.766 mmol) to give 3-(2-(1-aminoethyl)-6-fluoro-1H-benzo[d]imidazol-1-yl)benzonitrile as a colorless oil. LC-MS (ESI) m/z 281.1 [M+H]⁺.

4-Amino-6-(1-(1-(3-cyanophenyl)-6-fluoro-1H-benzo[d]imidazol-2-yl)ethylamino)pyrimidine-5-carbonitrile

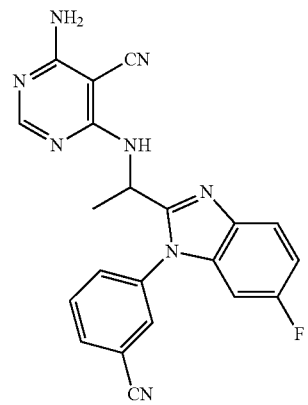 [SMILES: CC(Nc1ncnc(N)c1C#N)c1nc2ccc(F)cc2n1-c1cccc(C#N)c1]

Prepared according to Step D6 in General Procedure D using 3-(2-(1-aminoethyl)-6-fluoro-1H-benzo[d]imidazol-1-yl)benzonitrile (0.215 g, 0.767 mmol) to give 4-amino-6-

(1-(1-(3-cyanophenyl)-6-fluoro-1H-benzo[d]imidazol-2-yl)-ethylamino)pyrimidine-5-carbonitrile as an off-white solid. $^1$H NMR (400 MHz, DMSO-d$_6$) δ ppm 1.57 (d, J=6.85 Hz, 3H) 5.61 (quin, J=6.85 Hz, 1H) 7.00 (dd, J=8.90, 2.45 Hz, 1H) 7.09-7.17 (m, 1H) 7.18 (br. s., 2H) 7.63-7.79 (m, 3H) 7.81-7.94 (m, 3H) 8.07 (br. s., 1H). LC-MS (ESI) m/z 399.0 [M+H]$^+$.

4-Amino-6-(((1R)-1-(1-(3-cyanophenyl)-6-fluoro-1H-benzimidazol-2-yl)ethyl)amino)-5-pyrimidinecarbonitrile and 4-amino-6-(((1S)-1-(1-(3-cyanophenyl)-6-fluoro-1H-benzimidazol-2-yl)ethyl)amino)-5-pyrimidinecarbonitrile

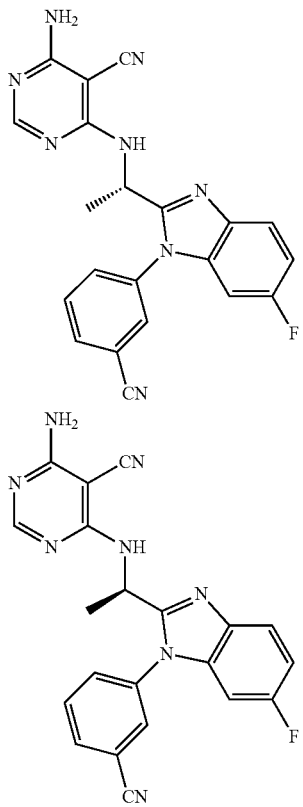

The racemic mixture (0.182 mg) was separated on AD-H column using preparative SFC to give two fractions. First peak on OD-H column: 4-amino-6-(((1S)-1-(1-(3-cyanophenyl)-6-fluoro-1H-benzimidazol-2-yl)ethyl)amino)-5-pyrimidinecarbonitrile (62 mg) LC-MS (ESI) m/z 399.0 [M+H]$^+$. $^1$H NMR (400 MHz, DMSO-d$_6$) δ ppm 1.58 (d, J=6.65 Hz, 3H) 5.55-5.68 (m, 1H) 7.01 (dd, J=9.00, 2.35 Hz, 1H) 7.09-7.25 (m, 3H) 7.67-7.74 (m, 2H) 7.76 (dd, J=8.80, 4.70 Hz, 1H) 7.82-7.88 (m, 2H) 7.90 (dt, J=7.68, 1.25 Hz, 1H) 8.08 (br. s., 1H). Second peak on OD-H column: 4-amino-6-(((1R)-1-(1-(3-cyanophenyl)-6-fluoro-1H-benzimidazol-2-yl)ethyl)amino)-5-pyrimidinecarbonitrile (60 mg), LC-MS (ESI) m/z 399.0 [M+H]$^+$. $^1$H NMR (400 MHz, DMSO-d$_6$) δ ppm 1.58 (d, J=6.65 Hz, 3H) 5.61 (quin, J=6.90 Hz, 1H) 7.01 (dd, J=9.00, 2.35 Hz, 1H) 7.08-7.25 (m, 3H) 7.67-7.74 (m, 2H) 7.76 (dd, J=8.90, 4.79 Hz, 1H) 7.83-7.88 (m, 2H) 7.90 (dt, J=7.63, 1.27 Hz, 1H) 8.08 (br. s., 1H).

Example 72

Preparation of 4-amino-6-(((1S)-1-(3-(2-pyridinyl)imidazo[1,2-a]pyrazin-2-yl)ethyl)amino)-5-pyrimidinecarbonitrile (1-Imidazo[1,2-a]pyrazin-2-yl-ethyl)-carbamic acid benzyl ester

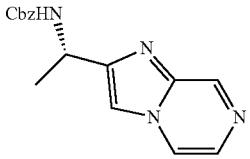 [SMILES: C[C@H](NC(=O)OCc1ccccc1)c1cn2ccncc2n1]

A mixture of pyrazin-2-ylamine (3 g, 31.5 mmol) and (3-bromo-1-methyl-2-oxopropyl)-carbamic acid benzyl ester (12 g, 41.05 mmol) in EtOH (20 mL) was heated to reflux overnight. After completion, the reaction mixture was cooled to rt. EtOH was removed in vacuo. The residue was dissolved in EtOAc and washed with satd. sodium bicarbonate solution. The organic layer was dried over sodium sulfate, filtered and concentrated in vacuo. The crude product was purified by column chromatography using silica gel (100-200 mesh) and 0-5% MeOH in DCM to provide (1-imidazo[1,2-a]pyrazin-2-yl-ethyl)-carbamic acid benzyl ester: LC-MS (ESI) m/z 297.2 [M+H]$^+$.

[1-(3-Iodo-imidazo[1,2-a]pyrazin-2-yl)-ethyl]-carbamic acid benzyl ester

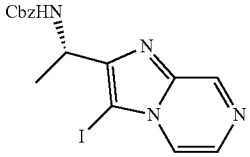 [SMILES: C[C@H](NC(=O)OCc1ccccc1)c1nc2cnccn2c1I]

To a solution of (1-imidazo[1,2-a]pyrazin-2-yl-ethyl)-carbamic acid benzyl ester (1.7 g, 5.74 mmol) in acetonitrile (10 mL) was added n-iodosuccinimide (1.3 g, 5.74 mmol) at rt and stirred overnight. After completion of the reaction, the mixture was diluted with water and extracted with EtOAc. The organic layer was washed with satd. sodium bicarbonate solution, dried over sodium sulfate, filtered and concentrated in vacuo. The crude product was purified by column chromatography using silica gel (100-200 mesh) and 0-4% MeOH in DCM to provide [1-(3-iodo-imidazo[1,2-a]pyrazin-2-yl)-ethyl]-carbamic acid benzyl ester: LC-MS (ESI) m/z 422.9 [M+H]$^+$.

[1-(3-Pyridin-2-yl-imidazo[1,2-a]pyrazin-2-yl)-ethyl]-carbamic acid benzyl ester

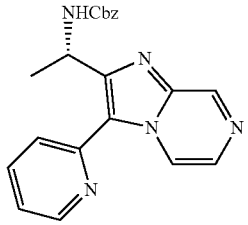 [SMILES: C[C@H](NC(=O)OCc1ccccc1)c1nc2cnccn2c1-c1ccccn1]

To a solution of [1-(3-iodo-imidazo[1,2-a]pyrazin-2-yl)-ethyl]-carbamic acid benzyl ester (1.6 g, 3.79 mmol) and 2-tributylstannanyl pyridine (4.1 g, 11.37 mmol) in 1,4-dioxane (20 mL) was added Pd(PPh₃)₄ (50 mg, 0.4 mmol) at rt. The reaction mixture was stirred overnight at 110° C. After completion of the reaction, the mixture was concentrated in vacuo. The crude product was purified by column chromatography using silica gel (100-200 mesh) and 0-40% acetone in hexane to provide [1-(3-pyridin-2-yl-imidazo 1,2-a]pyrazin-2-yl)-ethyl]-carbamic acid benzyl ester: LC-MS (ESI) m/z 374.1 [M+H]⁺.

1-(3-Pyridin-2-yl-imidazo[1,2-a]pyrazin-2-yl)-ethylamine

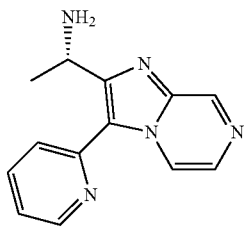 [SMILES: C[C@H](N)c1nc2cnccn2c1-c1ccccn1]

The mixture of [1-(3-pyridin-2-yl-imidazo[1,2-a]pyrazin-2-yl)-ethyl]-carbamic acid benzyl ester (450 mg, 1.2 mmol) and dimethylsulfide (1.0 mL) in TFA (4.0 mL) was stirred at rt overnight. The mixture was concentrated in vacuo, and the residue was dissolved in EtOAc. The organic layer was washed with satd. sodium bicarbonate solution, dried over sodium sulfate, filtered and concentrated in vacuo to provide 1-(3-pyridin-2-yl-imidazo[1,2-a]pyrazin-2-yl)-ethylamine: LC-MS (ESI) m/z 240.0 [M+H]⁺.

4-Amino-6-[1-(3-pyridin-2-yl-imidazo[1,2-a]pyrazin-2-yl)-ethylamino]-pyrimidine-5-carbonitrile

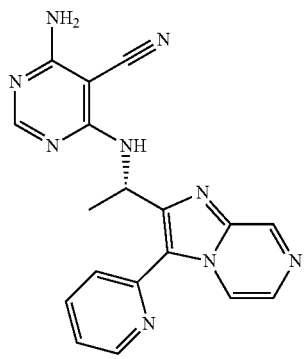 [SMILES: C[C@H](Nc1ncnc(N)c1C#N)c1nc2cnccn2c1-c1ccccn1]

To a mixture of 1-(3-pyridin-2-yl-imidazo[1,2-a]pyrazin-2-yl)-ethylamine (250 mg, 1.04 mmol) and 4-amino-6-chloro-pyrimidine-5-carbonitrile (160 mg 1.04 mmol) in n-butanol (3 mL) was added DIEA (1.7 mL, 10.04 mmol) at rt. The reaction mixture was stirred at 110° C. overnight. The mixture was concentrated in vacuo. The residue was purified by column chromatography using silica gel (100-200 mesh) and 0-40% acetone in hexane to provide 4-amino-6-[1-(3-pyridin-2-yl-imidazo[1,2-a]pyrazin-2-yl)-ethylamino]-pyrimidine-5-carbonitrile: ¹H NMR: (400 MHz, DMSO-d₆) δ 1.537 (d, J=6.8 Hz, 3H), 5.837-5.906 (m, 1H), 7.269 (br s, 2H), 7.471-7.502 (m, 1H), 7.572-7.594 (m, 1H), 7.887-7.907 (m, 1H), 7.983-8.043 (m, 3H), 8.814-8.826 (m, 1H), 8.928-8.944 (m, 1H), 9.180 (d, J=1.2 Hz, 1H); LC-MS (ESI) m/z 358.2 [M+H]⁺.

Example 73

Preparation of methyl 2-((1S)-1-((6-amino-5-cyano-4-pyrimidinyl)amino)ethyl)-3-phenylimidazo[1,2-a]pyridine-5-carboxylate (S)-Methyl-2-(1-(((benzyloxy)carbonyl)amino)ethyl)imidazo[1,2-a]pyridine-5-carboxylate

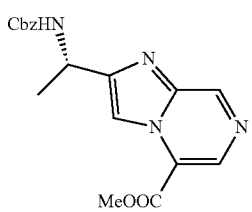 [SMILES: COC(=O)c1cncc2nc([C@H](C)NC(=O)OCc3ccccc3)cn12]

A mixture of 6-amino-pyridine-2-carboxylic acid methyl ester (1 g, 6.57 mmol) and (S)-benzyl (4-bromo-3-oxobutan-2-yl) carbamate (2.3 g, 7.88 mmol) in EtOH (25 mL) was heated to reflux overnight. After completion, the reaction mixture was cooled to 25° C. EtOH was removed in vacuo. The residue was dissolved in EtOAc and washed with satd. sodium bicarbonate. The organic layer was dried over sodium sulfate, filtered and concentrated in vacuo. The crude product was purified by column chromatography using silica gel (100-200 mesh) and 0-55% acetone in hexane to provide (S)-methyl-2-(1-(((benzyloxy)carbonyl)amino) ethyl) imidazo[1,2-a]pyridine-5-carboxylate: ¹H NMR: (400 MHz, DMSO-d₆) δ 1.4745 (d, J=6.8 Hz, 3H), 3.962 (s, 3H), 4.878-4.951 (m, 1H), 5.053 (s, 2H), 6.282 (br s, 1H), 7.312-7.380 (m, 5H), 7.782-7.803 (m, 1H), 7.851-7.899 (2H, m), 8.264 (m, 1H); LC-MS (ESI) m/z 354.1 [M+H]⁺.

(S)-Methyl 2-(1-(((benzyloxy)carbonyl)amino)ethyl)-3-iodoimidazo[1,2-a]-pyridine-5-carboxylate

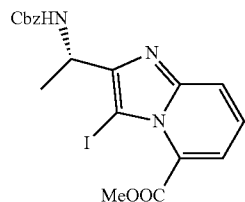 [SMILES: COC(=O)c1cccc2nc([C@H](C)NC(=O)OCc3ccccc3)c(I)n12]

To a solution of (S)-methyl-2-(1-(((benzyloxy)carbonyl)amino)ethyl)imidazo[1,2-a]pyridine-5-carboxylate (5.5 g, 7.93 mmol) in acetonitrile (50 mL) was added N-iodosuccinimide (2.3 g, 10.3 mmol) at 25° C. The reaction mixture was stirred at 25° C. overnight. After completion of the reaction, the mixture was diluted with water and extracted with EtOAc. The organic layer was washed with satd. sodium bicarbonate solution, dried over sodium sulfate, filtered and concentrated in vacuo. The crude product was purified by column chromatography using silica gel (100-200 mesh) and 0-50% EtOAc in hexane to provide (S)-methyl 2-(1-(((benzyloxy)carbonyl)amino)ethyl)-3-iodoimidazo[1,2-a]pyridine-5-carboxylate: ¹H NMR (CDCl₃, 400 MHz) δ 1.547 (d, J=6.8 Hz, 3H), 4.048 (s, 3H), 5.067-5.200 (m, 3H), 5.805 (d, J=7.2 Hz, 1H), 7.229-

7.260 (m, 2H), 7.292-7.350 (m, 5H), 7.675-7.708 (m, 1H); LC-MS (ESI) m/z 479.9 [M+H]+.

(S)-Methyl 2-(1-(((benzyloxy)carbonyl)amino) ethyl)-3-phenylimidazo[1,2-a]pyridine-5-carboxylate

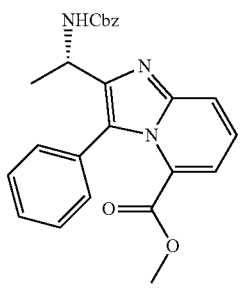 [SMILES: COC(=O)c1cccc2nc([C@H](C)NC(=O)OCc3ccccc3)c(-c3ccccc3)n12]

To a solution of (S)-methyl 2-(1-4(Benzyloxy)carbonyl) amino)ethyl)-3-iodoimidazo[1,2-a]pyridine-5-carboxylate (900 mg, 1.87 mmol) and phenyl boronic acid (275 mg, 2.25 mmol) in acetonitrile-water (12 mL) was added sodium carbonate (400 mg, 3.35 mmol) at 25° C. The reaction mixture was degassed with nitrogen for 30 min. To the mixture was added Pd(PPh$_3$)$_4$ (217 mg, 0.18 mmol) at 25° C. The reaction mixture was stirred at 95° C. overnight. After completion of the reaction water was added to reaction mixture and extracted with EtOAc. The organic layer was dried over sodium sulfate and concentrated in vacuo. The residue was purified by column chromatography using silica gel (100-200 mesh) and 0-70% EtOAcin hexane to provide (S)-methyl 2-(1-(((benzyloxy)carbonyl)amino)ethyl)-3-phenylimidazo [1,2-a]pyridine-5-carboxylate: LC-MS (ESI) m/z 430.0 [M+H]+.

(S)-Methyl 2-(1-aminoethyl)-3-phenylimidazo[1,2-a] pyridine-5-carboxylate

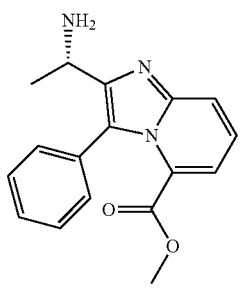

The mixture of (S)-methyl 2-(1-(((benzyloxy)carbonyl) amino)ethyl)-3-phenylimidazo[1,2-a]pyridine-5-carboxylate (600 mg, 1.3 mmol) and dimethylsulfide (0.4 mL) in TFA (1.2 mL) was stirred at 25° C. overnight. The mixture was concentrated in vacuo and the residue was dissolved in EtOAc. The organic layer was washed with satd. sodium bicarbonate, dried over sodium sulfate, filtered and concentrated in vacuo to provide (S)-methyl 2-(1-aminoethyl)-3-phenylimidazo-[1,2-a]pyridine-5-carboxylate (400 mg): LC-MS (ESI) m/z 296.2 [M+H]+. The crude product was used without further purification.

(S)-Methyl 2-[1-((6-Amino-5-cyanopyrimidin-4-yl) amino)ethyl]-3-phenylimidazo[1,2-a]pyridine-5-carboxylate

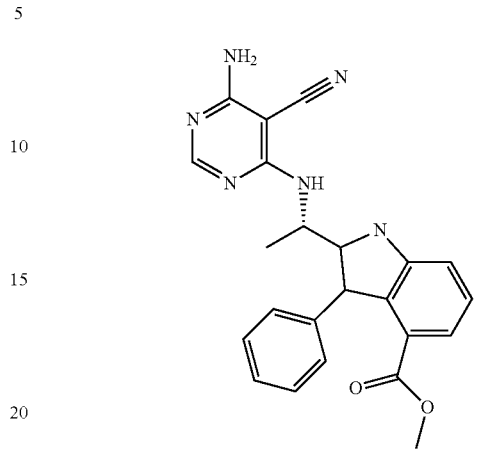

To the crude (S)-methyl 2-(1-aminoethyl)-3-phenylimidazo[1,2-a]pyridine-5-carboxylate (500 mg, 1.69 mmol) and 4-amino-6-chloro-pyrimidine-5-carbonitrile (268 mg, 1.69 mmol) in n-butanol (5 mL) was added DIEA (0.5 mL, 2.54 mmol) at 25° C. The reaction mixture was stirred at 110° C. for 5-6 h. The mixture was extracted with EtOAc. The organic layer was dried over sodium sulfate, filtered and concentrated in vacuo. The residue was purified by column chromatography using silica gel (100-200 mesh) and 0-40% acetone in hexane to provide (S)-methyl 2-[1-((6-Amino-5-cyanopyrimidin-4-yl)amino)ethyl]-3-phenylimidazo-[1,2-a]pyridine-5-carboxylate: $^1$H NMR (400 MHz, DMSO-d$_6$) δ 1.471 (d, J=6.8 Hz, 3H), 3.111 (s, 3H), 5.352-5.420 (m, 1H), 6.935-6.954 (m, 1H), 7.259-7.518 (m, 9H), 7.882-7.941 (m, 2H); LC-MS (ESI) m/z 414.1 [M+H]+.

Example 74

Preparation of 4-amino-6-(((1S)-1-(3-(2-pyridinyl) imidazo[1,2-b]pyridazin-2-yl)ethyl)amino)-5-pyrimidinecarbonitrile (1-Imidazo[1,2-b]pyridazin-2-yl-ethyl)-carbamic acid benzyl ester

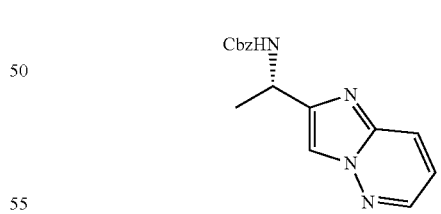

A mixture of pyridazin-3-ylamine (2 g, 21.05 mmol) and (3-bromo-1-methyl-2-oxopropyl)-carbamic acid benzyl ester (7.5 g, 25.26 mmol) in EtOH (25 mL) was heated to reflux overnight. After completion, the reaction mixture was cooled to rt. EtOH was removed in vacuo. The residue was dissolved in EtOAc. The organic layer was dried over sodium sulfate, filtered and concentrated in vacuo. The crude product was purified by column chromatography using silica gel (100-200 mesh) and 0-5% MeOH in DCM to provide (1-imidazo[1,2-b]pyridazin-2-yl-ethyl)-carbamic acid benzyl ester: LC-MS (ESI) m/z 297.3 [M+H]+.

[1-(3-Iodo-imidazo[1,2-b]pyridazin-2-yl)-ethyl]-carbamic acid benzyl ester

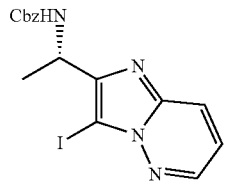 [SMILES: C[C@H](NC(=O)OCc1ccccc1)c1nc2cccnn2c1I]

To a solution of (1-imidazo[1,2-b]pyridazin-2-yl-ethyl)-carbamic acid benzyl ester (2.5 g, 8.44 mmol) in acetonitrile (30 mL) was added N-iodosuccinimide (2.3 g, 10.13 mmol) at rt and stirred overnight. After completion of the reaction, the mixture was diluted with water and extracted with EtOAc. The organic layer was washed with satd. sodium bicarbonate, dried over sodium sulfate, filtered and concentrated in vacuo. The crude product was purified by column chromatography using silica gel (100-200 mesh) and 0-5% MeOH in DCM to provide [1-(3-iodo-imidazo[1,2-b]pyridazin-2-yl)-ethyl]-carbamic acid benzyl ester: LC-MS (ESI) m/z 422.9 [M+H]$^+$.

[1-(3-Pyridin-2-yl-imidazo[1,2-b]pyridazin-2-yl)-ethyl]-carbamic acid benzyl ester

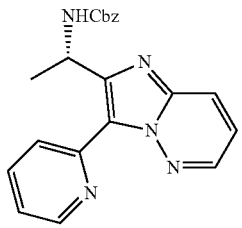 [SMILES: C[C@H](NC(=O)OCc1ccccc1)c1nc2cccnn2c1-c1ccccn1]

To a solution of [1-(3-iodo-imidazo[1,2-b]pyridazin-2-yl)-ethyl]-carbamic acid benzyl ester (3.0 g, 7.1 mmol) and 2-tributylstannanyl-pyridine (7.8 g, 21.32 mmol) in 1,4-dioxane (20 mL) was added Pd(PPh$_3$)$_4$ (820 mg, 0.71 mmol) at rt. The reaction mixture was stirred overnight at 110° C. After completion of the reaction, the mixture was concentrated in vacuo. The crude product was purified by column chromatography using silica gel (100-200 mesh) and 0-40% acetone in hexane to provide [1-(3-pyridin-2-yl-imidazo[1,2-b]pyridazin-2-yl)-ethyl]-carbamic acid benzyl ester: LC-MS (ESI) m/z 374.1 [M+H]$^+$.

1-(3-Pyridin-2-yl-imidazo[1,2-b]pyridazin-2-yl)-ethylamine

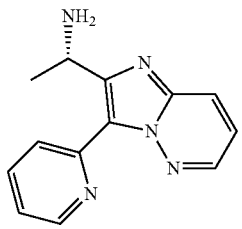 [SMILES: C[C@H](N)c1nc2cccnn2c1-c1ccccn1]

The mixture of [1-(3-pyridin-2-yl-imidazo[1,2-b]pyridazin-2-yl)-ethyl]-carbamic acid benzyl ester (600 mg, 1.6 mmol) and dimethylsulfide (1.2 mL) in TFA (7.5 mL)) was stirred at rt overnight. The mixture was concentrated in vacuo. The residue was dissolved in EtOAc. The organic layer was washed with satd. sodium bicarbonate solution, dried over sodium sulfate, filtered and concentrated in vacuo to provide 1-(3-pyridin-2-yl-imidazo[1,2-b]pyridazin-2-yl)-ethylamine (450 mg): LC-MS (ESI) m/z 240.0 [M+H]$^+$.

4-Amino-6-[1-(3-pyridin-2-yl-imidazo[1,2-b]pyridazin-2-yl)ethylamino]pyrimidine-5-carbonitrile

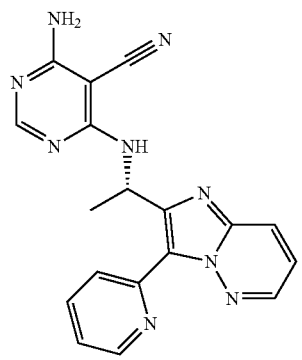 [SMILES: C[C@H](Nc1ncnc(N)c1C#N)c1nc2cccnn2c1-c1ccccn1]

To a mixture of 1-(3-pyridin-2-yl-imidazo[1,2-b]pyridazin-2-yl)-ethylamine (450 mg, 2.09 mmol) and 4-amino-6-chloro-pyrimidine-5-carbonitrile (325 mg, 2.09 mmol) in n-butanol (8 mL) was added DIEA (0.6 mL, 3.01 mmol) at rt. The reaction mixture was stirred at 110° C. overnight. The mixture was concentrated in vacuo. The residue was purified by column chromatography using silica gel (100-200 mesh) and 0-60% acetone in hexane to provide 4-amino-6-[1-(3-pyridin-2-yl-imidazo[1,2-b]pyridazin-2-yl)-ethyl amino]-pyrimidine-5-carbonitrile: $^1$H NMR (400 MHz, DMSO-d$_6$) δ 1.272 (d, J=6.4 Hz, 3H), 6.047-6.118 (m, 1H), 7.375 (br s, 2H), 7.446-7.477 (m, 2H), 8.022-8.060 (m, 2H), 8.230-8.280 (m, 1H), 8.400-8.490 (m, 2H), 8.727 (s, 1H), 8.878 (s, 1H). LC-MS (ESI) m/z 358.2 [M+H]$^+$.

Example 75

3-(5-Fluoro-2-nitrophenylamino)-N-methylbenzamide

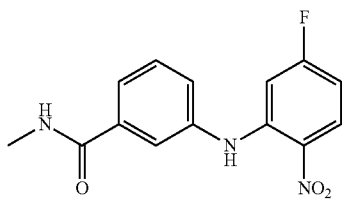 [SMILES: CNC(=O)c1cccc(Nc2cc(F)ccc2[N+](=O)[O-])c1]

Prepared according to Step D1 in General Procedure D using 3-aminobenzoyl-methylamide (2.360 g, 15.71 mmol) to give 3-(5-fluoro-2-nitrophenylamino)-N-methylbenzamide as an orange solid. LC-MS (ESI) m/z 290.0 [M+H]$^+$.

175

3-(2-Amino-5-fluorophenylamino)-N-methylbenzamide

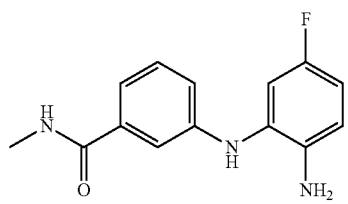

Prepared according to Step D2 in General Procedure D using 3-(5-fluoro-2-nitrophenylamino)-N-methylbenzamide (0.600 g, 2.07 mmol) to give 3-(2-amino-5-fluorophenylamino)-N-methylbenzamide as an orange solid. LC-MS (ESI) m/z 260.1 [M+H]$^+$.

(S)-tert-butyl 1-(4-fluoro-2-(3-(methylcarbamoyl)phenylamino)-phenylamino)-1-oxopropan-2-ylcarbamate

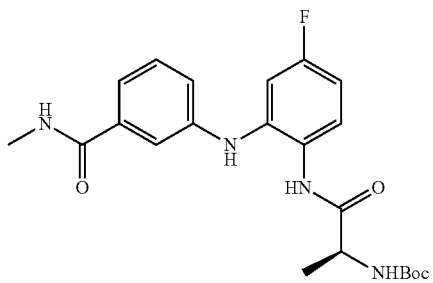 [SMILES: CNC(=O)c1cccc(Nc2cc(F)ccc2NC(=O)[C@H](C)NC(=O)OC(C)(C)C)c1]

Prepared according to Step D3 in General Procedure D using 3-(2-amino-5-fluorophenylamino)-N-methylbenzamide (0.538 g, 2.08 mmol) to give (S)-tert-butyl 1-(4-fluoro-2-(3-(methylcarbamoyl)phenylamino)phenylamino)-1-oxopropan-2-ylcarbamate as a yellow foam, quantitative yield assumed. LC-MS (ESI) m/z 453.0 [M+Na]$^+$.

3-(2-(1-Acetamidoethyl)-6-fluoro-1H-benzo[d]imidazol-1-yl)-N-methylbenzamide

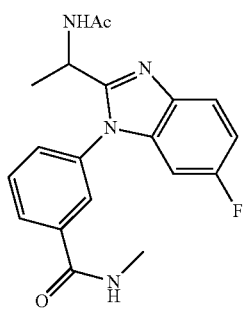 [SMILES: CNC(=O)c1cccc(-n2c(C(C)NC(C)=O)nc3ccc(F)cc32)c1]

Prepared according to Step D4 in General Procedure D using (S)-tert-butyl 1-(4-fluoro-2-(3-(methylcarbamoyl)phenylamino)phenylamino)-1-oxopropan-2-ylcarbamate (0.893 g, 2.074 mmol) to give afford 3-(2-(1-acetamidoethyl)-6-fluoro-1H-benzo[d]imidazol-1-yl)-N-methylbenzamide. LC-MS (ESI) m/z 355.1 [M+H]$^+$.

176

3-(2-(1-Aminoethyl)-6-fluoro-1H-benzo[d]imidazol-1-yl)-N-methylbenzamide

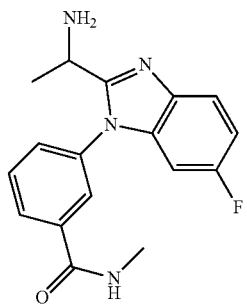 [SMILES: CNC(=O)c1cccc(-n2c(C(C)N)nc3ccc(F)cc32)c1]

Prepared according to Step D5a in General Procedure D using 3-(2-(1-acetamidoethyl)-6-fluoro-1H-benzo[d]imidazol-1-yl)-N-methylbenzamide (0.630 g, 1.78 mmol) to give 3-(2-(1-aminoethyl)-6-fluoro-1H-benzo[d]imidazol-1-yl)-N-methylbenzamide as an orange solid. MS (ESI) m/z 313.1 [M+H]$^+$.

3-(2-(1-(6-Amino-5-cyanopyrimidin-4-ylamino)ethyl)-6-fluoro-1H-benzo[d]-imidazol-1-yl)-N-methylbenzamide

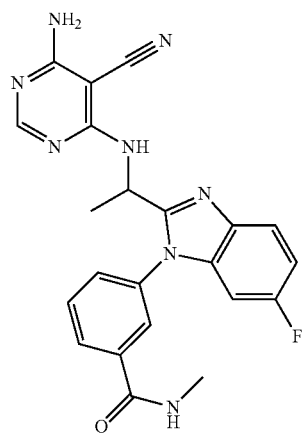

Prepared according to Step D6 in General Procedure D using 3-(2-(1-aminoethyl)-6-fluoro-1H-benzo[d]imidazol-1-yl)-N-methylbenzamide (430 mg, 1.38 mmol) to give 3-(2-(1-(6-amino-5-cyanopyrimidin-4-ylamino)ethyl)-6-fluoro-1H-benzo[d]imidazol-1-yl)-N-methylbenzamide as a white solid. $^1$H NMR (400 MHz, DMSO-d$_6$) δ ppm 1.52 (d, J=6.85 Hz, 3H) 2.81 (d, J=4.30 Hz, 3H) 5.32-5.59 (m, 1H) 6.92 (d, J=8.80 Hz, 1H) 7.08-7.17 (m, 1H) 7.19 (br. s., 2H) 7.56-7.78 (m, 4H) 7.83 (s, 1H) 7.91-8.10 (m, 2H) 8.49 (d, J=4.50 Hz, 1H). LC-MS (ESI) m/z 431.0 [M+H]$^+$ 3-(2-((1R)-1-((6-Amino-5-cyano-4-pyrimidinyl)amino)ethyl)-6-fluoro-1H-benzimidazol-1-yl)-N-methylbenzamide and 3-(2-((1S)-1-((6-amino-5-cyano-4-pyrimidinyl)amino)ethyl)-6-fluoro-1H-benzimidazol-1-yl)-N-methyl-benzamide

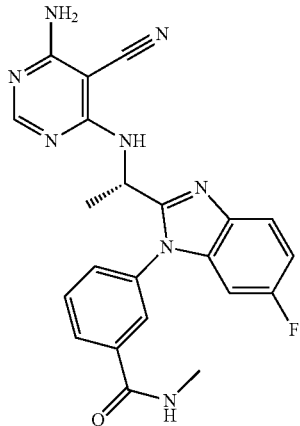 [SMILES: CNC(=O)c1cccc(-n2c(C(C)Nc3ncnc(N)c3C#N)nc3ccc(F)cc32)c1]

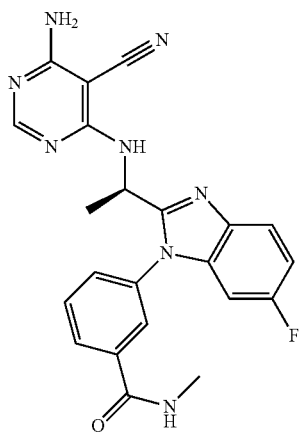

The racemic mixture (0.383 mg) was separated on AD-H column using preparative SFC to give two fractions. First peak on OD-H column: 3-(2-((1S)-1-(6-amino-5-cyano-4-pyrimidinyl)amino)ethyl)-6-fluoro-1H-benz-imidazol-1-yl)-N-methylbenzamide. $^1$H NMR (400 MHz, DMSO-d$_6$) δ ppm 1.52 (d, J=6.85 Hz, 3H) 2.81 (d, J=4.50 Hz, 3H) 5.39-5.52 (m, 1H) 6.92 (dd, J=8.90, 2.45 Hz, 1H) 7.14 (ddd, J=9.78, 8.80, 2.54 Hz, 1H) 7.19 (br. s., 2H) 7.59-7.72 (m, 3H) 7.75 (dd, J=8.80, 4.89 Hz, 1H) 7.83 (s, 1H) 7.92-8.06 (m, 2H) 8.49 (q, J=4.37 Hz, 1H)LC-MS (ESI) m/z 431.1 Second peak on OD-H column: 3-(2-((1R)-1-((6-amino-5-cyano-4-pyrimidinyl)amino)ethyl)-6-fluoro-1H-benzimidazol-1-yl)-N-methylbenzamide. $^1$H NMR (400 MHz, DMSO-d$_6$) δ ppm 1.52 (d, J=6.85 Hz, 3H) 2.81 (d, J=4.50 Hz, 3H) 5.37-5.55 (m, 1H) 6.92 (dd, J=8.90, 2.45 Hz, 1H) 7.14 (ddd, J=9.78, 8.80, 2.54 Hz, 1H) 7.19 (br. s., 2H) 7.60-7.72 (m, 3H) 7.75 (dd, J=8.80, 4.69 Hz, 1H) 7.83 (s, 1H) 7.92-8.05 (m, 2H) 8.49 (q, J=4.30 Hz, 1H). LC-MS (ESI) m/z 431.1 [M+H]$^+$.

Example 76

(S)-2-(1-((6-Amino-5-cyanopyrimidin-4-yl)amino)ethyl)-3-phenylimidazo[1,2-a]pyridine-5-carboxylic acid

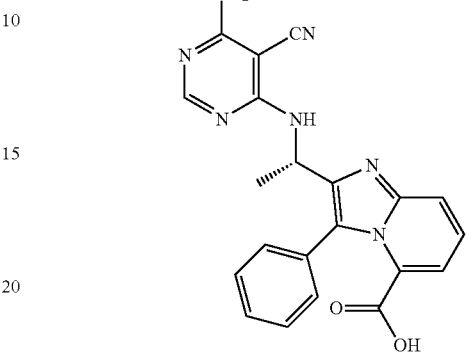

A solution of (S)-methyl 2-(1-(6-amino-5-cyanopyrimidin-4-ylamino)ethyl)-1-phenyl-1H-benzo[d]imidazole-7-carboxylate (0.244 g, 0.590 mmol) and lithium iodide (0.237 g, 1.771 mmol) in pyridine (3.11 mL) was stirred at 100° C. overnight. The solution was concentrated under reduced pressure to afford (S)-2-(1-((6-amino-5-cyanopyrimidin-4-yl)amino)ethyl)-3-phenylimidazo[1,2-a]pyridine-5-carboxylic acid as an off-white solid. LC-MS (ESI) m/z 400.1 [M+H]$^+$.

2-((1S)-1-((6-Amino-5-cyano-4-pyrimidinyl)amino)ethyl)-N-methyl-3-phenylimidazo[1,2-a]pyridine-5-carboxamide

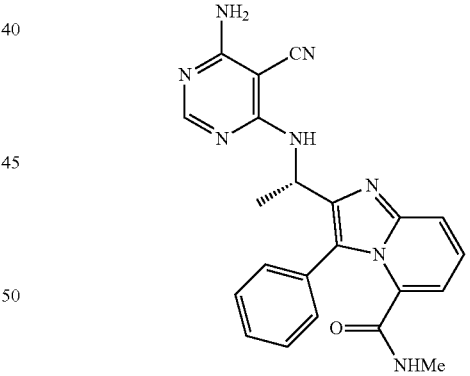

To a solution of DIEA (0.207 mL, 1.18 mmol), PyBOP (0.768 g, 1.475 mmol), and (S)-2-(1-((6-amino-5-cyanopyrimidin-4-yl)amino)ethyl)-3-phenylimidazo-[1,2-a]pyridine-5-carboxylic acid (0.236 g, 0.590 mmol) in DMF (3.93 mL) was added methanamine (2.0M in THF, 0.738 mL, 1.48 mmol). The solution was stirred at rt for 1 h then was loaded onto silica gel and purified by MPLC (eluted with a gradient of 0-10% MeOH in DCM) to afford a solid that was repurified by reverse phase analytical HPLC (eluted with a gradient of 10-60% MeCN in water with 0.1% TFA) to afford (S)-2-(14 (6-amino-5-cyanopyrimidin-4-yl)amino)-ethyl)-N-methyl-3-phenylimidazo[1,2-a]pyridine-5-carboxamide as a light yellow solid. $^1$H NMR (400 MHz, DMSO-d$_6$) δ ppm 1.44 (d, J=6.65 Hz, 3H) 2.16 (d, J=4.70 Hz, 3H) 5.29 (quin, J=6.90 Hz, 1H) 6.83 (d, J=7.63 Hz, 1H) 6.93 (dd, J=6.85, 1.17 Hz, 1H) 7.18-7.46 (m, 8H) 7.74 (dd, J=9.00, 1.17 Hz, 1H) 7.94 (s, 1H) 8.51 (q, J=4.56 Hz, 1H). LC-MS (ESI) m/z 413.1 [M+H]$^+$.

Example 77

5-Fluoro-N-(3-fluoro-2-nitrophenyl)pyridin-3-amine

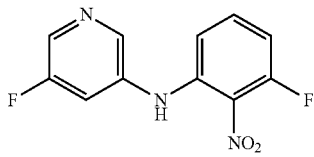

Prepared according to Step D1 in General Procedure D using 3-amino-5-fluoropyridine (2.114 g, 18.86 mmol) to give 5-fluoro-N-(3-fluoro-2-nitrophenyl)-pyridin-3-amine as an orange solid. LC-MS (ESI) m/z 252.1 [M+H]$^+$.

3-Fluoro-N1-(5-fluoropyridin-3-yl)benzene-1,2-diamine

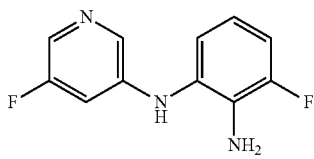 [SMILES: O=[N+]([O-])c1c(F)cccc1Nc1cncc(F)c1]

Prepared according to Step D2 in General Procedure D using 5-fluoro-N-(3-fluoro-2-nitrophenyl)pyridin-3-amine (3.40 g, 13.54 mmol) to give 3-fluoro-N1-(5-fluoropyridin-3-yl)benzene-1,2-diamine (2.92 g, 13.20 mmol, 98% yield) as a yellow solid. LC-MS (ESI) m/z 222.1 [M+H]$^+$.

(S)-tert-Butyl 1-(2-fluoro-6-(5-fluoropyridin-3-ylamino)phenylamino)-1-oxopropan-2-ylcarbamate

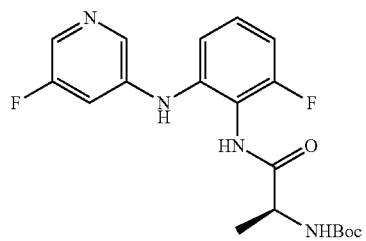 [SMILES: C[C@H](NC(=O)OC(C)(C)C)C(=O)Nc1c(F)cccc1Nc1cncc(F)c1]

Prepared according to Step D3 in General Procedure D using 3-fluoro-N1-(5-fluoropyridin-3-yl)benzene-1,2-diamine (2.92 g, 13.20 mmol) to give (S)-tert-butyl 1-(2-fluoro-6-(5-fluoropyridin-3-ylamino)phenylamino)-1-oxopropan-2-ylcarbamate as a beige solid. LC-MS (ESI) m/z 393.0 [M+H]$^+$.

N-(1-(4-Fluoro-1-(5-fluoropyridin-3-yl)-1H-benzo[d]imidazol-2-yl)-ethyl)acetamide

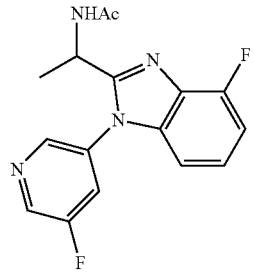 [SMILES: CC(=O)NC(C)c1nc2c(F)cccc2n1-c1cncc(F)c1]

Prepared according to Step D4 in General Procedure D using (S)-tert-butyl 1-(2-fluoro-6-(5-fluoropyridin-3-ylamino)phenylamino)-1-oxopropan-2-ylcarbamate (3.07 g, 7.82 mmol) to give N-(1-(4-fluoro-1-(5-fluoropyridin-3-yl)-1H-benzo[d]-imidazol-2-yl)ethyl)acetamide as a brown solid. LC-MS (ESI) m/z 317.1 [M+H]$^+$.

1-(4-Fluoro-1-(5-fluoropyridin-3-yl)-1H-benzo[d]imidazol-2-yl)ethanamine

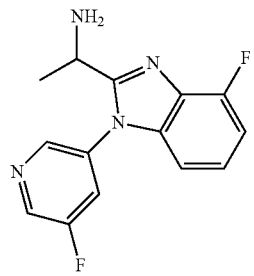 [SMILES: CC(N)c1nc2c(F)cccc2n1-c1cncc(F)c1]

Prepared according to Step D5a in General Procedure D using N-(1-(4-fluoro-1-(5-fluoropyridin-3-yl)-1H-benzo[d]imidazol-2-yl)ethyl)acetamide (2.30 g, 7.27 mmol) to give 1-(4-fluoro-1-(5-fluoropyridin-3-yl)-1H-benzo[d]imidazol-2-yl)ethanamine as a black oil. LC-MS (ESI) m/z 275.1 [M+H]$^+$.

4-Amino-6-(1-(4-fluoro-1-(5-fluoropyridin-3-yl)-1H-benzo[d]imidazol-2-yl)ethylamino)pyrimidine-5-carbonitrile

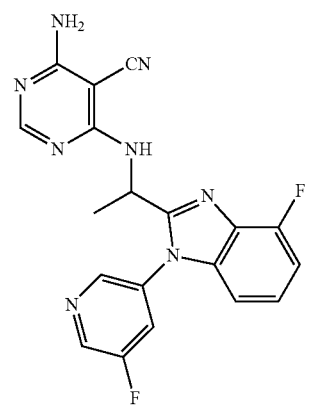 [SMILES: CC(Nc1ncnc(N)c1C#N)c1nc2c(F)cccc2n1-c1cncc(F)c1]

Prepared according to Step D6 in General Procedure D using 1-(4-fluoro-1-(5-fluoropyridin-3-yl)-1H-benzo[d]imidazol-2-yl)ethanamine (0.380 g, 1.39 mmol) to give 4-amino-6-(1-(4-fluoro-1-(5-fluoropyridin-3-yl)-1H-benzo[d]imidazol-2-yl)ethylamino)pyrimidine-5-carbonitrile as an off-white solid. $^1$H NMR (400 MHz, DMSO-d$_6$) δ ppm 1.62 (d, J=6.85 Hz, 3H) 5.60 (quin, J=6.99 Hz, 1H) 7.02 (dd, J=8.12, 0.68 Hz, 1H) 7.08-7.17 (m, 1H) 7.17-7.34 (m, 3H) 7.75-7.91 (m, 2H) 8.12 (d, J=8.61 Hz, 1H) 8.65 (s, 1H) 8.70 (d, J=2.54 Hz, 1H). LC-MS (ESI) m/z 393.0 [M+H]$^+$.

4-Amino-6-(((1R)-1-(4-fluoro-1-(5-fluoro-3-pyridinyl)-1H-benzimidazol-2-yl)ethyl)amino)-5-pyrimidinecarbonitrile and 4-amino-6-(((1S)-1-(4-fluoro-1-(5-fluoro-3-pyridinyl)-1H-benzimidazol-2-yl)ethyl)amino)-5-pyrimidinecarbonitrile

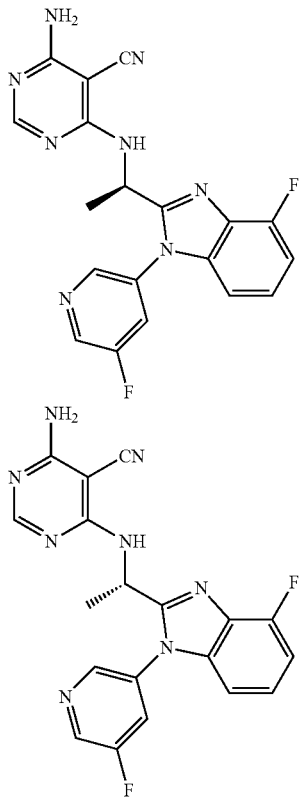

The racemic mixture (0.220 mg) was separated on AD-H column using preparative SFC to give two fractions. First peak on OD-H column: 4-Amino-6-(((1R)-1-(4-fluoro-1-(5-fluoro-3-pyridinyl)-1H-benzimidazol-2-yl)ethyl)amino)-5-pyrimidinecarbonitrile. LC-MS (ESI) m/z 393.0 [M+H]$^+$. $^1$H NMR (400 MHz, DMSO-d$_6$) δ ppm 1.61 (d, J=6.85 Hz, 3H) 5.59 (quin, J=6.94 Hz, 1H) 7.02 (d, J=8.02 Hz, 1H) 7.13 (dd, J=10.76, 7.82 Hz, 1H) 7.17-7.29 (m, 3H) 7.75-7.87 (m, 2H) 8.12 (d, J=8.22 Hz, 1H) 8.64 (s, 1H) 8.70 (d, J=2.74 Hz, 1H). Second peak on OD-H column: 4-Amino-6-((1S)-1-(4-fluoro-1-(5-fluoro-3-pyridinyl)-1H-benzimidazol-2-yl)ethyl)amino)-5-pyrimidinecarbonitrile (73 mg, 66.4%). LC-MS (ESI) m/z 393.0 [M+H]$^+$. $^1$H NMR (400 MHz, DMSO-d$_6$) δ ppm 1.61 (d, J=6.85 Hz, 3H) 5.59 (quin, J=6.90 Hz, 1H) 7.02 (d, J=8.02 Hz, 1H) 7.13 (dd, J=10.96, 8.02 Hz, 1H) 7.17-7.33 (m, 3H) 7.72-7.90 (m, 2H) 8.12 (d, J=7.43 Hz, 1H) 8.64 (s, 1H) 8.70 (d, J=2.54 Hz, 1H)

Example 78

4-Amino-6-(((1S)-1-(6-fluoro-1-(5-fluoro-3-pyridinyl)-1H-benzimidazol-2-yl)ethyl)amino)-5-pyrimidinecarboxamide

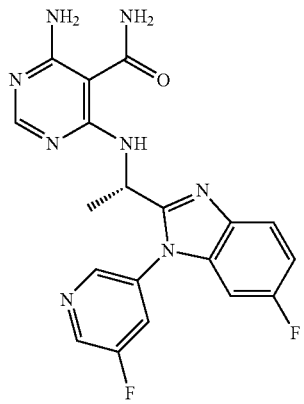 [SMILES: C[C@H](Nc1ncnc(N)c1C(N)=O)c1nc2ccc(F)cc2n1-c1cncc(F)c1]

To a solution of (S)-4-amino-6-(1-(6-fluoro-1-(5-fluoropyridin-3-yl)-1H-benzo[d]imidazol-2-yl)ethylamino)pyrimidine-5-carbonitrile (0.040 g, 0.10 mmol) in DMSO (1.02 mL) was added potassium carbonate (0.017 g, 0.122 mmol) followed by hydrogen peroxide (31% in water, 0.635 mL, 6.42 mmol). After stirring for 2 h the solution was poured into water and extracted with EtOAc. Organic extracts were concentrated and purified by MPLC (eluted with 0-100% (1:10:90 NH$_4$OH:MeOH:DCM) in DCM) to afford 4-amino-6-4 (1S)-1-(6-fluoro-1-(5-fluoro-3-pyridinyl)-1H-benzimidazol-2-yl)ethyl)amino)-5-pyrimidinecarboxamide as a white solid. $^1$H NMR (400 MHz, DMSO-d$_6$) δ ppm 1.51 (d, J=6.85 Hz, 3H) 5.34 (quin, J=6.94 Hz, 1H) 6.57 (s, 2H) 7.04-7.22 (m, 2H) 7.43 (br. s., 2H) 7.67-7.80 (m, 2H) 7.92 (d, J=7.63 Hz, 1H) 8.21 (dt, J=9.29, 2.10 Hz, 1H) 8.71 (s, 1H) 8.81 (d, J=2.74 Hz, 1H). LC-MS (ESI) m/z 411.0 [M+H]$^+$.

Example 79

Preparation of 2-((1S)-1-((5-amino-1,3,4-thiadiazol-2-yl)amino)ethyl)-1-cyclopropyl-N-methyl-1H-benzimidazole-7-carboxamide

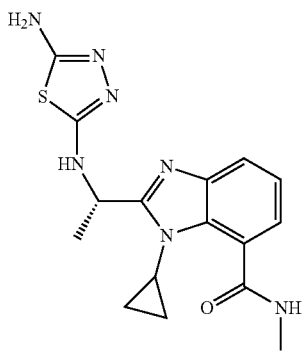 [SMILES: CNC(=O)c1cccc2nc([C@H](C)Nc3nnc(N)s3)n(C3CC3)c12]

A mixture of (S)-2-(1-aminoethyl)-1-cyclopropyl-N-methyl-1H-benzo[d]imidazole-7-carboxamide (prepared in example 20) (63.5 mg, 0.25 mmol), cesium carbonate (80 mg, 0.25 mmol) and 2-amino-5-bromo-[1,3,4]thiadiazole (44.3 mg, 0.25 mmol) in EtOH (5 mL) under $N_2$ was stirred at rt for 18 h. The reaction mixture was concentrated in vacuo. The residue was diluted with EtOAc, washed with water, brine, dried over magnesium sulfate, and concentrated in vacuo. Purification of the residue by flash chromatography over silica gel, using 0 to 10% gradient of MeOH in DCM with 0.2% $NH_4OH$ as eluent to give 2-((1S)-1-((5-amino-1,3,4-thiadiazol-2-yl)amino)ethyl)-1-cyclopropyl-N-methyl-1H-benzimidazole-7-carboxamide: $^1$H NMR (400 MHz, DMSO-$d_6$) δ 8.46-8.39 (1H, m); 7.62 (1H, d, J=8.0 Hz), 7.44 (1H, d, J=8.0 Hz), 7.24-7.16 (2H, m); 6.22 (2H, s), 5.46-5.37 (1H, m), 3.40-3.30 (1H, m), 2.82 (3H, d, J=4.0 Hz), 1.55 (3H, d, J=4.0 Hz), 1.22-1.15 (1H, m), 1.12-1.04 (1H, m), 1.01-0.92 (1H, m), 0.83-0.74 (1H, m); LC-MS (ESI) m/z 358.0 [M+H]$^+$.

Example 80

Preparation of 4-amino-6-(((1R)-1-(7-bromo-1-(5-fluoro-3-pyridinyl)-1H-benzimidazol-2-yl)ethyl) amino)-5-pyrimidinecarbonitrile and 4-amino-6-(((1S)-1-(7-bromo-1-(5-fluoro-3-pyridinyl)-1H-benzimidazol-2-yl)ethyl)amino)-5-pyrimidinecarbonitrile N-(2-Bromo-6-nitrophenyl)-5-fluoropyridin-3-amine

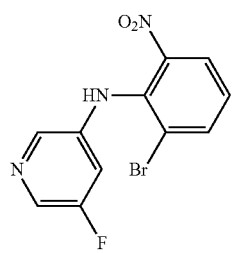 [SMILES: O=[N+]([O-])c1cccc(Br)c1Nc1cncc(F)c1]

To a solution of 1-bromo-2-fluoro-3-nitrobenzene (5.69 g, 25.9 mmol) and 3-amino-5-fluoropyridine (2.6373 g, 23.53 mmol) in DMF (39.2 mL) was added potassium tert-butoxide (5.28 g, 47.1 mmol) and the solution was stirred under nitrogen at rt overnight. After 5 additional h, the mixture was poured into water (150 mL) and extracted with EtOAc (2×100 mL). The organic extract was dried over $MgSO_4$. The solution was filtered and concentrated in vacuo to provide the crude material as a orange solid. The orange solid was purified by chromatography through a Redi-Sep™ pre-packed silica gel column (120 g), eluting with a gradient of 0% to 50% EtOAc in hexane, to provide N-(2-bromo-6-nitrophenyl)-5-fluoropyridin-3-amine as orange syrup: $^1$H NMR (400 MHz, DMSO-$d_6$) δ ppm 8.73 (1H, s), 8.09 (1H, dd, J=8.1, 1.5 Hz), 8.03 (1H, dd, J=8.2, 1.4 Hz), 7.97 (1H, d, J=2.5 Hz), 7.88 (1H, t, J=1.9 Hz), 7.44 (1H, t, J=8.1 Hz), 6.77 (1H, dt, J=11.2, 2.3 Hz); LC-MS (ESI) m/z 312.0 [M+H ($^{79}$Br)]$^+$ and 313.9 [M+H ($^{81}$Br)]$^+$.

6-Bromo-N1-(5-fluoropyridin-3-yl)benzene-1,2-diamine

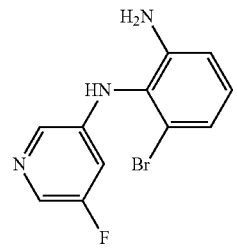 [SMILES: Nc1cccc(Br)c1Nc1cncc(F)c1]

A mixture of N-(2-bromo-6-nitrophenyl)-5-fluoropyridin-3-amine (5.686 g, 18.22 mmol) and tin(II) chloride dihydrate (20.56 g, 91 mmol) in EtOAc (121 mL) was heated under reflux with stirring. After 2.5 h, the mixture was cooled to rt. The cooled mixture was poured into 10M aqueous NaOH solution (150 mL). The mixture was extracted with EtOAC (100 mL×2) washed with water (100 mL×2), brine (100 mL×1), dried over $Mg_2SO_4$, filtered, and concentrated in vacuo. The crude material was absorbed onto a plug of silica gel and purified by chromatography through a Redi-Sep™ pre-packed silica gel column (120 g), eluting with a gradient of 0% to 30% EtOAc in hexane, to provide 6-bromo-N1-(5-fluoropyridin-3-yl)benzene-1,2-diamine as brown syrupy solid: $^1$H NMR (400 MHz, DMSO-$d_6$) δ ppm 7.84 (1H, s), 7.76-7.82 (2H, m), 6.91-6.98 (1H, m), 6.81-6.87 (1H, m), 6.77 (1H, dd, J=8.0, 1.4 Hz), 6.39 (1H, dt, J=11.7, 2.3 Hz), 5.28 (2H, s); LC-MS (ESI) m/z 282.0 [M+H ($^{79}$Br)]$^+$ and 283.9 [M+H ($^{81}$Br)]$^-$.

(S)-tert-Butyl 1-(3-bromo-2-(5-fluoropyridin-3-ylamino)phenylamino)-1-oxopropan-2-ylcarbamate

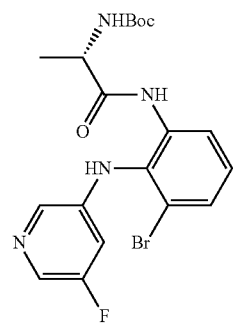 [SMILES: C[C@H](NC(=O)OC(C)(C)C)C(=O)Nc1cccc(Br)c1Nc1cncc(F)c1]

To a −10° C. solution (NaCl-ice bath) of Boc-L-Ala-OH (6.36 g, 33.6 mmol) and N-methylmorpholine (3.88 mL, 35.3 mmol) in DCM (84 mL) was added isobutyl chloroformate (4.40 mL, 33.6 mmol). The resulting cloudy colorless mixture was stirred at −10° C. for 30 min. To the mixture was then added a solution of 6-bromo-N1-(5-fluoropyridin-3-yl)benzene-1,2-diamine (4.7437 g, 16.81 mmol) in DCM (84 mL). The resulting mixture was allowed to warm to rt with stirring. After 20 h, satd. $NH_4Cl$ (100 mL) was added to the mixture. The cloudy organic layer was separated. The aqueous mixture was extracted with DCM (1×100 mL) and the organic extracts concentrated in vacuo to provide a crude product. The crude material was absorbed onto a plug of silica gel and purified by chromatography through a Redi-Sep pre-packed silica gel column (120 g), eluting with a gradient of 0% to 100% DCM:MeOH:NH₄OH (89:9:1) in DCM, to provide (S)-tert-butyl 1-(3-bromo-2-(5-fluoropyridin-3-ylamino)phenylamino)-1-oxopropan-2-ylcarbamate as orange solid: LC-MS (ESI) m/z 453.0 [M+H (⁷⁹Br)]⁺ and 455.0 [M+H (⁸¹Br)]⁺.

N-(1-(7-Bromo-1-(5-fluoropyridin-3-yl)-1H-benzo[d]imidazol-2-yl)ethyl)acetamide

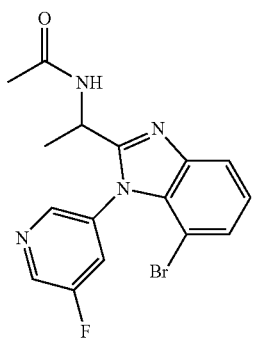 [SMILES: CC(=O)NC(C)c1nc2cccc(Br)c2n1-c1cncc(F)c1]

A solution of (S)-tert-butyl 1-(3-bromo-2-(5-fluoropyridin-3-ylamino)phenylamino)-1-oxopropan-2-ylcarbamate (2.4253 g, 5.35 mmol) in AcOH (17.83 mL) was heated at 100° C. with stirring. After 5 days, the mixture was removed from the heat and poured into a biphase of DCM (100 mL) and satd. sodium bicarbonate solution (100 mL). The mixture was basified with 10N NaOH (10 mL). The organic layer was washed with water (100 mL×3) and brine (100 mL X¹), dried over MgSO₄, filtered, and concentrated in vacuo to provide N-(1-(7-bromo-1-(5-fluoropyridin-3-yl)-1H-benzo[d]imidazol-2-yl)ethyl)acetamide as a dark brown solid: LC-MS (ESI) m/z 376.9 [M+H (⁷⁹Br)]⁺ and 379 [M+H (⁸¹Br)]⁺.

1-(7-Bromo-1-(5-fluoropyridin-3-yl)-1H-benzo[d]imidazol-2-yl)ethanamine

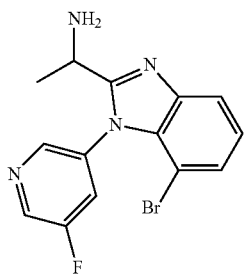 [SMILES: CC(N)c1nc2cccc(Br)c2n1-c1cncc(F)c1]

A solution of N-(1-(7-bromo-1-(5-fluoropyridin-3-yl)-1H-benzo[d]imidazol-2-yl)ethyl)acetamide (1.5652 g, 4.15 mmol) and 2N HCl (31.1 mL, 62.2 mmol) was heated at 100° C. After 6 h, the mixture was cooled to rt and partitioned between DCM (50 mL) and water (50 mL). The acidic aqueous mixture was washed with DCM (50 mL×4) to remove organic impurities and then basified to ~pH 12 with 10N NaOH (6 mL) and extracted with DCM (50 mL×3). The combined organic layers were washed with water (100 mL×1), brine (100 mL×1), dried over MgSO₄, filtered, and concentrated in vacuo to give a dark red syrup. The crude material was absorbed onto a plug of silica gel and purified by chromatography through a Redi-Sep™ pre-packed silica gel column (80 g), eluting with a gradient of 0% to 50% DCM:MeOH:NH₄OH (89:9:1) in DCM, to provide 1-(7-bromo-1-(5-fluoropyridin-3-yl)-1H-benzo[d]imidazol-2-yl)ethanamine as a brown syrupy solid: ¹H NMR (400 MHz, DMSO-d₆) δ ppm 8.86 (1H, t, J=2.8 Hz), 8.73 (1H, dt, J=13.5, 1.4 Hz), 8.23-8.33 (1H, m), 7.75 (1H, dd, J=8.0, 1.0 Hz), 7.41 (1H, d, J=7.4 Hz), 7.21 (1H, t, J=7.9 Hz), 3.76 (1H, q, J=6.7 Hz), 1.93 (2H, br. s.), 1.36 (3H, d, J=6.7 Hz); LC-MS (ESI) m/z 334.9 [M+H (⁷⁹Br)]⁺ and 337 [M+H (⁸¹Br)]⁺.

4-Amino-6-(1-(7-bromo-1-(5-fluoro-3-pyridinyl)-1H-benzimidazol-2-yl)-ethyl)amino)-5-pyrimidinecarbonitrile

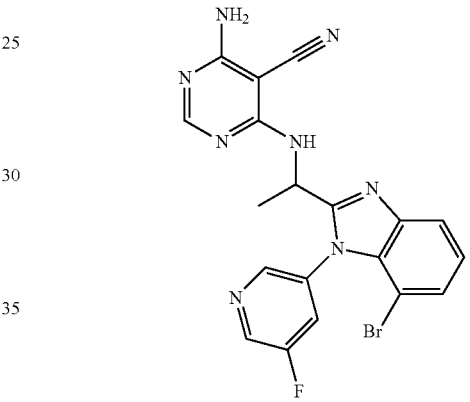

A mixture of 4-amino-6-chloropyrimidine-5-carbonitrile (0.368 g, 2.381 mmol), 1-(7-bromo-1-(5-fluoropyridin-3-yl)-1H-benzo[d]imidazol-2-yl)ethanamine (0.798 g, 2.38 mmol), and DIEA (1.24 mL, 7.14 mmol) in 1-butanol (23.8 mL) was stirred at 120° C. After 23 h, the mixture was removed from the heat and left at rt. After cooling, the mixture was concentrated in vacuo to give a dark purple solid. To the dark purple solid was added water (50 mL) followed by sonication. The resulting precipitate was collected by filtration, washed with water, and air-dried to give the product. The solid was absorbed onto a plug of silica gel and purified by chromatography through a Redi-Sep™ pre-packed silica gel column (80 g), eluting with a gradient of 0% to 50% DCM:MeOH:NH₄OH (89:9:1) in DCM, to provide a purple solid. The purple solid was suspended in EtOAc-hexane (1:5, 10 mL), filtered, and washed with EtOAc-hexane (1:5, 40 mL) to provide 4-amino-6-(1-(7-bromo-1-(5-fluoropyridin-3-yl)-1H-benzo[d]imidazol-2-yl)ethylamino)pyrimidine-5-carbonitrile as a purple solid: ¹H NMR (400 MHz, DMSO-d₆) δ ppm 8.47-8.79 (2H, m), 7.88-8.34 (1H, m), 7.67-7.85 (3H, m), 7.44 (1H, dd, J=7.8, 0.8 Hz), 7.22 (3H, t, J=7.9 Hz), 5.29-5.47 (1H, m), 1.57 (3H, d, J=6.8 Hz); LC-MS (ESI) m/z 453.0 [M+H (⁷⁹Br)]⁺ and 454.9 [M+H (⁸¹Br)]⁺.

4-Amino-6-(((1R)-1-(7-bromo-1-(5-fluoro-3-pyridinyl)-1H-benzimidazol-2-yl)ethyl)amino)-5-pyrimidinecarbonitrile and 4-amino-6-(((1S)-1-(7-bromo-1-(5-fluoro-3-pyridinyl)-1H-benzimidazol-2-yl)ethyl)amino)-5-pyrimidinecarbonitrile

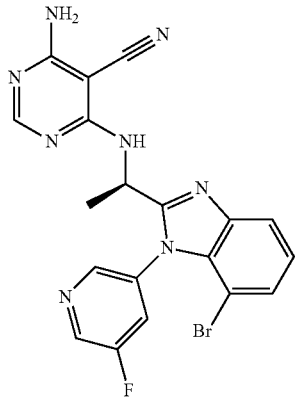

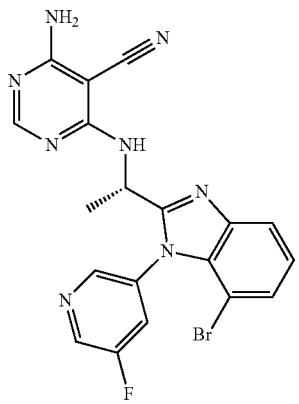 [SMILES: CC(Nc1ncnc(N)c1C#N)c1nc2cccc(Br)c2n1-c1cncc(F)c1]

The racemic mixture (0.1 g) was separated on AD-H column using preparative SFC to give two fractions: First peak on SFC AD-H column: 4-Amino-6-(((1R)-1-(7-bromo-1-(5-fluoro-3-pyridinyl)-1H-benzimidazol-2-yl)ethyl)amino)-5-pyrimidinecarbonitrile as a pink solid: $^1$H NMR (400 MHz, DMSO-$d_6$) δ ppm 8.50-8.78 (2H, m), 7.87-8.34 (1H, m), 7.71-7.84 (3H, m), 7.44 (1H, dd, J=7.8, 0.8 Hz), 7.22 (3H, t, J=7.9 Hz), 5.30-5.47 (1H, m), 1.57 (3H, d, J=6.7 Hz); LC-MS (ESI) m/z 453.0 [M+H ($^{79}$Br)]$^+$ and 455.0 [M+H ($^{81}$Br)]$^+$. Second peak on SFC AD-H column: 4-Amino-6-4(1S)-1-(7-bromo-1-(5-fluoro-3-pyridinyl)-1H-benzimidazol-2-yl)ethyl)amino)-5-pyrimidinecarbonitrile as a pink solid: $^1$H NMR (400 MHz, DMSO-$d_6$) δ ppm 8.51-8.77 (2H, m), 7.88-8.33 (1H, m), 7.71-7.84 (3H, m), 7.44 (1H, dd, J=7.8, 0.8 Hz), 7.22 (3H, t, J=7.9 Hz), 5.30-5.46 (1H, m), 1.57 (3H, d, J=6.7 Hz); LC-MS (ESI) m/z 453.0 [M+H ($^{79}$Br)]$^+$ and 455.0 [M+H ($^{81}$Br)]$^+$ at 1.650 min.

Example 81

Preparation of methyl 2-((1S)-1-((6-amino-5-cyano-4-pyrimidinyl)amino)ethyl)-3-(3-pyridinyl)imidazo[1,2-a]pyridine-5-carboxylate (S)-Methyl 2-(1-(((benzyloxy)carbonyl)amino)ethyl)-3-(pyridin-3-yl)imidazo-[1,2-a]pyridine-5-carboxylate

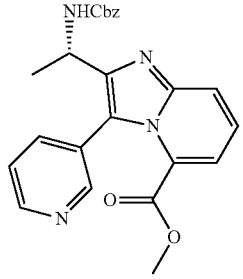 [SMILES: COC(=O)c1cccc2nc([C@H](C)NC(=O)OCc3ccccc3)c(-c3cccnc3)n12]

To a solution of (S)-methyl 2-(1-(((benzyloxy)carbonyl)amino)ethyl)-3-iodoimidazo[1,2-a]pyridine-5-carboxylate (prepared in example 73, 4.00 g, 8.35 mmol) and pyridin-3-ylboronic acid (1.00 g, 10.2 mmol) in toluene (48 mL), EtOH (32 mL), and water (16 mL) was added sodium carbonate (4.38 g, 41.8 mmol) at 25° C. The reaction mixture was degassed with nitrogen for 30 min and di-(triphenyl)phosphine)palladium(II) chloride (22 mg, 0.18 mmol) was added to reaction mixture at 25° C. The reaction mixture was stirred at 120° C. overnight. After completion of the reaction, water was added to reaction mixture and extracted with EtOAc. The organic layer was dried over sodium sulfate and concentrated in vacuo. The residue was purified by column chromatography using neutral alumina and 0-70% EtOAc in hexane to provide (S)-methyl 2-(1-(((benzyloxy)carbonyl)amino)ethyl)-3-(pyridin-3-yl)imidazo[1,2-a]pyridine-5-carboxylate ester: LC-MS (ESI) m/z 431.0 [M+H]$^+$.

(S)-Methyl 2-(1-aminoethyl)-3-(pyridin-3-yl)imidazo[1,2-a]pyridine-5-carboxylate

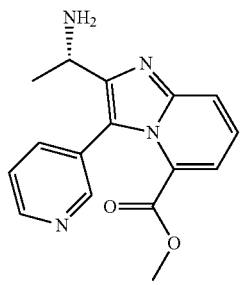 [SMILES: COC(=O)c1cccc2nc([C@H](C)N)c(-c3cccnc3)n12]

The mixture of (S)-methyl 2-(1-(((benzyloxy)carbonyl)amino)ethyl)-3-(pyridin-3-yl)imidazo[1,2-a]pyridine-5-carboxylate (450 mg, 1.04 mmol) and dimethylsulfide (0.4 mL) in TFA (1.2 mL)) was stirred at rt overnight. The mixture was concentrated in vacuo. The residue was dissolved in EtOAc. The organic layer was washed with satd. sodium bicarbonate solution, dried over sodium sulfate, filtered and concentrated in vacuo to provide (S)-methyl 2-(1-aminoethyl)-3-(pyridin- 3-yl)imidazo[1,2-a]pyridine-5-carboxylate: LC-MS (ESI) m/z 297.2 [M+H]+. The crude product was used without further purification.

(S)-Methyl 2-(1-((6-amino-5-cyanopyrimidin-4-yl)amino)ethyl)-3-(pyridin-3-yl)imidazo[1,2-a]pyridine-5-carboxylate

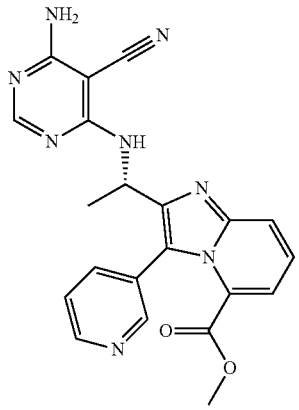 [SMILES: COC(=O)c1cccc2nc([C@H](C)Nc3ncnc(N)c3C#N)c(-c3cccnc3)n12]

To a mixture of (S)-methyl 2-(1-aminoethyl)-3-(pyridin-3-yl) imidazo[1,2-a]pyridine-5-carboxylate (300 mg, 1.013 mmol) and 4-amino-6-chloro-pyrimidine-5-carbonitrile (156 mg, 1.013 mmol) in n-butanol (3 mL) was added DIEA (0.3 mL, 1.519 mmol) at rt. The reaction mixture was stirred for 6 h and heated at 110° C. The mixture was diluted with and extracted with EtOAc. The organic layer was dried over sodium sulfate, filtered, and concentrated in vacuo. The residue was purified by column chromatography using silica gel (100-200 mesh) and 0-40% acetone in hexane to provide (S)-methyl 2-(1-((6-amino-5-cyanopyrimidin-4-yl)amino)ethyl)-3-(pyridin-3-yl)imidazo[1,2-a]pyridine-5-carboxylate: $^1$H NMR (400 MHz, DMSO-$d_6$) δ 1.514 (d, J=5.6 Hz, 3H), 3.226 (s, 3H), 5.313-5.382 (m, 1H), 7.064-7.082 (m, 1H), 7.220 (br s, 2H), 7.346-7.363 (m, 1H), 7.397-7.437 (m, 1H), 7.486-7.518 (m, 1H), 7.765 (br s, 1H), 7.875-7.926 (m, 2H), 8.552-8.605 (m, 2H); LC-MS (ESI) m/z 414.1 [M+H]+.

Example 82

Preparation of 4-amino-6-(((1S)-1-(1-(cyclopropylmethyl)-7-(trifluoromethyl)-1H-benzimidazol-2-yl)propyl)amino)-5-pyrimidinecarbonitrile 3-(Trifluoromethyl)benzene-1,2-diamine

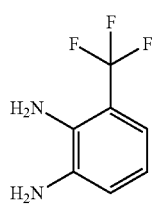

Using the general synthetic procedure for methyl 3-amino-2-(cyclopropylamino)benzoate in example 47, 3-(trifluoromethyl)benzene-1,2-diamine was prepared using 2-nitro-3-amino trifluorotoluene: LC-MS (ESI) m/z 177.1 [M+H]+.

(S)-tert-Butyl 1-(2-amino-3-(trifluoromethyl)phenylamino)-1-oxobutan-2-ylcarbamate

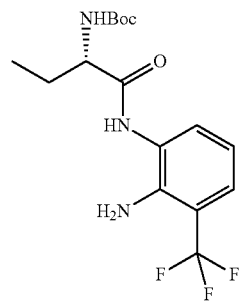 [SMILES: CC[C@H](NC(=O)OC(C)(C)C)C(=O)Nc1cccc(C(F)(F)F)c1N]

Using the general synthetic procedure for (S)-methyl 3-(2-(tert-butoxycarbonyl-amino)propanamido)-2-(cyclopropylamino)benzoate in example 47, (S)-tert-butyl 1-(2-amino-3-(trifluoromethyl)phenylamino)-1-oxobutan-2-ylcarbamate was prepared using 3-(trifluoromethyl)benzene-1,2-diamine and Boc-abu-OH: LC-MS (ESI) m/z 362.0 [M+H]+.

(S)-tert-Butyl 1-(2-(cyclopropylmethylamino)-3-(trifluoromethyl)phenylamino)-1-oxobutan-2-ylcarbamate

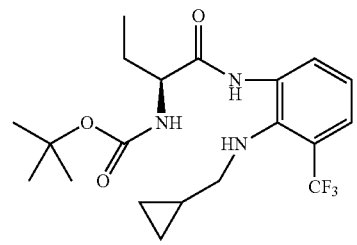 [SMILES: CC[C@H](NC(=O)OC(C)(C)C)C(=O)Nc1cccc(C(F)(F)F)c1NCC1CC1]

Using the general synthetic procedure for (S)-tert-butyl 1-(2-(cyclopropylmethylamino)-3-(methylsulfonyl)phenylamino)-1-oxopropan-2-ylcarbamate in example 66, (S)-tert-butyl 1-(2-(cyclopropylmethylamino)-3-(trifluoromethyl)phenylamino)-1-oxobutan-2-ylcarbamate was prepared using (S)-tert-butyl 1-(2-amino-3-(trifluoromethyl)phenylamino)-1-oxobutan-2-ylcarbamate: LC-MS (ESI) m/z 416.0 [M+H]+.

(S)-1-(1-(Cyclopropylmethyl)-7-(trifluoromethyl)-1H-benzo[d]imidazol-2-yl)propan-1-amine

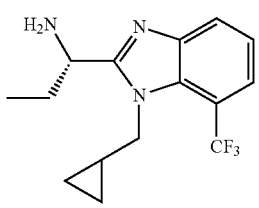 [SMILES: CC[C@H](N)c1nc2cccc(C(F)(F)F)c2n1CC1CC1]

Using the general synthetic procedure for (S)-methyl 2-(1-aminoethyl)-1-cyclopropyl-1H-benzo[d]imidazole-7-carboxylate in example 47, (S)-1-(1-(cyclopropylmethyl)-7-(trifluoromethyl)-1H-benzo[d]imidazol-2-yl)propan-1-amine was prepared using (S)-tert-butyl 1-(2-(cyclopropylmethylamino)-3-(trifluoromethyl)phenylamino)-1-oxobutan-2-ylcarbamate: LC-MS (ESI) m/z 298.0 [M+H]$^+$.

4-Amino-6-(((1S)-1-(1-(cyclopropylmethyl)-7-(trifluoromethyl)-1H-benzimidazol-2-yl)propyl)amino)-5-pyrimidinecarbonitrile

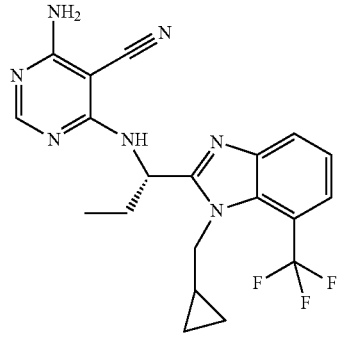 [SMILES: CC[C@H](Nc1ncnc(N)c1C#N)c1nc2cccc(C(F)(F)F)c2n1CC1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(cyclopropylmethyl)-7-(trifluoromethyl)-1H-benzimidazol-2-yl)propyl)amino)-5-pyrimidinecarbonitrile was prepared using (S)-1-(1-(cyclopropylmethyl)-7-(trifluoromethyl)-1H-benzo[d]imidazol-2-yl)propan-1-amine: $^1$H NMR (400 MHz, DMSO-d$_6$) δ 8.06 (1H, s), 8.01 (1H, d, J=8.0 Hz), 7.70-7.64 (2H, m), 7.40 (1H, t, J=8.0 Hz), 7.34 (2H, br), 5.70-5.60 (1H, m), 4.39 (1H, dd, J=16.0, 4.0 Hz), 4.38 (1H, dd, J=16.0, 4.0 Hz), 2.15-2.06 (2H, m), 1.20-2.10 (1H, m), 1.66 (3H, t, J=8.0 Hz), 0.58-0.48 (3H, m), 0.43-0.35 (1H, m); LC-MS (ESI) m/z 416.0 [M+H]$^+$.

Example 83

Preparation of 2-((1S)-1-((6-amino-5-cyano-4-pyrimidinyl)amino)propyl)-1-cyclopropyl-N-methyl-1H-benzimidazole-7-carboxamide

(S)-tert-Butyl 1-(2-(cyclopropylamino)-3-(methylcarbamoyl)phenylamino)-1-oxobutan-2-ylcarbamate

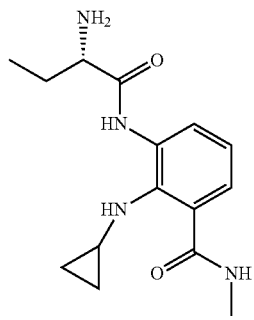 [SMILES: CC[C@H](N)C(=O)Nc1cccc(C(=O)NC)c1NC1CC1]

Using the general synthetic procedure for (S)-methyl 3-(2-(tert-butoxycarbonylamino)propanamido)-2-(cyclopropylamino)benzoate in example 47, (S)-tert-butyl 1-(2-(cyclopropylamino)-3-(methylcarbamoyl)phenylamino)-1-oxobutan-2-ylcarbamate was prepared using 3-amino-2-(cyclopropylamino)-N-methylbenzamide (Prepared in Example 20): LC-MS (ESI) m/z 391.1 [M+H]$^+$.

(S)-2-(1-Aminopropyl)-1-cyclopropyl-N-methyl-1H-benzo[d]imidazole-7-carboxamide

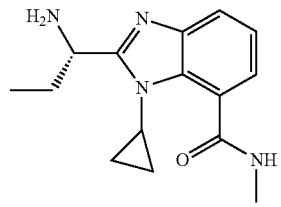 [SMILES: CC[C@H](N)c1nc2cccc(C(=O)NC)c2n1C1CC1]

Using the general synthetic procedure for (S)-methyl 2-(1-aminoethyl)-1-cyclopropyl-1H-benzo[d]imidazole-7-carboxylate in example 47, (S)-2-(1-amino-propyl)-1-cyclopropyl-N-methyl-1H-benzo[d]imidazole-7-carboxamide was prepared using (S)-tert-butyl 1-(2-(cyclopropylamino)-3-(methylcarbamoyl)phenylamino)-1-oxobutan-2-ylcarbamate: LC-MS (ESI) m/z 273.1 [M+H]$^+$.

2-((1S)-1-((6-Amino-5-cyano-4-pyrimidinyl)amino)propyl)-1-cyclopropyl-N-methyl-1H-benzimidazole-7-carboxamide

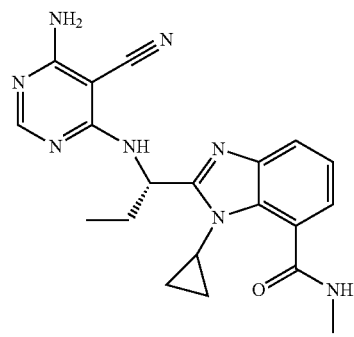 [SMILES: CC[C@H](Nc1ncnc(N)c1C#N)c1nc2cccc(C(=O)NC)c2n1C1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 2-((1S)-1-((6-amino-5-cyano-4-pyrimidinyl)amino)propyl)-1-cyclopropyl-N-methyl-1H-benzimidazole-7-carboxamide: $^1$H NMR (400 MHz, DMSO-d$_6$) δ 8.46-8.40 (1H, m); 8.03 (1H, s), 7.66 (1H, d, J=8.0 Hz), 7.44 (1H, d, J=8.0 Hz), 7.32 (2H, br), 7.26-7.16 (2H, m); 5.80-5.72 (1H, m), 2.82 (3H, d, J=4.0 Hz), 2.13-2.02 (2H, m), 1.20-1.08 (2H, m), 1.00-0.92 (4H, m), 0.82-0.74 (1H, m); LC-MS (ESI) m/z 391.1 [M+H]$^+$.

Example 84

4-Amino-6-(((1S)-1-(5-((4-methyl-1-piperazinyl)carbonyl)-3-phenylimidazo[1,2-a]pyridin-2-yl)ethyl)amino)-5-pyrimidinecarbonitrile

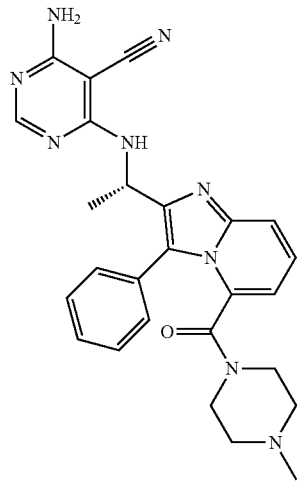 [SMILES: C[C@H](Nc1ncnc(N)c1C#N)c1nc2cccc(C(=O)N3CCN(C)CC3)n2c1-c1ccccc1]

A solution of N-methylpiperazine (0.040 mL, 0.356 mmol), (S)-2-(1-(6-amino-5-cyanopyrimidin-4-ylamino)ethyl)-3-phenylimidazo[1,2-a]pyridine-5-carboxylic acid (0.071 g, 0.178 mmol), PyBOP (0.185 g, 0.356 mmol) and DIEA (0.062 mL, 0.356 mmol) in DMF (1.78 mL) was stirred at rt for 1 h. The solution was loaded onto silica gel and purified by MPLC (eluted with a gradient of 0-10% MeOH in DCM) to afford an off-white solid that was repurified by MPLC (eluted with a gradient of 0-80% (1:10:90 NH$_4$OH:MeOH:DCM) solution in DCM) to afford 4-amino-6-(((1S)-1-(5-((4-methyl-1-piperazinyl)carbonyl)-3-phenylimidazo[1,2-a]pyridin-2-yl)ethyl)amino)-5-pyrimidinecarbonitrile as a white solid. $^1$H NMR (400 MHz, DMSO-d$_6$) δ ppm 1.43 (dd, J=14.18, 6.75 Hz, 3H) 1.88-2.01 (m, 1H) 2.03-2.10 (m, 1H) 2.12-2.44 (m, 6H) 3.00-3.14 (m, 1H) 3.22 (m, J=9.19 Hz, 1H) 3.40 (d, J=4.30 Hz, 1H) 5.13-5.34 (m, 1H) 6.75-6.98 (m, 2H) 7.16-7.53 (m, 8H) 7.75 (m, J=9.00, 5.09 Hz, 1H) 7.94 (d, J=6.85 Hz, 1H). LC-MS (ESI) m/z 482.1 [M+H]$^+$.

Example 85

Preparation of 4-amino-6-(((1S)-1-(1-(4-fluorobenzyl)-7-(tri-fluoromethyl)-1H-benzimidazol-2-yl)propyl)amino)-5-pyrimidinecarbonitrile (S)-tert-Butyl 1-(2-(4-fluorobenzylamino)-3-(trifluoromethyl)phenylamino)-1-oxobutan-2-ylcarbamate

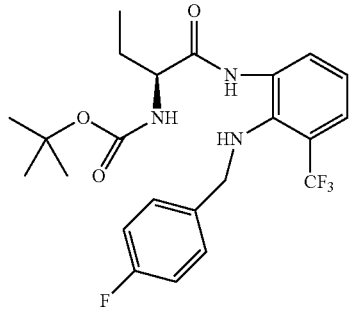 [SMILES: CC[C@H](NC(=O)OC(C)(C)C)C(=O)Nc1cccc(C(F)(F)F)c1NCc1ccc(F)cc1]

Using the general synthetic procedure for 4-amino-6-4(1S)-1-(1-(4-fluorobenzyl)-4-(methylsulfonyl)-1H-benzimidazol-2-yl)ethyl)amino)-5-pyrimidinecarbonitrile in example 59, (S)-tert-butyl 1-(2-(4-fluorobenzylamino)-3-(trifluoromethyl)-phenylamino)-1-oxobutan-2-ylcarbamate was prepared using (S)-tert-butyl 1-(2-amino-3-(trifluoromethyl)phenylamino)-1-oxobutan-2-ylcarbamate (Prepared in Example 82): LC-MS (ESI) m/z 470.2 [M+H]$^+$ (S)-1-(1-(4-Fluorobenzyl)-7-(trifluoromethyl)-1H-benzo[d]imidazol-2-yl)propan-1-amine

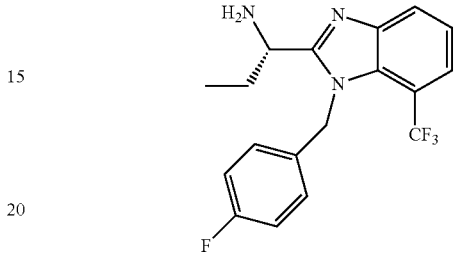

Using the general synthetic procedure for (S)-methyl 2-(1-aminoethyl)-1-cyclopropyl-1H-benzo[d]imidazole-7-carboxylate in example 47, (S)-1-(1-(4-fluorobenzyl)-7-(trifluoromethyl)-1H-benzo[d]imidazol-2-yl)propan-1-amine was prepared using (S)-tert-butyl 1-(2-(4-fluorobenzylamino)-3-(trifluoromethyl)phenylamino)-1-oxobutan-2-ylcarbamate: LC-MS (ESI) m/z 352.0 [M+H]$^+$.

4-Amino-6-(((1S)-1-(1-(4-fluorobenzyl)-7-(trifluoromethyl)-1H-benzimidazol-2-yl)propyl)amino)-5-pyrimidinecarbonitrile

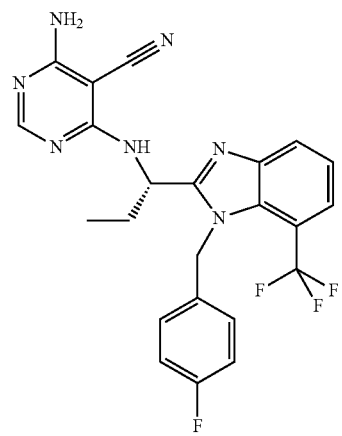 [SMILES: CC[C@H](Nc1ncnc(N)c1C#N)c1nc2cccc(C(F)(F)F)c2n1Cc1ccc(F)cc1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(4-fluorobenzyl)-7-(trifluoromethyl)-1H-benzimidazol-2-yl)propyl)amino)-5-pyrimidinecarbonitrile was prepared using (S)-1-(1-(4-fluorobenzyl)-7-(trifluoromethyl)-1H-benzo[d]imidazol-2-yl)propan-1-amine: $^1$H NMR (400 MHz, DMSO-d$_6$) δ 8.09 (1H, d, J=8.0 Hz), 7.97 (1H, s), 7.69-7.63 (2H, m), 7.44 (1H, t, J=8.0 Hz), 7.18 (2H, br), 7.04 (1H, d, J=8.0 Hz), 7.01 (1H, d, J=8.0 Hz), 6.83-6.76 (2H, m), 5.85 (2H, br), 5.53-5.45 (1H, m), 2.10-2.02 (1H, m), 1.20-1.14 (1H, m), 0.78 (3H, t, J=8.0 Hz); LC-MS (ESI) m/z 470.0 [M+H]$^+$.

Example 86

2-((1S)-1-(((6-Amino-5-cyano-4-pyrimidinyl)amino)ethyl)-N-cyclopropyl-3-phenylimidazo[1,2-a]pyridine-5-carboxamide

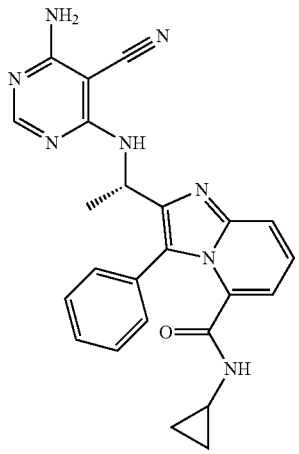 [SMILES: C[C@H](Nc1ncnc(N)c1C#N)c1nc2cccc(C(=O)NC3CC3)n2c1-c1ccccc1]

A solution of DIEA (0.062 mL, 0.356 mmol), cyclopropylamine (0.025 mL, 0.36 mmol), (S)-2-(1-(6-amino-5-cyanopyrimidin-4-ylamino)ethyl)-1-phenyl-1H-benzo[d]imidazole-7-carboxylic acid (0.071 g, 0.18 mmol), and PyBOP (0.185 g, 0.356 mmol) in DMF (1.18 mL) was stirred at rt for 1 h. The solution was loaded directly onto silica gel and purified by MPLC (eluted with 0-8% MeOH in DCM) to afford an off white solid that was repurified by MPLC (eluted with 0-100% (1:10:90 NH$_4$OH:MeOH:DCM) solution in DCM) to afford 2-((1S)-1-((6-amino-5-cyano-4-pyrimidinyl)amino)ethyl)-N-cyclopropyl-3-phenylimidazo[1,2-a]pyridine-5-carboxamide as a white solid. $^1$H NMR (400 MHz, DMSO-d$_6$) δ ppm 0.16-0.25 (m, 2H) 0.37-0.49 (m, 2H) 1.44 (d, J=6.65 Hz, 3H) 2.05 (tq, J=7.25, 3.64 Hz, 1H) 5.29 (quin, J=6.80 Hz, 1H) 6.84 (d, J=7.24 Hz, 1H) 6.94 (d, J=6.85 Hz, 1H) 7.12-7.51 (m, 8H) 7.75 (d, J=9.00 Hz, 1H) 7.95 (s, 1H) 8.67 (d, J=3.52 Hz, 1H). LC-MS (ESI) m/z 439.1 [M+H]$^+$.

Example 87

Preparation of 2-((1S)-1-((6-amino-5-cyano-4-pyrimidinyl)amino)ethyl)-1-(5-fluoro-3-pyridinyl)-1H-benzimidazole-7-carbonitrile and 2-((1R)-1-((6-amino-5-cyano-4-pyrimidinyl)amino)ethyl)-1-(5-fluoro-3-pyridinyl)-1H-benzimidazole-7-carbonitrile

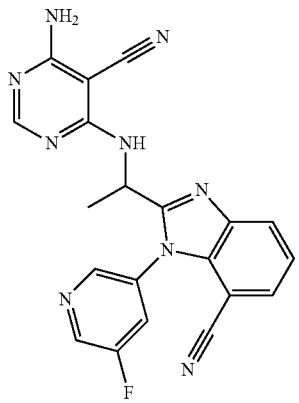 [SMILES: CC(Nc1ncnc(N)c1C#N)c1nc2cccc(C#N)c2n1-c1cncc(F)c1]

To a stirred solution of 4-amino-6-(1-(7-bromo-1-(5-fluoropyridin-3-yl)-1H-benzo[d]imidazol-2-yl)ethylamino)pyrimidine-5-carbonitrile (prepared in example 80, 0.157 g, 0.346 mmol) in DMF (1.73 mL) in a 3 neck round bottom flask fitted with a condenser was added Xphos™ precatalyst (0.031 g, 0.042 mmol) and potassium hydrogenphosphate (0.066 g, 0.38 mmol) and the mixture heated at 120° C. for 2 min. To the mixture was added dropwise tributylstannanecarbonitrile (0.109 g, 0.346 mmol) in DMF (1.73 mL) over 10 min and the mixture was heated at 120° C. with stirring. After 24 h, the mixture was cooled to rt and partitioned between EtOAc (50 mL) and 1.0M aqueous LiCl (50 mL). The separated aqueous layer was extracted with EtOAc (1×50 mL) and the combined organic extracts were washed with 1.0M aqueous LiCl (50 mL), dried over MgSO$_4$ and concentrated in vacuo. The crude material was absorbed onto a plug of silica gel and purified by chromatography through a Redi-Sep™ pre-packed silica gel column (40 g), eluting with a gradient of 0% to 100% DCM:MeOH:—NH$_4$OH (89:9:1) in DCM, to provide a solid. The solid was suspended in EtOAc-hexane (1:5, 10 mL), filtered, washed with EtOAc-hexane (1:5, 50 mL) to provide 2-(1-(6-amino-5-cyanopyrimidin-4-ylamino)ethyl)-1-(5-fluoropyridin-3-yl)-1H-benzo[d]imidazole-7-carbonitrile as a tan solid: $^1$H NMR (400 MHz, DMSO-d$_6$) δ ppm 8.58-8.84 (2H, m), 7.97-8.39 (2H, m), 7.69-7.87 (3H, m), 7.45 (1H, t, J=7.8 Hz), 7.22 (2H, br. s.), 5.43-5.57 (1H, m), 1.60 (3H, t, J=6.5 Hz); LC-MS (ESI) m/z 400.0 [M+H]$^+$.

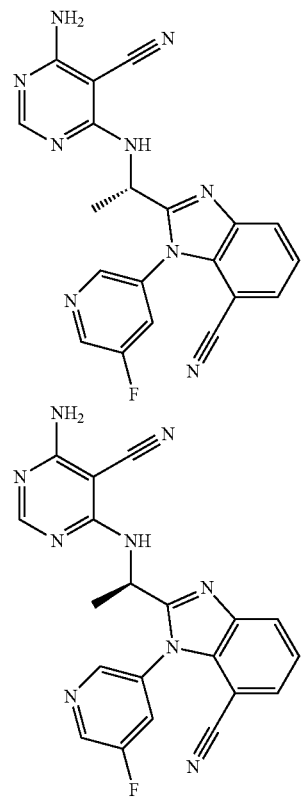

The racemic mixture (0.05 g) was separated on AD-H column using preparative SFC to give two fractions: First peak on SFC AD-H column: 2-((1S)-1-((6-amino-5-cyano-4-pyrimidinyl)amino)ethyl)-1-(5-fluoro-3-pyridinyl)-1H-benzimidazole-7-carbonitrile as an off-white solid: $^1$H NMR (400 MHz, DMSO-d$_6$) δ ppm 8.58-8.84 (2H, m), 7.98-8.38

(2H, m), 7.70-7.86 (3H, m), 7.45 (1H, t, J=7.9 Hz), 7.23 (2H, br. s.), 5.42-5.57 (1H, m), 1.60 (3H, t, J=6.5 Hz); LC-MS (ESI) m/z 400.0 [M+H]+. Second peak on SFC AD-H column: 2-((1R)-1-((6-amino-5-cyano-4-pyrimidinyl)amino)ethyl)-1-(5-fluoro-3-pyridinyl)-1H-benzimidazole-7-carbonitrile as an off-white solid: $^1$H NMR (400 MHz, DMSO-$d_6$) δ ppm 8.60-8.84 (2H, m), 7.98-8.39 (2H, m), 7.71-7.86 (3H, m), 7.45 (1H, t, J=7.9 Hz), 7.22 (2H, br. s.), 5.42-5.57 (1H, m), 1.60 (3H, t, J=6.5 Hz); LC-MS (ESI) m/z 400.0 [M+H]+.

Example 88

Preparation of N-((1S)-1-(1-(cyclopropylmethyl)-7-(trifluoromethyl)-1H-benzimidazol-2-yl)propyl)-9H-purin-6-amine

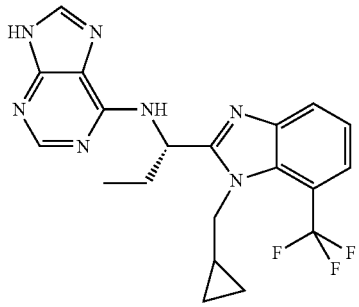 [SMILES: CC[C@H](Nc1ncnc2[nH]cnc12)c1nc2cccc(C(F)(F)F)c2n1CC1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, N-((1S)-1-(1-(cyclopropylmethyl)-7-(trifluoromethyl)-1H-benzimidazol-2-yl)propyl)-9H-purin-6-amine was prepared using (S)-1-(1-(cyclopropylmethyl)-7-(trifluoromethyl)-1H-benzo[d]imidazol-2-yl)propan-1-amine (prepared in example 82): $^1$H NMR (400 MHz, DMSO-$d_6$) δ 12.94 (1H, br), 8.25 (1H, s), 8.18 (1H, s), 8.00 (1H, d, J=8.0 Hz), 7.94 (2H, br), 7.67 (1H, d, J=8.0 Hz), 7.39 (1H, t, J=8.0 Hz), 5.79 (1H, br), 4.45 (1H, br), 2.23-2.12 (2H, m), 1.25-1.15 (1H, m), 1.02 (3H, t, J=8.0 Hz), 0.68-0.58 (1H, m), 0.58-0.48 (2H, m), 0.48-0.38 (1H, m); LC-MS (ESI) m/z 416.0 [M+H]+.

Example 89

Preparation of 4-amino-6-(((1S)-1-(1-(cyclopropyl-methyl)-7-(methylsulfonyl)-1H-benzimidazol-2-yl)propyl)amino)-5-pyrimidinecarbonitrile (S)-tert-Butyl 1-(2-amino-3-(methylsulfonyl)phenylamino)-1-oxobutan-2-ylcarbamate

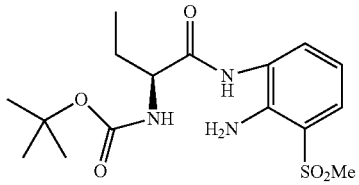

Using the general synthetic procedure for (S)-methyl 3-(2-(tert-butoxycarbonyl-amino)propanamido)-2-(cyclopropylamino)benzoate in example 47, (S)-tert-butyl 1-(2-amino-3-(methylsulfonyl)phenylamino)-1-oxobutan-2-ylcarbamate was prepared using 3-(methylsulfonyl)benzene-1,2-diamine (prepared in example 51) and Boc-abu-OH: LC-MS (ESI) m/z 372.1 [M+H]+.

(S)-tert-Butyl 1-(2-(cyclopropylmethylamino)-3-(methylsulfonyl)phenylamino)-1-oxobutan-2-ylcarbamate

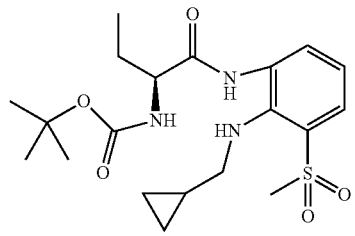 [SMILES: CC[C@H](NC(=O)OC(C)(C)C)C(=O)Nc1cccc(S(C)(=O)=O)c1NCC1CC1]

Using the general synthetic procedure for (S)-tert-butyl 1-(2-(cyclopropylmethylamino)-3-(methylsulfonyl)phenylamino)-1-oxopropan-2-ylcarbamate in example 66, (S)-tert-butyl 1-(2-(cyclopropylmethylamino)-3-(methylsulfonyl)phenylamino)-1-oxobutan-2-ylcarbamate was prepared using (S)-tert-butyl 1-(2-amino-3-(methylsulfonyl)phenylamino)-1-oxobutan-2-ylcarbamate: LC-MS (ESI) m/z 426.1 [M+H]+.

(S)-1-(1-(Cyclopropylmethyl)-7-(methylsulfonyl)-1H-benzo[d]imidazol-2-yl)propan-1-amine

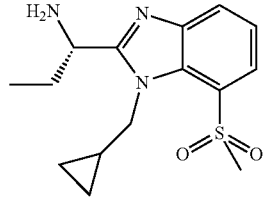 [SMILES: CC[C@H](N)c1nc2cccc(S(C)(=O)=O)c2n1CC1CC1]

Using the general synthetic procedure for (S)-methyl 2-(1-aminoethyl)-1-cyclopropyl-1H-benzo[d]imidazole-7-carboxylate in example 47, (S)-1-(1-(cyclopropylmethyl)-7-(methylsulfonyl)-1H-benzo[d]imidazol-2-yl)propan-1-amine was prepared using (S)-tert-butyl 1-(2-(cyclopropylmethylamino)-3-(methylsulfonyl)phenylamino)-1-oxobutan-2-ylcarbamate: LC-MS (ESI) m/z 308.0 [M+H]+.

4-Amino-6-(((1S)-1-(1-(cyclopropylmethyl)-7-(methylsulfonyl)-1H-benzimidazol-2-yl)propyl)amino)-5-pyrimidinecarbonitrile

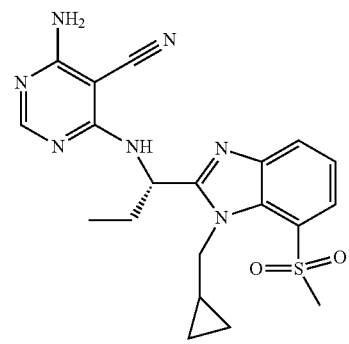 [SMILES: CC[C@H](Nc1ncnc(N)c1C#N)c1nc2cccc(S(C)(=O)=O)c2n1CC1CC1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(cyclopropylmethyl)-7-(methylsulfonyl)-1H-benzimidazol-2-yl)propyl)amino)-5-pyrimidinecarbonitrile was prepared using (S)-1-(1-(cyclopropylmethyl)-7-(methylsulfonyl)-1H-benzo[d]imidazol-2-yl)propan-1-amine: $^1$H NMR (400 MHz, DMSO-d$_6$) δ 8.08 (1H, s), 8.04 (1H, d, J=8.0 Hz), 7.90 (1H, d, J=8.0 Hz), 7.62 (1H, d, J=8.0 Hz), 7.44 (1H, t, J=8.0 Hz), 7.34 (2H, br), 5.75-5.66 (1H, m), 4.82 (1H, dd, J=16.0, 4.0 Hz), 4.59 (1H, dd, J=16.0, 4.0 Hz), 3.44 (3H, s), 2.17-2.06 (2H, m), 1.34-1.27 (1H, m), 0.97 (3H, t, J=8.0 Hz), 0.59-0.35 (4H, m); LC-MS (ESI) m/z 426.1 [M+H]$^+$.

Example 90

Preparation of 4-amino-6-(((1S)-1-(1-(4-fluorobenzyl)-7-(methylsulfonyl)-1H-benzimidazol-2-yl)propyl)amino)-5-pyrimidinecarbonitrile (S)-tert-Butyl 1-(2-(4-fluorobenzylamino)-3-(methylsulfonyl)phenylamino)-1-oxobutan-2-ylcarbamate

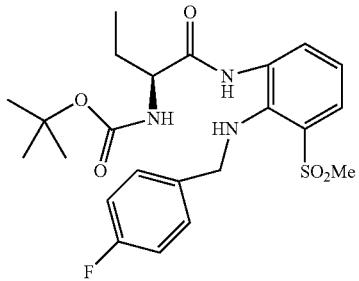 [SMILES: CC[C@H](NC(=O)OC(C)(C)C)C(=O)Nc1cccc(S(C)(=O)=O)c1NCc1ccc(F)cc1]

Using the general synthetic procedure for 4-amino-6-(((1S)-1-(1-(4-fluorobenzyl)-4-(methylsulfonyl)-1H-benzimidazol-2-yl)ethyl)amino)-5-pyrimidinecarbonitrile in example 59, (S)-tert-butyl 1-(2-(4-fluorobenzylamino)-3-(methylsulfonyl)phenylamino)-1-oxobutan-2-ylcarbamate was prepared using (S)-tert-butyl 1-(2-amino-3-(methylsulfonyl)phenylamino)-1-oxobutan-2-ylcarbamate (Prepared in Example 89): LC-MS (ESI) m/z 480.1 [M+H]$^+$.

(S)-1-(1-(4-Fluorobenzyl)-7-(methylsulfonyl)-1H-benzo[d]imidazol-2-yl)propan-1-amine

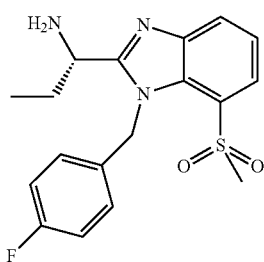 [SMILES: CC[C@H](N)c1nc2cccc(S(C)(=O)=O)c2n1Cc1ccc(F)cc1]

Using the general synthetic procedure for (S)-methyl 2-(1-aminoethyl)-1-cyclopropyl-1H-benzo[d]imidazole-7-carboxylate in example 47, (S)-1-(1-(4-fluorobenzyl)-7-(methylsulfonyl)-1H-benzo[d]imidazol-2-yl)propan-1-amine was prepared using (S)-tert-butyl 1-(2-(4-fluorobenzylamino)-3-(methylsulfonyl)phenylamino)-1-oxobutan-2-ylcarbamate: LC-MS (ESI) m/z 362.0 [M+H]$^+$.

4-Amino-6-(((1S)-1-(1-(4-fluorobenzyl)-7-(methylsulfonyl)-1H-benzimidazol-2-yl)propyl)amino)-5-pyrimidinecarbonitrile

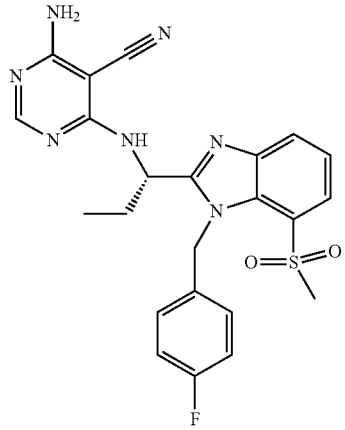 [SMILES: CC[C@H](Nc1ncnc(N)c1C#N)c1nc2cccc(S(C)(=O)=O)c2n1Cc1ccc(F)cc1]

Using the general synthetic procedure for (S)-methyl 2-(1-(6-amino-5-cyanopyrimidin-4-ylamino)ethyl)-1-cyclopropyl-1H-benzo[d]imidazole-7-carboxylate in example 47, 4-amino-6-(((1S)-1-(1-(4-fluorobenzyl)-7-(methylsulfonyl)-1H-benzimidazol-2-yl)propyl)amino)-5-pyrimidinecarbonitrile was prepared using (S)-1-(1-(4-fluorobenzyl)-7-(methylsulfonyl)-1H-benzo[d]imidazol-2-yl)propan-1-amine: $^1$H NMR (400 MHz, DMSO-d$_6$) δ 8.14 (1H, d, J=8.0 Hz), 7.99 (1H, s), 7.90 (1H, d, J=8.0 Hz), 7.65 (1H, d, J=8.0 Hz), 7.50 (1H, t, J=8.0 Hz), 7.21 (2H, br), 7.08 (1H, d, J=8.0 Hz), 7.06 (1H, d, J=8.0 Hz), 6.88-6.81 (2H, m), 6.06 (2H, br), 5.51-5.46 (1H, m), 3.00 (3H, s), 2.06-1.95 (2H, m), 0.76 (3H, t, J=8.0 Hz); LC-MS (ESI) m/z 480.1 [M+H]$^+$.

Example 91

5-Bromo-N-(5-fluoro-2-nitrophenyl)pyridin-3-amine

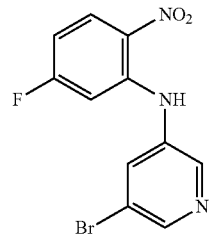 [SMILES: O=[N+]([O-])c1ccc(F)cc1Nc1cncc(Br)c1]

Prepared according to Step D1 in General Procedure D using 3-amino-5-bromopyridine (5.00 g, 28.9 mmol) to give 5-bromo-N-(5-fluoro-2-nitrophenyl)pyridin-3-amine as a brown solid. LC-MS (ESI) m/z 314.0 [M+H]$^+$.

Methyl 5-(2-amino-5-fluorophenylamino)nicotinate

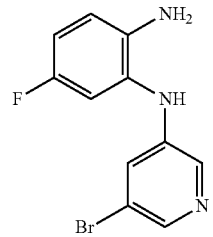 [SMILES: Nc1ccc(F)cc1Nc1cncc(Br)c1]

Prepared according to Step D2 in General Procedure D using 5-bromo-N-(5-fluoro-2-nitrophenyl)pyridin-3-amine (6.4 g, 20.5 mmol) to give N1-(5-bromopyridin-3-yl)-5-fluorobenzene-1,2-diamine as a crude black solid. LC-MS (ESI) m/z 282.0 [M+H]$^+$.

(S)-tert-butyl 1-(2-(5-bromopyridin-3-ylamino)-4-fluorophenylamino)-1-oxopropan-2-ylcarbamate

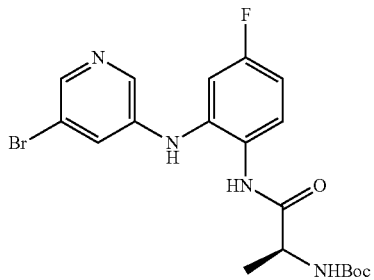 [SMILES: C[C@H](NC(=O)OC(C)(C)C)C(=O)Nc1ccc(F)cc1Nc1cncc(Br)c1]

Prepared according to Step D3 in General Procedure D using methyl 5-(2-amino-5-fluorophenylamino)nicotinate (5.50 g, 21.1 mmol) to give (S)-tert-butyl 1-(2-(5-bromopyridin-3-ylamino)-4-fluorophenylamino)-1-oxopropan-2-ylcarbamate. LC-MS (ESI) m/z 455.0 [M+H]$^+$.

N-(1-(1-(5-Bromopyridin-3-yl)-6-fluoro-1H-benzo[d]imidazol-2-yl)ethyl)acetamide

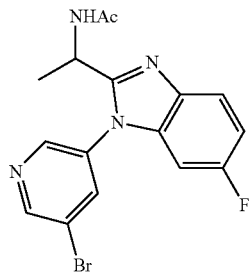 [SMILES: CC(=O)NC(C)c1nc2ccc(F)cc2n1-c1cncc(Br)c1]

Prepared according to Step D4 in General Procedure D using (S)-tert-butyl 1-(2-(5-bromopyridin-3-ylamino)-4-fluorophenylamino)-1-oxopropan-2-ylcarbamate (5.32 g, 11.74 mmol) to give N-(1-(1-(5-bromopyridin-3-yl)-6-fluoro-1H-benzo[d]imidazol-2-yl)ethyl)acetamide as a brown oil. LC-MS (ESI) m/z 377.0 [M+H]$^+$.

1-(1-(5-Bromopyridin-3-yl)-6-fluoro-1H-benzo[d]imidazol-2-yl)ethanamine

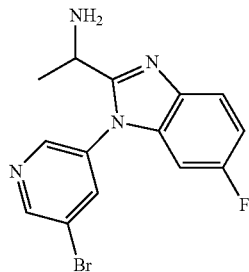 [SMILES: CC(N)c1nc2ccc(F)cc2n1-c1cncc(Br)c1]

Prepared according to Step D5a in General Procedure D using N-(1-(1-(5-bromopyridin-3-yl)-6-fluoro-1H-benzo[d]imidazol-2-yl)ethyl)acetamide (0.980 g, 2.60 mmol) to give 1-(1-(5-bromopyridin-3-yl)-6-fluoro-1H-benzo[d]imidazol-2-yl)ethanamine as a brown oil. LC-MS (ESI) m/z 337.0 [M+H]$^+$.

4-Amino-6-(1-(1-(5-bromopyridin-3-yl)-6-fluoro-1H-benzo[d]imidazol-2-yl)ethylamino)pyrimidine-5-carbonitrile

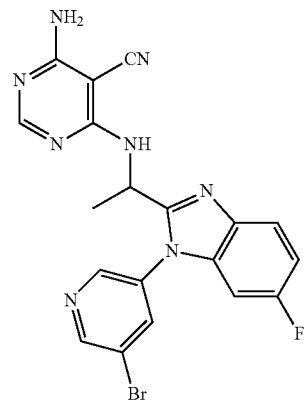 [SMILES: CC(Nc1ncnc(N)c1C#N)c1nc2ccc(F)cc2n1-c1cncc(Br)c1]

Prepared according to Step D6 in General Procedure D using 1-(1-(5-bromopyridin-3-yl)-6-fluoro-1H-benzo[d]imidazol-2-yl)ethanamine (0.769 g, 2.29 mmol) to give 4-amino-6-(1-(1-(5-bromopyridin-3-yl)-6-fluoro-1H-benzo[d]imidazol-2-yl)ethylamino)pyrimidine-5-carbonitrile as a light tan solid. $^1$H NMR (400 MHz, DMSO-d$_6$) δ ppm 1.59 (d, J=6.85 Hz, 3H) 5.63 (quin, J=6.70 Hz, 1H) 7.09 (dd, J=8.90, 2.45 Hz, 1H) 7.11-7.18 (m, 1H) 7.19 (br. s., 2H) 7.71-7.80 (m, 2H) 7.84 (s, 1H) 8.33 (br. s., 1H) 8.70 (d, J=1.17 Hz, 1H) 8.72 (d, J=1.96 Hz, 1H). LC-MS (ESI) m/z 452.9 [M+H]$^+$.

Example 92

Preparation of 4-amino-6-(((1S)-1-(5,6-difluoro-1-(5-fluoro-3-pyridinyl)-1H-benzimidazol-2-yl)ethyl)amino)-5-pyrimidinecarbonitrile (S)-tert-Butyl 1-(2-amino-4,5-difluorophenylamino)-1-oxopropan-2-ylcarbamate

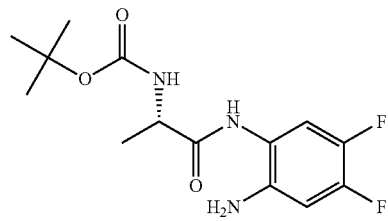 [SMILES: C[C@H](NC(=O)OC(C)(C)C)C(=O)Nc1cc(F)c(F)cc1N]

To the mixture of 1,2-diamino-4,5-difluorobenzene (2.00 g, 13.9 mmol) and Boc-L-Ala-OH (2.63 g, 13.9 mmol), and 1-(3-dimethylaminopropyl)-3-ethylcarbodiimide hydrochloride (5.85 g, 30.5 mmol) in DCM (139 mL) was added triethylamine (6.00 mL, 43.0 mmol) at rt and stirred for 3 h. The mixture was then concentrated in vacuo and absorbed onto a plug of silica gel and purified by chromatography through a Redi-Sep™ pre-packed silica gel column (80 g), eluting with a gradient of 0% to 100% EtOAc in hexane, to provide (S)-tert-butyl 1-(2-amino-4,5-difluorophenylamino)-1-oxopropan-2-ylcarbamate as orange solid: $^1$H NMR (400 MHz, DMSO-$d_6$) δ ppm 9.16 (1H, s), 7.21 (1H, dd, J=11.9, 8.8 Hz), 7.11 (1H, d, J=6.7 Hz), 6.65 (1H, dd, J=12.9, 8.0 Hz), 5.04 (2H, br. s.), 4.04-4.14 (1H, m), 1.39 (9H, s), 1.25 (3H, d, J=7.0 Hz); LC-MS (ESI) m/z 338.0 [M+Na]$^+$ and m/z 314.0 [M−H]$^−$.

(S)-tert-Butyl 1-(5,6-difluoro-1H-benzo[d]imidazol-2-yl)ethylcarbamate

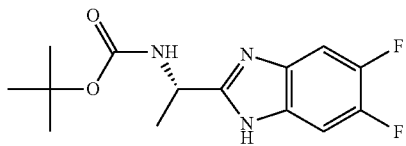 [SMILES: C[C@H](NC(=O)OC(C)(C)C)c1nc2cc(F)c(F)cc2[nH]1]

A mixture of (S)-tert-butyl 1-(2-amino-4,5-difluorophenylamino)-1-oxopropan-2-ylcarbamate (3.454 g, 10.96 mmol) in AcOH (21.91 mL) was heated at 75° C. After 50 min, the mixture was concentrated in vacuo. The residue was dissolved in DCM (100 mL), washed with satd. sodium bicarbonate solution (50 mL×2), water (100 mL×1), and brine (100 mL×1). The product was precipitated from DCM. In order to dissolve the precipitate, EtOAc (100 mL) was added. The combined organic layers were dried over MgSO$_4$, filtered, and concentrated in vacuo. The residue was absorbed onto a plug of silica gel and purified by chromatography through a Redi-Sep pre-packed silica gel column (80 g), eluting with a gradient of 0% to 100% EtOAc in hexane, to provide (S)-tert-butyl 1-(5,6-difluoro-1H-benzo[d]imidazol-2-yl)ethylcarbamate (2.5025 g, 8.42 mmol, 77% yield) as orange solid. The orange solid was suspended in DCM-hexane (1:1) and filtered to give (S)-tert-butyl 1-(5,6-difluoro-1H-benzo[d]imidazol-2-yl)ethylcarbamate (2.0003 g, 6.73 mmol, 61.4% yield) as a pink solid: $^1$H NMR (400 MHz, DMSO-$d_6$) δ ppm 12.34 (1H, br. s.), 7.47-7.57 (2H, m), 7.38 (1H, d, J=7.2 Hz), 4.83 (1H, quin, J=6.6 Hz), 1.45 (3H, d, J=7.0 Hz), 1.40 (9H, s); LC-MS (ESI) m/z 298.1 [M+H]$^+$.

(S)-tert-Butyl 1-(5,6-difluoro-1-(5-fluoropyridin-3-yl)-1H-benzo[d]imidazol-2-yl)ethylcarbamate

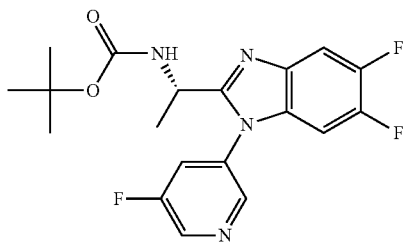 [SMILES: C[C@H](NC(=O)OC(C)(C)C)c1nc2cc(F)c(F)cc2n1-c1cncc(F)c1]

To a flask was added (S)-tert-butyl 1-(5,6-difluoro-1H-benzo[d]imidazol-2-yl)ethylcarbamate (0.506 g, 1.70 mmol), 5-fluoropyridine-3-boronic acid (0.480 g, 3.40 mmol), DCM (22.7 mL) and pyridine (0.28 mL, 3.4 mmol), and copper (II) acetate (0.464 g, 2.55 mmol). The mixture was stirred at rt for 57 days. The mixture was then partitioned with satd. aq. ammonium chloride solution (50 mL) and DCM (50 mL). The organic layer was washed with satd. aq. ammonium chloride solution (1×50 mL). The organic layer was dried over sodium sulfate, filtered, and concentrated in vacuo. The crude material was absorbed onto a plug of silica gel and purified by chromatography through a Redi-Sep™ pre-packed silica gel column (40 g), eluting with a gradient of 0% to 20% EtOAc in hexane, to provide a mixture of (S)-tert-butyl 1-(5,6-difluoro-1-(5-fluoropyridin-3-yl)-1H-benzo[d]imidazol-2-yl)ethylcarbamate and (5)-tert-butyl 1-(5,6-difluoro-1-(5-fluoropyridin-3-yl)-1H-benzo[d]imidazol-2-yl)ethylcarbamate as a solid: LC-MS (ESI) m/z 393.1 [M+H]$^+$.

(S)-1-(5,6-Difluoro-1-(5-fluoropyridin-3-yl)-1H-benzo[d]imidazol-2-yl)ethanamine

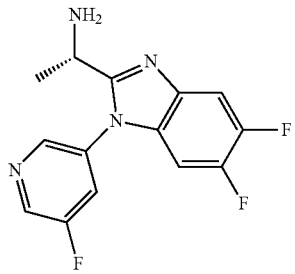 [SMILES: C[C@H](N)c1nc2cc(F)c(F)cc2n1-c1cncc(F)c1]

A mixture of (S)-tert-butyl 1-(5,6-difluoro-1-(5-fluoropyridin-3-yl)-1H-benzo[d]-imidazol-2-yl)ethylcarbamate (0.460 g, 1.17 mmol) in hydrochloric acid, 4 M solution in 1,4-dioxane (5.86 mL, 23.45 mmol) was stirred at rt. After 4 h, the mixture was partitioned between DCM (50 mL) and water (50 mL). The aqueous layer was washed with DCM (1×50 mL) to remove an organic impurity. The aqueous layer was treated with satd. aq. sodium bicarbonate solution (50 mL) and extracted with DCM (1×50 mL). The organic layer was dried over sodium sulfate, filtered, and concentrated in vacuo. The crude material was absorbed onto a plug of silica gel and purified by chromatography through a Redi-Sep™ pre-packed silica gel column (40 g), eluting with a gradient of 0% to 50% DCM:MeOH:NH$_4$OH (89:9:1) in DCM, to provide (S)-1-(5,6-difluoro-1-(5-fluoropyridin-3-yl)-1H-benzo[d]imidazol-2-yl)ethanamine as a colorless syrup: $^1$H NMR (400 MHz, DMSO-$d_6$) δ ppm 8.84 (1H, d, J=2.7 Hz), 8.75 (1H, s), 8.24 (1H, dt, J=9.4, 2.3 Hz), 7.79 (1H, dd, J=11.0, 7.4 Hz), 7.40 (1H, dd, J=10.4, 7.2 Hz), 3.96 (1H, q, J=6.6 Hz), 2.00 (2H, d, J=4.5 Hz), 1.37 (3H, d, J=6.7 Hz); LC-MS (ESI) m/z 293.0 [M+H]$^+$.

4-Amino-6-(((1S)-1-(5,6-difluoro-1-(5-fluoro-3-pyridinyl)-1H-benzimidazol-2-yl)ethyl)amino)-5-pyrimidinecarbonitrile

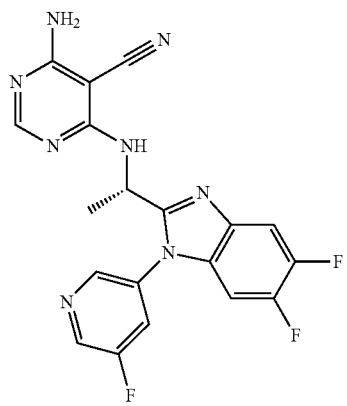 [SMILES: C[C@H](Nc1ncnc(N)c1C#N)c1nc2cc(F)c(F)cc2n1-c1cncc(F)c1]

A mixture of 4-amino-6-chloropyrimidine-5-carbonitrile (0.014 g, 0.091 mmol), (S)-1-(5,6-difluoro-1-(5-fluoropyridin-3-yl)-1H-benzo[d]imidazol-2-yl)ethanemine (0.0266 g, 0.091 mmol), and DIEA (0.048 mL, 0.273 mmol) in n-butanol (0.910 mL) was stirred at 120° C. After 20 h, the mixture was removed from the heat and concentrated in vacuo. To the residue was added water (50 mL) and the aqueous mixture was extracted with DCM (2×50 mL). The organic extract was dried over sodium sulfate, filtered, and concentrated in vacuo to provide the crude material. The crude material was absorbed onto a plug of silica gel and purified by chromatography through a Redi-Sep™ pre-packed silica gel column (40 g), eluting with a gradient of 0% to 50% DCM:MeOH:NH$_4$OH (89:9:1) in DCM, to provide 4-amino-6-(((1S)-1-(5,6-difluoro-1-(5-fluoro-3-pyridinyl)-1H-benzimidazol-2-yl)ethyl)amino)-5-pyrimidinecarbonitrile as a brown solid: $^1$H NMR (400 MHz, DMSO-d$_6$) δ ppm 8.67 (1H, d, J=2.5 Hz), 8.61 (1H, s), 8.06 (1H, d, J=8.2 Hz), 7.86 (1H, dd, J=11.0, 7.4 Hz), 7.82 (1H, s), 7.75 (1H, d, J=7.8 Hz), 7.39 (1H, dd, J=10.4, 7.2 Hz), 7.19 (2H, br. s.), 5.57 (1H, quin, J=7.0 Hz), 1.58 (3H, d, J=6.8 Hz); LC-MS (ESI)] m/z 411.0 [M+H]$^+$.

Example 93

4-Amino-6-(1-(1-(5-bromopyridin-3-yl)-6-fluoro-1H-benzo[d]imidazol-2-yl)ethylamino)pyrimidine-5-carbonitrile

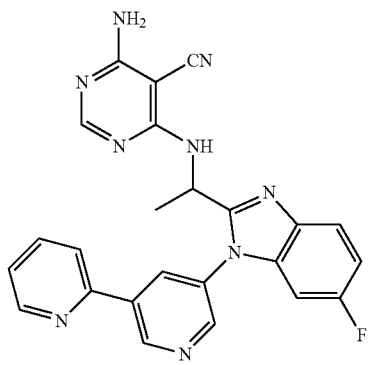 [SMILES: CC(Nc1ncnc(N)c1C#N)c1nc2ccc(F)cc2n1-c1cncc(-c2ccccn2)c1]

To a microwave vial was added 4-amino-6-(1-(1-(5-bromopyridin-3-yl)-6-fluoro-1H-benzo[d]imidazol-2-yl)ethylamino)pyrimidine-5-carbonitrile (0.130 g, 0.287 mmol), palladium(II) acetate (3.22 mg, 0.014 mmol), 2-tri-n-butylstannylpyridine (0.158 mL, 0.430 mmol), and 2-(dicyclohexylphosphino)-2',4',6'-triisopropyl1,1'-biphenyl (0.014 g, 0.029 mmol) in dioxane (1.91 mL). The solution was purged with nitrogen for 10 min then was stirred at 120° C. under microwave irradiation for 2 h. The solution was loaded directly onto silica gel and purified via MPLC (eluted with 0-8% MeOH in DCM) to afford an off-white solid. Repurification by MPLC (eluted with 0-6% MeOH in DCM) afforded 4-amino-6-(1-(1-(5-bromopyridin-3-yl)-6-fluoro-1H-benzo[d]imidazol-2-yl)ethylamino)pyrimidine-5-carbonitrile (0.130 g, 0.287 mmol) (racemic) as a white solid. LC-MS (ESI) m/z 452.2 [M+H]$^+$.

4-Amino-6-(((1R)-1-(1-(2,3'-bipyridin-5'-yl)-6-fluoro-1H-benzimidazol-2-yl)ethyl)amino)-5-pyrimidinecarbonitrile and 4-amino-6-(((1S)-1-(1-(2,3'-bipyridin-5'-yl)-6-fluoro-1H-benzimidazol-2-yl)ethyl)amino)-5-pyrimidinecarbonitrile

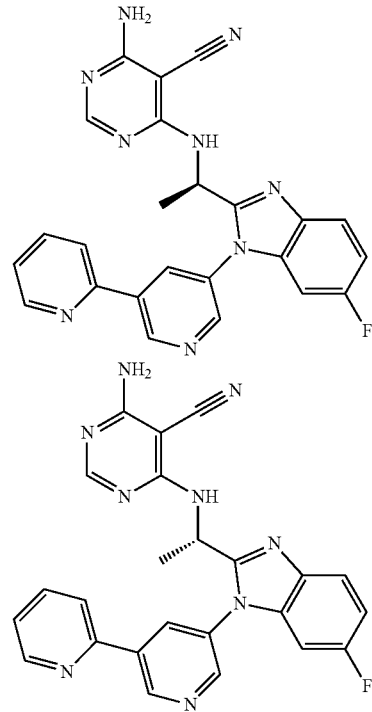

The racemic 4-(1-(1-(2,3'-bipyridin-5'-yl)-6-fluoro-1H-benzo[d]imidazol-2-yl)-ethylamino)-6-aminopyrimidine-5-carbonitrile (0.104 mg) was separated on AD-H column using preparative SFC to give two fractions. First peak on OD-H column: 4-amino-6-(((1R)-1-(1-(2,3'-bipyridin-5'-yl)-6-fluoro-1H-benzimidazol-2-yl)ethyl)amino)-5-pyrimidinecarbonitrile as a beige solid. $^1$H NMR (400 MHz, DMSO-d$_6$) δ ppm 1.60 (d, J=6.85 Hz, 3H) 5.51-5.71 (m, 1H) 6.94-7.26 (m, 4H) 7.46 (ddd, J=7.43, 4.89, 0.98 Hz, 1H) 7.66 (br. s., 1H) 7.74-7.86 (m, 2H) 7.96 (td, J=7.73, 1.76 Hz, 1H) 8.06 (d, J=8.02 Hz, 1H) 8.62 (s, 1H) 8.72 (d, J=4.11 Hz, 1H) 8.78 (d, J=1.37 Hz, 1H) 9.33 (d, J=1.76 Hz, 1H). LC-MS (ESI) m/z 452.0 [M+H]$^+$. Second peak on the OD-H column: 4-amino-6-((((S)-4-(1-(1-(2,3'-bipyridin-5'-yl)-6-fluoro-1H-benzo[d]imidazol-2-yl)ethylamino)-6-aminopyrimidine-5-carbonitrile as a beige solid. $^1$H NMR (400 MHz, DMSO-d$_6$) δ ppm 1.60 (d, J=6.85 Hz, 3H) 5.63 (br. s., 1H) 6.98-7.20 (m, 4H) 7.46 (ddd, J=7.43, 4.89, 0.98 Hz, 1H) 7.66 (br. s., 1H) 7.74-7.84 (m, 2H) 7.96 (td, J=7.73, 1.76 Hz, 1H) 8.06 (d, J=8.02

Hz, 1H) 8.62 (s, 1H) 8.72 (dt, J=4.79, 0.83 Hz, 1H) 8.78 (d, J=1.37 Hz, 1H) 9.33 (d, J=1.96 Hz, 1H). LC-MS (ESI) m/z 452.1 [M+H]⁺.

Example 94

N-(1-(6-Fluoro-1-(5-(methylsulfonamido)pyridin-3-yl)-1H-benzo[d]imidazol-2-yl)ethyl)acetamide

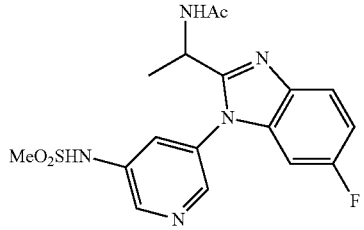

To a microwave vial was added cesium carbonate (1.30 g, 3.98 mmol), Pd₂(dba)₃ (0.146 g, 0.159 mmol), Xantphos (0.230 g, 0.398 mmol), N-(1-(1-(5-bromopyridin-3-yl)-6-fluoro-1H-benzo[d]imidazol-2-yl)ethyl)acetamide (0.600 g, 1.59 mmol), and methanesulfonamide (0.166 g, 1.75 mmol) in dioxane (7.95 mL). The suspension was purged with nitrogen for 5 min then was stirred at 120° C. for 3 h under microwave irradiation. The solution was loaded directly onto silica gel then purified by MPLC (eluted with a gradient of 0-10% MeOH in DCM) to afford N-(1-(6-fluoro-1-(5-(methylsulfonamido)pyridin-3-yl)-1H-benzo[d]imidazol-2-yl)ethyl)acetamide as an off-white solid. LC-MS (ESI) m/z 392.1 [M+H]⁺.

N-(5-(2-(1-Aminoethyl)-6-fluoro-1H-benzo[d]imidazol-1-yl)pyridin-3-yl)methanesulfonamide

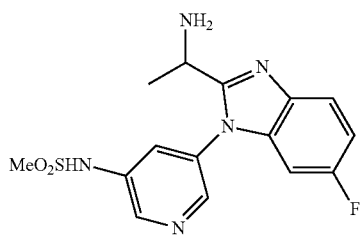

Prepared according to Step D5a in General Procedure D using N-(1-(6-fluoro-1-(5-(methylsulfonamido)pyridin-3-yl)-1H-benzo[d]imidazol-2-yl)ethyl)acetamide (0.389 g, 0.994 mmol) to give N-(5-(2-(1-aminoethyl)-6-fluoro-1H-benzo[d]-imidazol-1-yl)pyridin-3-yl)methanesulfonamide as a tan oil. LC-MS (ESI) m/z 350.1 [M+H]⁺.

N-(5-(2-(1-(6-Amino-5-cyanopyrimidin-4-ylamino)ethyl)-6-fluoro-1H-benzo[d]imidazol-1-yl)pyridin-3-yl)methanesulfonamide

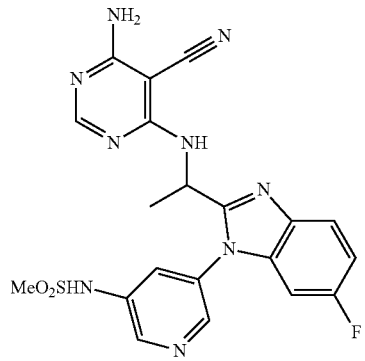

Prepared according to Step D6 in General Procedure D using N-(5-(2-(1-aminoethyl)-6-fluoro-1H-benzo[d]imidazol-1-yl)pyridin-3-yl)methanesulfonamide (0.175 g, 0.501 mmol) to give N-(5-(2-(1-(6-amino-5-cyanopyrimidin-4-ylamino)ethyl)-6-fluoro-1H-benzo[d]imidazol-1-yl)pyridin-3-yl)methanesulfonamide as an off-white solid. ¹H NMR (400 MHz, DMSO-d₆) δ ppm 1.57 (d, J=6.85 Hz, 3H) 3.15 (s, 3H) 5.50 (quin, J=6.94 Hz, 1H) 7.04 (dd, J=8.90, 2.45 Hz, 1H) 7.10-7.18 (m, 1H) 7.20 (br. s., 2H) 7.69-7.82 (m, 3H) 7.86 (s, 1H) 8.48 (d, J=2.15 Hz, 2H) 10.39 (br. s., 1H). LC-MS (ESI) m/z 468.0 [M+H]⁺.

N-(5-(2-((1R)-1-((6-Amino-5-cyano-4-pyrimidinyl)amino)ethyl)-6-fluoro-1H-benzimidazol-1-yl)-3-pyridinyl)methanesulfonamide and N-(5-(2-((1S)-1-((6-amino-5-cyano-4-pyrimidinyl)amino)ethyl)-6-fluoro-1H-benzimidazol-1-yl)-3-pyridinyl)methanesulfonamide

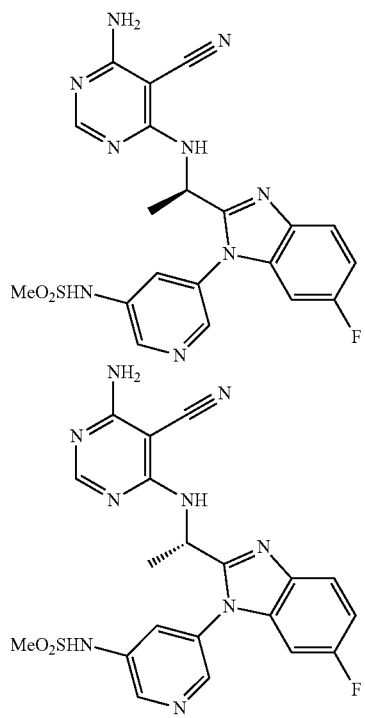

The racemic mixture (54 mg) was separated on AD-H column using preparative SFC to give two fractions. First peak on OD-H column: (R)—N-(5-(2-(1-(((6-amino-5-cyanopyrimidin-4-yl)amino)ethyl)-6-fluoro-1H-benzo[d]imidazol-1-yl)pyridin-3-yl)methanesulfonamide as a tan solid. $^1$H NMR (400 MHz, DMSO-d$_6$) δ ppm 1.56 (d, J=6.65 Hz, 3H) 3.14 (s, 3H) 5.50 (quin, J=6.90 Hz, 1H) 7.04 (dd, J=8.90, 2.25 Hz, 1H) 7.14 (td, J=9.29, 2.35 Hz, 1H) 7.20 (br. s., 2H) 7.69-7.81 (m, 3H) 7.85 (s, 1H) 8.47 (d, J=1.37 Hz, 2H) 10.39 (br. s., 1H). LC-MS (ESI) m/z 468.2 [M+H]$^+$. Second peak on the OD-H column: (S)—N-(5-(2-(1-(((6-amino-5-cyanopyrimidin-4-yl)amino)ethyl)-6-fluoro-1H-benzo[d]imidazol-1-yl)pyridin-3-yl)methanesulfonamide as a tan solid. $^1$H NMR (400 MHz, DMSO-d$_6$) δ ppm 1.56 (d, J=6.85 Hz, 3H) 3.14 (s, 3H) 5.50 (quin, J=6.94 Hz, 1H) 6.99-7.07 (m, 1H) 7.08-7.17 (m, 1H) 7.20 (br. s., 2H) 7.67-7.81 (m, 3H) 7.85 (s, 1H) 8.46 (s, 2H) 10.39 (br. s., 1H). LC-MS (ESI) m/z 468.2 [M+H]$^+$.

Example 95

4-Amino-6-(((1S)-1-(6-fluoro-1-(3-pyridinyl)-1H-benzimidazol-2-yl)ethyl)amino)-5-pyrimidinecarboxamide

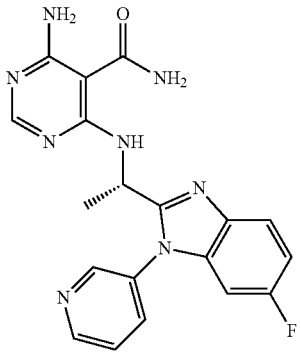 [SMILES: C[C@H](Nc1ncnc(N)c1C(N)=O)c1nc2ccc(F)cc2n1-c1cccnc1]

To an ice-cooled solution of potassium carbonate (0.027 g, 0.19 mmol) and (S)-4-amino-6-(1-(6-fluoro-1-(pyridin-3-yl)-1H-benzo[d]imidazol-2-yl)ethylamino)pyrimidine-5-carbonitrile (0.060 g, 0.16 mmol) in DMSO (1.60 mL) was added hydrogen peroxide (31.3% in water, 0.078 mL, 0.80 mmol) dropwise under nitrogen atmosphere. The solution was stirred at 0° C. for 1 h then was partitioned between water and EtOAc. Organic extracts were concentrated under reduced pressure then purified by MPLC (eluted with a gradient of 0-10% MeOH in DCM) to afford 4-amino-6-(((1S)-1-(6-fluoro-1-(3-pyridinyl)-1H-benzimidazol-2-yl)ethyl)amino)-5-pyrimidinecarboxamide as an off-white foam. $^1$H NMR (400 MHz, DMSO-d$_6$) d ppm 1.48 (d, J=6.85 Hz, 3H) 5.26 (quin, J=6.94 Hz, 1H) 6.57 (s, 2H) 6.98 (dd, J=8.90, 2.45 Hz, 1H) 7.14 (ddd, J=9.78, 8.80, 2.54 Hz, 1H) 7.46 (s, 2H) 7.65-7.70 (m, 1H) 7.74 (dd, J=8.80, 4.89 Hz, 1H) 7.77 (s, 1H) 7.94 (d, J=7.63 Hz, 1H) 8.05-8.12 (m, 1H) 8.78 (dd, J=4.79, 1.47 Hz, 1H) 8.82 (d, J=2.15 Hz, 1H). LC-MS (ESI) m/z 393.2 [M+H]$^+$.

Example 96

N-(3,5-Difluoro-2-nitrophenyl)pyridin-3-amine

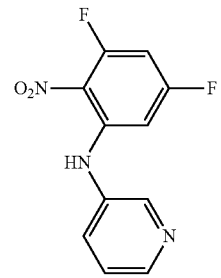 [SMILES: O=[N+]([O-])c1c(F)cc(F)cc1Nc1cccnc1]

Prepared according to Step D1 in General Procedure D using 1,3,5-trifluoro-2-nitrobenzene (5.28 mL, 45.2 mmol) and pyridin-3-amine (4.25 g, 45.2 mmol) to give N-(3,5-difluoro-2-nitrophenyl)pyridin-3-amine as a yellow solid. LC-MS (ESI) m/z 252.1 [M+H]$^+$.

3,5-Difluoro-N1-(pyridin-3-yl)benzene-1,2-diamine

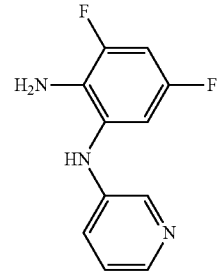

Prepared according to Step D2 in General Procedure D using N-(3,5-difluoro-2-nitrophenyl)pyridin-3-amine (6.7 g, 26.7 mmol) to give 3,5-difluoro-N1-(pyridin-3-yl)benzene-1,2-diamine as a brown solid. LC-MS (ESI) m/z 222.2 [M+H]$^+$.

tert-Butyl 1-(2,4-difluoro-6-(pyridin-3-ylamino)phenylamino)-1-oxopropan-2-ylcarbamate

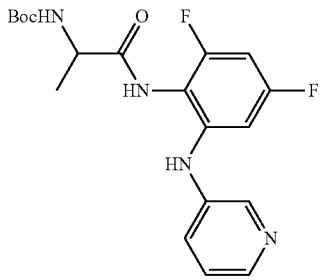 [SMILES: CC(NC(=O)OC(C)(C)C)C(=O)Nc1c(F)cc(F)cc1Nc1cccnc1]

Prepared according to Step D3 in General Procedure D using 3,5-difluoro-N1-(pyridin-3-yl)benzene-1,2-diamine (5.1 g, 23.06 mmol) to give tert-butyl 1-(2,4-difluoro-6-(pyridin-3-ylamino)phenylamino)-1-oxopropan-2-ylcarbamate as a pink solid. LC-MS (ESI) m/z 393.2 [M+H]$^+$.

N-(1-(4,6-Difluoro-1-(pyridin-3-yl)-1H-benzo[d]imidazol-2-yl)ethyl)acetamide

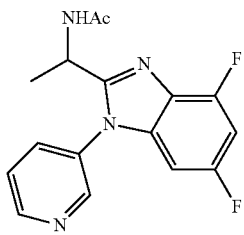 [SMILES: CC(=O)NC(C)c1nc2c(F)cc(F)cc2n1-c1cccnc1]

Prepared according to Step D4 in General Procedure D using tert-butyl 1-(2,4-difluoro-6-(pyridin-3-ylamino)phenylamino)-1-oxopropan-2-ylcarbamate (5.44 g, 13.86 mmol) to give N-(1-(4,6-difluoro-1-(pyridin-3-yl)-1H-benzo[d]imidazol-2-yl)ethyl)acetamide as a tan solid. LC-MS (ESI) m/z 317.1 [M+H]$^+$.

1-(4,6-Difluoro-1-(pyridin-3-yl)-1H-benzo[d]imidazol-2-yl)ethanamine

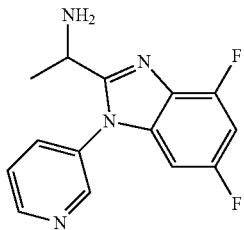 [SMILES: CC(N)c1nc2c(F)cc(F)cc2n1-c1cccnc1]

Prepared according to Step D5a in General Procedure D using N-(1-(4,6-difluoro-1-(pyridin-3-yl)-1H-benzo[d]imidazol-2-yl)ethyl)acetamide (1.29 g, 4.08 mmol) to give 1-(4,6-difluoro-1-(pyridin-3-yl)-1H-benzo[d]imidazol-2-yl)ethanamine as a dark purple solid. LC-MS (ESI) m/z 275.1 [M+H]$^+$.

4-Amino-6-(1-(4,6-difluoro-1-(pyridin-3-yl)-1H-benzo[d]imidazol-2-yl)ethylamino)pyrimidine-5-carbonitrile

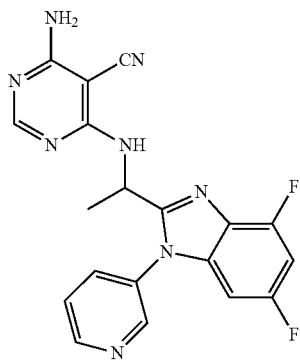 [SMILES: CC(Nc1ncnc(N)c1C#N)c1nc2c(F)cc(F)cc2n1-c1cccnc1]

Prepared according to Step D6 in General Procedure D using 1-(4,6-difluoro-1-(pyridin-3-yl)-1H-benzo[d]imidazol-2-yl)ethanamine (0.820 g, 2.99 mmol) to give 4-amino-6-(1-(4,6-difluoro-1-(pyridin-3-yl)-1H-benzo[d]imidazol-2-yl)ethylamino)pyrimidine-5-carbonitrile (0.850 g, 72.5% yield) as a light pink solid. $^1$H NMR (400 MHz, DMSO-d$_6$) δ ppm 1.57 (d, J=6.85 Hz, 3H) 5.47 (quin, J=6.94 Hz, 1H) 6.86 (dd, J=8.41, 2.15 Hz, 1H) 7.11-7.29 (m, 3H) 7.54-7.60 (m, 1H) 7.78-7.85 (m, 2H) 8.02 (d, J=8.02 Hz, 1H) 8.66 (dd, J=4.79, 1.47 Hz, 1H) 8.75 (d, J=2.15 Hz, 1H). LC-MS (ESI) m/z 393.2 [M+H]$^+$.

4-Amino-6-(((1R)-1-(4,6-difluoro-1-(3-pyridinyl)-1H-benzimidazol-2-yl)ethyl)amino)-5-pyrimidinecarbonitrile and 4-amino-6-(((1S)-1-(4,6-difluoro-1-(3-pyridinyl)-1H-benzimidazol-2-yl)ethyl)amino)-5-pyrimidinecarbonitrile

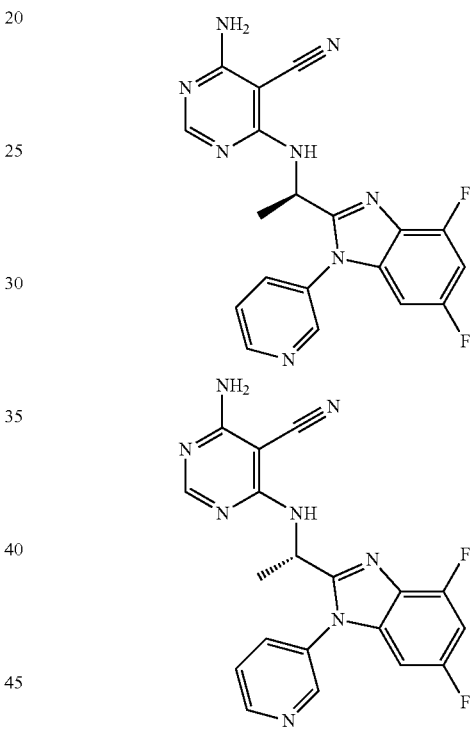

The racemic mixture (300 mg) was separated on AD-H column using preparative SFC to give two fractions. First peak on OD-H column: 4-amino-6-(((1R)-1-(4,6-difluoro-1-(3-pyridinyl)-1H-benzimidazol-2-yl)ethyl)amino)-5-pyrimidinecarbonitrile as a white solid. $^1$H NMR (400 MHz, DMSO-d$_6$) δ ppm 1.58 (d, J=6.85 Hz, 3H) 5.47 (quin, J=6.94 Hz, 1H) 6.87 (dd, J=8.51, 2.05 Hz, 1H) 7.10-7.28 (m, 3H) 7.57 (dd, J=8.12, 4.79 Hz, 1H) 7.77-7.85 (m, 2H) 8.02 (d, J=8.02 Hz, 1H) 8.67 (dd, J=4.79, 1.47 Hz, 1H) 8.75 (d, J=2.15 Hz, 1H). LC-MS (ESI) m/z 391.1 [M−H]$^−$. Second peak on OD-H column: 4-amino-6-(((1S)-1-(4,6-difluoro-1-(3-pyridinyl)-1H-benzimidazol-2-yl)ethyl)amino)-5-pyrimidinecarbonitrile as a white solid. LC-MS (ESI) m/z 391.1 [M−H]$^−$. $^1$H NMR (400 MHz, DMSO-d$_6$) δ ppm 1.58 (d, J=6.85 Hz, 3H) 5.47 (quin, J=6.94 Hz, 1H) 6.87 (dd, J=8.51, 2.05 Hz, 1H) 7.08-7.29 (m, 3H) 7.57 (dd, J=8.02, 4.89 Hz, 1H) 7.76-7.87 (m, 2H) 8.02 (d, J=7.83 Hz, 1H) 8.67 (dd, J=4.69, 1.37 Hz, 1H) 8.75 (d, J=1.96 Hz, 1H)

Example 97

Preparation of 4-amino-6-(((1S)-1-(6-fluoro-3-(3-pyridinyl)imidazo[1,2-a]pyridin-2-yl)ethyl)amino)-5-pyrimidinecarbonitrile (S)-Benzyl (1-(6-fluoroimidazo[1,2-a]pyridine-2-ylcarbamate

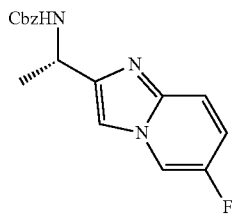 [SMILES: C[C@H](NC(=O)OCc1ccccc1)c1cn2cc(F)ccc2n1]

A solution of 2-Amino-5-fluoro pyridine (0.50 g, 4.45 mmol) and (S)-benzyl (4-bromo-3-oxobutan-2-yl) carbamate (1.3 g, 4.4 mmol) in EtOH (25 mL) was heated to reflux overnight. After completion, the reaction mixture was cooled to 25° C. and EtOH removed in vacuo. The residue was dissolved in EtOAc and washed with satd. sodium bicarbonate. The organic layer was dried over sodium sulfate, filtered and concentrated. The crude material was purified by column chromatography using silica gel (100-200 mesh) and 0-7% MeOH in DCM to provide (S)-benzyl (1-(6-fluoroimidazo[1,2-a]pyridine-2-ylcarbamate: $^1$H NMR (400 MHz, DMSO-$d_6$) δ 1.502 (d, J=6.8 Hz, 3H), 4.946-4.980 (m, 1H), 5.014-5.107 (m, 2H), 7.344-7.373 (m, 5H), 7.751-7.842 (m, 2H), 8.012-8.070 (m, 2H), 9.025 (s, 1H); LC-MS (ESI)] m/z 313.9 [M+H]$^+$.

(S)-Benzyl (1-(6-fluoro-3-iodoimidazo[1,2-a]pyridine-2-yl)ethyl)carbamate

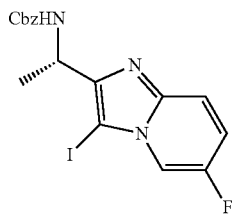 [SMILES: C[C@H](NC(=O)OCc1ccccc1)c1nc2ccc(F)cn2c1I]

To a solution of (S)-benzyl (1-(6-fluoroimidazo[1,2-a]pyridine-2-ylcarbamate (1.2 g, 3.8 mmol) in acetonitrile (19 mL) was added N-iodosuccinimide (0.861 g, 3.82 mmol) at 25° C. The reaction mixture was stirred overnight at 25° C. After completion of the reaction, the mixture was diluted with water and extracted with EtOAc. The organic layer was washed with satd. sodium bicarbonate, dried over sodium sulfate, filtered and concentrated. The crude product was purified by column chromatography using silica gel (100-200 mesh) and 0-40% EtOAc in hexane to provide (S)-benzyl (1-(6-fluoro-3-iodoimidazo[1,2-a]pyridine-2-yl)ethyl)carbamate: LC-MS (ESI)] m/z 439.8 [M+H]$^+$.

(S)-Benzyl (1-(6-fluoro-3-(pyridine-3-yl)imidazo[1,2-a]pyridine-2-yl)ethyl)carbamate

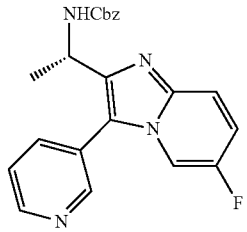 [SMILES: C[C@H](NC(=O)OCc1ccccc1)c1nc2ccc(F)cn2c1-c1cccnc1]

To a solution of (S)-benzyl (1-(6-fluoro-3-iodoimidazo[1,2-a]pyridine-2-yl)ethyl)carbamate (100 mg, 0.22 mmol) and pyridine 3-yl-boronic acid (30.7 mg, 0.25 mmol) in 1,4-dioxane (2 mL) was added cesium fluoride (66.8 mg, 0.440 mmol) at 25° C. The reaction mixture was degassed with nitrogen for 30 min and then tetrakis triphenylphosphine palladium(0) (13 mg, 0.011 mmol) was added at 25° C. The reaction mixture was stirred overnight at 100° C. After completion of the reaction water was added and the mixture extracted with EtOAc. The organic layer was dried over sodium sulfate and concentrated in vacuo. The residue was purified by column chromatography using silica gel (100-200 mesh) and 0-4% MeOH in DCM to provide (S)-Benzyl (1-(6-fluoro-3-(pyridine-3-yl)imidazo[1,2-a]pyridine-2-yl)ethyl)carbamate: LC-MS (ESI)] m/z 391.0 [M+H]$^+$.

(S)-Methyl 2-(1-aminoethyl)-3-phenylimidazo[1,2-a]pyridine-5-carboxylate

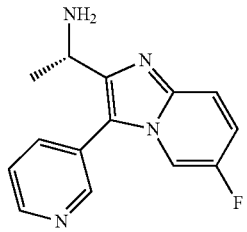 [SMILES: C[C@H](N)c1nc2ccc(F)cn2c1-c1cccnc1]

The mixture of (S)-benzyl (1-(6-fluoro-3-(pyridine-3-yl)imidazo[1,2-a]pyridine-2-yl)ethyl)carbamate (300 mg, 0.760 mmol) and DMS (0.3 mL) in TFA (1 mL) was stirred at 25° C. overnight. The mixture was concentrated in vacuo. The residue was dissolved in EtOAc and washed with satd. sodium bicarbonate solution. The organic layer was washed with satd. sodium bicarbonate solution, dried over sodium sulfate, filtered and concentrated in vacuo to provide (S)-methyl 2-(1-aminoethyl)-3-phenylimidazo[1,2-a]pyridine-5-carboxylate. The crude product was used without further purification.

4-Amino-6-(((1S)-1-(6-fluoro-3-(3-pyridinyl)imidazo[1,2-a]pyridin-2-yl)ethyl)amino)-5-pyrimidinecarbonitrile

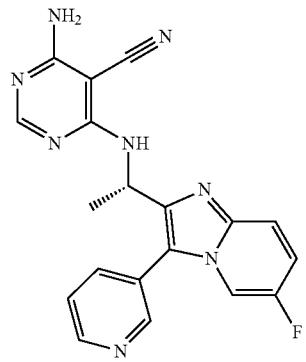 [SMILES: C[C@H](Nc1ncnc(N)c1C#N)c1nc2ccc(F)cn2c1-c1cccnc1]

To the crude (S)-methyl 2-(1-aminoethyl)-3-phenylimidazo[1,2-a]pyridine-5-carboxylate (190 mg, 0.74 mmol) and 4-amino-6-chloro-pyrimidine-5-carbonitrile (114 mg, 0.74 mmol) in n-butanol (4.4 mL) was added DIEA (0.36 mL, 2.2 mmol) at 25° C. The reaction mixture was stirred at 110° C. overnight. Water was added to reaction mixture and extracted with EtOAc. The organic layer was dried over sodium sulfate, filtered and concentrated in vacuo. The residue was purified by column chromatography using silica gel (100-200 mesh) and 0-3% MeOH in DCM to provide 4-amino-6-(((1S)-1-(6-fluoro-3-(3-pyridinyl)imidazo[1,2-a]-pyridin-2-yl)ethyl)amino)-5-pyrimidinecarbonitrile (25 mg): $^1$H NMR (400 MHz, DMSO-d$_6$) δ 1.522 (d, J=6.8 Hz, 3H), 5.398-5.466 (m, 1H), 7.036 (d, 1H, J=7.6 Hz), 7.229 (br s, 2H), 7.395-7.446 (m, 1H), 7.550-7.581 (m, 1H), 7.728-7.765 (m, 1H), 8.008 (d, 1H, J=8 Hz), 8.317-8.333 (m, 1H), 8.663-8.675 (m, 1H)., 8.717 (d, 1H, J=1.2 Hz); LC-MS (ESI)] m/z 375.16 [M+H]$^+$.

Biological Assays

Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expressed with Baculo virus in Hi5 insect cells. The γ isozyme was purified by sequential Ni-NTA, Superdex-200, Q-HP chromatography. The γ isozyme was stored frozen at −80° C. in NaH$_2$PO$_4$, pH 8, 0.2M NaCl, 1% ethylene glycol, 2 mM β-mercaptoethanol.

|  | Alpha | Beta | Delta | gamma |
|---|---|---|---|---|
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 h | 2 h | 2 h | 1 h |
| [Enzyme] | 15 nM | 40 nM | 15 nM | 50 nM |

In Vitro Enzyme Assays

Assays were performed in 25 μL with the above final concentrations of components in white polyproplyene plates (Costar 3355). Phospatidyl inositol phosphoacceptor, PtdIns (4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 μL) was added per test well, and the inhibition relative to reactions containing no compound, with and without enzyme was determined. After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM

Isolate Human B Cells:
Isolate PBMCs from Leukopac or from human fresh blood. Isolate human B cells by using Miltenyi protocol and B cell isolation kit II.—human B cells were Purified by using AutoMacs.column.
Activation of Human B Cells
Use 96 well Flat bottom plate, plate 50000/well purified B cells in B cell proliferation medium (DMEM+5% FCS, 10 mM Hepes, 50 μM 2-mercaptoethanol); 150 μL medium contain 250 ng/mL CD40L-LZ recombinant protein (Amgen) and 2 μg/mL anti-Human IgM antibody (Jackson ImmunoReseach Lab.#109-006-129), mixed with 50 μL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4

Isolate Human B Cells:
Isolate human PBMCs from Leukopac or from human fresh blood. Isolate human B cells using Miltenyi protocol—B cell isolation kit. Human B cells were Purified by AutoMacs.column.
Activation of Human B Cells
Use 96-well flat bottom plate, plate 50000/well purified B cells in B cell proliferation medium (DMEM+5% FCS, 50 μM 2-mercaptoethanol, 10 mM Hepes). The medium (150 μL) contain 250 ng/mL CD40L-LZ recombinant protein (Amgen) and 10 ng/mL IL-4 (R&D system #204-IL-025), mixed with 50 150 μL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll gradient. Use 96 well round-bottom plate and plate 2×10$^5$ PBMC/well with culture medium (RPMI1640+10% FCS, 50 uM 2-Mercaptoethanol, 10 mM Hepes). For IC$_{50}$ determinations, PI3K inhibitors was tested from 10 μM to 0.001 μM, in half log increments and in triplicate. Tetanus toxoid, T cell specific antigen (University of Massachusetts Lab) was added at 1 μg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane
Forkhead (FKHRL1) is a substrate for AKT1. It is cytoplasmic when phosphorylated by AKT (survival/growth). Inhibition of AKT (stasis/apoptosis)—forkhead translocation to the nucleus
FYVE domains bind to PI(3)P. the majority is generated by constitutive action of PI3K Class III
AKT membrane ruffling assay (CHO-1R-AKT1-EGFP cells/GE Healthcare)

Wash cells with assay buffer. Treat with compounds in assay buffer 1 h. Add 10 ng/mL insulin. Fix after 10 min at room temp and image Forkhead Translocation Assay (MDA MB468 Forkhead-DiversaGFP Cells)

Treat cells with compound in growth medium 1 h. Fix and image.

Class III PI(3)P Assay (U2OS EGFP-2XFYVE Cells/GE Healthcare)

Wash cells with assay buffer. Treat with compounds in assay buffer 1 h. Fix and image.

Control for all 3 assays is 10 uM Wortmannin:
AKT is cytoplasmic
Forkhead is nuclear
PI(3)P depleted from endosomes Biomarker Assay: B-Cell Receptor Stimulation of CD69 or B7.2 (CD86) Expression Heparinized human whole blood was stimulated with 10 µg/mL anti-IgD (Southern Biotech, #9030-01). 90 µL of the stimulated blood was then aliquoted per well of a 96-well plate and treated with 10 µL of various concentrations of blocking compound (from 10-0.0003 µM) diluted in IMDM+10% FBS (Gibco). Samples were incubated together for 4 h (for CD69 expression) to 6 h (for B7.2 expression) at 37° C. Treated blood (50 µL) was transferred to a 96-well, deep well plate (Nunc) for antibody staining with 10 µL each of CD45-PerCP (BD Biosciences, #347464), CD19-FITC (BD Biosciences, #340719), and CD69-PE (BD Biosciences, #341652). The second 50 µL of the treated blood was transferred to a second 96-well, deep well plate for antibody staining with 10 µL each of CD19-FITC (BD Biosciences, #340719) and CD86-PeCy5 (BD Biosciences, #555666). All stains were performed for 15-30 min in the dark at rt. The blood was then lysed and fixed using 450 µL of FACS lysing solution (BD Biosciences, #349202) for 15 min at rt. Samples were then washed 2× in PBS+2% FBS before FACS analysis. Samples were gated on either CD45/CD19 double positive cells for CD69 staining, or CD19 positive cells for CD86 staining.

Gamma Counterscreen Stimulation of Human Monocytes for Phospho-AKT Expression

A human monocyte cell line, THP-1, was maintained in RPMI+10% FBS (Gibco). One day before stimulation, cells were counted using trypan blue exclusion on a hemocytometer and suspended at a concentration of $1 \times 10^6$ cells per mL of media. 100 µL of cells plus media ($1 \times 10^5$ cells) was then aliquoted per well of 4-96-well, deep well dishes (Nunc) to test eight different compounds. Cells were rested overnight before treatment with various concentrations (from 10-0.0003 µM) of blocking compound. The compound diluted in media (12 µL) was added to the cells for 10 min at 37° C. Human MCP-1 (12 µL, R&D Diagnostics, #279-MC) was diluted in media and added to each well at a final concentration of 50 ng/mL. Stimulation lasted for 2 min at rt. Pre-warmed FACS Phosflow Lyse/Fix buffer (1 mL of 37° C.) (BD Biosciences, #558049) was added to each well. Plates were then incubated at 37° C. for an additional 10-15 min. Plates were spun at 1500 rpm for 10 min, supernatant was aspirated off, and 1 mL of ice cold 90% MeOH was added to each well with vigorous shaking Plates were then incubated either overnight at −70° C. or on ice for 30 min before antibody staining Plates were spun and washed 2× in PBS+2% FBS (Gibco). Wash was aspirated and cells were suspended in remaining buffer. Rabbit pAKT (50 µL, Cell Signaling, #4058L) at 1:100, was added to each sample for 1 h at rt with shaking Cells were washed and spun at 1500 rpm for 10 min. Supernatant was aspirated and cells were suspended in remaining buffer. Secondary antibody, goat anti-rabbit Alexa 647 (50 µL, Invitrogen, #A21245) at 1:500, was added for 30 min at rt with shaking Cells were then washed 1× in buffer and suspended in 150 µL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen Stimulation of Monocytes for Phospho-AKT Expression in Mouse Bone Marrow Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5 \times 10^6$ cells per 1 mL of media and 100 µL ($7.5 \times 10^5$ cells) was aliquoted per well into 4-96-well, deep well dishes (Nunc) to test eight different compounds. Cells were rested at 37° C. for 2 h before treatment with various concentrations (from 10-0.0003 µM) of blocking compound. Compound diluted in media (12 µL) was added to bone marrow cells for 10 min at 37° C. Mouse MCP-1 (12 µL, R&D Diagnostics, #479-JE) was diluted in media and added to each well at a final concentration of 50 ng/mL. Stimulation lasted for 2 min at rt. 1 mL of 37° C. pre-warmed FACS Phosflow Lyse/Fix buffer (BD Biosciences, #558049) was added to each well. Plates were then incubated at 37° C. for an additional 10-15 min. Plates were spun at 1500 rpm for 10 min. Supernatant was aspirated off and 1 mL of ice cold 90% MeOH was added to each well with vigorous shaking Plates were then incubated either overnight at −70° C. or on ice for 30 min before antibody staining Plates were spun and washed 2× in PBS+2% FBS (Gibco). Wash was aspirated and cells were suspended in remaining buffer. Fc block (2 µL, BD Pharmingen, #553140) was then added per well for 10 min at rt. After block, 50 µL, of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at RT with shaking Wash buffer was added to cells and spun at 1500 rpm for 10 min. Supernatant was aspirated and cells were suspended in remaining buffer. Secondary antibody; goat anti-rabbit Alexa 647 (50 µL, Invitrogen, #A21245) at 1:500, was added for 30 min at rt with shaking Cells were then washed 1x in buffer and suspended in 100 µL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mLs) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3X's and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3X's and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 µm cell strainer (BD Bioscience, Bedford, Mass.) into another 15 mL conical vial and washed with 9 mL of PBS. Splenocytes and blood are spun @ 2,000 rpms for 10 min (cold) and buffer is aspirated. Cells are resuspended in 2.0 mL of cold (−20° C.) 90% methyl alcohol (Mallinckrodt Chemicals, Phillipsburg, N.J.). MeOH is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 min and spun at 10,000 rpm in serum microtainer tubes (Becton Dickinson) for 10 min. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 µg of TNP-LPS (Biosearch Tech., #T-5065), 50 µg of TNP-Ficoll (Biosearch Tech., #F-1300), or 100 µg of TNP-KLH (Biosearch Tech., #T-5060) plus 1% alum (Brenntag, #3501) in PBS. TNP-KLH plus alum solution was prepared by gently inverting the mixture 3-5 times every 10 min for 1 h before immunization. On day 5, post-last treatment, mice were $CO_2$ sacrificed and cardiac punctured. Blood was allowed to clot for 30 min and spun at 10,000 rpm in serum microtainer tubes for 10 min. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 µg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 min depending on the Ig analyzed. The reaction was stopped with 2M sulfuric acid and plates were read at an OD of 450 nm.

PI3k δ Ki (µM) values are as follows:

| | |
|---|---|
| 1-cyclopropyl-N-methyl-2-((1S)-1-(9H-purin-6-ylamino)ethyl)-1H-benzimidazole-7-carboxamide | 0.0146 |
| 2-((1R)-1-((6-amino-5-cyano-4-pyrimidinyl)amino)ethyl)-1-(5-fluoro-3-pyridinyl)-N-methyl-1H-benzimidazole-7-carboxamide, 2-((1S)-1-((6-amino-5-cyano-4-pyrimidinyl)amino)ethyl)-1-(5-fluoro-3-pyridinyl)-N-methyl-1H-benzimidazole-7-carboxamide | 0.09010 |
| 2-((1R)-1-((6-amino-5-cyano-4-pyrimidinyl)amino)ethyl)-1-(5-fluoro-3-pyridinyl)-N-methyl-1H-benzimidazole-7-carboxamide | 1.37000 |
| 2-((1R)-1-((6-amino-5-cyano-4-pyrimidinyl)amino)ethyl)-1-(5-fluoro-3-pyridinyl)-1H-benzimidazole-7-carbonitrile, 2-((1S)-1-((6-amino-5-cyano-4-pyrimidinyl)amino)ethyl)-1-(5-fluoro-3-pyridinyl)-1H-benzimidazole-7-carbonitrile | 0.17700 |
| 2-((1R)-1-((6-amino-5-cyano-4-pyrimidinyl)amino)ethyl)-1-(5-fluoro-3-pyridinyl)-1H-benzimidazole-7-carbonitrile | 0.32500 |
| 2-((1S)-1-((6-amino-5-(4-(methylsulfonyl)phenyl)-4-pyrimidinyl)amino)ethyl)-1-cyclopropyl-N-methyl-1H-benzimidazole-7-carboxamide | 0.0105 |
| 2-((1S)-1-((6-amino-5-(methylsulfonyl)-4-pyrimidinyl)amino)ethyl)-1-cyclopropyl-N-methyl-1H-benzimidazole-7-carboxamide | 0.0300 |
| 2-((1S)-1-((6-amino-5-(trifluoromethyl)-4-pyrimidinyl)amino)ethyl)-1-cyclopropyl-N-methyl-1H-benzimidazole-7-carboxamide | 0.0370 |
| 2-((1S)-1-((6-amino-5-cyano-4-pyrimidinyl)amino)ethyl)-1-(5-fluoro-3-pyridinyl)-N-methyl-1H-benzimidazole-7-carboxamide | 0.01020 |
| 2-((1S)-1-((6-amino-5-cyano-4-pyrimidinyl)amino)ethyl)-1-(5-fluoro-3-pyridinyl)-1H-benzimidazole-7-carbonitrile | 0.17100 |
| 2-((1S)-1-((6-amino-5-cyano-4-pyrimidinyl)amino)ethyl)-1-cyclopropyl-N-methyl-1H-benzimidazole-7-carboxamide | 0.0071 |
| 2-((1S)-1-((6-amino-5-cyano-4-pyrimidinyl)amino)ethyl)-3-(5-fluoro-3-pyridinyl)-N-methylimidazo[1,2-a]pyridine-5-carboxamide | 0.08110 |
| 2-((1S)-1-((6-amino-5-cyano-4-pyrimidinyl)amino)ethyl)-N,1-dicyclopropyl-1H-benzimidazole-7-carboxamide | 0.01750 |
| 2-((1S)-1-((6-amino-5-cyano-4-pyrimidinyl)amino)ethyl)-N-cyclopentyl-1-cyclopropyl-1H-benzimidazole-7-carboxamide | 0.01840 |
| 2-((1S)-1-((6-amino-5-cyano-4-pyrimidinyl)amino)ethyl)-N-cyclopropyl-3-phenylimidazo[1,2-a]pyridine-5-carboxamide | 0.01740 |

| | |
|---|---|
| 2-((1S)-1-((6-amino-5-cyano-4-pyrimidinyl)amino)ethyl)-N-methyl-3-phenylimidazo[1,2-a]pyridine-5-carboxamide | 0.02620 |
| 2-((1S)-1-((6-amino-5-cyano-4-pyrimidinyl)amino)ethyl)-N-tert-butyl-1-cyclopropyl-1H-benzimidazole-7-carboxamide | 0.07380 |
| 2-((1S)-1-((6-amino-5-cyano-4-pyrimidinyl)amino)propyl)-1-cyclopropyl-N-methyl-1H-benzimidazole-7-carboxamide | 0.03900 |
| 3-(2-((1R)-1-((6-amino-5-cyano-4-pyrimidinyl)amino)ethyl)-6-fluoro-1H-benzimidazol-1-yl)-N-methylbenzamide, 3-(2-((1S)-1-((6-amino-5-cyano-4-pyrimidinyl)amino)ethyl)-6-fluoro-1H-benzimidazol-1-yl)-N-methylbenzamide | 0.03060 |
| 3-(2-((1R)-1-((6-amino-5-cyano-4-pyrimidinyl)amino)ethyl)-6-fluoro-1H-benzimidazol-1-yl)-N-methylbenzamide | 4.67000 |
| 3-(2-((1S)-1-((6-amino-5-cyano-4-pyrimidinyl)amino)ethyl)-6-fluoro-1H-benzimidazol-1-yl)-N-methylbenzamide | 0.01830 |
| 4-amino-6-(((1R)-1-(1-(2,3'-bipyridin-5'-yl)-6-fluoro-1H-benzimidazol-2-yl)ethyl)amino)-5-pyrimidinecarbonitrile | 1.19000 |
| 4-amino-6-(((1R)-1-(1-(2-pyridinyl)-1H-imidazo[4,5-b]pyridin-2-yl)ethyl)amino)-5-pyrimidinecarbonitrile, 4-amino-6-(((1S)-1-(1-(2-pyridinyl)-1H-imidazo[4,5-b]pyridin-2-yl)ethyl)amino)-5-pyrimidinecarbonitrile | 2.90000 |
| 4-amino-6-(((1R)-1-(1-(2-pyridinyl)-1H-imidazo[4,5-b]pyridin-2-yl)ethyl)amino)-5-pyrimidinecarbonitrile | Undefined |
| 4-amino-6-(((1R)-1-(1-(3,5-difluorophenyl)-1H-imidazo[4,5-b]pyridin-2-yl)ethyl)amino)-5-pyrimidinecarbonitrile, 4-amino-6-(((1S)-1-(1-(3,5-difluorophenyl)-1H-imidazo[4,5-b]pyridin-2-yl)ethyl)amino)-5-pyrimidinecarbonitrile | 0.34400 |
| 4-amino-6-(((1R)-1-(1-(3,5-difluorophenyl)-1H-imidazo[4,5-c]pyridin-2-yl)ethyl)amino)-5-pyrimidinecarbonitrile, 4-amino-6-(((1S)-1-(1-(3,5-difluorophenyl)-1H-imidazo[4,5-c]pyridin-2-yl)ethyl)amino)-5-pyrimidinecarbonitrile | 11.10000 |
| 4-amino-6-(((1R)-1-(1-(3,5-difluorophenyl)-4,6-difluoro-1H-benzimidazol-2-yl)ethyl)amino)-5-pyrimidinecarbonitrile | 0.25100 |
| 4-amino-6-(((1R)-1-(1-(3,5-difluorophenyl)-4-fluoro-1H-benzimidazol-2-yl)ethyl)amino)-5-pyrimidinecarbonitrile | 4.1800 |
| 4-amino-6-(((1R)-1-(1-(3,5-difluorophenyl)-6-fluoro-1H-benzimidazol-2-yl)ethyl)amino)-5-pyrimidinecarbonitrile | 0.0013 |
| 4-amino-6-(((1R)-1-(1-(3,5-difluorophenyl)-6-fluoro-1H-benzimidazol-2-yl)ethyl)amino)-5-pyrimidinecarbonitrile | 0.0390 |
| 4-amino-6-(((1R)-1-(1-(3,5-difluorophenyl)-7-fluoro-1H-benzimidazol-2-yl)ethyl)amino)-5-pyrimidinecarbonitrile | 0.0232 |
| 4-amino-6-(((1R)-1-(1-(3,5-difluorophenyl)-7-fluoro-1H-benzimidazol-2-yl)ethyl)amino)-5-pyrimidinecarbonitrile | 1.0600 |
| 4-amino-6-(((1R)-1-(1-(3-cyanophenyl)-6-fluoro-1H-benzimidazol-2-yl)ethyl)amino)-5-pyrimidinecarbonitrile, 4-amino-6-(((1S)-1-(1-(3-cyanophenyl)-6-fluoro-1H-benzimidazol-2-yl)ethyl)amino)-5-pyrimidinecarbonitrile | 0.02880 |
| 4-amino-6-(((1R)-1-(1-(3-cyanophenyl)-6-fluoro-1H-benzimidazol-2-yl)ethyl)amino)-5-pyrimidinecarbonitrile | 0.41100 |
| 4-amino-6-(((1R)-1-(1-(5-bromo-3-pyridinyl)-6-fluoro-1H-benzimidazol-2-yl)ethyl)amino)-5-pyrimidinecarbonitrile, 4-amino-6-(((1S)-1-(1-(5-bromo-3-pyridinyl)-6-fluoro-1H-benzimidazol-2-yl)ethyl)amino)-5-pyrimidinecarbonitrile | 0.04610 |
| 4-amino-6-(((1R)-1-(1-cyclopropyl-7-(methylsulfonyl)-1H-benzimidazol-2-yl)ethyl)amino)-5-pyrimidinecarbonitrile, 4-amino-6-(((1S)-1-(1-cyclopropyl-7-(methylsulfonyl)-1H-benzimidazol-2-yl)ethyl)amino)-5-pyrimidinecarbonitrile | 0.00376 |
| 4-amino-6-(((1R)-1-(1-cyclopropyl-7-(methylsulfonyl)-1H-benzimidazol-2-yl)ethyl)amino)-5-pyrimidinecarbonitrile | 1.00000 |
| 4-amino-6-(((1R)-1-(3-(3,5-difluorophenyl)-3H-imidazo[4,5-b]pyridin-2-yl)ethyl)amino)-5-pyrimidinecarbonitrile | Undefined |
| 4-amino-6-(((1R)-1-(4,6-difluoro-1-(3-pyridinyl)-1H-benzimidazol-2-yl)ethyl)amino)-5-pyrimidinecarbonitrile, 4-amino-6-(((1S)-1-(4,6-difluoro-1-(3-pyridinyl)-1H-benzimidazol-2-yl)ethyl)amino)-5-pyrimidinecarbonitrile | 0.02220 |
| 4-amino-6-(((1R)-1-(4,6-difluoro-1-(3-pyridinyl)-1H-benzimidazol-2-yl)ethyl)amino)-5-pyrimidinecarbonitrile | 1.29000 |
| 4-amino-6-(((1R)-1-(4-fluoro-1-(5-fluoro-3-pyridinyl)-1H-benzimidazol-2-yl)ethyl)amino)-5-pyrimidinecarbonitrile, 4-amino-6-(((1S)-1-(4-fluoro-1-(5-fluoro-3-pyridinyl)-1H-benzimidazol-2-yl)ethyl)amino)-5-pyrimidinecarbonitrile | 0.08610 |
| 4-amino-6-(((1R)-1-(5-fluoro-1-(2-pyridinyl)-1H-benzimidazol-2-yl)ethyl)amino)-5-pyrimidinecarbonitrile | 0.0070 |
| 4-amino-6-(((1R)-1-(5-fluoro-1-(3-(methylsulfanyl)phenyl)-1H-benzimidazol-2-yl)ethyl)amino)-5-pyrimidinecarbonitrile | 0.1280 |
| 4-amino-6-(((1R)-1-(5-fluoro-1-(3-(methylsulfanyl)phenyl)-1H-benzimidazol-2-yl)ethyl)amino)-5-pyrimidinecarbonitrile | 3.7400 |
| 4-amino-6-(((1R)-1-(5-fluoro-1-(3-(methylsulfonyl)phenyl)-1H-benzimidazol-2-yl)ethyl)amino)-5-pyrimidinecarbonitrile | >125 |

| | |
|---|---|
| 4-amino-6-(((1R)-1-(5-fluoro-1-(5-fluoro-3-pyridinyl)-1H-benzimidazol-2-yl)ethyl)amino)-5-pyrimidinecarbonitrile, 4-amino-6-(((1S)-1-(5-fluoro-1-(5-fluoro-3-pyridinyl)-1H-benzimidazol-2-yl)ethyl)amino)-5-pyrimidinecarbonitrile | 0.14800 |
| 4-amino-6-(((1R)-1-(5-fluoro-1-(5-fluoro-3-pyridinyl)-1H-benzimidazol-2-yl)ethyl)amino)-5-pyrimidinecarbonitrile | 2.82000 |
| 4-amino-6-(((1R)-1-(6-chloro-1-(3,5-difluorophenyl)-1H-benzimidazol-2-yl)ethyl)amino)-5-pyrimidinecarbonitrile | 0.0022 |
| 4-amino-6-(((1R)-1-(6-chloro-1-(3,5-difluorophenyl)-1H-benzimidazol-2-yl)ethyl)amino)-5-pyrimidinecarbonitrile | 1.3100 |
| 4-amino-6-(((1R)-1-(6-fluoro-1-(2-(methylsulfonyl)phenyl)-1H-benzimidazol-2-yl)ethyl)amino)-5-pyrimidinecarbonitrile | 0.1110 |
| 4-amino-6-(((1R)-1-(6-fluoro-1-(2-(methylsulfonyl)phenyl)-1H-benzimidazol-2-yl)ethyl)amino)-5-pyrimidinecarbonitrile | 7.0300 |
| 4-amino-6-(((1R)-1-(6-fluoro-1-(2-(methylsulfonyl)phenyl)-1H-benzimidazol-2-yl)ethyl)amino)-5-pyrimidinecarbonitrile | 2.0600 |
| 4-amino-6-(((1R)-1-(6-fluoro-1-(3-(2-pyridinyl)phenyl)-1H-benzimidazol-2-yl)ethyl)amino)-5-pyrimidinecarbonitrile | 0.1320 |
| 4-amino-6-(((1R)-1-(6-fluoro-1-(3-(methylsulfonyl)phenyl)-1H-benzimidazol-2-yl)ethyl)amino)-5-pyrimidinecarbonitrile | 0.0402 |
| 4-amino-6-(((1R)-1-(6-fluoro-1-(3-(methylsulfonyl)phenyl)-1H-benzimidazol-2-yl)ethyl)amino)-5-pyrimidinecarbonitrile | 9.15 |
| 4-amino-6-(((1R)-1-(6-fluoro-1-(3-fluorophenyl)-1H-benzimidazol-2-yl)ethyl)amino)-5-pyrimidinecarbonitrile | 0.3620 |
| 4-amino-6-(((1R)-1-(6-fluoro-1-(3-pyridinyl)-1H-benzimidazol-2-yl)ethyl)amino)-5-pyrimidinecarbonitrile, 4-amino-6-(((1S)-1-(6-fluoro-1-(3-pyridinyl)-1H-benzimidazol-2-yl)ethyl)amino)-5-pyrimidinecarbonitrile | 0.01390 |
| 4-amino-6-(((1R)-1-(6-fluoro-1-(3-pyridinyl)-1H-benzimidazol-2-yl)ethyl)amino)-5-pyrimidinecarbonitrile | 1.85000 |
| 4-amino-6-(((1R)-1-(6-fluoro-1-(4-fluorophenyl)-1H-benzimidazol-2-yl)ethyl)amino)-5-pyrimidinecarbonitrile | 0.0028 |
| 4-amino-6-(((1R)-1-(6-fluoro-1-(4-fluorophenyl)-1H-benzimidazol-2-yl)ethyl)amino)-5-pyrimidinecarbonitrile | 2.4800 |
| 4-amino-6-(((1R)-1-(6-fluoro-1-(5-fluoro-3-pyridinyl)-1H-benzimidazol-2-yl)ethyl)amino)-5-pyrimidinecarbonitrile | 0.0072 |
| 4-amino-6-(((1R)-1-(6-fluoro-1-(5-fluoro-3-pyridinyl)-1H-benzimidazol-2-yl)ethyl)amino)-5-pyrimidinecarbonitrile | 0.52700 |
| 4-amino-6-(((1R)-1-(6-fluoro-1-(6-fluoro-2-pyridinyl)-1H-benzimidazol-2-yl)ethyl)amino)-5-pyrimidinecarbonitrile, 4-amino-6-(((1S)-1-(6-fluoro-1-(6-fluoro-2-pyridinyl)-1H-benzimidazol-2-yl)ethyl)amino)-5-pyrimidinecarbonitrile | 0.02470 |
| 4-amino-6-(((1R)-1-(6-fluoro-1-(6-fluoro-2-pyridinyl)-1H-benzimidazol-2-yl)ethyl)amino)-5-pyrimidinecarbonitrile | 0.75500 |
| 4-amino-6-(((1R)-1-(7-bromo-1-(5-fluoro-3-pyridinyl)-1H-benzimidazol-2-yl)ethyl)amino)-5-pyrimidinecarbonitrile, 4-amino-6-(((1S)-1-(7-bromo-1-(5-fluoro-3-pyridinyl)-1H-benzimidazol-2-yl)ethyl)amino)-5-pyrimidinecarbonitrile | 0.06970 |
| 4-amino-6-(((1S)-1-(1-(2,3'-bipyridin-5'-yl)-6-fluoro-1H-benzimidazol-2-yl)ethyl)amino)-5-pyrimidinecarbonitrile | 0.24800 |
| 4-amino-6-(((1S)-1-(1-(2-pyridinyl)-1H-imidazo[4,5-b]pyridin-2-yl)ethyl)amino)-5-pyrimidinecarbonitrile | 1.62000 |
| 4-amino-6-(((1S)-1-(1-(3,5-difluorobenzyl)-7-(methylsulfonyl)-1H-benzimidazol-2-yl)ethyl)amino)-5-pyrimidinecarbonitrile | 0.29500 |
| 4-amino-6-(((1S)-1-(1-(3,5-difluorophenyl)-4,6-difluoro-1H-benzimidazol-2-yl)ethyl)amino)-5-pyrimidinecarbonitrile | 0.00260 |
| 4-amino-6-(((1S)-1-(1-(3,5-difluorophenyl)-4-fluoro-1H-benzimidazol-2-yl)ethyl)amino)-5-pyrimidinecarbonitrile | 0.0064 |
| 4-amino-6-(((1S)-1-(1-(3,5-difluorophenyl)-4-fluoro-1H-benzimidazol-2-yl)ethyl)amino)-5-pyrimidinecarbonitrile | 0.0021 |
| 4-amino-6-(((1S)-1-(1-(3,5-difluorophenyl)-6-fluoro-1H-benzimidazol-2-yl)ethyl)amino)-5-pyrimidinecarbonitrile | 0.0002 |
| 4-amino-6-(((1S)-1-(1-(3,5-difluorophenyl)-7-fluoro-1H-benzimidazol-2-yl)ethyl)amino)-5-pyrimidinecarbonitrile | 0.0037 |
| 4-amino-6-(((1S)-1-(1-(3-cyanophenyl)-6-fluoro-1H-benzimidazol-2-yl)ethyl)amino)-5-pyrimidinecarbonitrile | 0.01880 |
| 4-amino-6-(((1S)-1-(1-(4-fluorobenzyl)-4-(methylsulfonyl)-1H-benzimidazol-2-yl)ethyl)amino)-5-pyrimidinecarbonitrile | 2.41000 |
| 4-amino-6-(((1S)-1-(1-(4-fluorobenzyl)-7-(methylsulfonyl)-1H-benzimidazol-2-yl)ethyl)amino)-5-pyrimidinecarbonitrile | 0.02680 |
| 4-amino-6-(((1S)-1-(1-(4-fluorobenzyl)-7-(methylsulfonyl)-1H-benzimidazol-2-yl)propyl)amino)-5-pyrimidinecarbonitrile | 0.02740 |
| 4-amino-6-(((1S)-1-(1-(4-fluorobenzyl)-7-(trifluoromethyl)-1H-benzimidazol-2-yl)propyl)amino)-5-pyrimidinecarbonitrile | 0.46400 |
| 4-amino-6-(((1S)-1-(1-(cyclopropylmethyl)-5-fluoro-1H-benzimidazol-2-yl)ethyl)amino)-5-pyrimidinecarbonitrile | 0.0060 |
| 4-amino-6-(((1S)-1-(1-(cyclopropylmethyl)-5-fluoro-1H-benzimidazol-2-yl)ethyl)amino)-5-pyrimidinecarbonitrile | 0.0258 |
| 4-amino-6-(((1S)-1-(1-(cyclopropylmethyl)-6-fluoro-1H-benzimidazol-2-yl)ethyl)amino)-5-pyrimidinecarbonitrile | 0.0031 |

| | |
|---|---|
| 4-amino-6-(((1S)-1-(1-(cyclopropylmethyl)-7-(methylsulfonyl)-1H-benzimidazol-2-yl)ethyl)amino)-5-pyrimidinecarbonitrile | 0.00220 |
| 4-amino-6-(((1S)-1-(1-(cyclopropylmethyl)-7-(methylsulfonyl)-1H-benzimidazol-2-yl)propyl)amino)-5-pyrimidinecarbonitrile | 0.00219 |
| 4-amino-6-(((1S)-1-(1-(cyclopropylmethyl)-7-(trifluoromethyl)-1H-benzimidazol-2-yl)propyl)amino)-5-pyrimidinecarbonitrile | 0.05310 |
| 4-amino-6-(((1S)-1-(1-cyclopentyl-4-(methylsulfonyl)-1H-benzimidazol-2-yl)ethyl)amino)-5-pyrimidinecarbonitrile | 1.44000 |
| 4-amino-6-(((1S)-1-(1-cyclopropyl-5-fluoro-1H-benzimidazol-2-yl)ethyl)amino)-5-pyrimidinecarbonitrile | 0.0017 |
| 4-amino-6-(((1S)-1-(1-cyclopropyl-5-fluoro-1H-benzimidazol-2-yl)ethyl)amino)-5-pyrimidinecarbonitrile | 0.03150 |
| 4-amino-6-(((1S)-1-(1-cyclopropyl-6-fluoro-1H-benzimidazol-2-yl)ethyl)amino)-5-pyrimidinecarbonitrile | 0.00096 |
| 4-amino-6-(((1S)-1-(1-cyclopropyl-7-(methylsulfonyl)-1H-benzimidazol-2-yl)ethyl)amino)-5-pyrimidinecarbonitrile | 0.00283 |
| 4-amino-6-(((1S)-1-(1-cyclopropyl-7-fluoro-1H-benzimidazol-2-yl)ethyl)amino)-5-pyrimidinecarbonitrile | 0.0122 |
| 4-amino-6-(((1S)-1-(3-(2-pyridinyl)imidazo[1,2-a]pyrazin-2-yl)ethyl)amino)-5-pyrimidinecarbonitrile | 2.16000 |
| 4-amino-6-(((1S)-1-(3-(2-pyridinyl)imidazo[1,2-a]pyrimidin-2-yl)ethyl)amino)-5-pyrimidinecarbonitrile | 1.58000 |
| 4-amino-6-(((1S)-1-(3-(2-pyridinyl)imidazo[1,2-b]pyridazin-2-yl)ethyl)amino)-5-pyrimidinecarbonitrile | 2.01000 |
| 4-amino-6-(((1S)-1-(3-(3,5-difluorophenyl)-3H-imidazo[4,5-b]pyridin-2-yl)ethyl)amino)-5-pyrimidinecarbonitrile | 0.13800 |
| 4-amino-6-(((1S)-1-(3-(3,5-difluorophenyl)-6-fluoroimidazo[1,2-a]pyridin-2-yl)ethyl)amino)-5-pyrimidinecarbonitrile | 0.0114 |
| 4-amino-6-(((1S)-1-(3-(3-chloro-5-fluorophenyl)-6-fluoroimidazo[1,2-a]pyridin-2-yl)ethyl)amino)-5-pyrimidinecarbonitrile | 0.0088 |
| 4-amino-6-(((1S)-1-(3-(4-chlorophenyl)-6-fluoroimidazo[1,2-a]pyridin-2-yl)ethyl)amino)-5-pyrimidinecarbonitrile | 0.0251 |
| 4-amino-6-(((1S)-1-(3-(4-chlorophenyl)imidazo[1,2-a]pyridin-2-yl)ethyl)amino)-5-pyrimidinecarbonitrile | 0.0740 |
| 4-amino-6-(((1S)-1-(4,6-difluoro-1-(3-pyridinyl)-1H-benzimidazol-2-yl)ethyl)amino)-5-pyrimidinecarbonitrile | 0.00674 |
| 4-amino-6-(((1S)-1-(4-fluoro-1-(5-fluoro-3-pyridinyl)-1H-benzimidazol-2-yl)ethyl)amino)-5-pyrimidinecarbonitrile | 0.04700 |
| 4-amino-6-(((1S)-1-(5-((4-methyl-1-piperazinyl)carbonyl)-3-phenylimidazo[1,2-a]pyridin-2-yl)ethyl)amino)-5-pyrimidinecarbonitrile | 0.01180 |
| 4-amino-6-(((1S)-1-(5,6-difluoro-1-(5-fluoro-3-pyridinyl)-1H-benzimidazol-2-yl)ethyl)amino)-5-pyrimidinecarbonitrile | 0.05750 |
| 4-amino-6-(((1S)-1-(5-fluoro-1-(3-(methylsulfanyl)phenyl)-1H-benzimidazol-2-yl)ethyl)amino)-5-pyrimidinecarbonitrile | 0.0441 |
| 4-amino-6-(((1S)-1-(5-fluoro-1-(3-(methylsulfonyl)phenyl)-1H-benzimidazol-2-yl)ethyl)amino)-5-pyrimidinecarbonitrile | 0.4770 |
| 4-amino-6-(((1S)-1-(5-fluoro-1-(3-(methylsulfonyl)phenyl)-1H-benzimidazol-2-yl)ethyl)amino)-5-pyrimidinecarbonitrile | 0.0876 |
| 4-amino-6-(((1S)-1-(5-fluoro-1-(5-fluoro-3-pyridinyl)-1H-benzimidazol-2-yl)ethyl)amino)-5-pyrimidinecarbonitrile | 0.09640 |
| 4-amino-6-(((1S)-1-(5-fluoro-1-phenyl-1H-benzimidazol-2-yl)ethyl)amino)-5-pyrimidinecarbonitrile | 0.0017 |
| 4-amino-6-(((1S)-1-(6-chloro-1-(3,5-difluorophenyl)-1H-benzimidazol-2-yl)ethyl)amino)-5-pyrimidinecarbonitrile | 0.0027 |
| 4-amino-6-(((1S)-1-(6-fluoro-1-(2-(methylsulfonyl)phenyl)-1H-benzimidazol-2-yl)ethyl)amino)-5-pyrimidinecarbonitrile | 0.0535 |
| 4-amino-6-(((1S)-1-(6-fluoro-1-(2-(methylsulfonyl)phenyl)-1H-benzimidazol-2-yl)ethyl)amino)-5-pyrimidinecarbonitrile | 2.0800 |
| 4-amino-6-(((1S)-1-(6-fluoro-1-(3-(2-pyridinyl)phenyl)-1H-benzimidazol-2-yl)ethyl)amino)-5-pyrimidinecarbonitrile | 0.0089 |
| 4-amino-6-(((1S)-1-(6-fluoro-1-(3-(2-pyridinyl)phenyl)-1H-benzimidazol-2-yl)ethyl)amino)-5-pyrimidinecarbonitrile | 0.0038 |
| 4-amino-6-(((1S)-1-(6-fluoro-1-(3-(methylsulfonyl)phenyl)-1H-benzimidazol-2-yl)ethyl)amino)-5-pyrimidinecarbonitrile | 0.0342 |
| 4-amino-6-(((1S)-1-(6-fluoro-1-(3-fluorophenyl)-1H-benzimidazol-2-yl)ethyl)amino)-5-pyrimidinecarbonitrile | 0.0008 |
| 4-amino-6-(((1S)-1-(6-fluoro-1-(3-fluorophenyl)-1H-benzimidazol-2-yl)ethyl)amino)-5-pyrimidinecarbonitrile | 0.0004 |
| 4-amino-6-(((1S)-1-(6-fluoro-1-(3-pyridinyl)-1H-benzimidazol-2-yl)ethyl)amino)-5-pyrimidinecarbonitrile | 0.00805 |
| 4-amino-6-(((1S)-1-(6-fluoro-1-(3-pyridinyl)-1H-benzimidazol-2-yl)ethyl)amino)-5-pyrimidinecarboxamide | 0.06990 |
| 4-amino-6-(((1S)-1-(6-fluoro-1-(4-fluorophenyl)-1H-benzimidazol-2-yl)ethyl)amino)-5-pyrimidinecarbonitrile | 0.0018 |
| 4-amino-6-(((1S)-1-(6-fluoro-1-(5-fluoro-3-pyridinyl)-1H-benzimidazol-2-yl)ethyl)amino)-5-pyrimidinecarbonitrile | 0.00942 |
| 4-amino-6-(((1S)-1-(6-fluoro-1-(5-fluoro-3-pyridinyl)-1H-benzimidazol-2-yl)ethyl)amino)-5-pyrimidinecarboxamide | 0.15400 |

| | |
|---|---|
| 4-amino-6-(((1S)-1-(6-fluoro-1-(6-fluoro-2-pyridinyl)-1H-benzimidazol-2-yl)ethyl)amino)-5-pyrimidinecarbonitrile | 0.00889 |
| 4-amino-6-(((1S)-1-(6-fluoro-1-phenyl-1H-benzimidazol-2-yl)ethyl)amino)-5-pyrimidinecarbonitrile | 0.0002 |
| 4-amino-6-(((1S)-1-(6-fluoro-3-(2-(methylsulfonyl)phenyl)imidazo[1,2-a]pyridin-2-yl)ethyl)amino)-5-pyrimidinecarbonitrile | 0.0904 |
| 4-amino-6-(((1S)-1-(6-fluoro-3-(2-(methylsulfonyl)phenyl)imidazo[1,2-a]pyridin-2-yl)ethyl)amino)-5-pyrimidinecarbonitrile | 0.0401 |
| 4-amino-6-(((1S)-1-(6-fluoro-3-(2-(methylsulfonyl)phenyl)imidazo[1,2-a]pyridin-2-yl)ethyl)amino)-5-pyrimidinecarbonitrile | 1.0100 |
| 4-amino-6-(((1S)-1-(6-fluoro-3-(2-pyridinyl)imidazo[1,2-a]pyridin-2-yl)ethyl)amino)-5-pyrimidinecarbonitrile | 0.0099 |
| 4-amino-6-(((1S)-1-(6-fluoro-3-(3-(methylsulfonyl)phenyl)imidazo[1,2-a]pyridin-2-yl)ethyl)amino)-5-pyrimidinecarbonitrile | 0.0561 |
| 4-amino-6-(((1S)-1-(6-fluoro-3-(3-pyridinyl)imidazo[1,2-a]pyridin-2-yl)ethyl)amino)-5-pyrimidinecarbonitrile | 0.30600 |
| 4-amino-6-(((1S)-1-(6-fluoro-3-(4-fluorophenyl)imidazo[1,2-a]pyridin-2-yl)ethyl)amino)-5-pyrimidinecarbonitrile | 0.0083 |
| 4-amino-6-(((1S)-1-(6-fluoro-3-(5-fluoro-3-pyridinyl)imidazo[1,2-a]pyridin-2-yl)ethyl)amino)-5-pyrimidinecarbonitrile | 0.28600 |
| 4-amino-6-(((1S)-1-(6-fluoro-3-phenylimidazo[1,2-a]pyridin-2-yl)ethyl)amino)-5-pyrimidinecarbonitrile | 0.05440 |
| 4-amino-6-(((1S)-1-(7-(methylsulfonyl)-1H-benzimidazol-2-yl)ethyl)amino)-5-pyrimidinecarbonitrile | 0.04550 |
| 4-amino-6-(((1S)-1-(7-bromo-1-(5-fluoro-3-pyridinyl)-1H-benzimidazol-2-yl)ethyl)amino)-5-pyrimidinecarbonitrile | 0.04810 |
| 4-amino-6-(((1S)-1-(7-fluoro-1H-benzimidazol-2-yl)ethyl)amino)-5-pyrimidinecarbonitrile | 0.1730 |
| 4-amino-6-(((8-chloro-3-phenylimidazo[1,2-a]pyridin-2-yl)methyl)amino)-5-pyrimidinecarbonitrile | 0.2300 |
| 4-amino-6-((1-(3-(3,5-difluorophenyl)-1-benzothiophen-2-yl)ethyl)amino)-5-pyrimidinecarbonitrile | 0.00333 |
| 4-amino-6-((1-(3-phenyl-1-benzothiophen-2-yl)ethyl)amino)-5-pyrimidinecarbonitrile | 0.00266 |
| methyl 2-((1S)-1-((6-amino-5-cyano-4-pyrimidinyl)amino)ethyl)-3-(5-fluoro-3-pyridinyl)imidazo[1,2-a]pyridine-5-carboxylate | 0.31400 |
| methyl 2-((1S)-1-((6-amino-5-cyano-4-pyrimidinyl)amino)ethyl)-3-(3-pyridinyl)imidazo[1,2-a]pyridine-5-carboxylate | 0.14700 |
| methyl 2-((1S)-1-((6-amino-5-cyano-4-pyrimidinyl)amino)ethyl)-3-phenylimidazo[1,2-a]pyridine-5-carboxylate | 0.03900 |
| N-((1R)-1-(6-chloro-1-(3,5-difluorophenyl)-1H-benzimidazol-2-yl)ethyl)-9H-purin-6-amine | 0.0128 |
| N-((1R)-1-(6-chloro-1-(3,5-difluorophenyl)-1H-benzimidazol-2-yl)ethyl)-9H-purin-6-amine | 2.1600 |
| N-((1R)-1-(6-fluoro-1-(3-fluorophenyl)-1H-benzimidazol-2-yl)ethyl)-9H-purin-6-amine | 0.0015 |
| N-((1R)-1-(6-fluoro-1-(3-fluorophenyl)-1H-benzimidazol-2-yl)ethyl)-9H-purin-6-amine | 0.3950 |
| N-((1R)-1-(6-fluoro-1-(5-fluoro-3-pyridinyl)-1H-benzimidazol-2-yl)ethyl)-9H-purin-6-amine | 0.0145 |
| N-((1R)-1-(6-fluoro-1-(5-fluoro-3-pyridinyl)-1H-benzimidazol-2-yl)ethyl)-9H-purin-6-amine | 0.41800 |
| N-((1S)-1-(1-(cyclopropylmethyl)-7-(trifluoromethyl)-1H-benzimidazol-2-yl)propyl)-9H-purin-6-amine | 0.10000 |
| N-((1S)-1-(6-chloro-1-(3,5-difluorophenyl)-1H-benzimidazol-2-yl)ethyl)-9H-purin-6-amine | 0.0084 |
| N-((1S)-1-(6-fluoro-1-(3-fluorophenyl)-1H-benzimidazol-2-yl)ethyl)-9H-purin-6-amine | 0.0027 |
| N-((1S)-1-(6-fluoro-1-(5-fluoro-3-pyridinyl)-1H-benzimidazol-2-yl)ethyl)-9H-purin-6-amine | 0.00377 |
| N-((1S)-1-(7-fluoro-1H-benzimidazol-2-yl)ethyl)-9H-purin-6-amine | 0.6500 |
| N-(5-(2-((1R)-1-((6-amino-5-cyano-4-pyrimidinyl)amino)ethyl)-6-fluoro-1H-benzimidazol-1-yl)-3-pyridinyl)methanesulfonamide, N-(5-(2-((1S)-1-((6-amino-5-cyano-4-pyrimidinyl)amino)ethyl)-6-fluoro-1H-benzimidazol-1-yl)-3-pyridinyl)methanesulfonamide | 0.01440 |
| N-(5-(2-((1R)-1-((6-amino-5-cyano-4-pyrimidinyl)amino)ethyl)-6-fluoro-1H-benzimidazol-1-yl)-3-pyridinyl)methanesulfonamide | 0.60000 |
| N-(5-(2-((1S)-1-((6-amino-5-cyano-4-pyrimidinyl)amino)ethyl)-6-fluoro-1H-benzimidazol-1-yl)-3-pyridinyl)methanesulfonamide | 0.01190 |

For the treatment of PI3K$_6$-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI310-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq. or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethylformamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

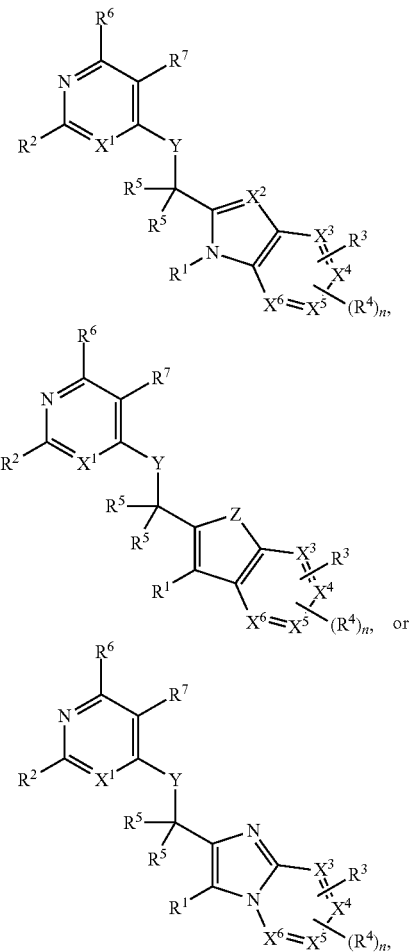

or any pharmaceutically-acceptable salt thereof, wherein:
$X^1$ is N;
$X^2$ is $C(R^{12})$ or N;
$X^3$ is C;
$X^4$ is C;
$X^5$ is C;
$X^6$ is C;
Y is $N(R^8)$, O or S;
Z is S, O, or $NR^{11}$;
n is 0, 1, 2 or 3;
$R^1$ is a direct-bonded, $C_{1-4}$alk-linked, $OC_{1-2}$alk-linked, $C_{1-2}$alkO-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; wherein the available carbon atoms of the ring are additionally substituted by 0, 1 or 2 oxo or thioxo groups; and wherein the ring is additionally substituted by 0 or 1 saturated 5- or 6-membered monocyclic ring containing 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk and cyano; or $R^1$ is $C_{1-4}$alk substituted by 1 or 2 substituents selected from cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^2$ is selected from H, halo, $C_{1-6}$alk, $C_{1-4}$haloalk, cyano, nitro, O$R^a$, N$R^aR^a$, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^3$ is selected from H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk, $C_{1-4}$haloalk, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^3$ is an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —O$C_{1-4}$alk, —NH$_2$, —NH$C_{1-4}$alk, —N($C_{1-4}$alk)$C_{1-4}$alk;

$R^4$ is, independently, in each instance, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk or $C_{1-4}$haloalk;

$R^5$ is, independently, in each instance, H, halo, $C_{1-6}$alk, $C_{1-4}$haloalk, or $C_{1-6}$alk substituted by 1, 2 or 3 substituents selected from halo, cyano, OH, O$C_{1-4}$alk, $C_{1-4}$alk, $C_{1-3}$haloalk, O$C_{1-4}$alk, NH$_2$, NH$C_{1-4}$alk, N($C_{1-4}$alk)$C_{1-4}$alk; or both $R^5$ groups together form a $C_{3-6}$-spiroalk substituted by 0, 1, 2 or 3 substituents selected from halo, cyano, OH, O$C_{1-4}$alk, $C_{1-4}$alk, $C_{1-3}$haloalk, O$C_{1-4}$alk, NH$_2$, NH$C_{1-4}$alk, N($C_{1-4}$alk)$C_{1-4}$alk;

$R^6$ is H, halo, NH$R^9$ or OH;

$R^7$ is selected from H, halo, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2R^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)

C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$ and C$_{1-6}$alk, wherein the C$_{1-6}$alk is substituted by 0, 1 2 or 3 substituents selected from halo, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, and the C$_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk; or R$^7$ and R$^8$ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$,—S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S (=O)$_2$NR$^a$R$^a$, —NR$^a$C$_{2-6}$alkNR$^a$R$^a$ and —NR$^a$C$_{2-6}$alkOR$^a$; or R$^7$ and R$^9$ together form a —N=C— bridge wherein the carbon atom is substituted by H, halo, C$_{1-6}$alk, C$_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$;

R$^8$ is H or C$_{1-6}$alk;

R$^9$ is H, C$_{1-6}$alk or C$_{1-4}$haloalk;

R$^{10}$ is H, H halo, C$_{1-3}$alk, C$_{1-3}$haloalk or cyano;

R$^{11}$ is H or C$_{1-4}$alk;

R$^{12}$ is H or C$_{1-4}$alk;

R$^a$ is independently, at each instance, H or R$^b$; and

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk.

2. A compound according to claim 1, wherein the compound has the general structure:

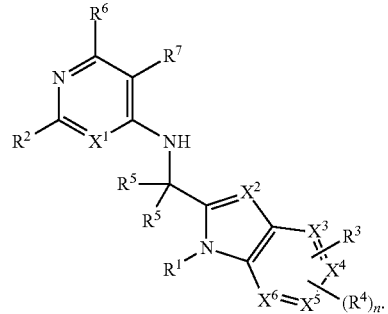

3. A compound according to claim 1, wherein the compound has the general structure:

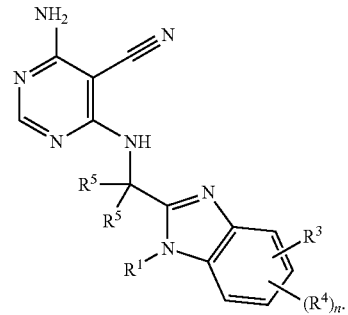

4. A compound according to claim 1, wherein the compound is selected from:

1-cyclopropyl-N-methyl-2-((1S)-1-(9H-purin-6-ylamino)ethyl)-1H-benzimidazole-7-carboxamide, 2-((1R)-1-((6-amino-5-cyano-4-pyrimidinyl)amino)ethyl)-1-(5-fluoro-3-pyridinyl)-N-methyl-1H-benzimidazole-7-carboxamide, 2-((1S)-1-((6-amino-5-cyano-4-pyrimidinyl)amino)ethyl)-1-(5-fluoro-3-pyridinyl)-N-methyl-1H-benzimidazole-7-carboxamide, 2-((1R)-1-((6-amino-5-cyano-4-pyrimidinyl)amino)ethyl)-1-(5-fluoro-3-pyridinyl)-N-methyl-1H-benzimidazole-7-carboxamide, 2-((1R)-1-((6-amino-5-cyano-4-pyrimidinyl)amino)ethyl)-1-(5-fluoro-3-pyridinyl)-1H-benzimidazole-7-carbonitrile, 2-((1S)-1-((6-amino-5-cyano-4-pyrimidinyl)amino)ethyl)-1-(5-fluoro-3-pyridinyl)-1H-benzimidazole-7-carbonitrile, 2-((1R)-1-((6-amino-5-cyano-4-pyrimidinyl)amino)ethyl)-1-(5-fluoro-3-pyridinyl)-1H-benzimidazole-7-carbonitrile, 2-((1S)-1-(6-amino-5-(4-(methylsulfonyl)phenyl)-4-pyrimidinyl)amino)ethyl)-1-cyclopropyl-N-methyl-1H-benzimidazole-7-carboxamide, 2-((1S)-1-(6-amino-5-(methylsulfonyl)-4-pyrimidinyl)amino)ethyl)-1-cyclopropyl-N-methyl-1H-benzimidazole-7-carboxamide, 2-((1S)-1-((6-amino-5-(trifluoromethyl)-4-pyrimidinyl)amino)ethyl)-1-cyclopropyl-N-methyl-1H-benzimidazole-7-carboxamide, 2-((1S)-1-(6-amino-5-cyano-4-pyrimidinyl)amino)ethyl)-1-(5-fluoro-3-pyridinyl)-N-methyl-1H-benzimidazole-7-carboxamide, 2-((1S)-1-(6-amino-5-cyano-4-pyrimidinyl)amino)ethyl)-1-(5-fluoro-3-pyridinyl)-1H-benzimidazole-7-carbonitrile, 2-((1S)-1-(6-amino-5-cyano-4-pyrimidinyl)amino)ethyl)-1-cyclopropyl-N-methyl-1H-benzimidazole-7-carboxamide,
2-((1S)-1-(6-amino-5-cyano-4-pyrimidinyl)amino)ethyl)-3-(5-fluoro-3-pyridinyl)-N-methylimidazo[1,2-a]pyridine-5-carboxamide,
2-((1S)-1-(6-amino-5-cyano-4-pyrimidinyl)amino)ethyl)-N,1-dicyclopropyl-1H-benzimidazole-7-carboxamide,
2-((1S)-1-((6-amino-5-cyano-4-pyrimidinyl)amino)ethyl)-N-cyclopentyl-1-cyclopropyl-1H-benzimidazole-7-carboxamide,
2-((1S)-1-(6-amino-5-cyano-4-pyrimidinyl)amino)ethyl)-N-cyclopropyl-3-phenylimidazo[1,2-a]pyridine-5-carboxamide,
2-((1S)-1-(6-amino-5-cyano-4-pyrimidinyl)amino)ethyl)-N-methyl-3-phenylimidazo[1,2-a]pyridine-5-carboxamide,
2-((1S)-1-(6-amino-5-cyano-4-pyrimidinyl)amino)ethyl)-N-tert-butyl-1-cyclopropyl-1H-benzimidazole-7-carboxamide,
2-((1S)-1-((6-amino-5-cyano-4-pyrimidinyl)amino)propyl)-1-cyclopropyl-N-methyl-1H-benzimidazole-7-carboxamide,
3-(2-((1R)-1-((6-amino-5-cyano-4-pyrimidinyl)amino)ethyl)-6-fluoro-1H-benzimidazol-1-yl)-N-methylbenzamide, 3-(2-((1S)-1-((6-amino-5-cyano-4-pyrimidinyl)amino)ethyl)-6-fluoro-1H-benzimidazol-1-yl)-N-methylbenzamide,
3-(2-((1R)-1-((6-amino-5-cyano-4-pyrimidinyl)amino)ethyl)-6-fluoro-1H-benzimidazol-1-yl)-N-methylbenzamide,
3-(2-((1S)-1-((6-amino-5-cyano-4-pyrimidinyl)amino)ethyl)-6-fluoro-1H-benzimidazol-1-yl)-N-methylbenzamide,
4-amino-6-(((1R)-1-(1-(2,3'-bipyridin-5'-yl)-6-fluoro-1H-benzimidazol-2-yl)ethyl)amino)-5-pyrimidinecarbonitrile,
4-amino-6-(((1R)-1-(1-(2-pyridinyl)-1H-imidazo[4,5-b]pyridin-2-yl)ethyl)amino)-5-pyrimidinecarbonitrile, 4-amino-6-(((1S)-1-(1-(2-pyridinyl)-1H-imidazo[4,5-b]pyridin-2-yl)ethyl)amino)-5-pyrimidinecarbonitrile,
4-amino-6-(((1R)-1-(1-(2-pyridinyl)-1H-imidazo[4,5-b]pyridin-2-yl)ethyl)amino)-5-pyrimidinecarbonitrile,
4-amino-6-(((1R)-1-(1-(3,5-difluorophenyl)-1H-imidazo[4,5-b]pyridin-2-yl)ethyl)amino)-5-pyrimidinecarbonitrile, 4-amino-6-(((1S)-1-(1-(3,5-difluorophenyl)-1H-imidazo[4,5-b]pyridin-2-yl)ethyl)amino)-5-pyrimidinecarbonitrile,
4-amino-6-(((1R)-1-(1-(3,5-difluorophenyl)-1H-imidazo[4,5-c]pyridin-2-yl)ethyl)amino)-5-pyrimidinecarbonitrile, 4-amino-6-(((1S)-1-(1-(3,5-difluorophenyl)-1H-imidazo[4,5-c]pyridin-2-yl)ethyl)amino)-5-pyrimidinecarbonitrile,
4-amino-6-(((1R)-1-(1-(3,5-difluorophenyl)-4,6-difluoro-1H-benzimidazol-2-yl) ethyl)amino)-5-pyrimidinecarbonitrile,
4-amino-6-(((1R)-1-(1-(3,5-difluorophenyl)-4-fluoro-1H-benzimidazol-2-yl) ethyl)amino)-5-pyrimidinecarbonitrile,
4-amino-6-(((1R)-1-(1-(3,5-difluorophenyl)-6-fluoro-1H-benzimidazol-2-yl)ethyl)amino)-5-pyrimidinecarbonitrile,
4-amino-6-(((1R)-1-(1-(3,5-difluorophenyl)-6-fluoro-1H-benzimidazol-2-yl)ethyl)amino)-5-pyrimidinecarbonitrile,
4-amino-6-(((1R)-1-(1-(3,5-difluorophenyl)-7-fluoro-1H-benzimidazol-2-yl)ethyl)amino)-5-pyrimidinecarbonitrile,
4-amino-6-(((1R)-1-(1-(3,5-difluorophenyl)-7-fluoro-1H-benzimidazol-2-yl)ethyl)amino)-5-pyrimidinecarbonitrile,
4-amino-6-(((1R)-1-(1-(3-cyanophenyl)-6-fluoro-1H-benzimidazol-2-yl)ethyl)amino)-5-pyrimidinecarbonitrile, 4-amino-6-(((1S)-1-(1-(3-cyanophenyl)-6-fluoro-1H-benzimidazol-2-yl) ethyl)amino)-5-pyrimidinecarbonitrile,
4-amino-6-(((1R)-1-(1-(3-cyanophenyl)-6-fluoro-1H-benzimidazol-2-yl)ethyl)amino)-5-pyrimidinecarbonitrile,
4-amino-6-(((1R)-1-(1-(5-bromo-3-pyridinyl)-6-fluoro-1H-benzimidazol-2-yl)ethyl)amino)-5-pyrimidinecarbonitrile, 4-amino-6-(((1S)-1-(1-(5-bromo-3-pyridinyl)-6-fluoro-1H-benzimidazol-2-yl)ethyl)amino)-5-pyrimidinecarbonitrile,
4-amino-6-(((1R)-1-(1-cyclopropyl-7-(methylsulfonyl)-1H-benzimidazol-2-yl)ethyl)amino)-5-pyrimidinecarbonitrile, 4-amino-6-(((1S)-1-(1-cyclopropyl-7-(methylsulfonyl)-1H-benzimidazol-2-yl)ethyl)amino)-5-pyrimidinecarbonitrile,
4-amino-6-(((1R)-1-(1-cyclopropyl-7-(methylsulfonyl)-1H-benzimidazol-2-yl)ethyl)amino)-5-pyrimidinecarbonitrile,
4-amino-6-(((1R)-1-(3-(3,5-difluorophenyl)-3H-imidazo[4,5-b]pyridin-2-yl)ethyl)amino)-5-pyrimidinecarbonitrile,
4-amino-6-(((1R)-1-(4,6-difluoro-1-(3-pyridinyl)-1H-benzimidazol-2-yl)ethyl)amino)-5-pyrimidinecarbonitrile, 4-amino-6-(((1S)-1-(4,6-difluoro-1-(3-pyridinyl)-1H-benzimidazol-2-yl) ethyl)amino)-5-pyrimidinecarbonitrile,
4-amino-6-(((1R)-1-(4,6-difluoro-1-(3-pyridinyl)-1H-benzimidazol-2-yl)ethyl)amino)-5-pyrimidinecarbonitrile,
4-amino-6-(((1R)-1-(4-fluoro-1-(5-fluoro-3-pyridinyl)-1H-benzimidazol-2-yl)ethyl)amino)-5-pyrimidinecarbonitrile, 4-amino-6-(((1S)-1-(4-fluoro-1-(5-fluoro-3-pyridinyl)-1H-benzimidazol-2-yl)ethyl)amino)-5-pyrimidinecarbonitrile,
4-amino-6-(((1R)-1-(5-fluoro-1-(2-pyridinyl)-1H-benzimidazol-2-yl)ethyl)amino)-5-pyrimidinecarbonitrile,
4-amino-6-(((1R)-1-(5-fluoro-1-(3-(methylsulfanyl)phenyl)-1H-benzimidazol-2-yl) ethyl)amino)-5-pyrimidinecarbonitrile,
4-amino-6-(((1R)-1-(5-fluoro-1-(3-(methylsulfanyl)phenyl)-1H-benzimidazol-2-yl) ethyl)amino)-5-pyrimidinecarbonitrile,
4-amino-6-(((1R)-1-(5-fluoro-1-(3-(methylsulfonyl)phenyl)-1H-benzimidazol-2-yl) ethyl)amino)-5-pyrimidinecarbonitrile,
4-amino-6-(((1R)-1-(5-fluoro-1-(5-fluoro-3-pyridinyl)-1H-benzimidazol-2-yl)ethyl)amino)-5-pyrimidinecarbonitrile, 4-amino-6-(((1S)-1-(5-fluoro-1-(5-fluoro-3-pyridinyl)-1H-benzimidazol-2-yl)ethyl)amino)-5-pyrimidinecarbonitrile,
4-amino-6-(((1R)-1-(5-fluoro-1-(5-fluoro-3-pyridinyl)-1H-benzimidazol-2-yl)ethyl)amino)-5-pyrimidinecarbonitrile,
4-amino-6-(((1R)-1-(6-chloro-1-(3,5-difluorophenyl)-1H-benzimidazol-2-yl)ethyl)amino)-5-pyrimidinecarbonitrile, 4-amino-6-(((1R)-1-(6-chloro-1-(3,5-difluorophenyl)-1H-benzimidazol-2-yl)ethyl)amino)-5-pyrimidinecarbonitrile,
4-amino-6-(((1R)-1-(6-fluoro-1-(2-(methylsulfonyl)phenyl)-1H-benzimidazol-2-yl) ethyl)amino)-5-pyrimidinecarbonitrile,
4-amino-6-(((1R)-1-(6-fluoro-1-(2-(methylsulfonyl)phenyl)-1H-benzimidazol-2-yl) ethyl)amino)-5-pyrimidinecarbonitrile,
4-amino-6-(((1R)-1-(6-fluoro-1-(2-(methylsulfonyl)phenyl)-1H-benzimidazol-2-yl) ethyl)amino)-5-pyrimidinecarbonitrile,
4-amino-6-(((1R)-1-(6-fluoro-1-(3-(2-pyridinyl)phenyl)-1H-benzimidazol-2-yl)ethyl)amino)-5-pyrimidinecarbonitrile,
4-amino-6-(((1R)-1-(6-fluoro-1-(3-(methylsulfonyl)phenyl)-1H-benzimidazol-2-yl) ethyl)amino)-5-pyrimidinecarbonitrile,
4-amino-6-(((1R)-1-(6-fluoro-1-(3-(methylsulfonyl)phenyl)-1H-benzimidazol-2-yl) ethyl)amino)-5-pyrimidinecarbonitrile,
4-amino-6-(((1R)-1-(6-fluoro-1-(3-fluorophenyl)-1H-benzimidazol-2-yl)ethyl)amino)-5-pyrimidinecarbonitrile,
4-amino-6-(((1R)-1-(6-fluoro-1-(3-pyridinyl)-1H-benzimidazol-2-yl)ethyl)amino)-5-pyrimidinecarbonitrile, 4-amino-6-(((1S)-1-(6-fluoro-1-(3-pyridinyl)-1H-benzimidazol-2-yl) ethyl)amino)-5-pyrimidinecarbonitrile,
4-amino-6-(((1R)-1-(6-fluoro-1-(3-pyridinyl)-1H-benzimidazol-2-yl)ethyl)amino)-5-pyrimidinecarbonitrile,
4-amino-6-(((1R)-1-(6-fluoro-1-(4-fluorophenyl)-1H-benzimidazol-2-yl)ethyl)amino)-5-pyrimidinecarbonitrile,
4-amino-6-(((1R)-1-(6-fluoro-1-(4-fluorophenyl)-1H-benzimidazol-2-yl)ethyl)amino)-5-pyrimidinecarbonitrile,
4-amino-6-(((1R)-1-(6-fluoro-1-(5-fluoro-3-pyridinyl)-1H-benzimidazol-2-yl)ethyl)amino)-5-pyrimidinecarbonitrile,
4-amino-6-(((1R)-1-(6-fluoro-1-(5-fluoro-3-pyridinyl)-1H-benzimidazol-2-yl)ethyl)amino)-5-pyrimidinecarbonitrile,
4-amino-6-(((1R)-1-(6-fluoro-1-(6-fluoro-2-pyridinyl)-1H-benzimidazol-2-yl)ethyl)amino)-5-pyrimidinecarbonitrile, 4-amino-6-(((1S)-1-(6-fluoro-1-(6-fluoro-2-pyridinyl)-1H-benzimidazol-2-yl)ethyl)amino)-5-pyrimidinecarbonitrile,
4-amino-6-(((1R)-1-(6-fluoro-1-(6-fluoro-2-pyridinyl)-1H-benzimidazol-2-yl)ethyl)amino)-5-pyrimidinecarbonitrile,
4-amino-6-(((1R)-1-(7-bromo-1-(5-fluoro-3-pyridinyl)-1H-benzimidazol-2-yl)ethyl)amino)-5-pyrimidinecarbonitrile, 4-amino-6-(((1S)-1-(7-bromo-1-(5-fluoro-3-pyridinyl)-1H-benzimidazol-2-yl)ethyl)amino)-5-pyrimidinecarbonitrile,
4-amino-6-(((1S)-1-(1-(2,3'-bipyridin-5'-yl)-6-fluoro-1H-benzimidazol-2-yl)ethyl)amino)-5-pyrimidinecarbonitrile,
4-amino-6-(((1S)-1-(1-(2-pyridinyl)-1H-imidazo[4,5-b]pyridin-2-yl)ethyl)amino)-5-pyrimidinecarbonitrile,
4-amino-6-(((1S)-1-(1-(3,5-difluorobenzyl)-7-(methylsulfonyl)-1H-benzimidazol-2-yl) ethyl)amino)-5-pyrimidinecarbonitrile,
4-amino-6-(((1S)-1-(1-(3,5-difluorophenyl)-4,6-difluoro-1H-benzimidazol-2-yl)ethyl)amino)-5-pyrimidinecarbonitrile,
4-amino-6-(((1S)-1-(1-(3,5-difluorophenyl)-4-fluoro-1H-benzimidazol-2-yl)ethyl)amino)-5-pyrimidinecarbonitrile,
4-amino-6-(((1S)-1-(1-(3,5-difluorophenyl)-4-fluoro-1H-benzimidazol-2-yl)ethyl)amino)-5-pyrimidinecarbonitrile,
4-amino-6-(((1S)-1-(1-(3,5-difluorophenyl)-6-fluoro-1H-benzimidazol-2-yl)ethyl)amino)-5-pyrimidinecarbonitrile,
4-amino-6-(((1S)-1-(1-(3,5-difluorophenyl)-7-fluoro-1H-benzimidazol-2-yl)ethyl)amino)-5-pyrimidinecarbonitrile,
4-amino-6-(((1S)-1-(1-(3-cyanophenyl)-6-fluoro-1H-benzimidazol-2-yl)ethyl)amino)-5-pyrimidinecarbonitrile,
4-amino-6-(((1S)-1-(1-(4-fluorobenzyl)-4-(methylsulfonyl)-1H-benzimidazol-2-yl) ethyl)amino)-5-pyrimidinecarbonitrile,
4-amino-6-(((1S)-1-(1-(4-fluorobenzyl)-7-(methylsulfonyl)-1H-benzimidazol-2-yl) ethyl)amino)-5-pyrimidinecarbonitrile,
4-amino-6-(((1S)-1-(1-(4-fluorobenzyl)-7-(methylsulfonyl)-1H-benzimidazol-2-yl) propyl)amino)-5-pyrimidinecarbonitrile,
4-amino-6-(((1S)-1-(1-(4-fluorobenzyl)-7-(trifluoromethyl)-1H-benzimidazol-2-yl) propyl)amino)-5-pyrimidinecarbonitrile,
4-amino-6-(((1S)-1-(1-(cyclopropylmethyl)-5-fluoro-1H-benzimidazol-2-yl)ethyl)amino)-5-pyrimidinecarbonitrile,
4-amino-6-(((1S)-1-(1-(cyclopropylmethyl)-5-fluoro-1H-benzimidazol-2-yl)ethyl)amino)-5-pyrimidinecarbonitrile,
4-amino-6-(((1S)-1-(1-(cyclopropylmethyl)-6-fluoro-1H-benzimidazol-2-yl)ethyl)amino)-5-pyrimidinecarbonitrile,
4-amino-6-(((1S)-1-(1-(cyclopropylmethyl)-7-(methylsulfonyl)-1H-benzimidazol-2-yl) ethyl)amino)-5-pyrimidinecarbonitrile,
4-amino-6-(((1S)-1-(1-(cyclopropylmethyl)-7-(methylsulfonyl)-1H-benzimidazol-2-yl) propyl)amino)-5-pyrimidinecarbonitrile,
4-amino-6-(((1S)-1-(1-(cyclopropylmethyl)-7-(trifluoromethyl)-1H-benzimidazol-2-yl) propyl)amino)-5-pyrimidinecarbonitrile,
4-amino-6-(((1S)-1-(1-cyclopentyl-4-(methylsulfonyl)-1H-benzimidazol-2-yl)ethyl)amino)-5-pyrimidinecarbonitrile,
4-amino-6-(((1S)-1-(1-cyclopropyl-5-fluoro-1H-benzimidazol-2-yl)ethyl)amino)-5-pyrimidinecarbonitrile,
4-amino-6-(((1S)-1-(1-cyclopropyl-5-fluoro-1H-benzimidazol-2-yl)ethyl)amino)-5-pyrimidinecarbonitrile,
4-amino-6-(((1S)-1-(1-cyclopropyl-6-fluoro-1H-benzimidazol-2-yl)ethyl)amino)-5-pyrimidinecarbonitrile,
4-amino-6-(((1S)-1-(1-cyclopropyl-7-(methylsulfonyl)-1H-benzimidazol-2-yl)ethyl)amino)-5-pyrimidinecarbonitrile,
4-amino-6-(((1S)-1-(1-cyclopropyl-7-fluoro-1H-benzimidazol-2-yl)ethyl)amino)-5-pyrimidinecarbonitrile,
4-amino-6-(((1S)-1-(3-(2-pyridinyl)imidazo[1,2-a]pyrazin-2-yl)ethyl)amino)-5-pyrimidinecarbonitrile,
4-amino-6-(((1S)-1-(3-(2-pyridinyl)imidazo[1,2-a]pyrimidin-2-yl)ethyl)amino)-5-pyrimidinecarbonitrile,
4-amino-6-(((1S)-1-(3-(2-pyridinyl)imidazo[1,2-b]pyridazin-2-yl)ethyl)amino)-5-pyrimidinecarbonitrile, 4-amino-6-(((1S)-1-(3-(3,5-difluorophenyl)-3H-imidazo[4,5-b]pyridin-2-yl)ethyl)amino)-5-pyrimidinecarbonitrile,
4-amino-6-(((1S)-1-(3-(3,5-difluorophenyl)-6-fluoroimidazo[1,2-a]pyridin-2-yl)ethyl)amino)-5-pyrimidinecarbonitrile,
4-amino-6-(((1S)-1-(3-(3-chloro-5-fluorophenyl)-6-fluoroimidazo[1,2-a]pyridin-2-yl) ethyl)amino)-5-pyrimidinecarbonitrile,
4-amino-6-(((1S)-1-(3-(4-chlorophenyl)-6-fluoroimidazo[1,2-a]pyridin-2-yl)ethyl)amino)-5-pyrimidinecarbonitrile,
4-amino-6-(((1S)-1-(3-(4-chlorophenyl)imidazo[1,2-a]pyridin-2-yl)ethyl)amino)-5-pyrimidinecarbonitrile,
4-amino-6-(((1S)-1-(4,6-difluoro-1-(3-pyridinyl)-1H-benzimidazol-2-yl)ethyl)amino)-5-pyrimidinecarbonitrile,
4-amino-6-(((1S)-1-(4-fluoro-1-(5-fluoro-3-pyridinyl)-1H-benzimidazol-2-yl)ethyl)amino)-5-pyrimidinecarbonitrile,
4-amino-6-(((1S)-1-(5-((4-methyl-1-piperazinyl)carbonyl)-3-phenylimidazo[1,2-a]pyridin-2-yl)ethyl)amino)-5-pyrimidinecarbonitrile,
4-amino-6-(((1S)-1-(5,6-difluoro-1-(5-fluoro-3-pyridinyl)-1H-benzimidazol-2-yl) ethyl)amino)-5-pyrimidinecarbonitrile,
4-amino-6-(((1S)-1-(5-fluoro-1-(3-(methylsulfanyl)phenyl)-1H-benzimidazol-2-yl) ethyl)amino)-5-pyrimidinecarbonitrile,
4-amino-6-(((1S)-1-(5-fluoro-1-(3-(methylsulfonyl)phenyl)-1H-benzimidazol-2-yl) ethyl)amino)-5-pyrimidinecarbonitrile,
4-amino-6-(((1S)-1-(5-fluoro-1-(3-(methylsulfonyl)phenyl)-1H-benzimidazol-2-yl) ethyl)amino)-5-pyrimidinecarbonitrile,
4-amino-6-(((1S)-1-(5-fluoro-1-(5-fluoro-3-pyridinyl)-1H-benzimidazol-2-yl) ethyl)amino)-5-pyrimidinecarbonitrile,
4-amino-6-(((1S)-1-(5-fluoro-1-phenyl-1H-benzimidazol-2-yl)ethyl)amino)-5-pyrimidinecarbonitrile,
4-amino-6-(((1S)-1-(6-chloro-1-(3,5-difluorophenyl)-1H-benzimidazol-2-yl)ethyl)amino)-5-pyrimidinecarbonitrile,
4-amino-6-(((1S)-1-(6-fluoro-1-(2-(methylsulfonyl)phenyl)-1H-benzimidazol-2-yl) ethyl)amino)-5-pyrimidinecarbonitrile,
4-amino-6-(((1S)-1-(6-fluoro-1-(2-(methylsulfonyl)phenyl)-1H-benzimidazol-2-yl) ethyl)amino)-5-pyrimidinecarbonitrile,
4-amino-6-(((1S)-1-(6-fluoro-1-(3-(2-pyridinyl)phenyl)-1H-benzimidazol-2-yl)ethyl)amino)-5-pyrimidinecarbonitrile,
4-amino-6-(((1S)-1-(6-fluoro-1-(3-(2-pyridinyl)phenyl)-1H-benzimidazol-2-yl)ethyl)amino)-5-pyrimidinecarbonitrile,
4-amino-6-(((1S)-1-(6-fluoro-1-(3-(methylsulfonyl)phenyl)-1H-benzimidazol-2-yl) ethyl)amino)-5-pyrimidinecarbonitrile,
4-amino-6-(((1S)-1-(6-fluoro-1-(3-fluorophenyl)-1H-benzimidazol-2-yl)ethyl)amino)-5-pyrimidinecarbonitrile,
4-amino-6-(((1S)-1-(6-fluoro-1-(3-fluorophenyl)-1H-benzimidazol-2-yl)ethyl)amino)-5-pyrimidinecarbonitrile,
4-amino-6-(((1S)-1-(6-fluoro-1-(3-pyridinyl)-1H-benzimidazol-2-yl)ethyl)amino)-5-pyrimidinecarbonitrile,
4-amino-6-(((1S)-1-(6-fluoro-1-(3-pyridinyl)-1H-benzimidazol-2-yl)ethyl)amino)-5-pyrimidinecarboxamide,
4-amino-6-(((1S)-1-(6-fluoro-1-(4-fluorophenyl)-1H-benzimidazol-2-yl)ethyl)amino)-5-pyrimidinecarbonitrile,
4-amino-6-(((1S)-1-(6-fluoro-1-(5-fluoro-3-pyridinyl)-1H-benzimidazol-2-yl)ethyl)amino)-5-pyrimidinecarbonitrile,
4-amino-6-(((1S)-1-(6-fluoro-1-(5-fluoro-3-pyridinyl)-1H-benzimidazol-2-yl)ethyl)amino)-5-pyrimidinecarboxamide,
4-amino-6-(((1S)-1-(6-fluoro-1-(6-fluoro-2-pyridinyl)-1H-benzimidazol-2-yl)ethyl)amino)-5-pyrimidinecarbonitrile,
4-amino-6-(((1S)-1-(6-fluoro-1-phenyl-1H-benzimidazol-2-yl)ethyl)amino)-5-pyrimidinecarbonitrile,
4-amino-6-(((1S)-1-(6-fluoro-3-(2-(methylsulfonyl)phenyl)imidazo[1,2-a]pyridin-2-yl) ethyl)amino)-5-pyrimidinecarbonitrile,
4-amino-6-(((1S)-1-(6-fluoro-3-(2-(methylsulfonyl)phenyl)imidazo[1,2-a]pyridin-2-yl) ethyl)amino)-5-pyrimidinecarbonitrile,
4-amino-6-(((1S)-1-(6-fluoro-3-(2-(methylsulfonyl)phenyl)imidazo[1,2-a]pyridin-2-yl)ethyl)amino)-5-pyrimidinecarbonitrile,
4-amino-6-(((1S)-1-(6-fluoro-3-(2-pyridinyl)imidazo[1,2-a]pyridin-2-yl)ethyl)amino)-5-pyrimidinecarbonitrile,
4-amino-6-(((1S)-1-(6-fluoro-3-(3-(methylsulfonyl)phenyl)imidazo[1,2-a]pyridin-2-yl) ethyl)amino)-5-pyrimidinecarbonitrile,
4-amino-6-(((1S)-1-(6-fluoro-3-(3-pyridinyl)imidazo[1,2-a]pyridin-2-yl)ethyl)amino)-5-pyrimidinecarbonitrile,
4-amino-6-(((1S)-1-(6-fluoro-3-(4-fluorophenyl)imidazo[1,2-a]pyridin-2-yl)ethyl)amino)-5-pyrimidinecarbonitrile,
4-amino-6-(((1S)-1-(6-fluoro-3-(5-fluoro-3-pyridinyl)imidazo[1,2-a]pyridin-2-yl) ethyl)amino)-5-pyrimidinecarbonitrile,
4-amino-6-(((1S)-1-(6-fluoro-3-phenylimidazo[1,2-a]pyridin-2-yl)ethyl)amino)-5-pyrimidinecarbonitrile,
4-amino-6-(((1S)-1-(7-(methylsulfonyl)-1H-benzimidazol-2-yl)ethyl)amino)-5-pyrimidinecarbonitrile,
4-amino-6-(((1S)-1-(7-bromo-1-(5-fluoro-3-pyridinyl)-1H-benzimidazol-2-yl)ethyl)amino)-5-pyrimidinecarbonitrile,
4-amino-6-(((1S)-1-(7-fluoro-1H-benzimidazol-2-yl) ethyl)amino)-5-pyrimidinecarbonitrile,
4-amino-6-(((8-chloro-3-phenylimidazo[1,2-a]pyridin-2-yl)methyl)amino)-5-pyrimidinecarbonitrile,
4-amino-6-((1-(3-(3,5-difluorophenyl)-1-benzothiophen-2-yl)ethyl)amino)-5-pyrimidinecarbonitrile,
4-amino-6-((1-(3-phenyl-1-benzothiophen-2-yl)ethyl) amino)-5-pyrimidinecarbonitrile,
methyl 2-((1S)-1-((6-amino-5-cyano-4-pyrimidinyl) amino)ethyl)-3-(5-fluoro-3-pyridinyl) imidazo[1,2-a] pyridine-5-carboxylate,
methyl 2-((1S)-1-((6-amino-5-cyano-4-pyrimidinyl) amino)ethyl)-3-(3-pyridinyl)imidazo[1,2-a]pyridine-5-carboxylate,
methyl 2-((1S)-1-((6-amino-5-cyano-4-pyrimidinyl) amino)ethyl)-3-phenylimidazo[1,2-a]pyridine-5-carboxylate,
N-((1R)-1-(6-chloro-1-(3,5-difluorophenyl)-1H-benzimidazol-2-yl)ethyl)-9H-purin-6-amine, N-((1R)-1-(6-chloro-1-(3,5-difluorophenyl)-1H-benzimidazol-2-yl)ethyl)-9H-purin-6-amine,
N-((1R)-1-(6-fluoro-1-(3-fluorophenyl)-1H-benzimidazol-2-yl)ethyl)-9H-purin-6-amine,
N-((1R)-1-(6-fluoro-1-(3-fluorophenyl)-1H-benzimidazol-2-yl)ethyl)-9H-purin-6-amine,
N-((1R)-1-(6-fluoro-1-(5-fluoro-3-pyridinyl)-1H-benzimidazol-2-yl)ethyl)-9H-purin-6-amine,
N-((1R)-1-(6-fluoro-1-(5-fluoro-3-pyridinyl)-1H-benzimidazol-2-yl)ethyl)-9H-purin-6-amine,
N-((1S)-1-(1-(cyclopropylmethyl)-7-(trifluoromethyl)-1H-benzimidazol-2-yl)propyl)-9H-purin-6-amine,
N-((1S)-1-(6-chloro-1-(3,5-difluorophenyl)-1H-benzimidazol-2-yl)ethyl)-9H-purin-6-amine,
N-((1S)-1-(6-fluoro-1-(3-fluorophenyl)-1H-benzimidazol-2-yl)ethyl)-9H-purin-6-amine,
N-((1S)-1-(6-fluoro-1-(5-fluoro-3-pyridinyl)-1H-benzimidazol-2-yl)ethyl)-9H-purin-6-amine,
N-((1S)-1-(7-fluoro-1H-benzimidazol-2-yl)ethyl)-9H-purin-6-amine,
N-(5-(2-((1R)-1-((6-amino-5-cyano-4-pyrimidinyl)amino)ethyl)-6-fluoro-1H-benzimidazol-1-yl)-3-pyridinyl)methanesulfonamide, N-(5-(2-((1S)-1-((6-amino-5-cyano-4-pyrimidinyl) amino)ethyl)-6-fluoro-1H-benzimidazol-1-yl)-3-pyridinyl)methanesulfonamide,
N-(5-(2-((1R)-1-((6-amino-5-cyano-4-pyrimidinyl)amino)ethyl)-6-fluoro-1H-benzimidazol-1-yl)-3-pyridinyl)methanesulfonamide, and
N-(5-(2-((1S)-1-((6-amino-5-cyano-4-pyrimidinyl)amino)ethyl)-6-fluoro-1H-benzimidazol-1-yl)-3-pyridinyl)methanesulfonamide, and any pharmaceutically acceptable salts thereof.

5. A pharmaceutical composition comprising a compound according to claim 1 and a pharmaceutically-acceptable diluent or carrier.

* * * * *